United States Patent
Marzano et al.

(10) Patent No.: US 12,272,899 B2
(45) Date of Patent: Apr. 8, 2025

(54) COMMON HOUSING FOR A PLURALITY OF TERMINAL PIN CONNECTORS FOR USE IN AN IMPLANTABLE MEDICAL DEVICE

(71) Applicant: Greatbatch Ltd., Clarence, NY (US)

(72) Inventors: Thomas Marzano, East Amherst, NY (US); Keith W. Seitz, Clarence Center, NY (US); Robert A. Stevenson, Canyon Country, CA (US); Christine A. Frysz, Orchard Park, NY (US); Marc Gregory Martino, Westlake Village, CA (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 18/736,643

(22) Filed: Jun. 7, 2024

(65) Prior Publication Data
US 2024/0322483 A1   Sep. 26, 2024

Related U.S. Application Data

(63) Continuation of application No. 17/561,048, filed on Dec. 23, 2021, now Pat. No. 12,149,021, which is a
(Continued)

(51) Int. Cl.
*H01R 13/52* (2006.01)
*A61N 1/375* (2006.01)
(Continued)

(52) U.S. Cl.
CPC ....... *H01R 13/5224* (2013.01); *A61N 1/3754* (2013.01); *H01G 4/35* (2013.01);
(Continued)

(58) Field of Classification Search
None
See application file for complete search history.

(56) References Cited

U.S. PATENT DOCUMENTS

| 2,685,073 A | 7/1954 | Damon |
| 3,200,355 A | 8/1965 | Dahlen |
| (Continued) | | |

FOREIGN PATENT DOCUMENTS

EP   4 349 397   10/2024

OTHER PUBLICATIONS

European Search , Application No. 23202461.2, dated Feb. 9, 2024
(Continued)

*Primary Examiner* — James Harvey
(74) *Attorney, Agent, or Firm* — Michael F. Scalise

(57) ABSTRACT

A feedthrough terminal pin connector assembly for an active implantable medical device (AIMD) includes first and second terminal pin connectors, each comprising a sidewall having an exterior surface spaced from an interior surface defining a connector opening extending along a longitudinal axis. At least a first portion of the sidewall is electrically conductive. An electrically conductive compliant structure is supported by the electrically conductive portion of the sidewall in each of the first and second connector openings. A common housing contains the first and second terminal pin connectors with an insulative material electrically isolating the first and second electrically conductive sidewall portions from each other. The common housing is configured to be supported on a circuit board having at least a first and a second electrical circuits with the first and second electrically conductive portions being electrically connected to the respective first and second electrical circuits.

23 Claims, 56 Drawing Sheets

Related U.S. Application Data continuation of application No. 16/809,676, filed on Mar. 5, 2020, now Pat. No. 11,211,741, which is a continuation-in-part of application No. 15/628,741, filed on Jun. 21, 2017, now Pat. No. 10,587,073, which is a continuation of application No. 14/747,582, filed on Jun. 23, 2015, now Pat. No. 9,692,173, which is a continuation-in-part of application No. 13/487,293, filed on Jun. 4, 2012, now Pat. No. 9,065,224.

(60) Provisional application No. 61/492,828, filed on Jun. 3, 2011.

(51) Int. Cl.
    *H01G 4/35* (2006.01)
    *H01R 13/426* (2006.01)
    *H01R 13/719* (2011.01)

(52) U.S. Cl.
    CPC ......... *H01R 13/426* (2013.01); *H01R 13/521* (2013.01); *H01R 13/719* (2013.01); *Y10T 29/49204* (2015.01)

(56) References Cited

U.S. PATENT DOCUMENTS

| | | | |
|---|---|---|---|
| 3,621,445 A | 11/1971 | Horecky et al. |
| 4,187,605 A | 2/1980 | Selvin et al. |
| 4,421,378 A | 12/1983 | Sanford et al. |
| 4,424,551 A | 1/1984 | Stevenson et al. |
| 4,666,222 A | 5/1987 | Gallusser et al. |
| 4,767,342 A | 8/1988 | Sato |
| 4,824,380 A | 4/1989 | Matthews |
| 5,055,055 A | 10/1991 | Bakker |
| 5,103,818 A | 4/1992 | Maston et al. |
| 5,168,876 A | 12/1992 | Quedens et al. |
| 5,333,095 A | 7/1994 | Stevenson et al. |
| 5,376,012 A | 12/1994 | Clark |
| 5,591,039 A | 1/1997 | Matthews |
| 5,893,779 A | 4/1999 | Bianca et al. |
| 6,059,600 A | 5/2000 | Vanbesien |
| 6,183,301 B1 | 2/2001 | Paagman |
| 6,224,404 B1 | 5/2001 | Sauer |
| 6,443,749 B2 | 9/2002 | Brownell et al. |
| 6,632,107 B1 | 10/2003 | Vanbesien |
| 6,643,903 B2 | 11/2003 | Stevenson et al. |
| 6,765,779 B2 | 7/2004 | Stevenson et al. |
| 6,765,780 B2 | 7/2004 | Brendel et al. |
| 6,852,925 B2 | 2/2005 | Wolf et al. |
| 6,932,658 B2 | 8/2005 | Liang |
| 7,035,076 B1 | 4/2006 | Stevenson |
| 7,038,900 B2 | 5/2006 | Stevenson et al. |
| 7,068,081 B2 | 6/2006 | Naffziger et al. |
| 7,167,749 B2 | 1/2007 | Biggs et al. |
| 7,172,467 B1 | 2/2007 | Yohn et al. |
| 7,195,523 B2 | 3/2007 | Naviaux |
| 7,249,981 B2 | 7/2007 | Chen |
| 7,295,123 B2 | 11/2007 | Engelberg et al. |
| 7,391,601 B1 | 6/2008 | Imani |
| 7,630,768 B1 | 12/2009 | Coffed et al. |
| 7,751,893 B2 | 7/2010 | Biggs et al. |
| 7,794,256 B1 | 9/2010 | Sochor |
| 7,806,729 B2 * | 10/2010 | Nguyen ............ H01R 13/6585 |
| | | | 439/607.23 |
| 7,812,691 B1 | 10/2010 | Fisk et al. |
| 7,822,477 B2 | 10/2010 | Rey et al. |
| 7,917,219 B2 | 3/2011 | Stevenson et al. |
| 7,931,507 B2 | 4/2011 | Yu et al. |
| 8,065,009 B2 | 11/2011 | Biggs |
| 8,096,838 B2 | 1/2012 | Dilmaghanian |
| 8,103,348 B1 | 1/2012 | Coffed et al. |
| 8,112,152 B2 | 2/2012 | Taylor et al. |
| 8,179,658 B2 | 5/2012 | Stevenson et al. |
| 8,195,295 B2 | 6/2012 | Stevenson et al. |
| 8,422,195 B2 | 4/2013 | Stevenson |
| 8,433,410 B2 | 4/2013 | Dabney et al. |
| 8,437,855 B2 | 5/2013 | Sjostedt et al. |
| 8,468,664 B2 | 6/2013 | Brendel et al. |
| 8,543,209 B2 | 9/2013 | Tyers et al. |
| 8,577,453 B1 | 11/2013 | Stevenson et al. |
| 8,642,887 B1 | 2/2014 | Li et al. |
| 8,653,384 B2 | 2/2014 | Tang et al. |
| 8,659,870 B2 | 2/2014 | Brendel et al. |
| 8,855,785 B1 | 10/2014 | Johnson et al. |
| 8,868,189 B2 | 10/2014 | Stevenson et al. |
| 8,900,008 B2 | 12/2014 | Day et al. |
| 8,938,309 B2 | 1/2015 | Marzano et al. |
| 9,014,808 B2 | 4/2015 | Dabney et al. |
| 9,064,640 B2 | 6/2015 | Brendel et al. |
| 9,065,224 B2 | 6/2015 | Marzano et al. |
| 9,108,066 B2 | 8/2015 | Woods et al. |
| 9,223,253 B2 | 12/2015 | Lior et al. |
| 9,352,150 B2 | 5/2016 | Stevenson et al. |
| 9,427,596 B2 | 8/2016 | Brendel et al. |
| 9,463,329 B2 | 10/2016 | Frysz et al. |
| 9,511,220 B2 | 12/2016 | Marzano et al. |
| 9,692,173 B2 | 6/2017 | Marzano et al. |
| 9,757,558 B2 | 9/2017 | Stevenson et al. |
| 9,764,129 B2 | 9/2017 | Stevenson et al. |
| 9,806,443 B1 | 10/2017 | Thackston |
| RE46,699 E | 2/2018 | Woods et al. |
| 9,889,306 B2 | 2/2018 | Stevenson et al. |
| 9,895,534 B2 | 2/2018 | Stevenson et al. |
| 9,931,514 B2 | 4/2018 | Frysz et al. |
| 9,937,354 B2 | 4/2018 | Barry et al. |
| RE46,837 E | 5/2018 | Tyers et al. |
| 9,993,650 B2 | 6/2018 | Seitz et al. |
| 10,080,889 B2 | 9/2018 | Marzano et al. |
| 10,092,749 B2 | 10/2018 | Stevenson et al. |
| 10,099,051 B2 | 10/2018 | Stevenson et al. |
| 10,124,164 B2 | 11/2018 | Stevenson et al. |
| 10,249,415 B2 | 4/2019 | Seitz et al. |
| 10,272,252 B2 | 4/2019 | Seitz et al. |
| 10,272,253 B2 | 4/2019 | Seitz et al. |
| 10,350,421 B2 | 7/2019 | Stevenson et al. |
| 10,376,688 B2 | 8/2019 | Chen et al. |
| 2001/0033478 A1 | 10/2001 | Ortiz et al. |
| 2003/0139096 A1 | 7/2003 | Stevenson et al. |
| 2006/0089682 A1 | 4/2006 | Kronich et al. |
| 2006/0167522 A1 | 7/2006 | Malinowski |
| 2006/0221543 A1 | 10/2006 | Stevenson et al. |
| 2007/0134985 A1 | 6/2007 | Frysz et al. |
| 2007/0203530 A1 | 8/2007 | Hubing et al. |
| 2007/0260282 A1 | 11/2007 | Taylor et al. |
| 2009/0068863 A1 | 3/2009 | Walter |
| 2009/0259265 A1 | 10/2009 | Stevenson et al. |
| 2010/0192355 A1 | 8/2010 | Zhao et al. |
| 2011/0106189 A1 | 5/2011 | Seeley et al. |
| 2011/0237122 A1 * | 9/2011 | Schwarz ............... H01R 24/50 |
| | | | 439/578 |
| 2011/0303458 A1 | 12/2011 | Sutay et al. |
| 2012/0309237 A1 | 12/2012 | Marzano et al. |
| 2013/0274820 A1 | 10/2013 | Malinowski et al. |
| 2013/0338747 A1 | 12/2013 | Kondabatni et al. |
| 2014/0272457 A1 | 9/2014 | Watada |
| 2015/0245468 A1 | 8/2015 | Barry et al. |
| 2015/0295349 A1 | 10/2015 | Marzano et al. |
| 2017/0266451 A1 | 9/2017 | Lim et al. |
| 2019/0356097 A1 | 11/2019 | Landwehr et al. |
| 2022/0115806 A1 | 4/2022 | Marzano et al. |
| 2024/0115867 A1 * | 4/2024 | Stevenson ............ A61N 1/3754 |
| 2024/0322483 A1 * | 9/2024 | Marzano ............. A61N 1/3754 |

OTHER PUBLICATIONS

European Search , Application No. 12170625.3, dated Oct. 4, 2012.
Stevenson, Bob , "Dissipation Factor Testing is Inadequate for Medical Implant EMI Filters and Other High Frequency MLC Capacitor Applications", 23rd Capacitor and Resistor Technology

(56) References Cited

OTHER PUBLICATIONS

Symposium, CARTS 2003, Mar. 31-Apr. 3, 2003, Chaparral Suites Resort, Scottsdale, Arizona.

* cited by examiner

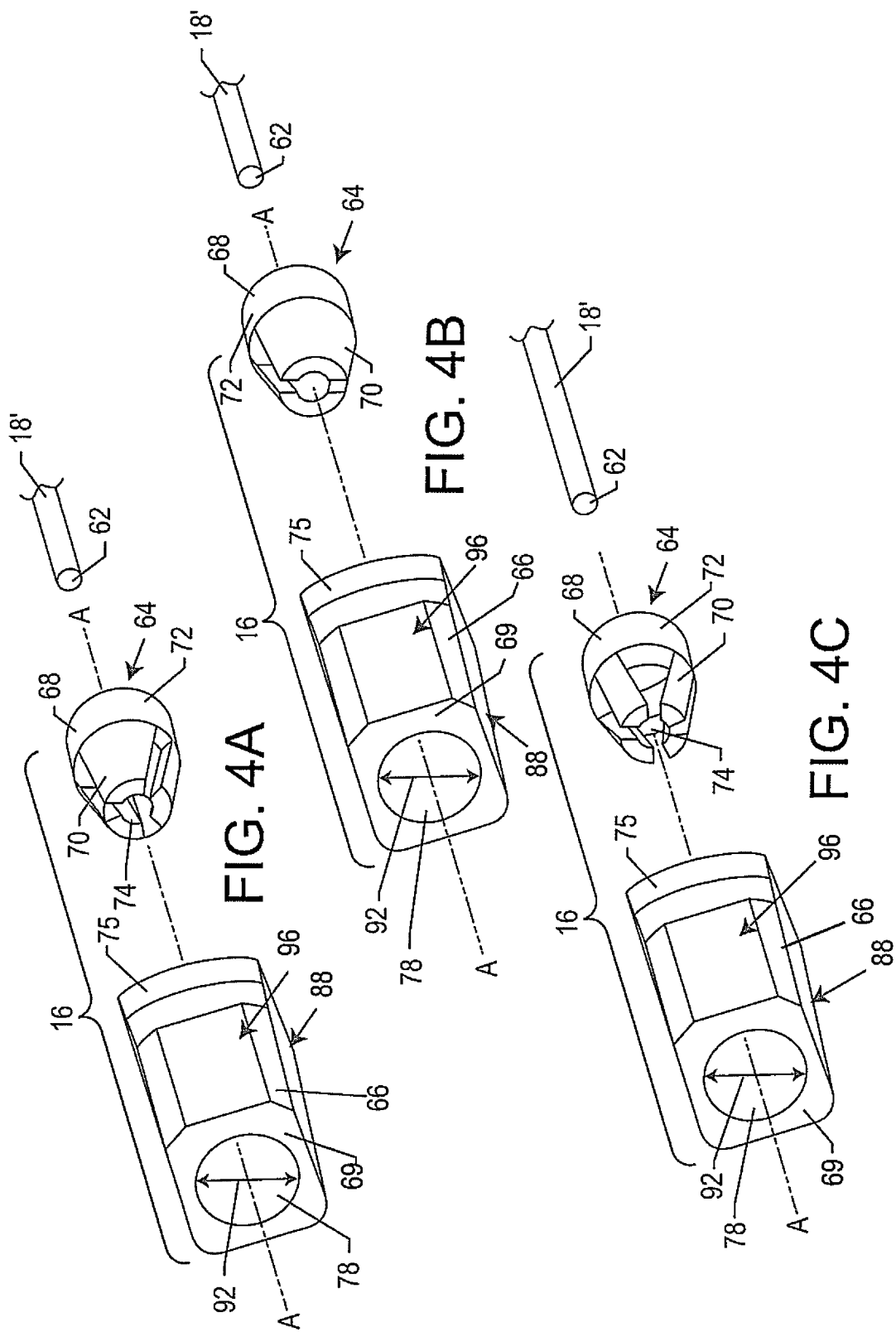

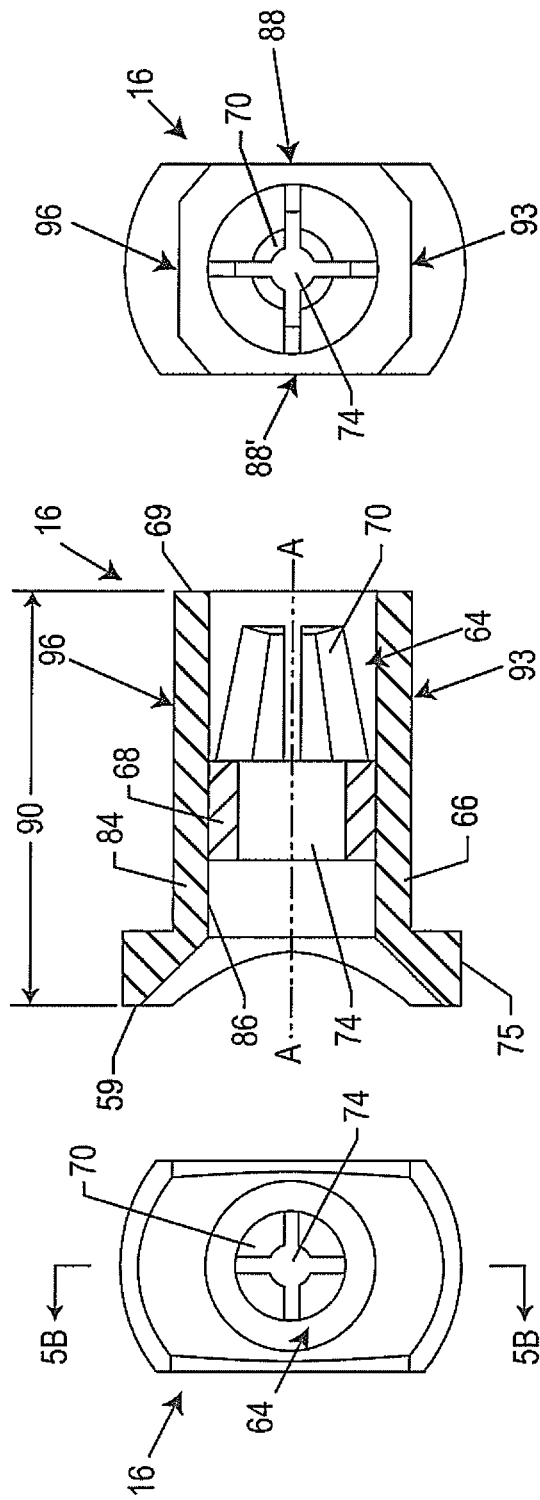

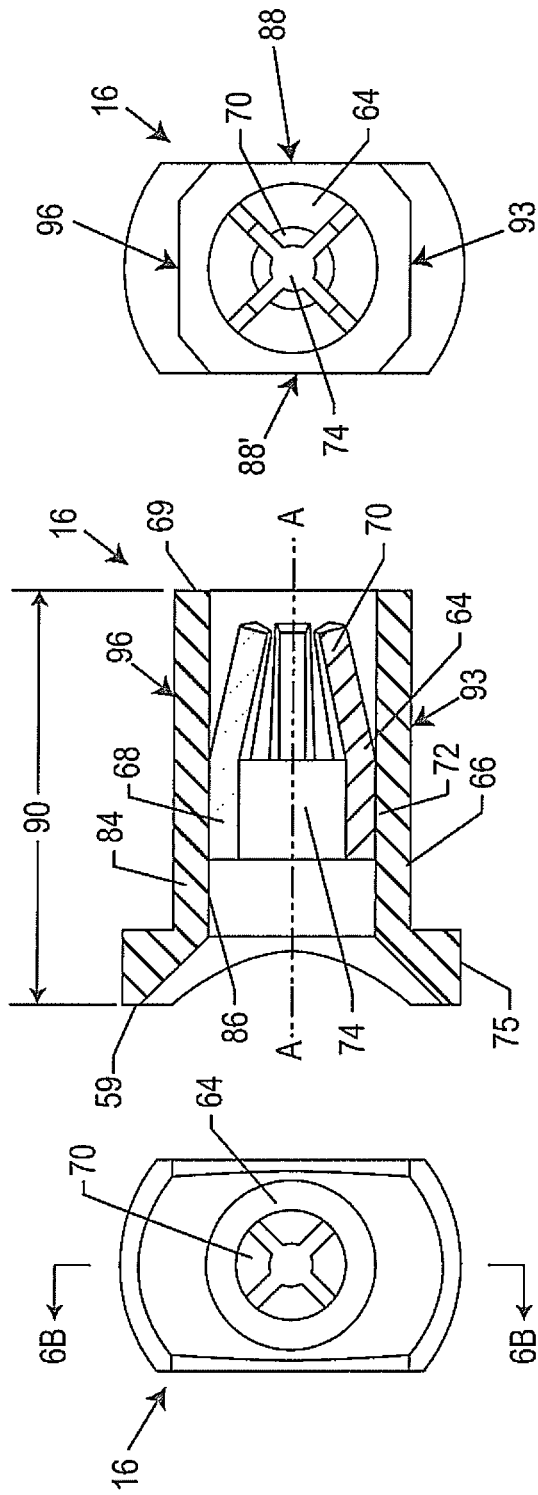

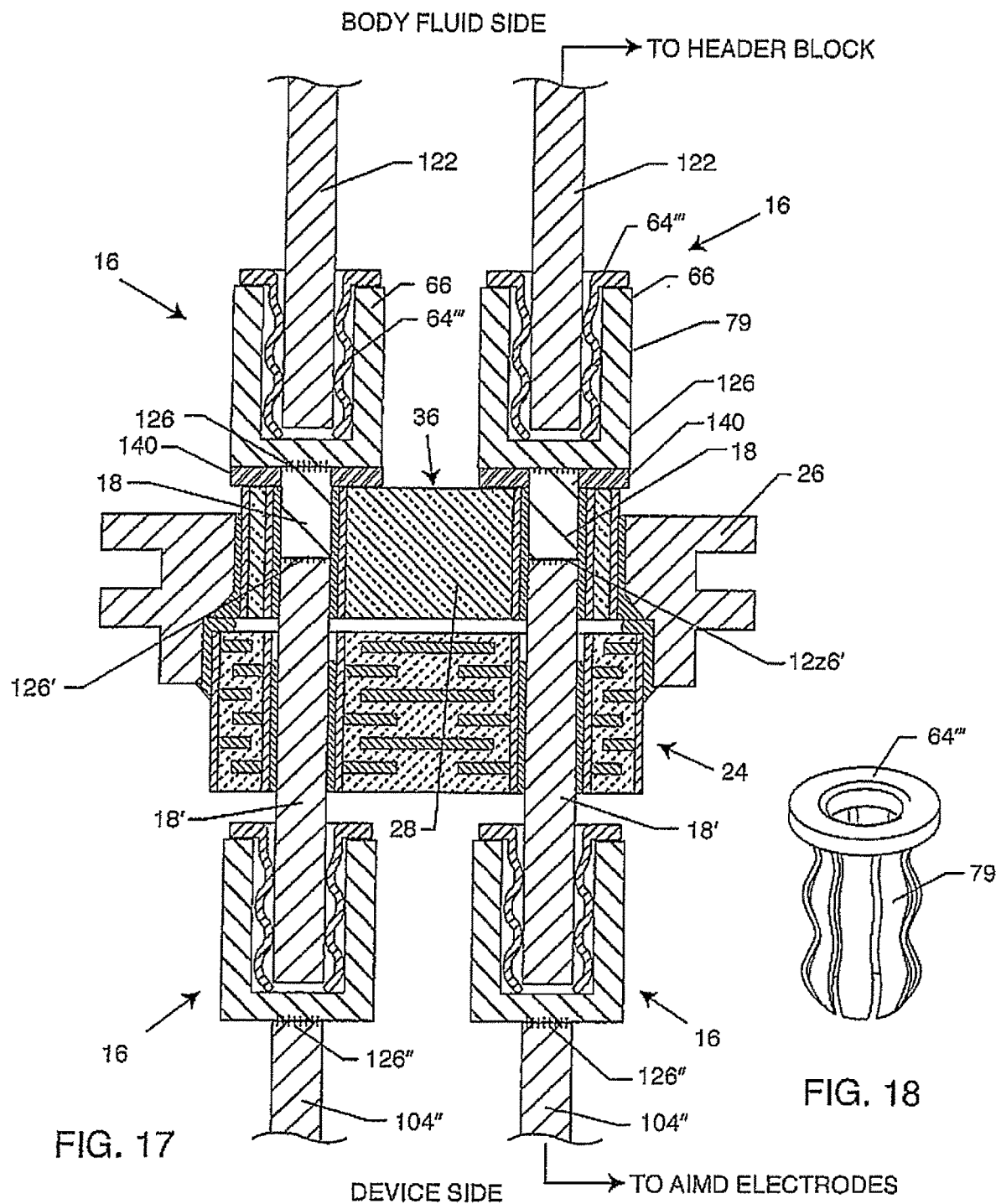

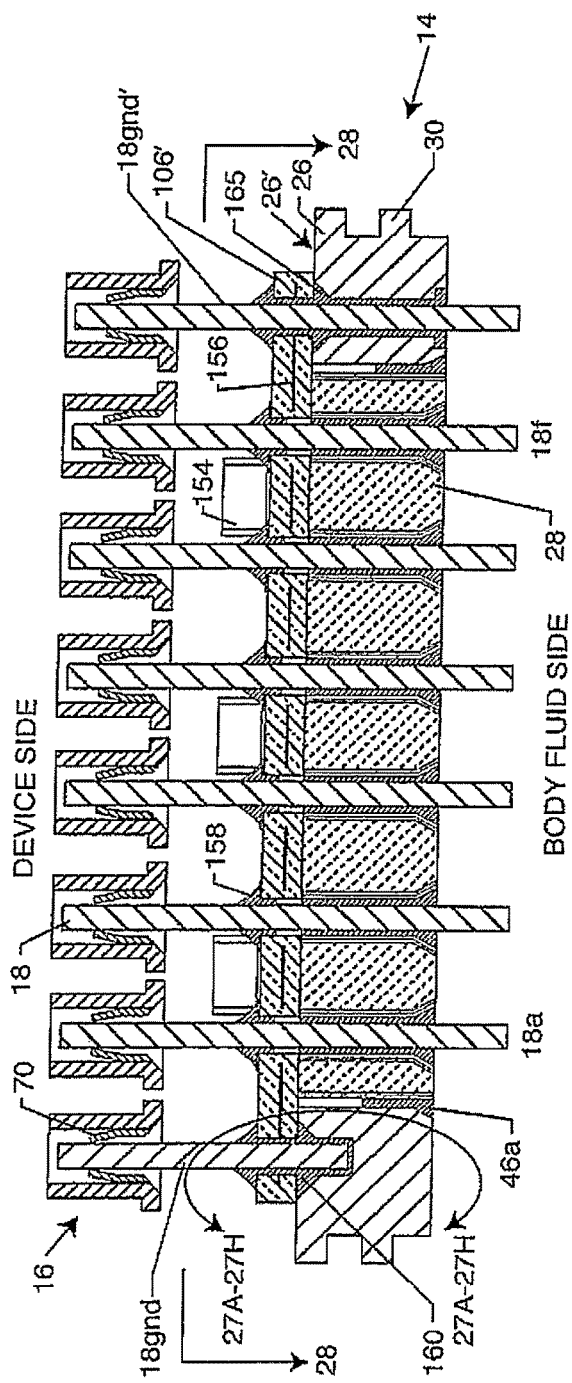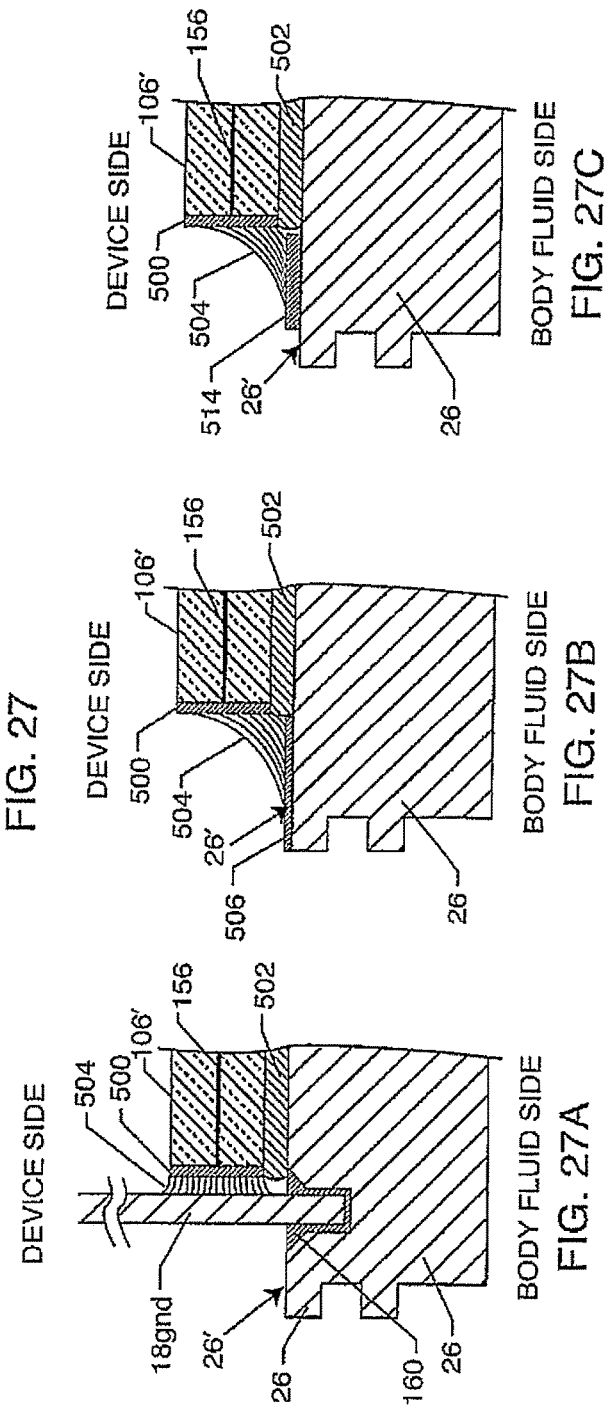

(TOP VIEW OF DEVICE SIDE)

(TOP VIEW OF DEVICE SIDE)

(TOP VIEW OF DEVICE SIDE)

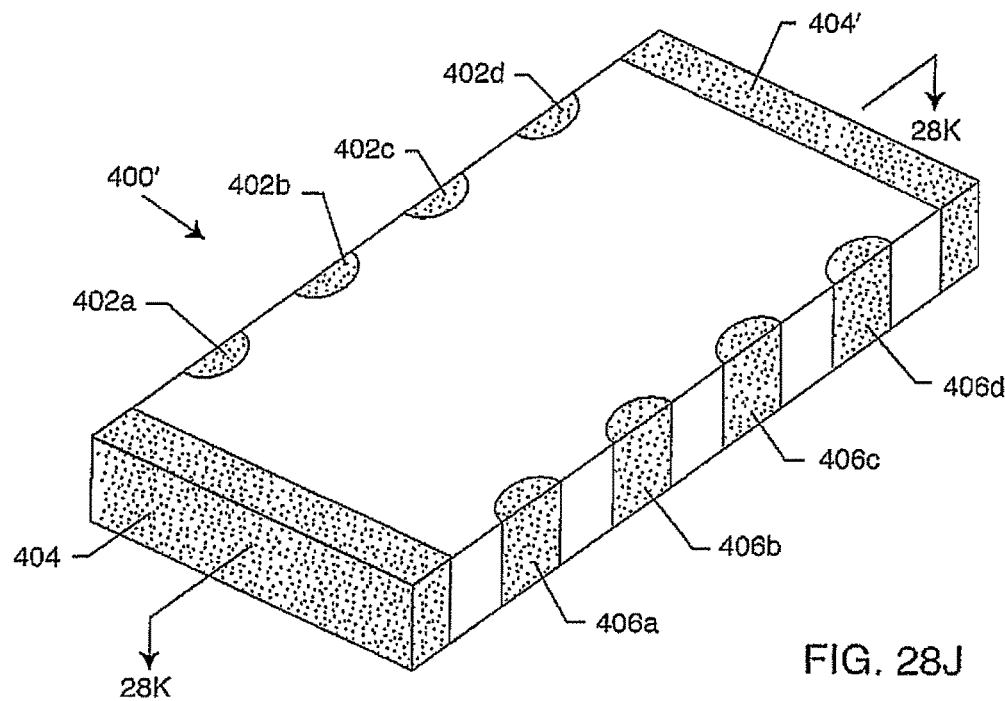
FIG. 28J
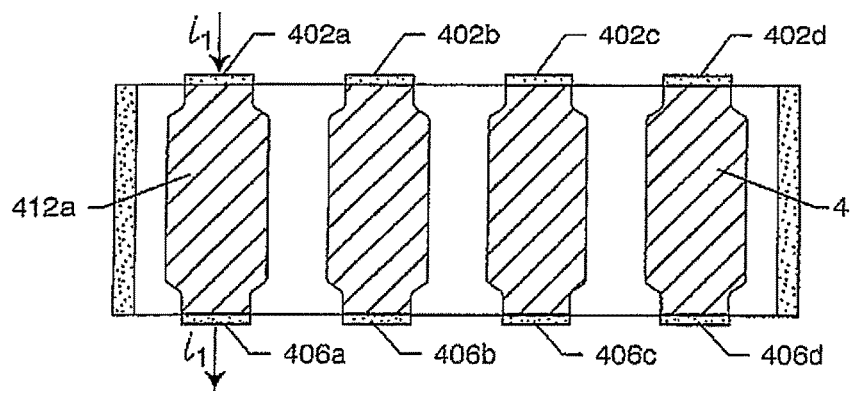
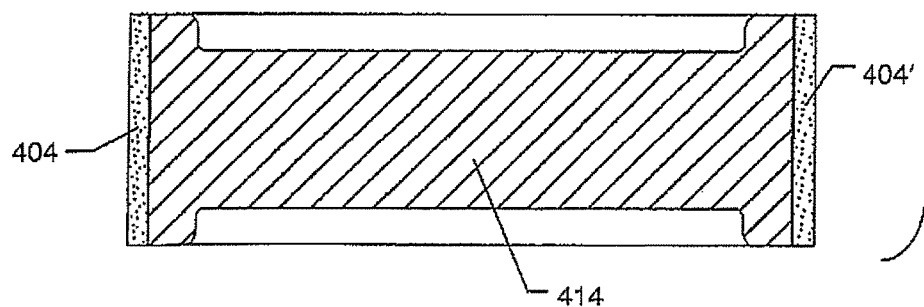
FIG. 28K

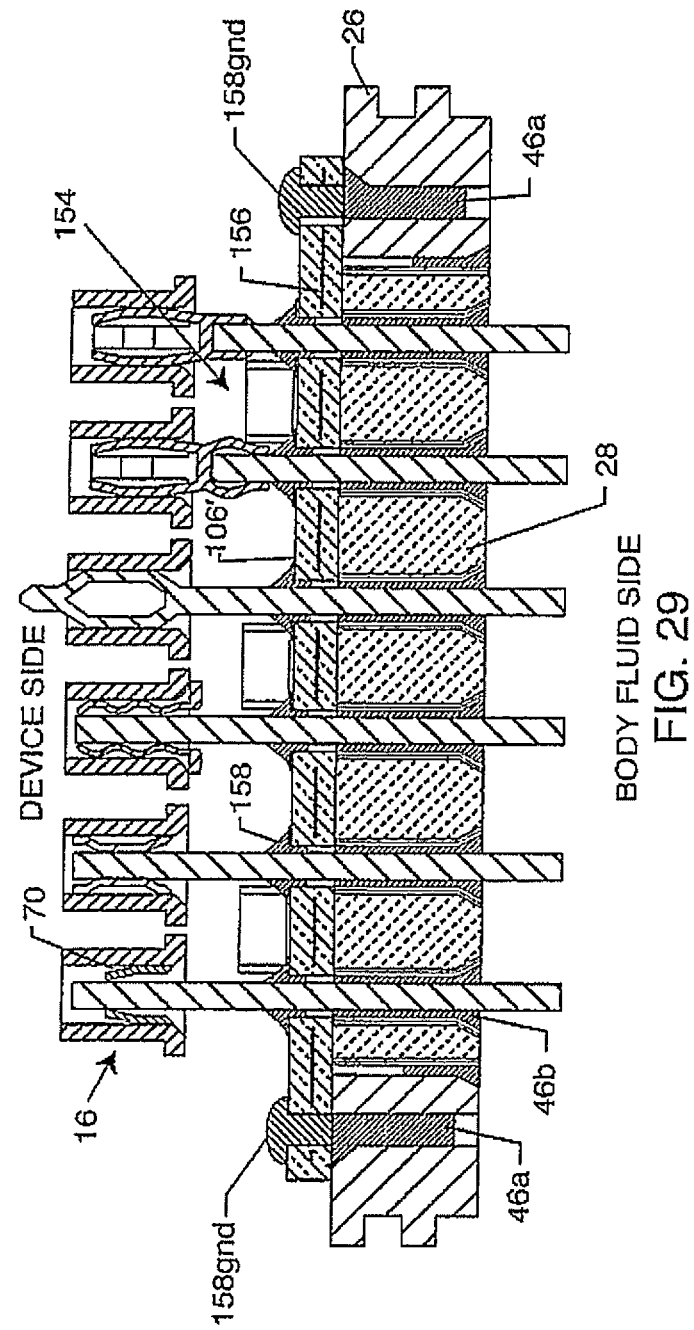

COMMON HOUSING FOR A PLURALITY OF TERMINAL PIN CONNECTORS FOR USE IN AN IMPLANTABLE MEDICAL DEVICE

CROSS-REFERENCE TO RELATED APPLICATIONS

This application is a continuation of U.S. patent application Ser. No. 17/561,048, filed on Dec. 23, 2021, now U.S. Pat. No. 12,149,021, which is a continuation of U.S. patent application Ser. No. 16/809,676, filed on Mar. 5, 2020, now U.S. Pat. No. 11,211,741, which is a continuation-in-part application to U.S. application Ser. No. 15/628,741, filed on Jun. 21, 2017, now U.S. Pat. No. 10,587,073, which is a continuation application to U.S. application Ser. No. 14/747,582, filed on Jun. 23, 2015, now U.S. Pat. No. 9,692,173, which is a continuation-in-part application to U.S. application Ser. No. 13/487,293, filed on Jun. 4, 2012, now U.S. Pat. No. 9,065,224, which claims priority to U.S. provisional application Ser. No. 61/492,828, filed on Jun. 3, 2011.

FIELD OF THE INVENTION

This invention relates generally to a hermetic feedthrough terminal pin assembly, usually of the type incorporating a filter capacitor, for use in implantable medical devices such as cardiac pacemakers, cardioverter defibrillators, and the like, to facilitate connection of the feedthrough terminal pin to a circuit board within the implantable medical device. More specifically, this invention relates to a removable connector assembly comprising various novel structures taught herein that allow rework and/or replacement of various electrical components, if necessary, after testing discovers a potential malfunction or problem, thereby saving time, expense and resources.

BACKGROUND OF THE INVENTION

Feedthrough assemblies are generally well known by those skilled in the art of active implantable medical devices for use in connecting electrical signals through the housing, can, casing or case of an electronic instrument or device. For example, in an implantable medical device, such as a cardiac pacemaker, defibrillator, or neurostimulator, the feedthrough assembly comprises one or more conductive terminal pins supported by an insulator structure for passage of electrical signals from the exterior to the interior of the medical device. The conductive terminals are fixed into place using a metallization and gold braze process, which provides a hermetic seal between the pin and insulative material.

Conventionally, the ends of the terminal pin distal ends are permanently electrically connected directly within the active implantable medical device to circuit boards inside the casing or to an AIMD header block outside the casing. As an example, the terminal pin distal end may be electrically connected directly to an electrical circuit board residing within the device by using a soldering or welding attachment process. This connection is readily achievable utilizing platinum or platinum alloy based terminal pins of the prior art.

However, once this electrical connection is made, it is very hard to replace various components if a problem is detected during testing. The present invention, therefore, facilitates the testing and removal and/or exchange of various electrical components, such as the circuit board, so that significant cost, time, and resources can be saved.

SUMMARY OF THE INVENTION

Referring generally to FIGS. 1 to 9, an exemplary embodiment of the present invention includes a hermetic feedthrough terminal pin connector assembly for an active implantable medical device (AIMD) comprising: a) an electrically conductive ferrule configured to hermetically seal an opening of a casing of the AIMD, the ferrule configured to prevent a leakage of a body fluid in a human implant application to an inside of the casing of the AIMD; b) an electrical insulator hermetically sealing a ferrule opening, the insulator configured to prevent the leakage of the body fluid in the human implant application to the inside of the casing of the AIMD; c) a feedthrough terminal pin hermetically sealed to and disposed through the insulator, the feedthrough terminal pin extending outwardly beyond the insulator on the inside of the casing of the AIMD; d) a circuit board disposed on the inside of the casing of the AIMD; and e) a terminal pin connector, comprising: i) an electrically conductive connector housing disposed on the circuit board, wherein the connector housing is electrically connected to at least one electrical circuit disposed on the circuit board; and ii) at least one electrically conductive prong supported by the connector housing, the at least one prong contacting and compressed against the feedthrough terminal pin extending outwardly beyond the insulator on the inside of the casing of the AIMD. Circuit boards include multilayer boards, multilayer alumina boards, printed circuit boards (otherwise known as PCBs or printed circuits), FR-4 or FR4 boards and the like.

In other exemplary embodiments, the at least one prong may comprise at least two prongs, each prong contacting and compressed against the feedthrough terminal pin extending outwardly beyond the insulator on the inside of the casing of the AIMD. Alternatively, the at least one prong may comprise a plurality of prongs, each prong of the plurality of prongs contacting and compressed against the feedthrough terminal pin extending outwardly beyond the insulator on the inside of the casing of the AIMD.

The connector housing may be electrically connected to the at least one electrical circuit with a solder, a braze, an electrically conductive adhesive or a weld.

The terminal pin connector may be configured to allow multiple insertions and retractions of the feedthrough terminal pin extending outwardly beyond the insulator on the inside of the casing of the AIMD without affecting reliability and enabling rework or pre-assembly testing.

The connector housing may comprise a housing sidewall defining a housing opening surrounded by a housing inner surface, wherein the at least one prong comprises at least two prongs that extend from a base, the base supported by the housing inner surface, wherein the at least two prongs are angled inwardly towards a central axis that extends longitudinally through a through-bore of the base, wherein the feedthrough terminal pin extending outwardly beyond the insulator on the inside of the casing of the AIMD is disposed through the through-bore of the base. The housing sidewall may comprise at least one planar surface attached to and contacting the circuit board.

A ground terminal pin may be electrically connected to the ferrule and include a second terminal pin connector disposed on the circuit board, wherein the ground terminal pin is electrically connected to the second terminal pin connector. A second ground terminal pin may be electrically connected to the ferrule and include a third terminal pin connector disposed on the circuit board, wherein the second ground terminal pin is electrically connected to the third terminal pin connector.

A feedthrough capacitor may be included having at least one active electrode plate disposed apart and parallel to at least one ground electrode plate within a capacitor dielectric, wherein the at least one active electrode plate is electrically connected to the feedthrough terminal pin and the at least one ground electrode plate is electrically connected to the ferrule, wherein the feedthrough terminal pin extends outwardly beyond the feedthrough capacitor on the inside of the casing of the AIMD.

Another exemplary embodiment of the present invention includes a terminal pin connector assembly for an active implantable medical device (AIMD), the terminal pin connector assembly comprising: a) a circuit board configured to be disposed on an inside of a casing of the AIMD; and b) a terminal pin connector, comprising: i) an electrically conductive connector housing disposed on the circuit board, wherein the connector housing is electrically connected to at least one electrical circuit disposed on the circuit board; and ii) at least one electrically conductive prong supported by the connector housing, the at least one prong configured to contact and compress against a terminal pin; iii) wherein the terminal pin connector is configured to accept a hermetically sealed feedthrough terminal pin extending into a casing of the AIMD.

In other exemplary embodiments, the at least one prong may comprise at least two prongs, each prong configured to contact and compress against the terminal pin. Alternatively, the at least one prong may comprise a plurality of prongs, each prong of the plurality of prongs configured to contact and compress against the terminal pin.

The connector housing may be electrically connected to the at least one electrical circuit with a solder, a braze, an electrically conductive adhesive or a weld.

The terminal pin connector may be configured to allow multiple insertions and retractions of the terminal pin without affecting reliability and enabling rework or pre-assembly testing.

The connector housing may comprise a housing sidewall defining a housing opening surrounded by a housing inner surface, wherein the at least one prong comprises at least two prongs that extend from a base, the base supported by the housing inner surface, wherein the at least two prongs are angled inwardly towards a central axis that extends longitudinally through a through-bore of the base, wherein the terminal pin is configured to be disposed through the through-bore of the base. The housing sidewall may comprise at least one planar surface contacting the circuit board.

Referring generally to FIGS. 10-18, another exemplary embodiment of the present invention includes a hermetic feedthrough terminal pin connector assembly configured for attachment to a casing of an active implantable medical device (AIMD), the hermetic feedthrough terminal pin connector assembly comprising: a) an electrically conductive ferrule configured to hermetically seal an opening of the casing of the AIMD; b) an electrically nonconductive insulator hermetically sealing a ferrule opening; c) wherein the ferrule and the insulator are configured to prevent a leakage of a body fluid in a human implant application from a body fluid side of the casing to a device side of the casing; d) a feedthrough terminal pin hermetically sealed to and disposed through the insulator, the feedthrough terminal pin extending outwardly beyond the insulator on the body fluid side of the casing; e) a header configured to be attached to the casing of the AIMD, the header comprising: i) a terminal pin connector, wherein the terminal pin connector comprises: 1) an electrically conductive connector housing; and 2) at least one electrically conductive elastically resilient termination structure supported by the connector housing, the at least one elastically resilient termination structure contacting and compressed against the feedthrough terminal pin extending outwardly beyond the insulator on the body fluid side of the casing; and ii) a lead plug port configured to receive a distal end of an implanted lead; and iii) a conductor electrically connecting the lead plug port to the connector housing.

The connector housing and the at least one electrically conductive elastically resilient termination structure of the terminal pin connector may be made from materials which are biocompatible, non-toxic, and biostable.

The terminal pin connector may be configured to be removable to allow multiple insertions and retractions of the feedthrough terminal pin extending outwardly beyond the insulator on the body fluid side of the casing of the AIMD without affecting reliability and enabling rework or pre-assembly testing.

Alternatively, the at least one elastically resilient termination structure contacting and compressed against the feedthrough terminal pin may contact the terminal pin sidewall in a grip-tight engagement preventing inadvertent removal of the feedthrough terminal pin from the terminal pin connector, while still allowing removability for rework or replacement.

Another exemplary embodiment of the present invention includes a terminal pin connector header assembly for an active implantable medical device (AIMD), the terminal pin connector header assembly comprising: a) a terminal pin connector, wherein the terminal pin connector comprises: i) an electrically conductive connector housing; and ii) at least one electrically conductive elastically resilient termination structure supported by the connector housing, the at least one elastically resilient termination structure contacting and compressed against the feedthrough terminal pin extending outwardly beyond the insulator on the body fluid side of the casing; b) a lead plug port configured to receive a distal end of an implanted lead; and c) a conductor electrically connecting the lead plug port to the connector housing; e) wherein the connector housing, the at least one electrically conductive elastically resilient termination structure and the conductor are disposed within a header body.

In other exemplary embodiments, the connector housing and the at least one electrically conductive elastically resilient termination structure of the terminal pin connector may be made from materials which are biocompatible, non-toxic, and biostable.

The terminal pin connector may be configured to allow multiple insertions and retractions of the feedthrough terminal pin extending outwardly beyond the insulator on the body fluid side of the casing of the AIMD without affecting reliability and enabling rework or pre-assembly testing.

Alternatively, the at least one elastically resilient termination structure contacting and compressed against the feedthrough terminal pin may contact the terminal pin sidewall in a grip-tight engagement preventing inadvertent removal of the feedthrough terminal pin from the terminal pin connector.

Referring generally to FIGS. 27-28, another exemplary embodiment of the present invention includes a hermetic feedthrough terminal pin connector assembly for an active implantable medical device (AIMD), the hermetic feedthrough terminal pin connector assembly comprising: a) an electrically conductive ferrule configured to hermetically seal an opening of a casing of the AIMD, the ferrule configured to prevent a leakage of a body fluid in a human implant application to an inside of the casing of the AIMD; b) an electrical insulator hermetically sealing a ferrule opening, the insulator configured to prevent the leakage of the body fluid in the human implant application to the inside of the casing of the AIMD; c) a first EMI filter circuit board disposed on the inside of the casing of the AIMD, the first EMI filter circuit board disposed on, near or adjacent to the electrical insulator and/or the electrically conductive ferrule; d) a feedthrough terminal pin hermetically sealed to and disposed through the insulator, the feedthrough terminal pin extending outwardly beyond the insulator and outwardly beyond the first EMI filter circuit board on the inside of the casing of the AIMD; e) a chip filter capacitor disposed on the first EMI filter circuit board, the chip filter capacitor having at least one active electrode plate disposed apart and parallel to at least one ground electrode plate within a capacitor dielectric, wherein the at least one active electrode plate is electrically connected to the feedthrough terminal pin and the at least one ground electrode plate is electrically connected to the ferrule; f) a second circuit board disposed on the inside of the casing of the AIMD; and g) a terminal pin connector, comprising: i) an electrically conductive connector housing disposed on the second circuit board, wherein the connector housing is electrically connected to at least one electrical circuit disposed on the second circuit board; and ii) at least one electrically conductive elastically resilient termination structure supported by the connector housing, the at least one elastically resilient termination structure contacting and compressed against the feedthrough terminal pin extending outwardly beyond the insulator and the first EMI filter circuit board on the inside of the casing of the AIMD.

In other exemplary embodiments, the at least one elastically resilient termination structure may comprise at least one prong, the at least one prong contacting and compressed against the feedthrough terminal pin extending outwardly beyond the insulator on the inside of the casing of the AIMD. In other exemplary embodiments, the at least one elastically resilient termination structure may comprise at least two prongs, each prong contacting and compressed against the feedthrough terminal pin extending outwardly beyond the insulator on the inside of the casing of the AIMD. Alternatively, the at least one elastically resilient termination structure may comprise a plurality of prongs, each prong of the plurality of prongs contacting and compressed against the feedthrough terminal pin extending outwardly beyond the insulator on the inside of the casing of the AIMD.

In yet other exemplary embodiments, the at least one elastically resilient termination structure may include one or more additional elastically resilient termination structures, the one or more additional elastically resilient termination structures being all the same configuration, each of a different configuration, or any configuration combination between all the same and all different, each elastically resilient termination structure contacting and compressed against the feedthrough terminal pin extending outwardly beyond the insulator on the inside of the casing of the AIMD.

The connector housing may be electrically connected to the at least one electrical circuit with a solder, a braze, an electrically conductive adhesive or a weld.

The terminal pin connector may be configured to allow multiple insertions and retractions of the feedthrough terminal pin extending outwardly beyond the insulator on the inside of the casing of the AIMD without affecting reliability and enabling rework or pre-assembly testing.

The connector housing may comprise a housing sidewall defining a housing opening surrounded by a housing inner surface, wherein the at least one elastically resilient termination structure comprises at least two prongs that extend from a base, the base supported by the housing inner surface, wherein the at least two prongs are angled inwardly towards a central axis that extends longitudinally through a throughbore of the base, wherein the feedthrough terminal pin extending outwardly beyond the insulator on the inside of the casing of the AIMD is disposed through the through-bore of the base. The housing sidewall may comprise at least one planar surface attached to and contacting the circuit board.

A first ground terminal pin may be electrically connected to the ferrule and including a second terminal pin connector disposed on the second circuit board, wherein the first ground terminal pin is electrically connected to the second terminal pin connector. A second ground terminal pin may be electrically connected to the ferrule and including a third terminal pin connector disposed on the second circuit board, wherein the second ground terminal pin is electrically connected to the third terminal pin connector.

Referring generally to FIGS. 28A-D, another exemplary embodiment of the present invention includes a hermetic feedthrough terminal pin connector assembly for an active implantable medical device (AIMD), the hermetic feedthrough terminal pin connector assembly comprising: a) an electrically conductive ferrule configured to hermetically seal an opening of a casing of the AIMD, the ferrule configured to prevent a leakage of a body fluid in a human implant application to an inside of the casing of the AIMD; b) an electrical insulator hermetically sealing a ferrule opening, the insulator configured to prevent the leakage of the body fluid in the human implant application to the inside of the casing of the AIMD; c) a first EMI filter circuit board disposed on the inside of the casing of the AIMD, the first EMI filter circuit board disposed on, near or adjacent to the electrical insulator and/or the electrically conductive ferrule; d) a first feedthrough terminal pin hermetically sealed to and disposed through the insulator, the first feedthrough terminal pin extending outwardly beyond the insulator and outwardly beyond the first EMI filter circuit board on the inside of the casing of the AIMD; e) a second feedthrough terminal pin hermetically sealed to and disposed through the insulator, the second feedthrough terminal pin extending outwardly beyond the insulator and outwardly beyond the first EMI filter circuit board on the inside of the casing of the AIMD; f) an X2Y attenuator filter capacitor disposed on the first EMI filter circuit board, the X2Y attenuator filter capacitor having at least one first and second active electrode plates disposed apart and parallel to at least one ground electrode plate within a capacitor dielectric, wherein the at least one first active electrode plate is electrically connected to the first feedthrough terminal pin, wherein the at least one second active electrode plate is electrically connected to the second feedthrough terminal pin, and wherein the at least one ground electrode plate is electrically connected to the ferrule; g) a second circuit board disposed on the inside of the casing of the AIMD; h) a first terminal pin connector, comprising: i) an electrically conductive first connector housing disposed on the second circuit board, wherein the first connector housing is electrically connected to at least one first electrical circuit disposed on the second circuit board; and ii) at least one first electrically conductive elastically resilient termination structure supported by the first connector housing, the at least one first elastically resilient termination structure contacting and compressed against the first feedthrough terminal pin extending outwardly beyond the first EMI filter circuit board on the inside of the casing of the AIMD; and i) a second terminal pin connector, comprising: i) an electrically conductive second connector housing disposed on the second circuit board, wherein the second connector housing is electrically connected to at least one second electrical circuit disposed on the second circuit board; and ii) at least one second electrically conductive elastically resilient termination structure supported by the second connector housing, the at least one second elastically resilient termination structure contacting and compressed against the second feedthrough terminal pin extending outwardly beyond the first EMI filter circuit board on the inside of the casing of the AIMD.

Referring now generally to FIGS. 28E-H, another exemplary embodiment of the present invention includes a hermetic feedthrough terminal pin connector assembly for an active implantable medical device (AIMD), the hermetic feedthrough terminal pin connector assembly comprising: a) an electrically conductive ferrule configured to hermetically seal an opening of a casing of the AIMD, the ferrule configured to prevent a leakage of a body fluid in a human implant application to an inside of the casing of the AIMD; b) an electrical insulator hermetically sealing a ferrule opening, the insulator configured to prevent the leakage of the body fluid in the human implant application to the inside of the casing of the AIMD; c) a first EMI filter circuit board disposed on the inside of the casing of the AIMD, the first EMI filter circuit board disposed on, near or adjacent to the electrical insulator and/or the electrically conductive ferrule; d) a first feedthrough terminal pin hermetically sealed to and disposed through the insulator, the first feedthrough terminal pin extending outwardly beyond the insulator on the inside of the casing of the AIMD; e) a second terminal pin attached to the first EMI filter circuit board, the second terminal pin extending outwardly beyond the first EMI filter circuit board on the inside of the casing of the AIMD; f) a flat-thru filter capacitor disposed on the first EMI filter circuit board, the flat-thru filter capacitor having at least one active electrode plate disposed apart and parallel to at least one ground electrode plate within a capacitor dielectric, wherein the at least one active electrode plate is electrically connected to the first feedthrough terminal pin at a first end of the at least one active electrode plate, wherein the at least one active electrode plate is electrically connected to the second terminal pin at a second end of the at least one active electrode plate, and wherein the at least one ground electrode plate is electrically connected to the ferrule; g) a second circuit board disposed on the inside of the casing of the AIMD; and h) a terminal pin connector, comprising: i) an electrically conductive connector housing disposed on the second circuit board, wherein the connector housing is electrically connected to at least one electrical circuit disposed on the second circuit board; and ii) at least one electrically conductive elastically resilient termination structure supported by the connector housing, the at least one elastically resilient termination structure contacting and compressed against the second terminal pin extending outwardly beyond the first EMI filter circuit board on the inside of the casing of the AIMD.

Referring now generally to FIG. 19, another exemplary embodiment of the present invention includes a hermetic feedthrough terminal pin connector assembly for an active implantable medical device (AIMD), the hermetic feedthrough terminal pin connector assembly comprising: a) an electrically conductive ferrule configured to hermetically seal an opening of a casing of the AIMD, the ferrule configured to prevent a leakage of a body fluid in a human implant application to an inside of the casing of the AIMD; b) an electrical insulator hermetically sealing a ferrule opening, the insulator configured to prevent the leakage of the body fluid in the human implant application to the inside of the casing of the AIMD; c) a feedthrough terminal pin hermetically sealed to and disposed through the insulator, the feedthrough terminal pin extending outwardly beyond the insulator on the inside of the casing of the AIMD, wherein the feedthrough terminal pin extending outwardly beyond the insulator on the inside of the casing of the AIMD includes an elastically resilient termination structure; and d) a circuit board disposed on the inside of the casing of the AIMD, the circuit board comprising a formed or stamped metallic eyelet electrically connected to a circuit trace; e) wherein the elastically resilient termination structure of the feedthrough terminal pin is at least partially disposed within the metallic eyelet electrically connecting the feedthrough terminal pin and the metallic eyelet.

Referring now generally to FIGS. 22, 23, 24, another exemplary embodiment of the present invention includes a hermetic feedthrough terminal pin connector assembly for an active implantable medical device (AIMD), the hermetic feedthrough terminal pin connector assembly comprising: a) an electrically conductive ferrule configured to hermetically seal an opening of a casing of the AIMD, the ferrule configured to prevent a leakage of a body fluid in a human implant application to an inside of the casing of the AIMD; b) an electrical insulator hermetically sealing a ferrule opening, the insulator configured to prevent the leakage of the body fluid in the human implant application to the inside of the casing of the AIMD; c) wherein the insulator comprises a ceramic insulator body co-sintered with an electrically conductive filled via, wherein the electrically conductive filled via comprises a pure platinum or a ceramic reinforced metal composite; d) wherein the electrically conductive filled via comprises a counterbore formed therein; and e) an electrically conductive wire having at least one electrically conductive elastically resilient termination structure supported at a distal end of the electrically conductive wire; f) wherein the at least one electrically conductive elastically resilient termination structure is contacting and compressed against an inside of the counterbore of the electrically conductive filled via electrically connecting the electrically conductive wire to the electrically conductive filled via.

Referring now generally to FIGS. 30-32, another exemplary embodiment of the present invention includes a hermetic feedthrough terminal pin connector assembly for an active implantable medical device (AIMD), the hermetic feedthrough terminal pin connector assembly comprising: a) an electrically conductive ferrule configured to hermetically seal an opening of a casing of the AIMD, the ferrule configured to prevent a leakage of a body fluid in a human implant application to an inside of the casing of the AIMD; b) an electrical insulator hermetically sealing a ferrule opening, the insulator configured to prevent the leakage of the body fluid in the human implant application to the inside of the casing of the AIMD; c) a feedthrough terminal pin hermetically sealed to and disposed through the insulator, the feedthrough terminal pin extending outwardly beyond the insulator on the inside of the casing of the AIMD; d) a circuit board disposed on the inside of the casing of the AIMD; e) an electrically conductive terminal pin half pad disposed on the circuit board and electrically connected to at least one circuit trace disposed on the circuit board; f) a terminal pin capture pad disposed opposite the electrically conductive terminal pin, wherein the terminal pin capture pad is attached to the circuit board with a fastener; g) wherein at least a portion of the feedthrough terminal pin is disposed between and is compressed by the electrically conductive terminal pin half pad and the terminal pin capture pad, wherein the feedthrough terminal pin is electrically connected to the electrically conductive terminal pin half pad.

Referring now generally to FIG. 33, another exemplary embodiment of the present invention includes a hermetic feedthrough terminal pin connector assembly for an active implantable medical device (AIMD), the hermetic feedthrough terminal pin connector assembly comprising: a) an electrically conductive ferrule configured to hermetically seal an opening of a casing of the AIMD, the ferrule configured to prevent a leakage of a body fluid in a human implant application to an inside of the casing of the AIMD; b) an electrical insulator hermetically sealing a ferrule opening, the insulator configured to prevent the leakage of the body fluid in the human implant application to the inside of the casing of the AIMD; c) a feedthrough terminal pin hermetically sealed to and disposed through the insulator, the feedthrough terminal pin extending outwardly beyond the insulator on the body fluid side of the casing of the AIMD; d) a header block disposed on the outside of the casing of the AIMD; e) an electrically conductive terminal pin half pad disposed on the header block and electrically connected to at least one conductor disposed in the header block, the at least one conductor electrically connected to at least one port disposed within the header block, wherein a distal electrode in contact with body tissue is configured to be plugged into the at least port; and f) a terminal pin capture pad disposed opposite the electrically conductive terminal pin, wherein the terminal pin capture pad is attached to the header block with a fastener; g) wherein at least a portion of the feedthrough terminal pin is disposed between and is compressed by the electrically conductive terminal pin half pad and the terminal pin capture pad, wherein the feedthrough terminal pin is electrically connected to the electrically conductive terminal pin half pad.

Referring now generally to FIGS. 34-34E, another exemplary embodiment of the present invention includes a hermetic feedthrough terminal pin connector assembly for an active implantable medical device (AIMD), the hermetic feedthrough terminal pin connector assembly comprising: a) an electrically conductive ferrule configured to hermetically seal an opening of a casing of the AIMD, the ferrule configured to prevent a leakage of a body fluid in a human implant application to an inside of the casing of the AIMD; b) an electrical insulator hermetically sealing a ferrule opening, the insulator configured to prevent the leakage of the body fluid in the human implant application to the inside of the casing of the AIMD; c) a feedthrough terminal pin hermetically sealed to and disposed through the insulator, the feedthrough terminal pin extending outwardly beyond the insulator on the inside of the casing of the AIMD; d) a circuit board disposed on the inside of the casing of the AIMD; and e) an elastically resilient metallic clip disposed on the circuit board and electrically connected to at least one circuit trace disposed on the circuit board, the elastically resilient metallic clip having an opening configured for insertion of the feedthrough terminal pin; f) wherein at least a portion of the feedthrough terminal pin extending outwardly beyond the insulator on the inside of the casing is inserted through the opening in the elastically resilient metallic clip electrically connecting the feedthrough terminal pin to the elastically resilient metallic clip.

Referring now generally to FIG. 20, another exemplary embodiment of the present invention includes a hermetic feedthrough terminal pin connector assembly for an active implantable medical device (AIMD), the hermetic feedthrough terminal pin connector assembly comprising: a) an electrically conductive ferrule configured to hermetically seal an opening of a casing of the AIMD, the ferrule configured to prevent a leakage of a body fluid in a human implant application to an inside of the casing of the AIMD; b) an electrical insulator hermetically sealing a ferrule opening, the insulator configured to prevent the leakage of the body fluid in the human implant application to the inside of the casing of the AIMD; c) a feedthrough terminal pin hermetically sealed to and disposed through the insulator, the feedthrough terminal pin extending outwardly beyond the insulator on the inside of the casing of the AIMD and supporting at least one electrically conductive elastically resilient termination structure; d) a circuit board disposed on the inside of the casing of the AIMD; and e) an electrically conductive connector housing disposed on the circuit board, wherein the connector housing is electrically connected to at least one electrical circuit disposed on the circuit board; f) wherein the at least one elastically resilient termination structure is contacting and compressed against an inside surface of the electrically conductive connector housing electrically connecting the connector housing and the feedthrough terminal pin.

Referring now generally to FIG. 24A, another exemplary embodiment of the present invention includes a hermetic feedthrough terminal pin connector assembly for an active implantable medical device (AIMD), the hermetic feedthrough terminal pin connector assembly comprising: a) an electrically conductive ferrule configured to hermetically seal an opening of a casing of the AIMD, the ferrule configured to prevent a leakage of a body fluid in a human implant application to an inside of the casing of the AIMD; b) an electrical insulator hermetically sealing a ferrule opening, the insulator configured to prevent the leakage of the body fluid in the human implant application to the inside of the casing of the AIMD; c) wherein the insulator comprises a ceramic insulator body co-sintered with an electrically conductive filled via, wherein the electrically conductive filled via comprises a pure platinum or a ceramic reinforced metal composite; d) an electrically conductive connector housing disposed at least partially on the electrically conductive filled via electrically connecting the connector housing to the filled via; and e) at least one electrically conductive prong and at least one electrically conductive wire, wherein either: i) the at least one electrically conductive prong is supported by the conductive wire, wherein the at least one prong is contacting and compressed against an inside surface of the connector housing electrically connecting the connector housing and the wire; or ii) the at least one electrically conductive prong is supported by the connector housing, the at least one prong contacting and compressed against the wire electrically connecting the connector housing and the wire.

Referring now generally to FIGS. 8, 9, 9A, 9B, 14, another exemplary embodiment of the present invention includes a hermetic feedthrough terminal pin connector assembly for an active implantable medical device (AIMD), the hermetic feedthrough terminal pin connector assembly comprising: a) an electrically conductive ferrule configured to hermetically seal an opening of a casing of the AIMD, the ferrule configured to prevent a leakage of a body fluid in a human implant application to an inside of the casing of the AIMD; b) an electrical insulator hermetically sealing a ferrule opening, the insulator configured to prevent the leakage of the body fluid in the human implant application to the inside of the casing of the AIMD; c) a feedthrough terminal pin hermetically sealed to and disposed through the insulator, the feedthrough terminal pin extending outwardly beyond the insulator on the inside of the casing of the AIMD; d) a circuit board disposed on the inside of the casing of the AIMD; and e) a terminal pin connector, comprising: i) an electrically conductive connector housing disposed on the circuit board, wherein the connector housing is electrically connected to at least one electrical circuit disposed on the circuit board, and wherein the connector housing comprises at least one flange outwardly extending outwardly beyond a side surface of the connector housing; and ii) at least one electrically conductive elastically resilient termination structure supported by the connector housing, the at least one elastically resilient termination structure contacting and compressed against the feedthrough terminal pin extending outwardly beyond the insulator on the inside of the casing of the AIMD; f) wherein the side surface of the connector housing abuts the circuit board, wherein the at least one flange is disposed overhanging an edge of the circuit board.

These and other objects and advantages of the present invention will become increasingly more apparent by a reading of the following description in conjunction with the appended drawings.

BRIEF DESCRIPTION OF THE DRAWINGS

FIGS. 4A-4C illustrate embodiments of the clip of the connector housing of the terminal pin connector.

FIG. 5A shows a proximal end view of an embodiment of the terminal pin connector.

FIG. 5B shows a cross-sectional view of the terminal pin connector of FIG. 5A taken along lines 5B-5B.

FIG. 5C shows a distal end view of the terminal pin connector of FIG. 5A.

FIG. 6A shows a proximal end view of an embodiment of the terminal pin connector.

FIG. 6B shows a cross-sectional view of the terminal pin connector of FIG. 6A taken along lines 6B-6B.

FIG. 6C shows a distal end view of the terminal pin connector of FIG. 6A.

FIG. 17 shows a cross-sectional view of an alternative embodiment of a feedthrough capacitor connector assembly.

FIG. 18 is a perspective view of the clip of FIG. 17.

FIG. 27 shows a cross-sectional view of an embodiment of the feedthrough connector assembly taken along lines 27-27. Illustrated are terminal pin connectors attached to terminal pins. It is noted that the terminal pins are actually also attached to an AIMD active electronic circuit board (not shown) of the device side of an AIMD.

FIG. 27A illustrates an embodiment of an electrical connection to the ground pin and the at least one ground electrode plate of an EMI filter circuit board.

FIG. 27B illustrates an embodiment of an alternative electrical connection to the ground pin and the at least one ground electrode plate of an EMI filter circuit board.

FIG. 27C illustrates an embodiment of an alternative electrical connection to the ground pin and the at least one ground electrode plate of an EMI filter circuit board.

FIG. 28J is a perspective view of a quad polar flat-thru capacitor.

FIG. 28K is a sectional view taken along lines 28K-28K of FIG. 28J showing the active and ground electrode plates of the quad polar flat-thru capacitor.

FIG. 29 shows a cross-sectional view of an alternative embodiment of a feedthrough connector assembly comprising various compliant termination structures. Illustrated are terminal pin connectors attached to terminal pins. It is noted that the terminal pins are actually also attached to an AIMD active electronic circuit board (not shown) of the device side of an AIMD.

DETAILED DESCRIPTION OF THE PREFERRED EMBODIMENTS

Figure 1:
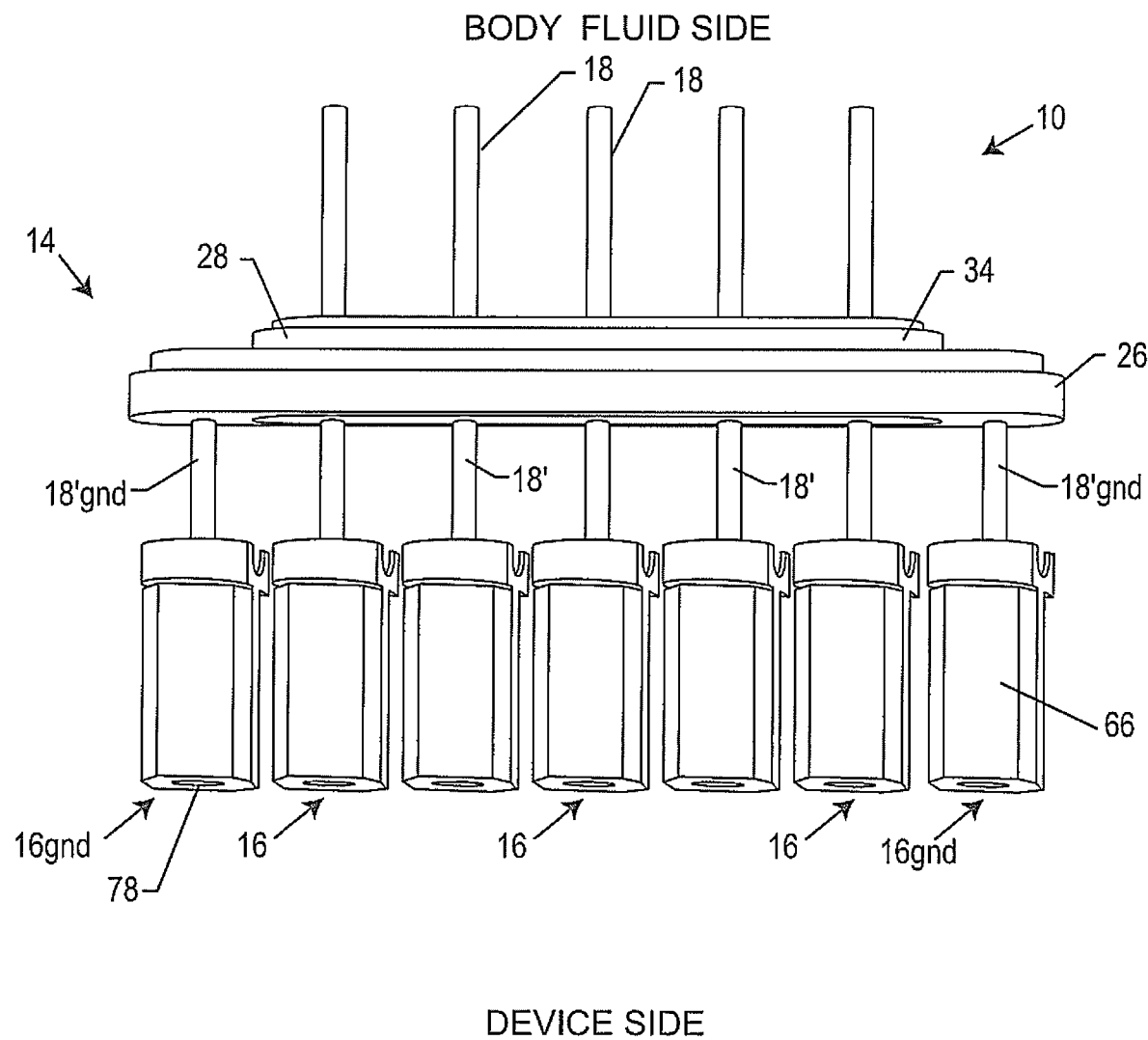
FIG. 1 illustrates a side perspective view of an embodiment of the AIMD feedthrough connector assembly.

Modern active implantable medical devices (AIMDs) 12, such as implantable cardiac pacemakers, implantable cardioverter defibrillators, cardiac resynchronization devices, such as cardiac resynchronization pacemakers and defibrillators, all have remote telemetry capability and programming capabilities. The AIMD active electronic circuit boards 106 are extremely complex because they contain not only digital circuits, but also biological sensing circuits (analogue circuits). A modern AIMD may have over 4,500 programmable functions and also may have extensive memory storage capability where doctors can retrieve waveforms after a cardiac event. When an active electronic circuit board is built for such AIMDs, it is placed on a large test console where computers extensively check every function of the circuit board. The active electronic circuit board becomes a defective circuit board if there is any single bit error or logic error. Once the active electronic circuit board and the battery are installed and the AIMD is hermetically sealed, the AIMD then undergoes final testing.

If the AIMD active electronic circuit board is found to be defective at final testing, it is too late to replace the defective circuit board. As used herein, active circuit boards are defined as AIMD active electronic circuit boards which require a power source and have one or more electronic components, including microchips and the like. The term active as used herein also apply to active terminal pins or active co-sintered conductive vias, which constitute conductive pathways that pass through the hermetic terminal insulator to circuits that are active circuits. In this context, active is defined as a terminal pin or circuit or even implanted therapy delivery leadwire which conducts therapeutic pacing pulses and/or senses biological signals. In general, active circuits require a power source such as a primary or secondary battery. This is in contrast to ground terminal pins or ground circuit traces, which are generally at the potential of the AIMD casing 32.

Circuit boards come in a multitude of sizes, shapes, and materials. They may be single layer or multi-layer with surface circuit traces, embedded circuit traces or both, and surface ground electrode plates, embedded ground electrode plates or both, including through-hole, surface mount, and/or optional embedded components. Typical circuit board materials include fiberglass, alumina ceramic, FR-4 (or FR4) and the like. Circuit boards are often called printed circuit boards (PCBs), which refer to how circuit traces are laid out. Circuit boards typically have a number of active and ground conductive paths (sometimes called conductive pathways).

Referring now to the Provisional Patent Application No. 61/492,828 filed on Jun. 3, 2011, the following paragraphs are excerpts taken from the '828 Provisional. Wording shown in quotation marks are quoted directly.

The '828 Provisional states: "How was the problem addressed before invention: 1) Use of expensive, but solderable biostable feedthrough wire material, such as platinum or palladium; 2) Use of additional coatings on feedthrough wires using expensive processes, such as selective physical vapor deposition or selective electro (or electroless) plating to make surface to wire solderable; 3) Additional coatings on wire materials that have marginal or poor solderability, such as nickel or platinum-iridium alloys, by using a hot solder dipping operation after feedthroughs have been assembled; 4) Use of laser welding feedthrough wires to printed circuit board mounted contacts or contact clips; 5) Use of resistance welding feedthrough wires to printed circuit board mounted contacts or contact clips." The foregoing lists issues with how prior art connections between unfiltered feedthroughs and/or filtered feedthrough assemblies and an AIMD active electronic circuit board.

The '828 Provisional also states: "What are short-comings of previous ways to solve the problem: 1) Feedthrough wires made from solderable material that are also biostable and biocompatible are, in comparison, very expensive; 2) Feedthrough wires coated with physical vapor deposition and/or electro (and electroless) plating are, in comparison, very expensive; 3) Feedthrough wires connected to printed circuit boards using laser welding or resistance welding is, in comparison, very expensive; 4) Feedthrough wires connected by all of the above processes are not disconnected without destructive techniques (e.g. once welded or soldered, the feedthrough and/or printed circuit board are mated for the product's life without damage to either both the feedthrough and/or printed circuit board.)" As such, the '828 provisional discloses that once the AIMD active electronic circuit board is connected, it is permanently attached and cannot realistically be removed. In the case of a defective circuit board, this means the entire AIMD must be scrapped or at least most of the AIMD pulse generator, including a casing half, a battery, among possibly other costly components, such as high energy storage capacitors if the AIMD is an implantable cardioverter defibrillator (ICD).

As previously disclosed, a modern AIMD circuit board is complex, having over 4,500 programmable functions and can also be capable of storing biological wave forms, for example, but not limited to, cardiac wave forms for a pacemaker or an ICD. The prior art methods of connecting feedthrough wires to the circuit board involve processes, such as thermal sonic bonding, wire bonding, welding, soldering or the like, typically apply heat and pressure to the components being connected. Hence, even though AIMD active electronic circuit boards are pretested through an automated test system, which is costly in and of itself, such connection methods using thermal energy and mechanical force, can and do damage AIMD active electronic and other circuit boards. The embodiments of the present application resolves these issues, as the novel connectors of the present application allow equally reliable connection of AIMD components without introducing damaging amounts of thermal energy or mechanical force, while enabling insertion and retraction of components so that defective components can be removed for replacement or rework (replacement and rework of defective components being more cost-effective compared to scrapping costly assemblies and/or fully assembled products).

Continuing on, the '828 Provisional states: "By modifying existing commercially available connectors to meet wire pitch requirements, a mechanical and electrical connection can be made to feedthrough wires. This connector could be populated on the circuit board at the same time, all other components are populated and reflowed." As used therein, the word "populated" is a very common term of art applied to circuit board assembly and implies that robots can be used to pick and place all of these components, including the terminal pin connectors 16 disclosed herein (which would also be automatically populated). Typically, once the board is populated, then all the electrical connections, such as BGA or solder joints, are made at the same time. After the board is populated and cleaned, it goes through extensive electrical and functional testing. Typically, an automated test console is used to check all of its programmable and non-programmable functions. It is very important that after this testing, the board be handled very gently and not be exposed to undo mechanical forces or thermal shocks, such as soldering or welding. This is because such mechanical forces or thermal shocks result in residual stresses and strains that can induce immediate or latent defects in the circuit board. Latent defects are a very worrisome risk as these types of defects are often not discovered until a device has been in the field (implanted in the human) for months or years. The connectors taught herein allow the AIMD active electronic circuit board 106 insertion and retraction (removability) without imparting undo mechanical or thermal stresses.

The '828 Provisional states: "This connector could also be attached through feedthrough wires at the end of the feedthrough assembly process. This connector allows multiple insertions/retractions without affecting reliability, thus enabling rework or pre-assembly testing. The connector could be mounted in one unique-body insulating structure or kept as individual components." It is understood that the feedthrough wires mentioned are the terminal pins 18 taught herein. What this paragraph is saying is that the connector disclosed allows multiple insertions/retractions without affecting reliability. This means that a reworked or a new circuit board could easily be plugged in to replace a defective circuit board. In general, removal of defective circuit boards and plugging in a replacement or reworked circuit board would be preferred but is not possible without the embodiments taught herein. Additionally, the connector embodiments disclosed herein also apply to an AIMD header block, such that a defective AIMD header block could be removed and reworked or replaced.

Hence, as the '828 provisional teaches, "by modifying existing commercially available connectors" such that the commercially available connectors can be integrated with AIMD circuit boards and AIMD header blocks, wherein the connectors integrated with AIMD circuit boards and AIMD header blocks can be removably connected not only resolves the issues associated with the present AIMD circuit board and AIMD header blocks, but also forms an equally reliable connection while also minimizing production scrap levels thereby lowering manufacturing financial losses. Exemplary embodiments of novel modifications of commercially available AIMD connectors available from, for example, but not limited to, Mill-Max®, Samtec, Amphenol, ITT, Airborn, Smiths Interconnect, ODU GmbH & Co. KG, Positronic, Molex, 3M, Interplex Industries, preci-dip, TE Connectivity, NEPCON, KEL Corporation, among others, in addition to various custom novel connector embodiments, are taught and disclosed herein.

The present patent application thus relates to removable connector assemblies that allow rework and/or replacement of defective circuit boards. With the present invention, extensive testing of any circuit board of an AIMD can be completed before welding the final can half thereby hermetically sealing the AIMD. The term "can" is defined herein as a case, a casing, or a housing of an AIMD. In the event that a defective circuit board is discovered, the present invention makes it easy to remove the defective circuit board from its AIMD subassembly and then plug in a new functional replacement circuit board. By doing this, one saves a number of expensive components, including the AIMD casing (can half), the AIMD hermetically sealed feedthrough, if present, the EMI filter of the AIMD hermetically sealed feedthrough, the AIMD power source (s), for example, a battery, or, in the case of a defibrillator, the high energy storage capacitors, other potentially costly mounting components, other hardwired additional circuit boards, or potentially costly high-voltage switches.

As present-day feedthrough assemblies for modern AIMDs may comprise sintered conductors, such as, but not limited to, a co-sintered conductive paste-filled via, instead of conventional terminal pins, such sintered conductors present additional challenges for creating robust and reliable circuit board connections. For example, conventional AIMD feedthroughs typically comprise one or more terminal pins 18, which generally have some length extending outwardly beyond either the body fluid side insulator surface 36, the device side insulator surface 38, or both the body fluid and device side insulator surfaces 36, 38 of the AIMD hermetically sealed feedthrough 14. Either one or both ends of the terminal pin (s) 18 is/are electrically directly connectable to one of a circuit board within the active implantable medical device 14, to one or more components, a subassembly, an assembly, or combinations thereof outside of the active implantable medical device 14, or in various combinations of both the inside and the outside of the active implantable medical device 14. As used herein, inside the active implantable medical device is defined herein as the device side of the active implantable medical device, and outside the active implantable medical device is defined herein as the body fluid side of the active implantable medical device. In the device side case, the terminal pin distal end 62 is typically electrically connected to an active electrical circuit residing within the AIMD casing. In the body fluid side case, the terminal pin distal end is typically electrically connected to a structure configured for electrical stimulation, for example, an AIMD header block to which implantable leads with electrodes connect. In either case, electrical connection is typically made by a soldering or a welding attachment process. While this connection is readily achievable in the prior art, these processes are often complex and time consuming, lowering throughput efficiencies, and sometimes even requiring manual operations. These processes also can be difficult and can pose risk of damage to the parts being connected, which includes an AIMD active electronic circuit board 106 and/or an EMI filter circuit board 106'. Furthermore, in the case of soldering, depending on the solder process, flux residues or solder balls may occur, adding further manufacturing complications. As a result, such soldering and welding processes can additionally involve complex and time-consuming cleaning, testing and inspection protocols. Of particular significance, however, is that these processes may be prohibitively costly when pre-assembled parts are found to be out of specification during inspection or have failed testing and/or evaluation requirements and cannot be reworked or replaced. Moreover, the cost of failure can be particularly substantial, even excessive, when a device is at an almost completed stage of manufacturing and is either not reworkable or if re-workability is unreasonable. Accordingly, the novel removable terminal pin connectors 16 of the present application provide cost-effective electrical connection without sacrificing AIMD quality, reliability, and performance, and provides connector embodiments that resolve these concerns. The removable terminal pin connectors 16 additionally provide options for insertable and retractable AIMD header blocks. As such, the present invention teaches the use of various removable terminal pin connectors for use on the body fluid, the device side, or both the body fluid and the device sides of AIMDs.

The removable terminal pin connectors as taught herein, include some commercially available non-AIMD connectors and how the commercially available parts can be integrated with an AIMD such that removability from the AIMD permits replacement or rework of a defective component, subassembly, assembly, portion, or part, thereby reducing costs of quality associated with product failures. Of particular significance is that such commercially available electrical connectors as taught herein were not contemplated or intended for use in AIMDs by those skilled in the art. Moreover, removable terminal pin connectors are still not being used today in active implantable medical devices. This is because those skilled in the art failed to teach, suggest, or appreciate a way to test AIMD circuit boards or header blocks after being fully or partially installed in or on an AIMD. Furthermore, those skilled in the art would not even have been motivated to teach, suggest, or appreciate replacement or rework of AIMD circuit boards or header blocks because, once installed using processes such as soldering and welding, removability was considered impossible or impractical. Hence, even if those skilled in the art could test for defective AIMD circuit boards or header blocks, then the defective AIMD circuit boards or header blocks, and the associated other components of the assembly at the time the defect was identified, were considered irrecoverable internal failure costs due to product performance failure.

The present application teaches that a defective component, subassembly, assembly, portion, or part of an AIMD can indeed be either replaced or reworked. For example, in the case of circuit boards, the present application teaches that a defective circuit board can either be easily removed and replaced with a new functional circuit board or that a defective circuit board could be removed and then reworked such that the defective circuit board functionality is acceptably restored. Similarly, this reasoning can be applied to AIMD header blocks. Moreover, the ability to install and test an AIMD circuit board or a header block after installation such that the defective component, subassembly, assembly, portion, or part of the AIMD can be replaced or reworked provides cost and time saving advantages that were previously considered irrecoverable internal failure costs.

The use of connectors that facilitate insertion and retraction of either AIMD circuit boards and/or AIMD header blocks was particularly counter-intuitive since such connectors take up both space and add weight to the overall AIMD. All the thinking by those skilled in the art in the AIMD industry is directly contrary to improving, adding, or innovating 'anything' that would add any size or weight to active implantable medical devices. In fact, research related to modern AIMDs focused heavily on miniaturization of AIMDs. As such, it has been and still is particularly important for all active implantable medical devices that they be very small and very thin for patient comfort and patient safety. Using an implantable cardiac pacemaker as an example, it is typically inserted in the pectoral area of the human chest either submuscular (sub-pectoral) or subcutaneous (under the skin). Early model pacemakers that were thicker caused a very unpleasant bulge under the patient's skin, which many patients found to be uncomfortable and irritating. Accordingly, adding additional components, such as AIMD circuit board and/or header block connectors, is contrary to the entire industry trend to those of skill in the art who were ideating and innovating to make things smaller and smaller and lighter and lighter. It is only when the present inventors understood that circuit boards for AIMDs had become so complex and the other associated components so costly that the ability to replace a defective circuit board overcame the disadvantages of adding additional components, that potentially might add some size and/or weight to an AIMD. During the development of the removable AIMD circuit board invention, the inventors also understood the need for and the ability to rework an AIMD header block on the body fluid side of AIMDs, thereby conceiving the removable AIMD header block.

The inventors performed due diligence regarding a wide variety of connector art, including various types of circuit board connectors and connectors for potential use with other AIMD components like AIMD header blocks. None of the prior art discovered by the inventors were designed or in any way intended or contemplated for use in any active implantable medical device. More specifically, no AIMD discovery for removable/replaceable AIMD circuit boards or header blocks even emerged during the due diligence process. Additionally, discovered AIMD circuit board or header block related patents do not even address the unique requirements for or even consider the concept of a replaceable AIMD circuit board or a header block for an active implantable medical device. Such discovered patents include U.S. Pat. Nos. 3,621,445; 5,893,779; 6,183,301; 7,249,981; 8,900,008; and 9,806,443, the contents of all of which are fully incorporated herein by these references.

Accordingly, to date, the inventors are not aware of any teaching of connectors being used in active implantable medical devices 12 in order to permit removability of an AIMD circuit board and/or a header block. Additionally, none of the prior art discovered taught structures and/or configurations for a terminal pin (s) 18 and/or the via configurations of a co-sintered paste-filled via(s) 146 that include a hermetically sealed ferrule 26, an insulator 28, and either a feedthrough capacitor 24, 24', 24" or an EMI filter circuit board 106' that could take advantage of the terminal pin connectors 16 of the present invention such that at least one of an AIMD active electronic circuit board 106, an EMI filter circuit board 106', an AIMD header block 118, or combinations thereof are removable. Furthermore, none of the prior art taught the use of terminal pin connectors 16 for use on the body fluid side of an AIMD, which permit removability and are biocompatible, non-toxic, and biostable. For at least these reasons, the embodiments of the present application are indeed novel and are being disclosed for the first time by the teaching of this and the applications of the priority chain herein.

The removable electrical terminal pin connector 16 of the present application is specifically for use in AIMDs, the removable electrical terminal pin connector 16 providing electrical connection between one or more components of the AIMD and one or more feedthrough conductive pathways, wherein the one or more feedthrough conductive pathways are selected from the group consisting of a terminal pin, a pin, a leadwire, a lead wire, a two-part pin, a lead conductor, a sintered paste-filled via, a co-sintered via, a co-sintered via with one or more metallic inserts, or combinations thereof, and wherein the component of the AIMD comprises one of a circuit, a circuit board, an electrical component, a header, a header block, or combinations thereof. An AIMD component being connected to a feedthrough conductive pathway may reside on either a device side or on a body fluid side of the AIMD. The term "component" as used herein is defined as either an individual part or element, or one or more parts or elements that make up a subassembly or an assembly (like an AIMD active circuit electronic board or a header block) of an AIMD.

The removable terminal pin connectors 16 of the present application do not substantially increase resistance and/or impedance at the point of connection and do not compromise the intended electromechanical performance of the AIMD, yet such terminal pin connectors 16 permit insertion and retraction of an AIMD component from the one or more hermetically sealed feedthrough conductive pathways (such as terminal pin 18 or co-sintered conductive paste-filled via 146) without damage to either the component or the one or more feedthrough conductive pathways being connected. Further, the insertion and retraction capability of the terminal pin connectors 16 disclosed herein provides re-workability and/or replacement of any portion of the AIMD that has been determined to be out of specification, or that has failed quality, reliability, testing or evaluation requirements. In summary, the AIMD component being connected to the one or more hermetically sealed feedthrough conductive pathways may comprise one of an assembly, a subassembly, a structure, a body, an element, a part, a circuit, a circuit board, a header, a header block, or combinations thereof. Hermetically sealed feedthrough conductive pathways may comprise terminal pins, leadwires, lead wires, two-part pins, co-sintered insulator vias, co-sintered metallic inserts, co-sintered connector components and combinations thereof.

The removable connectors of the present application provide some embodiments comprising compliant designs. The term "compliant" is defined herein as an elastically resilient structure (i.e., a structure that resists a distorting influence and returns to its original form when that influence or force is removed, meaning its elastic limit or yield point was not reached) that may comprise a prong, a tine, a finger, an elongated member or a spring-like structure and that also provides a mechanical and an electrical interface between a component (such as an AIMD active electronic circuit board, an EMI filter circuit board or an AIMD header block) and a hermetically sealed feedthrough conductive pathway. The compliant design further permits insertion and retraction of an AIMD component from a hermetically sealed feedthrough conductive pathway. The compliant design may either be a separate independent structure, a part of a connector housing, or an integral part of the hermetically sealed feedthrough conductive pathway. Additionally, a terminal pin connector 16 may comprise either a one-piece construction, a two-piece construction, or a multi-piece construction. In some embodiments described herein, compliant terminations may comprise one or more prongs. As used herein, prong is defined as a projecting part, a tapering projection, or an elongate extension from a base structure. The term "prong" is used within this application interchangeably with the term "tine" and are synonymous. In some embodiments described herein, compliant designs may comprise a bi-spring design, known in the industry as "eye of the needle".

Figure 9:
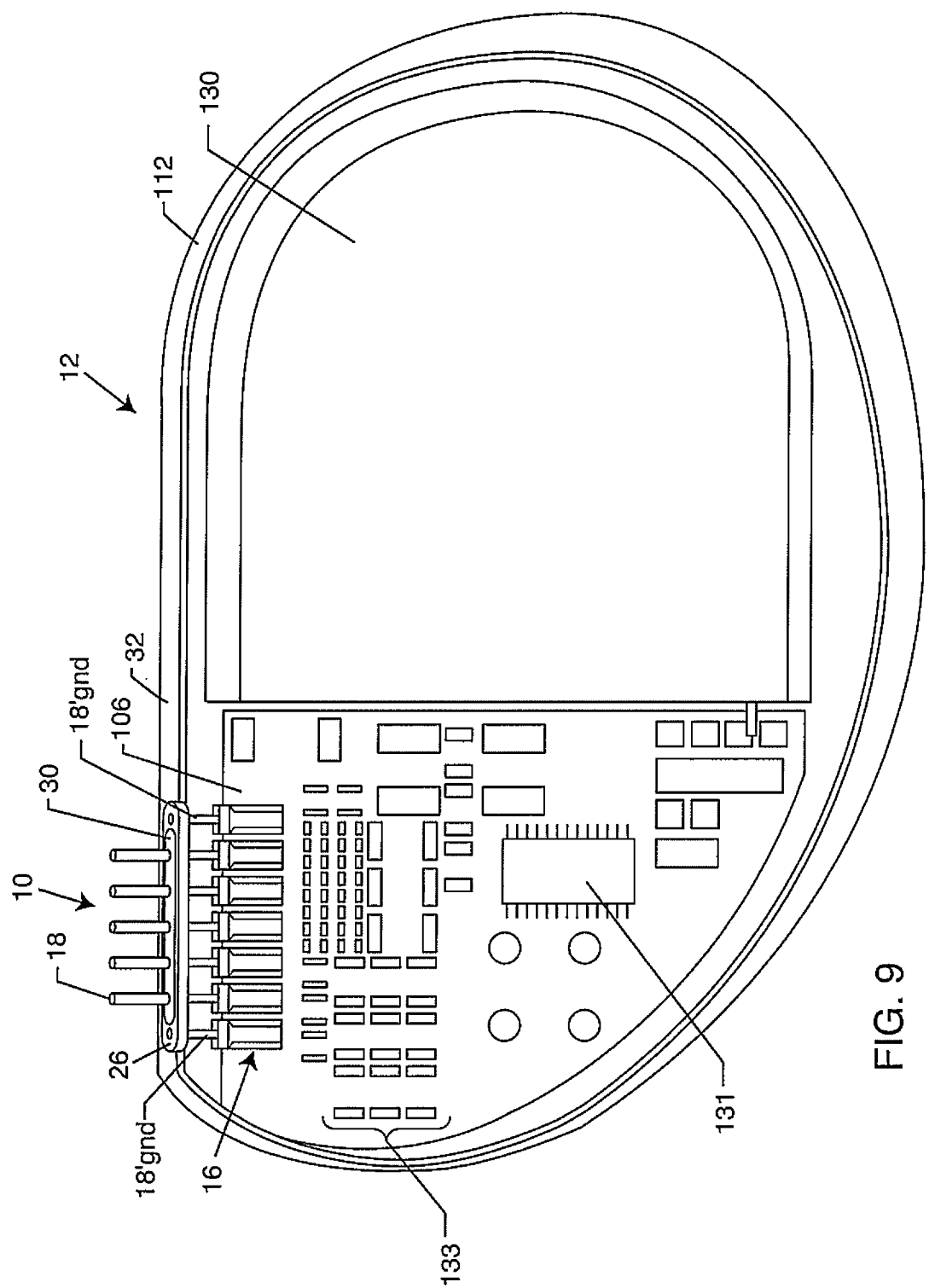
FIG. 9 illustrates a perspective view of an embodiment of an AIMD feedthrough connector assembly positioned within an AIMD casing half.

The following detailed description and figures teach various embodiments of the novel terminal pin connectors 16 for an AIMD feedthrough connector assembly 10 of the present invention. The AIMD feedthrough connector assembly 10 is useful with medical devices, such as an active implantable medical device (AIMD) 12 as shown in FIG. 9 which can be a pacemaker, cardiac defibrillator, cardioverter defibrillator, cochlear implant, neurostimulator, drug pump, deep brain stimulator, hearing assist device, incontinence device, obesity treatment device, Parkinson's disease therapy device, bone growth stimulator, spinal cord stimulator and other such devices, which are either implanted, temporarily implanted, or otherwise external the human body.

As shown in FIG. 1, the AIMD feedthrough connector assembly 10 comprises an AIMD hermetically sealed feedthrough 14 and a terminal pin connector 16. The AIMD hermetically sealed feedthrough 14 of the AIMD feedthrough connector assembly 10 includes terminal pins 18' and 18'gnd that provide for conducting electrical signals to and from body tissue, such as a patient's heart, while hermetically sealing the interior (device side) of the AIMD 12 (not shown) against ingress of patient body fluids that could otherwise disrupt AIMD operation or cause AIMD malfunction.

Figure 2:
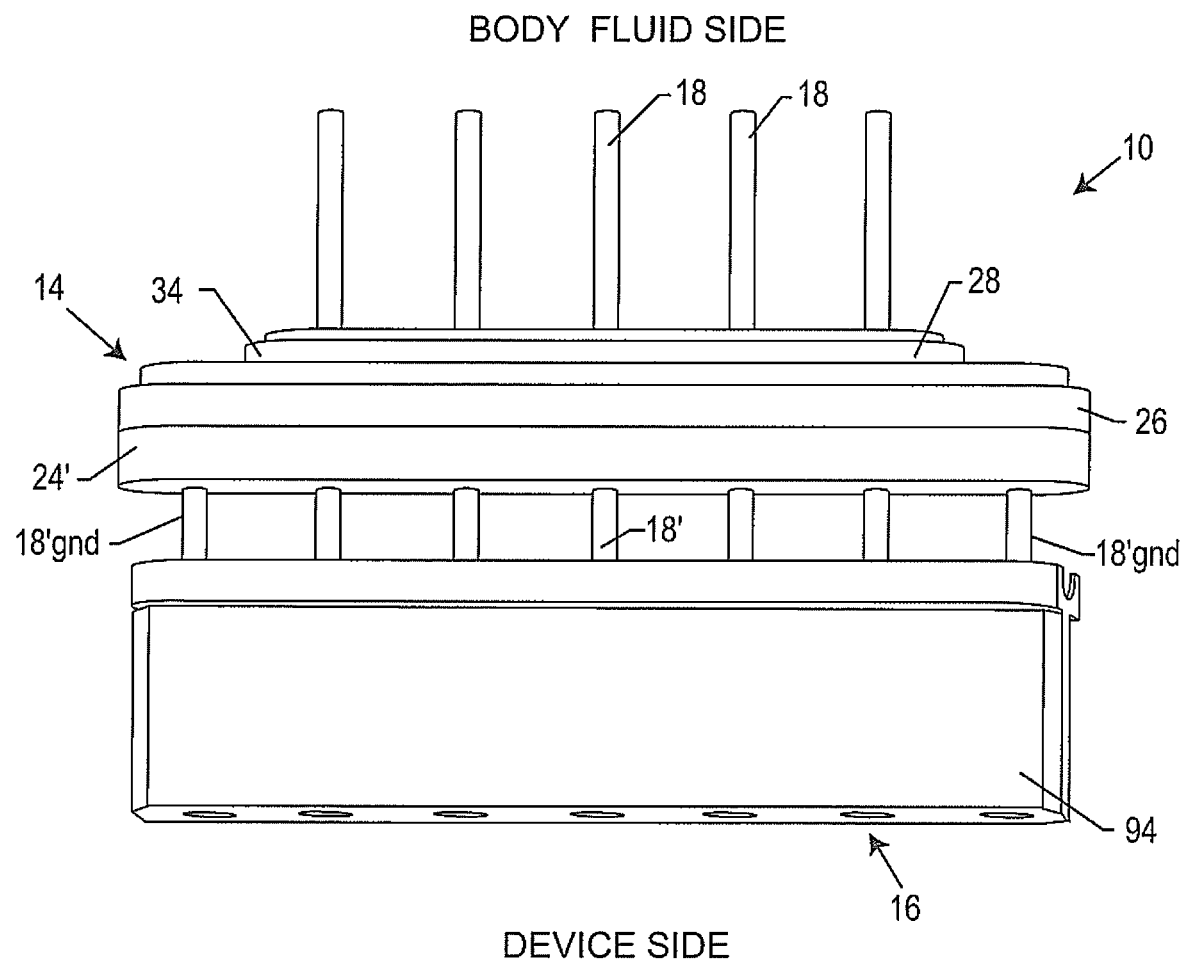
FIG. 2 illustrates an alternative embodiment of the AIMD feedthrough connector assembly comprising a one-piece housing.

FIG. 2 is very similar to FIG. 1, except that the AIMD feedthrough connector assembly 10 now includes an internally grounded feedthrough capacitor 24', as illustrated. Internally grounded feedthroughs are taught by U.S. Pat. No. 5,905,627, the contents of which are fully incorporated herein by this reference. As illustrated, the internally grounded feedthrough capacitor 24' is disposed on the device side of the AIMD feedthrough connector assembly 10. In accordance with the present invention, illustrated in the embedment of FIG. 2 are terminal pin connectors 16 all contained within a common housing body 94. The common housing body 94 may comprises a metallic structure, a ceramic structure, or a structure comprising a ceramic and a metal. The common housing body 94 may further be an insulated housing body comprising a ceramic structure, or a ceramic structure with metal structures optionally positioned in, on or about the ceramic structure. In the case where the common housing body 94 is metallic, it is contemplated that an insulating material would be contained inside the common housing body 94, the insulating material positioned to thereby electrically insulate each of the terminal pins 18', 18'gnd one from the other. The individual terminal pin connectors 16 are not shown as they are embedded in the common housing body 94. It is contemplated that the common housing body 94 may comprise terminal pin connectors 16 having similar or the same shape and configuration as the terminal pin connectors 16 previously described in FIG. 1 or may comprise any of the connector structures disclosed herein. The common housing body 94 may further comprise any combination of connector structures disclosed, including terminal pin connector 16. As used herein, the term "common housing body" is defined as one connector housing in which two or more connector structures or terminal pin connectors reside.

Referring once again to FIG. 2, one will see the internally grounded feedthrough capacitor 24' is shown vertically aligned with the ferrule 26 structure. The illustrated internally grounded feedthrough capacitor 24' is exemplary only, including how the internally grounded feedthrough capacitor may be attached to a ferrule 26. There are various ways feedthrough capacitors may be attached. For example, attachment of externally grounded feedthrough capacitors 24 to AIMD hermetically sealed feedthroughs 14 is well known in the prior art and includes, U.S. Pat. No. 5,333,095, (otherwise known as the Surface Mount patent); and U.S. Pat. Nos. 5,978,204; 5,905,627 (Internal Ground patents, which would require the addition of at least one internally grounded terminal pin 18gnd that would be connected to the ferrule 26), the contents of which are fully incorporated herein by these references. Following are additional patents that disclose externally grounded feedthrough capacitors 24: U.S. Pat. Nos. 6,643,903; 6,765,779; 7,035,076; 7,917,219; 8,179,658; 8,422,195; 8,433,410; 8,468,664; 8,543,209; 8,577,453; 8,659,870; 8,653,384; 8,855,785; 8,868,189; 9,014,808; 9,064,640; 9,108,066; 9,352,150; 9,427,596; 9,463,329; 9,757,558; 9,764,129; re-issue 46,699; re-issue 46,837; 9,895,534; 9,889,306; 9,931,514; 9,993,650; 10,080,889; 10,092,749; 10,099,051; 10,124,164; 10,249, 415; 10,272,252: 10,272,253 and 10,350,421, the contents of which are also fully incorporated herein by these references.

Figure 3:
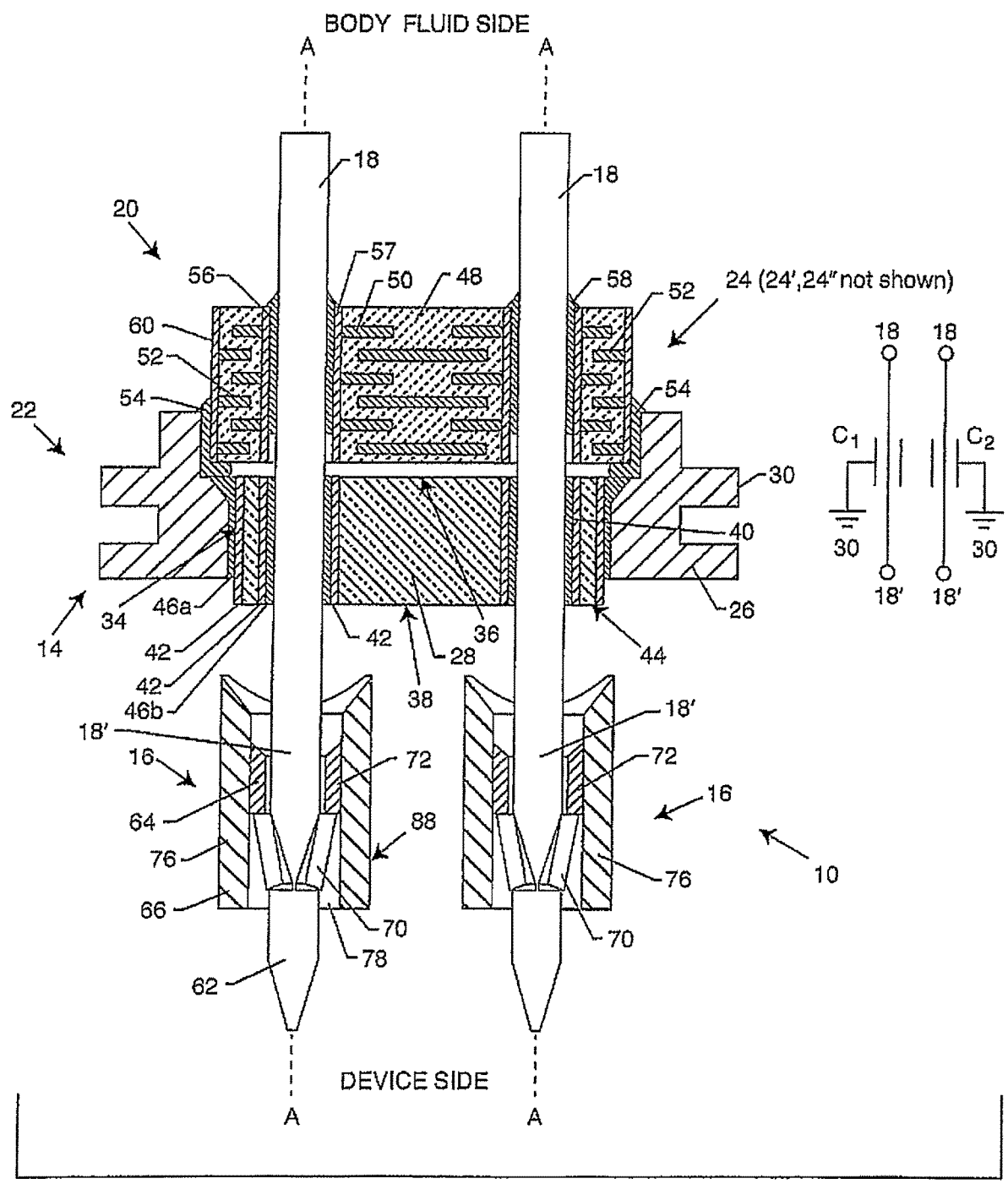
FIG. 3 shows a cross-sectional view of an embodiment of the AIMD feedthrough connector assembly.

FIG. 3 illustrates a cross-sectional view of an alternative embodiment of an externally grounded feedthrough capacitor 24 of the feedthrough capacitor connector assembly 20 disclosed herein. Externally grounded feedthrough capacitors 24 are also known in the industry as conventionally grounded feedthrough capacitors. Internally grounded feedthrough capacitors 24' and hybrid feedthrough capacitors 24" can alternatively be used in feedthrough capacitor connector assemblies 20. Hybrid feedthrough capacitors 24" comprise both an external ground and an internal ground. As used herein, a filtered feedthrough assembly 22 comprises an AIMD hermetically sealed feedthrough 14 and a filter capacitor 24 (24', 24" not shown), the filter capacitor comprising one of an externally grounded feedthrough capacitor 24, an internally grounded feedthrough capacitor 24' or a hybrid feedthrough capacitor 24", wherein the filter capacitor is mounted or attached to the AIMD hermetically sealed feedthrough 14. Also, as used herein, a feedthrough capacitor connector assembly 20 comprises a filtered feedthrough assembly 22 and terminal pin connectors 16. In summary, it is contemplated that the feedthrough capacitor could be an externally grounded feedthrough capacitor 24, an internally grounded feedthrough capacitor 24' (see U.S. Pat. No. 5,905,627 incorporated herein fully by reference), or a hybrid feedthrough capacitor 24" (see U.S. Pat. No. 6,765, 780 incorporated herein fully by reference), which includes both the features of the internally grounded feedthrough capacitor 24' and the externally grounded feedthrough capacitor 24.

Referring once again to FIG. 3, shown is a cross sectional view of feedthrough capacitor connector assembly 20 comprising an externally grounded feedthrough capacitor 24. As previously disclosed, feedthrough capacitor connector assemblies 20 may incorporate both an externally grounded feedthrough capacitor 24 as shown, or an internally grounded feedthrough capacitor 24' (not shown), or a hybrid feedthrough capacitor 24" (also not shown), the hybrid feedthrough capacitor 24" comprising both an external ground and an internal ground. As illustrated, the external ground of FIG. 3 comprises an external ground electrical path comprising an outer metallization layer 60 residing on the externally grounded feedthrough capacitor 24, an electrical connection material 54, a braze material 46a residing between the ferrule 26 and the insulator 28 of the AIMD hermetically sealed feedthrough 14, and the ferrule 26. The terms "hermetic", "hermetically sealed" and "hermetic seal" refer to an enclosure, a feedthrough, and/or a seal comprising a leak rate no greater than $1 \times 10^{-7}$ std cc He/sec. It is understood that insulator 28 could comprise one of a ceramic, a glass, a glass-ceramic, or combinations thereof. As previously disclosed, the feedthrough capacitor connector assembly 20 may alternatively comprise an internal ground as taught by U.S. Pat. No. 6,765,780 incorporated herein fully by reference. One is referred to FIG. 42 of the '780 patent as an exemplary internal ground electrical path. The feedthrough capacitor connector assembly 20 of FIG. 3 may also optionally incorporate the teachings of a number of other patents, including U.S. Pat. Nos. 4,424,551; 5,333,095; 6,643,903; and 6,765,779, the contents all of which are fully incorporated herein by these references.

As illustrated in FIG. 3 the feedthrough capacitor connector assembly 20 comprises a filtered feedthrough assembly 22 comprising an externally grounded feedthrough capacitor 24 that is attached to the AIMD hermetically sealed feedthrough 14. Like the AIMD feedthrough connector assembly 10 of FIG. 1, the feedthrough capacitor connector assembly 20 of FIG. 3 comprises terminal pin connectors 16. In this embodiment, the externally grounded feedthrough capacitor 24 is attached to the body fluid side of the AIMD hermetically sealed feedthrough 14 such that undesirable electromagnetic interference (EMI) signals and noise transmission into the interior (device side) of the medical device are suppressed or decoupled as taught by U.S. Pat. No. 7,917,219, the contents of which are fully incorporated herein by this reference. More particularly, the AIMD hermetically sealed feedthrough 14 of the AIMD feedthrough connector assembly 10 of FIG. 1 and the filtered feedthrough assembly 22 of FIG. 3, comprises a an electrically conductive ferrule 26 comprising a ferrule opening extending to a ferrule body fluid side opposite a ferrule device side and an insulator 28 residing in the ferrule opening where a gold braze 46a hermetically seals the insulator 28 to the ferrule 26. Suitable electrically conductive materials for the ferrule 26 include titanium, tantalum, niobium, stainless steel, or combinations of alloys thereof, titanium being preferred. The ferrule 26 may be of any geometry; non-limiting examples being curved, round, oval, rectangular, square, and oblong. A ferrule 26 may comprise a flange 30, the flange extending from and surrounding the ferrule 26 to facilitate attachment of the feedthrough 14 to an AIMD casing 32 (not shown) of the active implantable medical device 12 (also not shown). The flange 30 of the ferrule 26 illustrated in FIG. 3 is a capture flange, also known as an H-flange, which captures the AIMD casing halves 112, 114 (not shown) for subsequent joining. While FIG. 3 illustrates an H-flange, flange 30 may alternatively be an L-flange, an F-flange, an indent flange or a barrel flange. The method of attachment of the ferrule 26 comprising flange 30 to the AIMD casing 32 may be by laser welding, brazing, soldering or other suitable joining methods. The insulator 28 is of an insulative material such as a ceramic, glass or glass-ceramic, or combinations thereof. Suitable ceramic insulating materials may be selected from the group consisting of alumina, zirconia, zirconia toughened alumina, aluminum nitride, boron nitride, silicon carbide, or combinations thereof. Suitable biostable glass insulating materials may be selected from the group consisting of $SiO_2$, $Al_3O_3$, MgO, Cao, $Na_2O$, $B_2O_3$, SrO, or combinations thereof, and wherein the SiO content of the biostable glass is at least about 60%. Suitable biostable glass-ceramic insulating materials may be selected from the group consisting of alumina, zirconia, zirconia toughened alumina, aluminum nitride, boron nitride, silicon carbide, $SiO_2$, $Al_2O_3$, MgO, Cao, $Na_2O$, $B_2O_3$, SrO, or combinations thereof. In some embodiments, the insulating material is alumina, which is high purity aluminum oxide, and comprises an insulator sidewall 34 extending to a body fluid side insulator surface 36 (which may be a first or upper side) and a device side insulator surface 38 (which may be a second or lower side). The insulator 28 is also provided with insulator bores 40 that receive the terminal pins 18 passing therethrough. The insulator 28 comprises an insulator sidewall 34 and one or more insulator bores 40, the one or more insulator bores comprising an insulator bore sidewall 44. The insulator sidewall 34 and the insulator bore sidewalls 44 each comprise a layer of metal, defined herein as a metallization layer 42. It is understood that the metallization layer 42 may comprise one or more layers of metal. The metallization layers 42 on the insulator sidewall 34 and the insulator bore sidewalls 44 of the insulator 28 are applied so that during a brazing process, a first braze material 46a may form a hermetic seal between the ferrule 26 and the insulator sidewall 34 of the insulator 28, and a second braze material 46b may form a hermetic seal between the terminal pins 18 and the insulator bore sidewall 44 of the one or more insulator bores 40 of the insulator 28. Hermetic sealing of the terminal pins 18 to the insulator 28 and the insulator 28 to the ferrule 26 may be done in a single brazing process, wherein the braze material is of the same composition. Alternatively, the brazing process may a step-brazing process, wherein two different braze materials are used for each hermetic seal, wherein each braze material has a different melting temperature. In one embodiment, the braze materials 46a and 46b may be selected from the group consisting of gold, silver, gold alloys, silver alloys, or combinations thereof. Referring again to the metallization layer 42, is understood that the metallization layers 42 are intended to facilitate wetting of the braze materials 46a, 46b to the insulator sidewall 34 and the insulator bore sidewalls 44 respectively such that contact and metallurgical bonding of the insulator 28 with the ferrule 26 and with the terminal pins 18 establishes a hermetic seal each therebetween thereby forming the AIMD hermetically sealed feedthrough 14.

As further shown in FIG. 3, the filtered feedthrough assembly 22 includes the externally grounded feedthrough capacitor 24 that provides filtering of undesirable EMI signals before they can enter the AIMD casing 32 via the terminal pins 18. The externally grounded feedthrough capacitor 24 comprises a capacitor dielectric 48, the capacitor dielectric comprising a ceramic or a ceramic-based dielectric. The capacitor dielectric 48 of the externally grounded feedthrough capacitor 24 supports at least one active electrode plate 50 interleaved in a capacitive relationship with at least one ground electrode plate 52, and wherein the at least one active electrode plate 50 is conductively connected to the conductive pathway, which is, as illustrated in FIG. 3, terminal pins 18, and the at least one ground electrode plate 52 is conductively coupled to the ferrule 26. The capacitor dielectric 48 may be a monolithic ceramic, such as a multi-layer ceramic capacitor (MLCC), or may alternatively be stacked film, tantalum, or electrolytic capacitors. It is understood that the capacitor dielectric 48 may support a plurality of spaced-apart layers of active electrode plates 50 or first electrode plates in spaced relationship with a plurality of spaced apart layers of ground electrode plates 52 or second electrode plates. Additionally, the capacitor dielectric 48 may be shaped to match the shape of the ferrule 26, or may alternatively have an oval, round, square or rectangular shape that either differs from, approaches, or is essentially similar to the shape of the ferrule 26. The externally grounded feedthrough capacitor 24 may be attached to the AIMD hermetically sealed feedthrough 14 adjacent to the insulator 28 at the body fluid side insulator surface 36 by an electrical connection material 54, such as a thermal-setting conductive adhesive, a solder, and the like. As shown in FIG. 3, it is important that the electrical connection material 54 contact the braze material 46a, for example gold, so that an oxide-resistant attachment is made as taught in U.S. Pat. No. 6,765,779, the contents of which are fully incorporated herein by this reference. The capacitor dielectric 48 includes one or more capacitor dielectric bores 56, the one or more capacitor dielectric bores comprising a metallization layer 57 on an inner surface of each capacitor dielectric bore 56, each capacitor dielectric bore capable of receiving a terminal pin 18. Terminal pins 18 passing through the one or more capacitor dielectric bores 56 are electrically connected to the active electrode plates 50 of the externally grounded feedthrough capacitor 24 by an electrical connection material 58, such as a thermal-setting conductive adhesive, a solder and the like. The electrical connection material 58, electrically connects the terminal pin 18 and the metallization layer 57 residing on the inner surface of the capacitor dielectric bore 56.

Referring once again to the filtered feedthrough assembly 22 of FIG. 3, the externally grounded feedthrough capacitor 24 in this embodiment is disposed on the body fluid side. This is a different location compared to the internally grounded feedthrough capacitor 24' of FIG. 2, which is disposed on the device side. The advantage of having the feedthrough capacitor on the device side is that it is inside the hermetically sealed AIMD casing 32 and is therefore, not exposed to body fluid. It is noted that the hermetically sealed body of the AIMD is disclosed herein as a casing 32 instead of a housing, even though, as a general term of art, including in the prior art, the hermetically sealed body of the AIMD is generally disclosed as a housing. Nevertheless, for particular differentiation between an AIMD housing and a connector housing, the present application specifically and consistently discloses the hermetically sealed body of the AIMD as an AIMD casing 32, while the use of the term "housing" is particularly disclosed in relation to the terminal pin connector 16, more specifically, to the connector housing 66 of the terminal pin connector 16. Hence throughout this specification the hermetically sealed body of the AIMD is termed an AIMD casing 32 and the terminal pin connector body is termed connector housing 66. Regarding feedthrough capacitors, in the case of feedthrough capacitors residing on the body fluid side, of significance is that regular capacitor materials of construction are not compatible with body fluid, hence, when in contact with body fluid, its electronic component would rapidly short out. As such, the feedthrough capacitor of FIG. 3 is a specially designed feedthrough capacitor specifically configured to be biocompatible, non-toxic and biostable in the presence of body fluids. One is referred to U.S. Pat. No. 6,985,347, which describes an EMI filter capacitor assembly that utilizes biocompatible and non-migratable materials to adapt electronic components for direct body fluid exposure, the contents of which are fully incorporated herein by this reference.

Referring again to FIG. 3, an exemplary electrical schematic is shown. Represented are two terminal pins 18, which suggests a bipolar capacitor, meaning there are two active terminal pins 18 passing through the capacitor dielectric bore 56 of the externally grounded feedthrough capacitor 24. As the structure shown with the electrical schematic of FIG. 3 is only a cross-sectional view illustrating a single plane of the three-dimensional body illustrated, it is understood that the externally grounded feedthrough capacitor 24 could alternatively be a quad polar capacitor or a long rectangular capacitor comprising more than four terminal pins 18 (or even n number of pins). Hence, it is understood that there could be many other capacitor designs other than just the two terminal pins shown in the exemplary electrical schematic. This exemplary electrical schematic represents two feedthrough capacitors C1 and C2, which are both disposed such that they are connected to the ferrule 26 and, in turn, to the AIMD casing 32 (not shown). Feedthrough capacitors C1 and C2 act as filters or high frequency diverters, which prevent electromagnetic interference (EMI) originating from the body fluid side (the EMI can undesirably couple to implanted leads or AIMD header block wiring) thereby, protecting such dangerous electromagnetic interference from entering into the device side of the AIMD 12 where the EMI could interfere with a sensitive AIMD active electronic circuit board 106. Feedthrough capacitors are known in the industry as three-terminal devices and because they have extremely low inductance, they provide very broadband filtering up to frequencies of 3 GHZ-10 GHz (and even above 10 GHz). Other three-terminal capacitors will be described later in the present application, including flat-thru capacitors and some X2Y attenuator designs. Two-terminal capacitors will also be described, including MLCCs and some X2Y attenuator designs. It is noted that two-terminal capacitors typically do not offer filtering at extremely high frequencies, however, when carefully designed, two-terminal capacitors can be effectively used in AIMDs. It is understood by one skilled in the art that electromagnetic interference could confuse the AIMD and create various life-threatening situations. This is extremely dangerous for cardiac pacemaker dependent patients who rely on pacemakers to keep their hearts beating. If the cardiac pacemaker becomes confused, it could stop stimulating the heart and the patient would die.

Figure 3A:
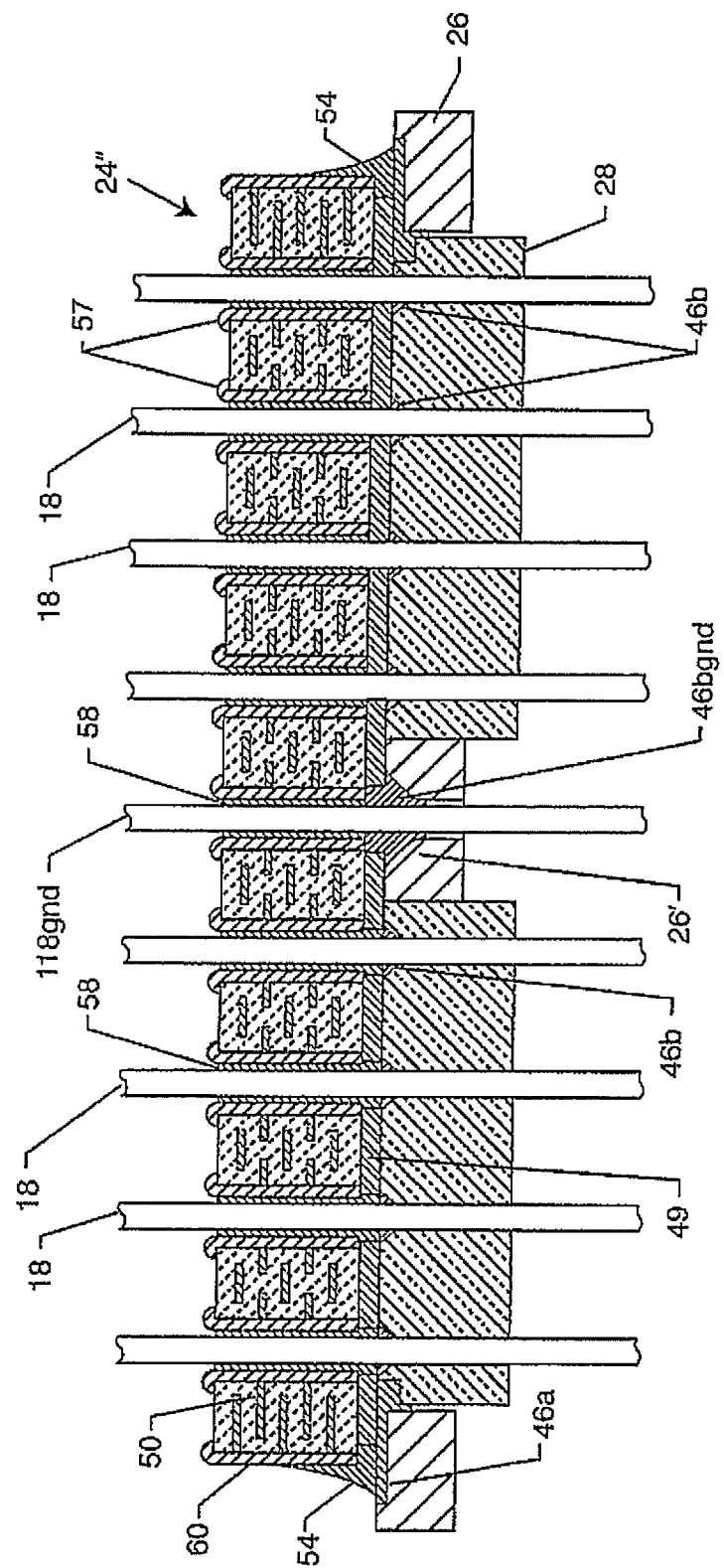
FIG. 3A shows a cross-sectional view of an alternative embodiment of the AIMD feedthrough connector assembly.

FIG. 3A is very similar to FIG. 3, except that the feedthrough capacitor of the embodiment of FIG. 3A is a hybrid capacitor 24", meaning that it has both an external ground path, which, as shown is only one external ground path example, that comprises exemplary elements 60, 54, 46a and 26 (and 32 not shown), and an internal ground path, which, as shown is only one internal ground path example, that comprises exemplary elements 26, 18gnd, 58, and 57. It is contemplated that the terminal pin connectors 16 of FIG. 3 are not shown in FIG. 3A, however understood that the terminal pin connectors 16 can be disposed on either the device side or the body fluid side of the AIMD 12. It is also noted in FIG. 3A that the body fluid side and the device side of the AIMD 12 are not labeled, as it is also understood that the capacitor, if it is a biocompatible capacitor, could also be disposed on either the body fluid side or the device side of the AIMD. In an embodiment, the terminal pin connectors 16 could be disposed on the side of FIG. 3A towards the AIMD active electronic circuit board 106 (in other words, the device side). FIG. 3A is taken from FIG. 42 of U.S. Pat. No. 6,765,780, the contents of which are fully incorporated herein by this reference.

As shown in FIGS. 1, 2, 3, 3B, 3C, 7A, 7B, 8, 9, 12, 15, 16 and 17, the terminal pin connector 16 of the present invention attaches to at least one terminal pin 18 of the AIMD hermetically sealed feedthrough 14. The terminal pin connector 16 may also be attached to the terminal pin 18 of an unfiltered AIMD hermetically sealed feedthrough 14 as shown in FIG. 1 or to a terminal pin 18 of the externally grounded feedthrough filter capacitor 22, as illustrated in FIG. 2. More specifically, the terminal pin connector 16 is attached to a terminal pin distal end 62. For identification purposes, the terminal pin distal end 62 is defined as the portion of the terminal pin 18 inside the AIMD casing 32 of the active implantable medical device (AIMD) 12.

Figure 4:
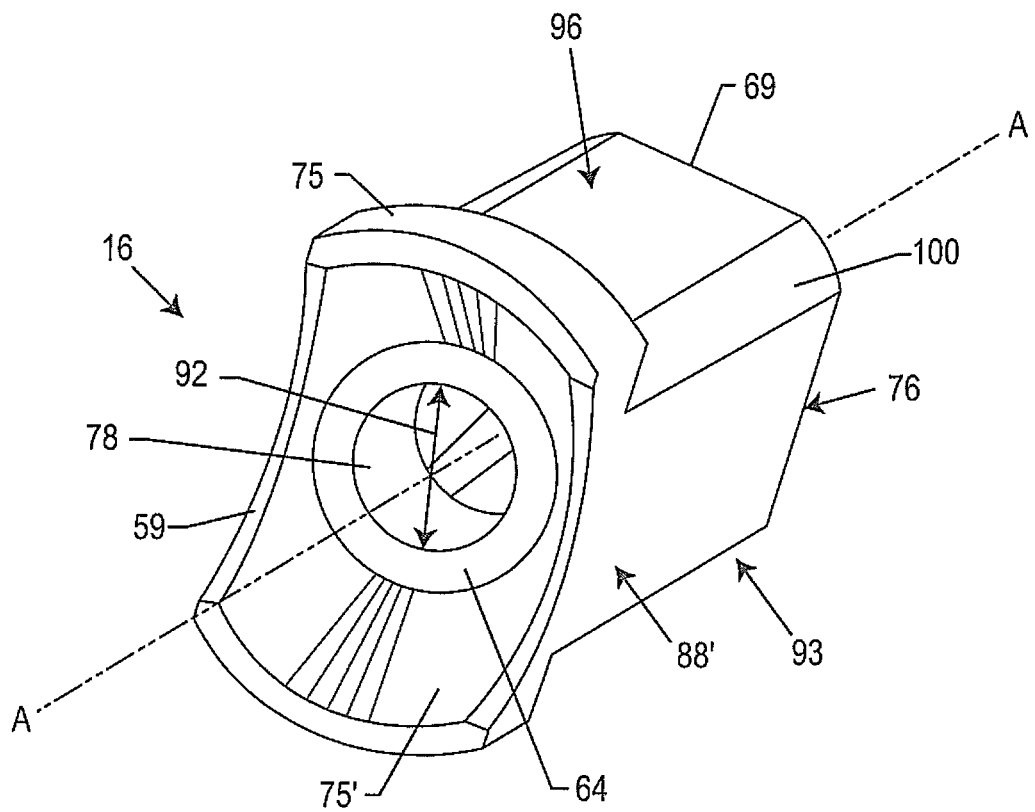
FIG. 4 shows a perspective view of an embodiment of the terminal pin connector.
Figure 7A:
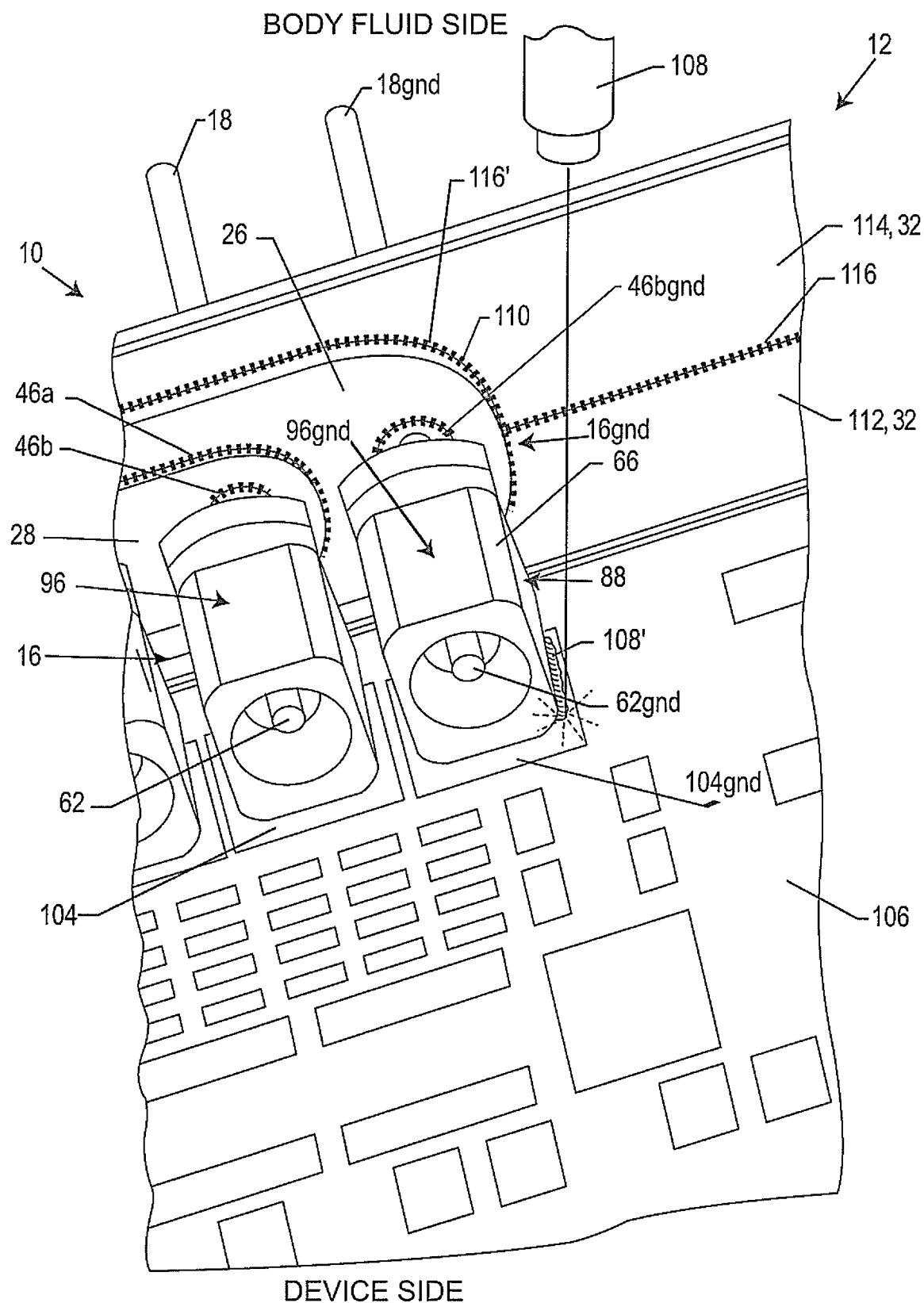
FIG. 7A illustrates an embodiment of the terminal pin connector attached to an electrical connection pad of an AIMD active electronic circuit board.

FIGS. 4, 4A-4C and 5A-5E illustrate embodiments of the present invention. In these embodiments, the shape of the connector housing 66 of the terminal pin connector 16 may comprise a square or rectangular shape, the connector housing 66 thereby having at least two flat surfaces, which are shown as an exterior sidewall comprising a planar surface 88' and a planar surface 96 in the connector housing 66 of at least FIG. 4 (note: the connector housing 66 can also have a round shape as shown in FIG. 7C, or an oval or hexagonal shape, not shown). The terminal pin connector 16 includes an alignment feature 75', the alignment feature of the embodiment of FIG. 4 comprising an inwardly tapering surface, which helps to guide an off-center terminal pin 18' to the center bore diameter 92. As used herein, the term "alignment feature" is defined as an outwardly projecting and/or outwardly protruding flange, edge, rim, collar, or rib on a structure serving to locate, register, guide and/or align a first object for attaching, connecting, or mating to a second object. The alignment feature may either be a continuous, a discontinuous, or a partial projection or protrusion around the circumference or the perimeter of a connector housing 66. The connector housing 66 of FIG. 4 is particularly designed having a square or rectangular shape to intentionally narrow down and/or restrict the width of the terminal pin connectors 16 so that they can be aligned closely together on an AIMD active electronic circuit board 106 (not shown) with very close spacing (otherwise known as close pitched). This is very important particularly for high density or high-count conductor pathway or terminal pin 18' assemblies, which necessitate close pitch spacing requirements (one example of an AIMD 12 having high density or high-count conductive pathways would be spinal cord neurostimulators, which generally have more than 24 terminal pins 18'). As defined herein, a square or a rectangular connector housing 66 comprises at least two flat surfaces (similar to or such as the exemplary exterior planar surfaces 88' and 93' of FIG. 4) for close placement when multiple terminal pin connectors 16 are required in a limited space (known as close pitch), and wherein each terminal pin connector 16 is capable of attachment to at least one circuit board electrical connection pad 104 either being directly physically and electrically connected, or electrically connected by an electrical connection material 107.

As used herein, the term "electrical connection pad" is herein defined as a small surface of metal, such as copper or other suitable electrically conductive material, on or within a circuit board or alternatively somewhere on the perimeter edge of the thickness of a printed circuit board that allows attaching a component to the circuit board. An electrical connection pad 104 may comprise a circuit board land (as shown in FIG. 7A), be part of a circuit trace (as shown in FIG. 7C) or be part of the perimeter edge of the thickness of a circuit board (such as, for example, where the electrical connection pad 104 of FIG. 9B resides on the perimeter edge of the thickness of the circuit board (not shown) instead of on the surface of the circuit board as shown. The edge metallization 500 shown in FIG. 27A has either an electrical connection pad 104 as part of the metallization structure, or the edge metallization may be discontinuous to form an electrical connection pad 104, or, instead of an edge metallization 500, the perimeter edge may comprise an electrical connection pad 104 (a perimeter edge comprising an electrical connection pad 104 does not necessarily require an edge metallization 500).

As shown in FIG. 4, the alignment feature 75, which is shown as a discontinuous flange projecting from each one of the pair of the housing planar surfaces 96 of the connector housing 66, allows for the alignment feature 75 of the terminal pin connector 16 to be positioned such that either one or the other of the two discontinuous flanges overhanging the AIMD active electronic circuit board 106 (not shown) places its associated housing planar surface 96 directly against (and in electrical connection to) the circuit board electrical connection pad 104. The housing planar surface 96 of the connector housing 66 of the terminal pin connector 16 can be directly physically connected to the circuit board electrical connection pad 104 by an electrical connection material 107. The central axis A-A of the clip through-bore 72 and the connector housing through-bore 78 of the terminal pin connector 16 as illustrated in FIG. 4 is the axis along which the terminal pin 18' will be inserted.

As illustrated in FIGS. 3, 3B, 3C, 3D, 4, 4A-4C, 5A-5E, and 6A-6C, the terminal pin connector 16 comprises a clip 64 that resides within a connector housing 66. The clip 64 is designed to accept terminal pin 18 so that, when the terminal pin 18' is inserted into the terminal pin connector 16, the clip 64 surrounds the circumference or perimeter of the terminal pin 18' such that the clip 64 grasps the exterior surface of the terminal pin 18 by at least one prong 70. In the embodiment shown in FIGS. 4, 4A-4C and 5A-5E, the clip 64 comprises a clip base 68 and a plurality of prongs 70 that extend from the clip base 68. Clip 64 may comprise a single construction, the clip further comprising a single material, as indicated in the cross-sectional view of FIG. 6B (clip 64 is shown having the same cross-hatch for the clip base 68 and the prong 70).

Alternatively, the clip 64 may comprise multiple components, and multiple materials, for example, the clip base 68 may be one component and one or more prong 70 each may be a different component, wherein the clip base 68, and the one or more prongs 70 are each of a different material. As shown, the clip base 68 comprises a clip sidewall 72, which, in this case, is annular. The exemplary annular clip sidewall 72 comprises a clip through-bore 74. This clip through-bore 74 is the opening that accepts the terminal pin 18' such that terminal pin 18' longitudinally extends and is grasped by prong (s) 70 of the clip 64. The clip through-bore 74 is dimensioned such that the terminal pin 18 of a multitude of diameters can pass therethrough with an interference fit making electrical contact between the terminal pin 18 and the clip 64.

Referring once again to prong 70, shown in FIGS. 4A-4C, is that the clip 64 comprises at least one prong 70 or finger that extends from the clip base 68. As shown, the prongs 70 are preferably angled inwardly towards a central (longitudinal) axis A-A that extends longitudinally through/along the clip through-bore 74 of the clip base 68. This inward orientation enables the prongs 70 to flex and make contact to compress against the exterior surface of the perimeter of the terminal pin 18' gripping the terminal pin 18' therewithin.

In addition, the inward orientation of the prongs 70 creates a wedging relationship between the terminal pin 18 and prongs 70. As the end of the prongs 70 compress against the sidewall of the terminal pin 18', the pin 18' becomes wedged against the prongs 70. The wedging of the prong 70 against the terminal pin 18 importantly assures that a very low resistance electrical connection will be achieved. It is very important that a reliable and very low resistance connection be achieved from the circuit board to the connector housing 66 to the clip 64 and in turn, to the prong 70 and to the terminal pin 18. This path is highly conductive both at DC and at RF frequencies. Such a wedging relationship helps prevent the terminal pin 18' from inadvertently disengaging with the clip 64. However, in the embodiments shown in FIGS. 4-6 the terminal pins 18' can be removed from the clip 64, when necessary, such that the terminal pins 18 can be inserted and removed from the clip 64, for example, when AIMD active electronic circuit board 106 replacement is deemed necessary.

Regarding the clip 64 and terminal pins 18 of FIGS. 4A through 6C, a terminal pin (s) 18' can freely slide longitudinally within the prong (s) 70 along axis A-A without disengaging from the terminal pin connector (s) 16 even though the terminal pin (s) 18' is gripped tightly by the prong (s) 70. This is extremely important, especially during final laser welding of the AIMD casing 32 of the active implantable medical device 12, because once the AIMD feedthrough connector assembly 10 is installed to a first casing half 112, and the AIMD active electronic circuit board 106 is plugged in using the terminal pin connector (s) 16 residing on the circuit board, a final laser weld is performed to complete a hermetic enclosure (that is, the AIMD casing 12), which now comprises the AIMD feedthrough connector assembly 10 and the two AIMD can halves (that is, the first casing half 112 and the second casing half 114). The final laser weld introduces heat, which can create significant stress in an assembly, a subassembly, or between components that are not free to move, due to differences in the coefficient of linear thermal expansion (CTE), a material property of each component of the AIMD 12. Since CTE is a material property, different materials will expand on heating at different rates, depending on a material's composition, structure, and thermal properties. When CTE mismatch exists, for example, between the AIMD active electronic circuit board 106, the circuit board holding fixture and the AIMD casing halves 112, 114, there is a higher potential for developing fractures, cracks, delamination, and detachment within an assembly. In the exemplary case of final laser welding, as the AIMD casing 32 expands and contracts, the terminal pin (s) 18' are capable of sliding within the prong (s) 70 without disengaging from the terminal pin connector (s) 16, thereby preventing the buildup of stresses at this connection. This is of particular benefit, in that, when terminal pin (s) 18' are welded or soldered to an AIMD component or subassembly, such as an AIMD active electronic circuit board 106, an EMI filter board 106', an AIMD header block 118, or combinations thereof, the weld or solder joint could lead to fracture, cracking, delamination or detachment resulting in failure and rejection of the final laser welded AIMD assembly, along with all the subassemblies and components that are now hermetically sealed within the AIMD casing 32.

Further referring to clip 64, as a terminal pin 18 is introduced through the clip base 68 of the clip 64, the space between the prong (s) 70 expands to thereby allow the terminal pin 18 to proceed therebetween. In the embodiment shown in FIG. 3, the prongs 70 of the clip 64 are designed to allow the terminal pin 18 to proceed in one direction between the prong ends such that the terminal pin 18 is prohibited from moving in the reverse direction. In these embodiments, the terminal pin 18 proceeds in a distal direction through the clip through-bore 74 residing within the connector housing 66 of the clip 64. Once positioned within the clip through-bore 74, the angled prong orientation grips terminal pin 18 and inhibits or prevents the terminal pin from markedly moving in the reverse proximal direction mitigating disengagement from the terminal pin connector 16.

Figure 3B:
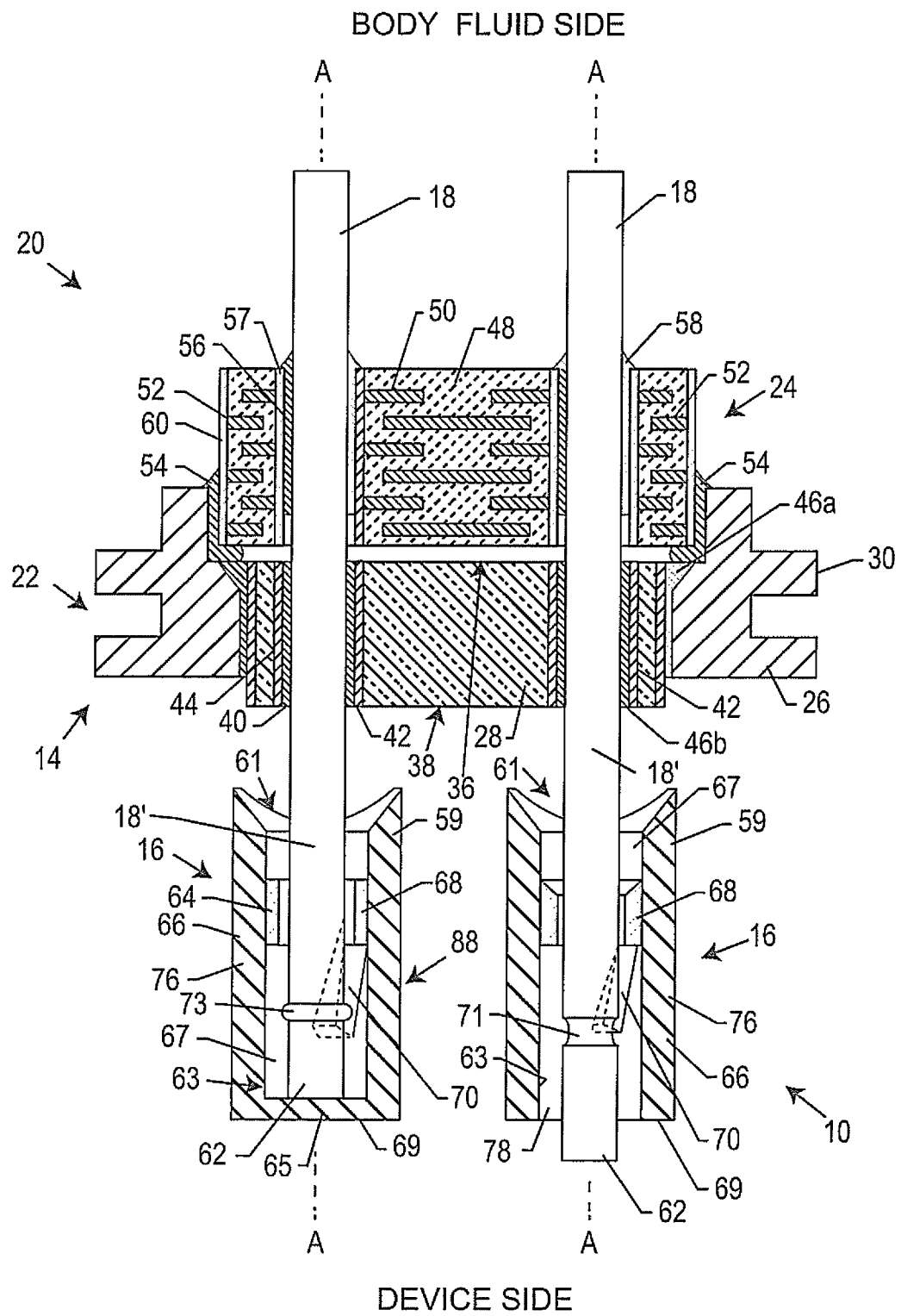
FIG. 3B shows a cross-sectional view of an alternative embodiment of the AIMD feedthrough connector.

FIG. 3B illustrates an alternative embodiment of clip 64 and connector housing 66 of terminal pin connector 16 of the present invention. As shown, at least one prong 70 extends from the base 68 of the clip 64. In addition, the connector housing 66 comprises a housing opening 67 that at least partially extends through the thickness of the connector housing 66 from a first connector housing end 59 towards a second connector housing end 69. On the right-hand side of FIG. 3B, the housing opening 67 has a first diameter that extends through the first connector housing end 59. On the left-hand side of FIG. 3B, the housing opening 67 extends axially along longitudinal axis A-A through at least a portion of the connector housing thickness to a connector housing end wall 65 located at the second connector housing end 69, thereby forming a blind hole within the connector housing 66. As defined herein a "blind hole" is a hole that is formed, such as by reaming, drilling, or milling, to a specified depth without breaking through a connector housing end wall 65 of the workpiece. Accordingly, the terminal pin distal end 62 is at least partially positioned within the housing opening 67 of the blind hole shown, thereby positioning the terminal pin 18 such that a length of terminal pin 18 extends along longitudinal axis A-A. The terminal pin distal end 62 when inserted into the blind hole housing opening 67 further positions terminal pin 18 proximate a connector housing interior surface 63 such that the terminal pin distal end 62 may be optionally bottomed out (or contacting) the connector housing end wall 65. Referring once again to the left-hand side of FIG. 3B, one can see that when terminal pin 18' is bottomed out against the connector housing end wall 65 of the blind hole, the terminal pin 18' cannot be inserted any further into the terminal pin connector 16. Consequently, in the embodiment shown on the left-hand side of FIG. 3B, the terminal pin distal end 62 cannot extend past the blind hole because the connector end wall 65 stops any further insertion movement. Hence, the blind hole on the left-hand side of FIG. 3B is an important feature in that the prong 70 cannot fully slide over the rim of the terminal pin ridge 73, which could thereby challenge or otherwise inhibit removal or replacement of a defective circuit board. The terminal pin ridge 73 also advantageously imparts added deflection of prong 70, which enhances grip thereby ensuring a high reliability, low resistance, low impedance, and a removable electrical connection. Now referring to the right-hand side, FIG. 3B illustrates prong 70 engaging the terminal pin recess 71. The transition corner from the diameter of terminal pin 18' to the terminal pin recess 71 is curved and radiused to facilitate terminal pin 18' removability from clip 64 even though terminal pin 18 may extend through and optionally outwardly beyond the connector housing through-bore 78 of the connector housing 66. The curved and radiused portion of the terminal pin recess 71 provides a smooth surface on which terminal pin 18 can slide in and out of clip 64 when a push or a pull force is applied. Hence, the connector housing end wall 65, which forms a blind hole on the left-hand side of FIG. 3B in the connector housing 66, is not important or even necessary, and therefore may only optionally be included. Referring back to the right-hand side of FIG. 3B, the embodiment illustrated lacks the connector housing end wall 65 shown in the left-hand side of FIG. 3, and instead comprises the connector housing through-bore 78. In this case, the terminal pin distal end 62 optionally protrudes outwardly beyond the terminal pin connector 16. This can be an important feature during final visual inspection of the assembled AIMD active electronic circuit board 106 and AIMD hermetically sealed feedthrough 14 as the protruding terminal pin distal end 62 provides a visual indicator to making sure that all of the terminal pins 18' are fully inserted into their respective terminal pin connectors 16.

In addition, at least one prong 70 is shown extending distally from the annular clip sidewall 72. The end of the at least one prong 70 contacts a portion of an exterior surface of the terminal pin 18' along the terminal pin distal end 62 that resides within the housing opening 67. The prong 70 is angled inwardly towards the central axis A-A that extends longitudinally through the clip through-bore 74 of the base 68 and into the blind hole of the housing opening 67. As previously mentioned, this inward orientation enables the prong 70 to contact and compress against the exterior surface of the perimeter of the terminal pin 18' gripping the terminal pin 18 therewithin. Furthermore, the prong 70 creates a wedging relationship between the exterior surface of the terminal pin 18 and the annular clip sidewall 72.

In some embodiments, a terminal pin recess 71 as shown on the right-hand side of FIG. 3B, may partially extend within an exterior surface of terminal pin 18 about the terminal pin distal end 62 thereof. The terminal pin recess 71 of FIG. 3B is shown positioned such that the recess annularly extends around the circumference (the exterior surface) of the terminal pin distal end 62 of terminal pin 18'. The terminal pin recess 71 may enhance the grip of the prong 70 along the terminal pin's exterior surface as the terminal pin recess 71 provides a groove within the exterior pin surface so that the end of the prong 70 can be positioned therewithin.

Alternatively, in lieu of the terminal pin recess 71, an outwardly extending terminal pin ridge 73 may be at least partially constructed about the terminal pin distal end 62 of the terminal pin 18'. Referring once again to features 71 and 73 of FIG. 3B, the terminal pin recess and the terminal pin ridge are desirably radiused such that a defective circuit board with applied pull force, could still be removed from the terminal pins 18' such that a replacement or reworked circuit board can be installed. As shown on the left-hand side of FIG. 3B, the terminal pin ridge 73 may be positioned annularly extending around the circumference (the exterior surface) of the terminal pin distal end 62 of terminal pin 18 similarly to the terminal pin recess 71. Also, similarly to the recess 71, the terminal pin ridge 73 helps prevent inadvertent disengagement of the prong (s) 70 of the clip 64 from the terminal pin 18'. When the terminal pin 18' is positioned within the connector housing 66, the terminal pin ridge 73 is positioned proximal the end of prong 70.

Referring once again to FIG. 3B, on the left-hand side, one will see that the ring has curved and radiused surfaces (convex shaped). Referring to the right-hand side, one will see that the angular notch is also curved and radiused (concave shaped). This is to allow the terminal pin 18' to be retracted when a pull force is applied. The curves are designed such that the prong 70, will still slip over or into the concave or convex shapes respectively even when the concave or convex shapes induces resistance to such movement. It is contemplated that, for example, on the right-hand side of FIG. 3B, the notch could be a rectangular notch instead of the concave shaped curved notch, as shown. In the case where the notch is rectangular, the resistance to pull may be increased such that a tool may be required for disengaging and retracting the terminal pin 18' from the terminal pin connector 16. In this case, it would be grip-tight, but still optionally be removable with the help of a tool.

Referring once again to FIG. 3B, on the left-hand side, one can see that the prong 70 overlies the terminal pin ridge 73. Importantly, the terminal pin distal end 62 of the terminal pin 18' inserted into the terminal pin connector 16, which extends fully through the feedthrough capacitor connector assembly 20 including the filtered feedthrough assembly 22, is designed such that the terminal pin distal end 62 bottoms out at the connector housing interior surface 63 of the blind hole of the connector housing 66. This feature is very important because that means that the prong 70 is pushed against the outside radius of terminal pin ridge 73. This has two very important results. The first result is that the terminal pin ridge 73, as it is shown positioned, facilitates retraction of a circuit board (such as an AIMD active electronic circuit board 106 or an EMI filter circuit board 106' not shown). As described throughout the specification, the connector housing 66 is designed to be mechanically and electrically attached to a circuit board land or a circuit trace of an AIMD active electronic circuit board 106 or an EMI filter circuit board 106' (not shown). Once the AIMD active electronic circuit board 106 or the EMI filter circuit board 106' is installed and the flange 30 of the ferrule 26 is laser welded into the AIMD casing 32, longitudinal movement of terminal pin 18' is restricted. So, it is really only during circuit board installation and removal that the terminal pin 18 slides in and out of the connector housing 66 comprising clip 64 and its associated prong (s) 70. As such, the curved and radiused feature of both the left-hand and the right-hand sides of FIG. 3B positions the prong (s) 70 such that the AIMD active electronic circuit board 106 is removable thereby allowing replacement or rework and re-installation of the circuit board in the case the circuit board is deemed defective. Optionally, not shown, a secondary tool could be used to assist release of prong (s) 70 from the terminal pin (s) 18 thereby facilitating removal of the AIMD active electronic circuit board 106 for replacement or rework and re-installation.

Referring to U.S. Pat. No. 9,692,173, one will see that FIG. 3B of the present specification is identical to FIG. 3 of the '173 patent, which is in the present priority chain and is further incorporated herein by this reference. One will see that the terminal pin connector 16 has one or more prongs 70 that engage terminal pin 18. In this case, terminal pin 18 has been specially formed or machined. This provides movement resistance to terminal pin 18' when prongs 70 engages terminal pin 18, thereby forming a grip-tight relationship between the prongs 70 and the machined feature in terminal pin 18. This is to help prevent inadvertent movement of the terminal pin 18 along the longitudinal axis A-A out from within the connector opening 67, while still allowing for terminal pin 18 removability.

Referring once again to FIGS. 3, 3B and 3C, as these are cross-sections, the characteristics of the clip through-bore 74 only illustrates a single plane of the through-bore, hence, to better appreciate the features and functionality of the clip through-bore 74, one is referred to FIGS. 4A through 4C and FIGS. 5A through 5C.

In any of the embodiments herein, the clip 64 or connector housing 66 may comprise an electrically conductive material, such as an electrically conductive metal. For example, the clip 64 may comprise copper, tin, iron, steel, stainless steel, aluminum, titanium, gold, silver, platinum, palladium, rhodium, brass, molybdenum, tungsten, niobium, and alloys and/or combinations thereof; constantan, beryllium copper, beryllium nickel, Nitinol, aluminum alloys, titanium alloys, gold alloys, silver alloys, platinum alloys, palladium alloys, copper alloys, tin alloys, rhodium alloys, niobium alloys, nickel-chromium alloys, associated alloys and combinations thereof; electrically conductive carbons, including the 'super' carbon developed by the international collaboration between Yanshan University and the Carnegie Institution of Science, the 'super' carbon being hard, elastic like rubber, ultra strong, lightweight and electrically conductive; and electrically conductive composites, the electrically conductive composites being made from two or more constituent materials that have different physical and chemical properties, such that, when combined, produce a composite material with characteristics different from the individual components, and which can be customized to specifically address, for example, degree of electrical conductivity, thermal management, electrical and/or magnetic field management, electromagnetic interference (EMI) mitigation, noise susceptibility shielding, weight, cost, and other such material property requirements. Any of these materials may be used alone or in combination with each other. Clip 64 may also comprise a plating, wherein the plating may further comprise electroplating, electrodeposition, electroless plating, barrel plating, or mechanical plating. The plating may be provided to increase strength and durability, allow solderability if needed, improve electrical conductivity, increase surface hardness, provide wear resistance, impart anti-galling properties, afford antifriction properties, offer insertion/retraction lubricity, or increase friction to impart resistance to movement or to enhance grip, or permit property customization of clip 64 to address a specific requirement of an implantable medical application. The plating may comprise gold, silver, palladium, rhodium, platinum, titanium, aluminum magnesium, tin, copper, zinc, nickel, chrome, stainless steel, bronze and combinations thereof. The plating may further comprise palladium/nickel, palladium/cobalt, tin/lead, zinc/nickel, zinc/cobalt, alloy plating, composite plating, or combinations thereof. Additionally, clip 64 may comprise a gold flash over any plated material, for example, steel with a tin plating, nickel plated steel, aluminum with electroless nickel plating, beryllium copper with gold over copper plating, brass with a tin plating, brass with gold over a copper plating, copper alloy with gold over copper plating, phosphor bronze with gold over copper plating, zinc plating with a chromate seal, zinc plating with a tin plating, passivated stainless steel and combinations thereof.

In preferred embodiments of the present application, it would be desirable if the connector components, including the connector assemblies, prongs, fingers, tines, clips and the like, consist primarily of non-ferromagnetic materials, so that patients having AIMD implants can undergo magnetic resonance imaging (MRI) when indicated. For example, it is now possible to obtain pacemakers, implantable cardioverter defibrillators, and even neurostimulators that have been "MRI Conditionally Approved" by the FDA. In an MRI environment, when AIMDs comprise components having a lot of magnetic and/or ferromagnetic material, the presence of such magnetic and/or electromagnetic materials can be problematic for a number of reasons. These include: 1) increased force and torque on the AIMD due to the static magnetic field of the MRI; 2) increased image artifact in the immediate area of the AIMD caused by the interaction of the MRI fields with the ferromagnetic materials and dipole movements; and 3) during RF field exposure from MRI, components that have high magnetic and/or ferromagnetic materials can exhibit undesirable heating through dipole flipping. Therefore, non-magnetic and/or non-ferromagnetic materials are excellent options for addressing these issues. As used herein, magnetic materials or ferro-magnetic materials mean any materials that are attracted to a magnetic force or highly saturate in the presence of a magnetic field. Non-magnetic or non-ferromagnetic refers to those materials which are either not attracted or only weakly attracted to a magnetic force, and which either do not or minimally saturate in the presence of a magnetic field. Nonlimiting examples of non-ferromagnetic materials include: aluminum, beryllium, copper, gold, lead, platinum, rhodium, silver, tin, titanium, zinc, and alloys or combinations thereof. Also included are brass, bronze, 304 stainless steel, 316 stainless steel and the like. Any of these materials can also be used to coat, plate, or otherwise cover any of the listed materials above.

Alternatively, the clip 64 may have an electrically conductive coating, such as an electrically conductive foil, metallization, plating or a vapor deposited film. Coating processes may include: physical vapor deposition, chemical vapor deposition, electrostatic spray assisted vapor deposition (ESAVD), electron beam physical vapor deposition (EBPVD), ion plating, ion beam assisted deposition (IBAD), magnetron sputtering, pulsed laser deposition, sputter deposition, vacuum deposition, pulsed electron deposition (PED), plating, electroless plating, electroplating, spraying, painting, plasma spraying, thermal spraying, spin coating, dip coating, metal foil lamination, and thin film deposited layers. The electrically conductive coating may comprise one or more layers. The electrically conductive coating may comprise, but not limited to, copper, tin, stainless steel, aluminum, titanium, gold, platinum, palladium, carbon, palladium alloys, associated alloys, and combinations thereof. The clip 64 (base 68 and prong (s) 70) is designed to provide an electrical connection between the terminal pin 18' of the AIMD hermetically sealed feedthrough 14 and the connector housing 66.

Figure 3C:
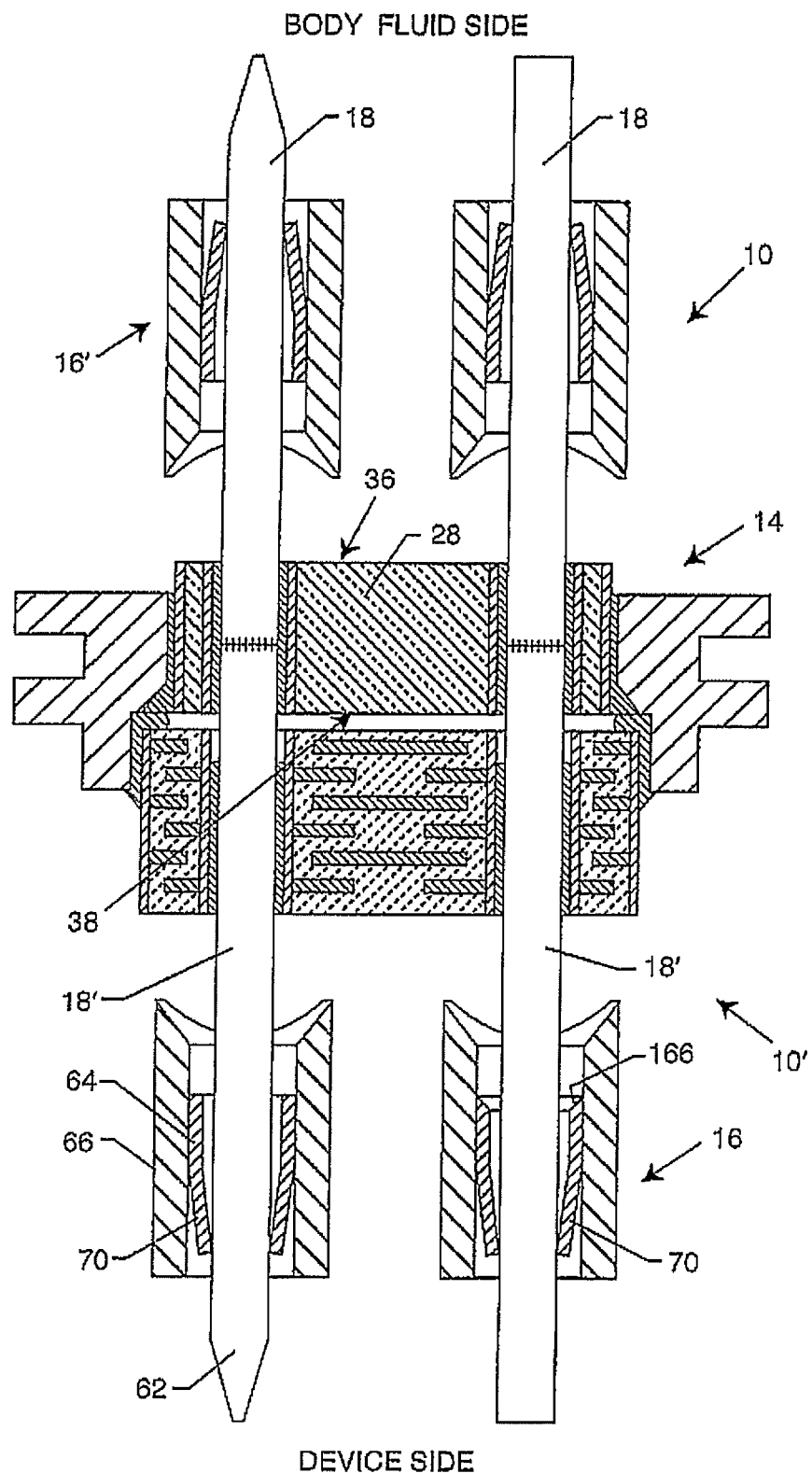
FIG. 3C shows a cross-sectional view of an alternative embodiment of the AIMD feedthrough connector.
Figure 3D:
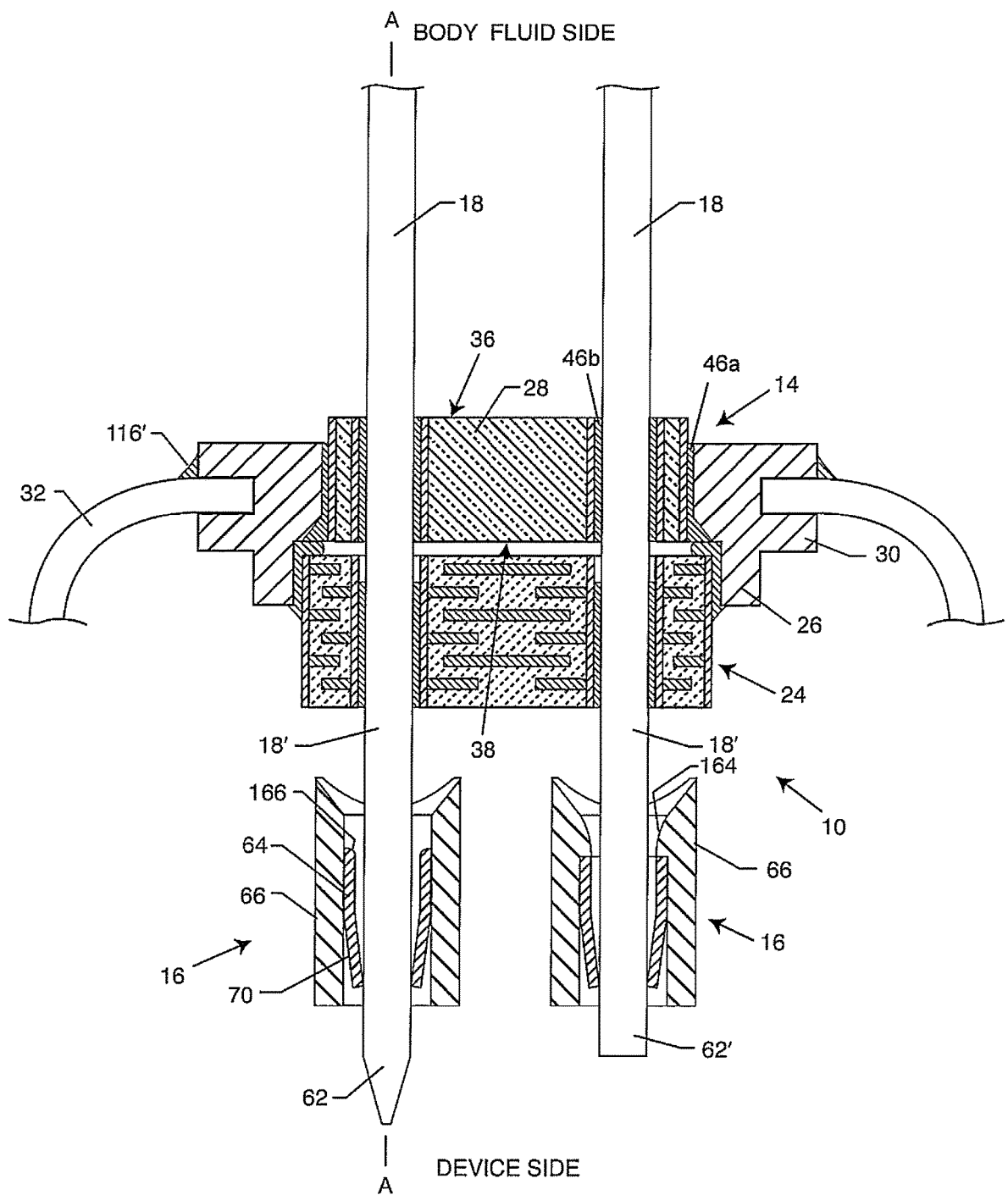
FIG. 3D shows a cross-sectional view of an alternative embodiment of the AIMD feedthrough connector assembly.

Referring now to FIG. 3D, shown are embodiments of the terminal pin connector 16 of the present invention disposed on the terminal pin distal ends 62, 62' of the terminal pin 18' on the device side. As previously disclosed, the terminal pin connectors 16 would be mounted and electrically attached to AIMD active electronic circuit board lands or circuit traces. Mounting of terminal pin connectors 16 to circuit board lands or circuit traces is more thoroughly disclosed in FIGS. 7A, 7B, 8 and 9. Referring once again to FIG. 3D, illustrated is an AIMD hermetically sealed feedthrough 14 to which an externally grounded feedthrough capacitor 24 is mounted, thereby forming a filter feedthrough. The purpose of feedthrough capacitors is to decouple or divert dangerous electromagnetic interference (EMI) signals that may be picked up on the body fluid side of the AIMD 12 by the implanted leads connected to the header block of the AIMD. The terminal pin connectors 16 of the present application, which are located and mounted on an AIMD active electronic circuit board (not shown), are disposed such that the terminal pins 18 of the filter feedthrough are capable of literally plugging into their respective terminal pin connectors 16 so that the terminal pin connectors 16 are adjacent the feedthrough capacitor 24.

Referring once again to FIG. 3D, illustrated is a laser weld 116' that connects the flange 30 of the ferrule 26 to the AIMD casing 32, which is generally of titanium. During AIMD pulse generator assembly, a tack weld, as opposed to a continuous laser weld, is made to hold the ferrule into an AIMD first casing half or clam shell. After AIMD active electronic circuit board testing and acceptance, then an AIMD second casing half is mated to the first casing half and a continuous laser weld is made all around the can halves and around the flange 30 of the ferrule 26, thereby, completely hermetically sealing the AIMD electronics battery and associated components within the AIMD casing 32.

Referring once again to FIG. 3D, illustrated embodiments of the two terminal pins 18, both of which are hermetically sealed to the insulator 28. The ferrule 26 is also hermetically sealed to the insulator 28. The terminal pins 18 pass through the insulator 28 in non-conductive relation with the ferrule. A ground pin 18$gnd$ (not shown) may also optionally be electrically and mechanically connected to the ferrule. Referring now to the terminal pin distal ends 62, 62', illustrated on the left-hand side is an embodiment of a terminal pin distal end 62 that is pointed [which may alternately be rounded (not shown)] thereby, facilitating insertion into the terminal pin connector 16. On the right-hand side, illustrated is an embodiment of a terminal pin distal end 62' that is flat, in other words, squared off [the corners of which may alternately be radiused (not shown) to eliminate sharp corners]. Either of these two terminal pin distal end embodiments will facilitate insertion of the terminal pins 18.

FIG. 3D also illustrates two terminal pin connector 16 embodiments. The embodiment on the right-hand side of FIG. 3D illustrates an entry portion of the through-bore of the connector housing 66 comprising a smooth transition 164 to help guide the flat terminal pin distal end 62' into the terminal pin connector 16. It is possible that, for the unique application of an active implantable medical device, in order to plug in an AIMD active electronic circuit board (not shown), the circuit board may be tilted at a slight angle relative to the terminal pins 18 of the hermetically sealed feedthrough 14. Therefore, the smooth transition 164 of the terminal pin connector 16 shown on the right-hand side of FIG. 3D is a configuration for effectively guiding the terminal pin 18 when the terminal pin is not perfectly parallel to and/or coaxially aligned with the connector housing 66 so that the terminal pin 18 can be securely gripped within the prongs 70 of the clip 64.

The embodiment on the left-hand side of FIG. 3D illustrates a connector housing 66 comprising a chambered entry portion in a clip 64 residing within the connector housing 66 wherein the entry portion of the through-bore of the clip 64 comprises a radiused edge 166. Accordingly, this embodiment is an alternate configuration for effectively guiding the terminal pin 18 into the clip 64 so that the terminal pin 18 can be securely gripped with the prongs of the clip 64. In this embodiment, a pointed (or rounded) terminal pin distal end 62 would work in concert with the radiused edge 166 of the clip 64 in facilitating insertion of an off-centered terminal pin 18. It will be understood by one skilled in the art, that any of the embodiments taught herein to facilitate terminal pin connector insertion can be used concurrently or in various combinations pending application requirements.

The present invention is a continuation-in-part application to U.S. Pat. No. 10,587,073, which resides in a family that includes U.S. Pat. Nos. 9,065,224 and 9,692,173, the contents of which all are fully incorporated herein by this reference. The following is quoted from the Abstract of the '224 patent: "The connector clip mechanically attaches to the terminal pin of the feedthrough and exterior surface of the housing electrically contacts the circuit board, creating an electrical connection therebetween." This is a general description of the present invention and covers terminal pin connector 16, wherein a through-pin 18 connected to the terminal pin connector 16 is insertable into and retractable from its terminal pin connector 16, thus removable. Some embodiments of the terminal pin 18 of the present application provide for a terminal pin 18 residing within a terminal pin connector 16 such that the terminal pin 18 is grasped in a grip-tight manner such that inadvertent longitudinal movement is prevented while still allowing removability of the terminal pin 18 from the terminal pin connector 16 when a pull force is applied. Now quoting from column 4 lines 58 and on from the '224 invention, we have, "as illustrated in FIGS. 4, 4A-4C and 5A-5C, the terminal pin connector 16 comprises a clip 64 that resides within a connector housing 66. The clip 64 is designed to be positioned around the perimeter of the terminal pin 18 such that, the clip 64 grasps the exterior surface of the terminal pin 18." This is a very clear description of FIG. 3D of the present invention. Referring once again to FIG. 3D, the clip or prongs 64, 70 reside within the connector housing 66 wherein, the clip and its prong 70 are, "designed to be positioned around the terminal pin 18 such that, the clips 64 grasp the exterior surface of the terminal pin 18." This is a description of an embodiment that allows longitudinal movement of the pin 18 within the terminal pin connector 16. Again, quoting from column 4 of the '224 invention, from line 65 and on, "the base through-bore 74 is dimensioned such that, the terminal pin 18 of a multitude of diameters can pass therethrough." Hence, the terminal pin connector 16 can accommodate insertion and retraction of a family of terminal pin 18 diameters in the event a defective component connected by terminal pin connector 16 requires replacement or rework. Quoting from column 5 of the '224 invention, starting on line 1, stated is, "As shown in FIGS. 4A-4C, the clip 64 comprises at least two prongs or fingers 70 that extend from the base 68. As shown, the prongs 70 are preferably angled inwardly towards a central axis A-A that extends longitudinally through the clip through-bore 74 of the base 68. This inward orientation enables the prong 70 to contact and compress against the exterior surface of the perimeter of the terminal pin 18 gripping the pin therewith." This is the description in the present invention of FIG. 3D where the prong 70 grips the exterior of the terminal pin 18.

Referring now to FIG. 3B, one can see that features 73 and 71 of the terminal pin 18 are curved. This curved feature mitigates inadvertent longitudinal movement of the terminal pin 18 out of the terminal pin connector 16, however is still removable with an applied pull force, thereby allowing replacement or rework of a defective component connected by terminal pin connector 16.

Referring once again to the '224 specification column 5, line 11, it says, "The prong 70 of the clip 64 are preferably designed to allow the terminal pin 18 to proceed in one direction between the prong ends such that, the terminal pin 18 is prohibited from moving in the reverse direction." Referring to FIGS. 4A-4C of the present application to which this language refers, illustrated are embodiments of the prongs 70 of the clip 64 through which the terminal pin 18 proceeds. FIG. 4A comprises three prongs, FIG. 4C comprises two prongs and FIG. 4C comprised four prongs. As the terminal pin 18 is intended for insertion into the terminal pin connector 16 by way of the through-bore of the base 68 of the clip 64 as shown, retraction would be prohibited unless a component attached by the terminal pin connector 16 is defective and requires removal for replacement or rework. Hence, the term "prohibit" means that an inserted terminal pin 18 is not to be retracted from terminal pin connector 16 unless the component connected by the terminal connector is deemed defective and requires removal for replacement or rework. As such, a designer would consider a desired grip strength when designing prong 70 of clip 64 such that terminal pin 18 is preferably prohibited from moving in the reverse of the insertion direction unless retraction is required due to defect. If a component is deemed defective, the pull force required for retraction from the terminal pin connector must be greater than the push force required to insert the terminal pin 18 into the terminal pin connector 16. Embodiments are disclosed herein, wherein the design of one of a terminal pin, a terminal pin connector, a clip of a terminal pin connector, a prong of a clip of a terminal pin connector, a compliant termination structure, or combinations thereof consists of a pull force for retraction greater than a push force for insertion. In some embodiments, a tool is used to facilitate retraction. In other embodiments a memory-shape alloy may be used to facilitate retraction.

Now referring again to FIG. 3, one can see that the terminal pins 18 are "preferably designed" such that the terminal pins themselves 18 are alternatively notched to thereby engage the prong 70. As can be seen in FIG. 3, the terminal pins 18 and their distal end 62 are easily inserted through the prongs 70, but once the prongs engage the terminal pin, which optionally has a machined recess, then the prongs engage the pin in such a way that they are prohibitively retractable without using a tool. This embodiment can be extremely important especially when the terminal pin connectors 16 are disposed on the device side of the casing 32.

Referring to FIGS. 4, 4A-C, 5A-C and 6B, the connector housing 66 may comprise a housing sidewall 76 which encompasses a connector housing through-bore 78 along the A-A axis that extends longitudinally therethrough, or at least partially therethrough when the connector housing 66 comprises a blind hole. In the embodiments shown, the connector housing 66 is designed similarly to that of a tube having an opening that extends from a proximal housing end 59 to a distal housing end 69. The connector housing 66 comprises a housing sidewall thickness 84 that extends from a housing interior sidewall surface 86 to a housing exterior sidewall surface 88. In certain embodiments, the terminal pin connector 16 may have a terminal pin connector length 90 ranging from about 0.025 inches to about 0.300 inches and a through-bore diameter 92 that ranges from about 0.01 inches to about 0.030 inches.

As shown and taught, the clip 64 is positioned within a connector housing 66 by an interference fit. This interference fit configuration prevents the clip 64 from moving inward or outward of the connector housing 66 when insertion or retraction of the terminal pin 18 occurs. Instead of an interference fit, it is contemplated that the individual clip 64 can be positioned within the connector housing 66 and then electrically and mechanically attached through various processes, including soldering, welding, brazing and the like. It will be further appreciated that these structures, such as the clip 64, may be formed by 3D printing processes. The clip 64 and the connector housing 66 could be 3D printed as a monolithic structure or as two separate pieces, which are subsequently joined, as described above. 3D printing includes stereolithography 3D printing. Additionally, the clip 64 and connector housing 66 could comprise a single co-sintered metal. Furthermore, a shape-memory alloy, such as Nitinol, may be used for clip 64, wherein the insertion could be done at one temperature and then the Nitinol would expand when it reaches body temperature. If Nitinol is used, the Nitinol can further be modified as described earlier to impart different spring constants at different points of the clip 64'.

Referring to FIG. 4, illustrated is an embodiment of the connector housing 66 comprising a housing perimeter. The housing perimeter comprises four planar surfaces comprising two planar pairs, each planar pair of the planar surfaces having planes opposite each other. A first planar pair comprises housing planar surfaces 88, 88', the planes of which are depicted in FIG. 4 at the 'right-hand side' labelled 88, 88' and at the 'left-hand side' (not labelled) of the terminal pin connector 16. A second planar pair comprises housing planar surfaces 93, 96 the planes of which are depicted in FIG. 4 at the 'top' labelled 93 and at the 'bottom' (not labelled) of the terminal pin connector 16. It is contemplated that angled, curved or radiused transitions 100 from one housing planar surface 88, 88' to another housing planar surface 93, 96 may be included as illustrated for the purpose of eliminating corners. Alternatively, the connector housing 66 of the terminal pin connector 16 may comprise fewer than four or more than four planar surfaces, such as may occur in, for example, triangular or hexagonal connector housing shapes. It is contemplated that the connector housing 66 could be round, which would eliminate planar surfaces 88, 88' and 93, 96.

In summary, the connector housing 66 as illustrated in FIG. 4, is electrically connected to a circuit board electrical connection pad 104. Therefore, the terminal pin connector 16, comprising the connector housing 66 and the clip 64 (with a base 68 and/or prongs 70) are all in electrical contact to the circuit board electrical connection pad 104. When the AIMD active electronic circuit board 106 is plugged into either a filtered or an unfiltered AIMD hermetically sealed feedthrough 14, this establishes an electrical connection between the terminal pins 18 through the terminal pin connector 16 to the circuit board electrical connection pads 104. These circuit board electrical connection pads 104 would each be routed through either internal or external AIMD active circuit board 106 conductive paths such as circuit traces. The conductive paths comprise one of an active conductive path, a ground conductive path, or both an active path and a ground path. These conductive paths are not shown for simplicity.

Figure 5D:
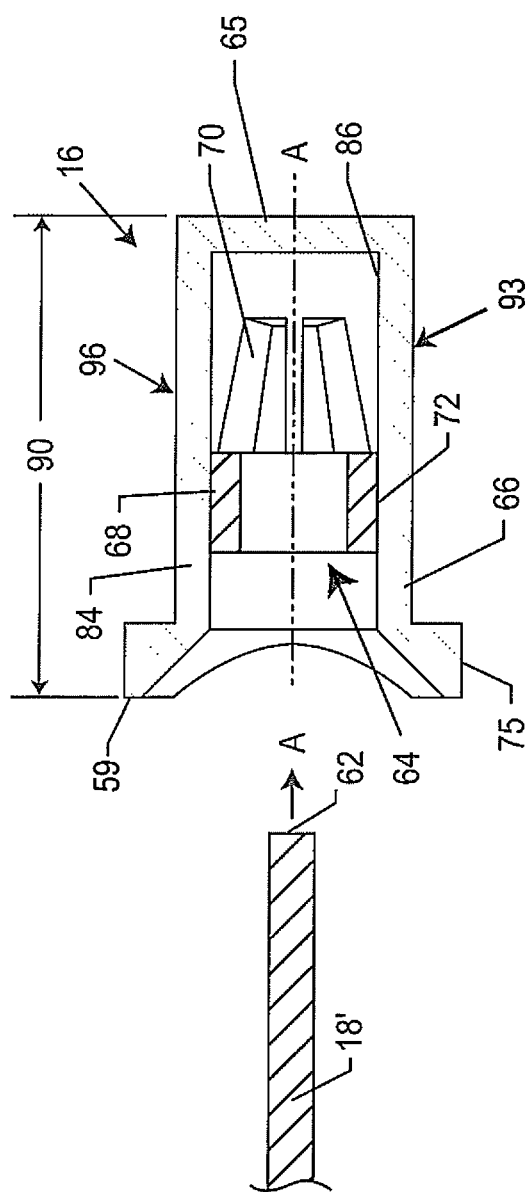
FIG. 5D shows a cross-sectional view similar to FIG. 5B illustrating an alternative embodiment of the terminal pin connector.

FIG. 5D is very similar to FIGS. 4, 4B, 4C and FIGS. 5A, 5B and 5C. FIG. 5D shows the terminal pin 18' ready to be inserted inside the connector housing 16, as illustrated. Once the terminal pin 18' is inserted, the prong (s) 70 deflect (there must be at least one prong). It is important that the material of the prongs 70 have a spring constant such that, once the terminal pin 18' is inserted, the prongs tightly grasp the outside diameter of the terminal pin 18', thereby providing a low resistance/low impedance electrical connection and a robust mechanical connection. Referring once again to FIG. 5D, in this embodiment, there is a blind hole with a connector housing end wall 65. It is contemplated that the connector housing 66 could also be an open-bore or through-bore. In FIG. 5D, the terminal pin 18' shown is a formed pin (generally drawn and extruded), which, once the terminal pin is slipped tightly within the prong 70, the terminal pin 18' can be removed. In other words, a defective circuit board to a terminal pin connector 16 is attached (not shown) would be removable for replacement or rework.

Figure 5E:
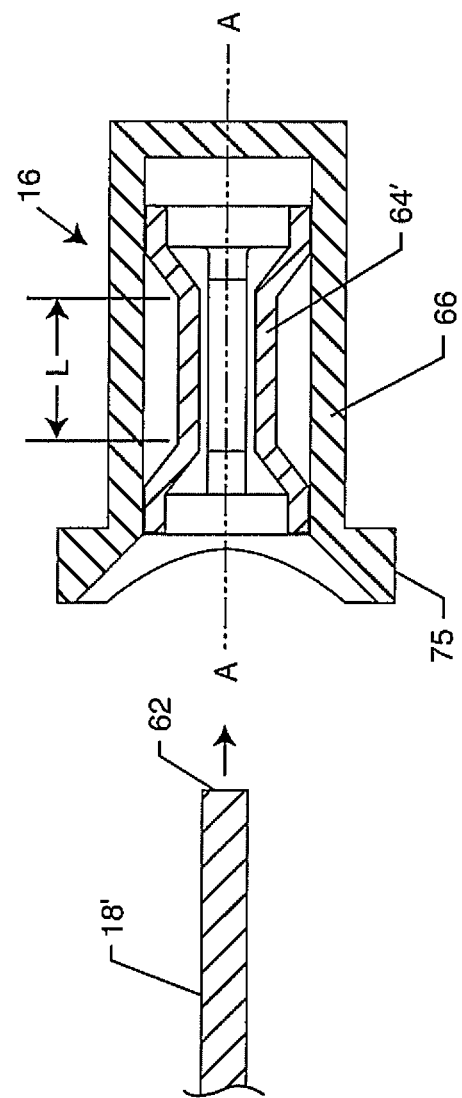
FIG. 5E shows a cross-sectional view similar to FIG. 5B illustrating an alternative embodiment of the terminal pin connector.

FIG. 5E is very similar to FIG. 5D, except that prong 70 has been replaced by a spring clip 64'. Instead of prong 70, the spring clip 64' residing within the connector housing 66 comprises a clip base at each end and one or more elongated members therebetween so that the inside diameter formed by the elongated members is less than the inside diameter of the clip bases. The one or more elongated members are connected to each clip base. While it is preferable for the spring clip 64' to comprise multiple elongated members, some applications may alternatively allow the clip bases to be connected by a single compliant elongated member connected to the clip bases at each end of the spring clip 64'. The material of spring clip 64' has a spring rate such that it will expand as the terminal pin 18 is being inserted. Therefore, one has to insert the terminal pin connector 16 (and circuit board not shown) onto terminal pin 18 and then apply a push force such that the side wall or walls of the elongated members of the clip spring 64' of terminal pin connector 16 expands and then grips against the terminal pin 18, thereby forming a very low resistance and low impedance electrical connection. Referring once again to FIG. 5E, in order to facilitate flexure, the structure 64' having a single elongated member, the single elongated member between the clip bases being continuous around the full circumference of the clip bases, however, in this case the single continuous elongated member also comprises an elongated member wall thickness less than the wall thickness of the base clips. It is contemplated in FIG. 5E, that the cross section shown may be understood to illustrate a single continuous elongated member or two or more, even "n" number of separate elongated members. Referring once again to FIG. 5E, one will appreciate that the overall length L of the spring clip 64' can be adjusted so that a desired electrical contact force to the terminal pin 18 is made. The number of elongated members can also be adjusted (as a high number of elongated members will require less contact force while a smaller number of elongated members will require higher contact force).

Referring once again to FIG. 5E, it is contemplated that the spring clip 64' is electrically and mechanically connected to the inside diameter of the connector housing 66 of the terminal pin connector 16. The connector housing 66 could be angled inward (chamfered) so that the spring clip 64' compresses while it is being inserted or a tool could be used, similar to a piston ring compressor for the pistons of an automobile. One could also use a shape-memory alloy for any of the configurations just described, such as Nitinol, wherein the insertion could be done at one temperature and then the material would expand when it reaches body temperature. If Nitinol is used, the Nitinol can further be modified as described earlier to impart different spring constants at different points of the spring clip 64'.

Figure 22:
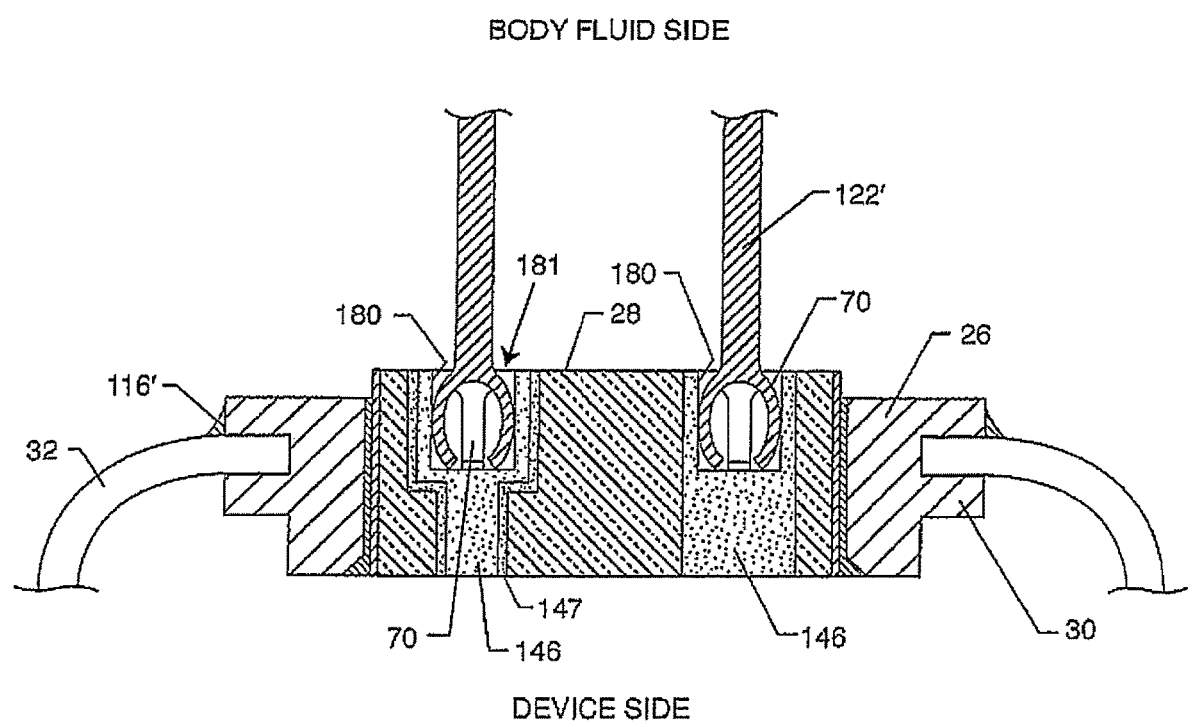
FIG. 22 shows a cross-sectional view of an alternative embodiment of an AIMD feedthrough connector assembly.
Figure 23:
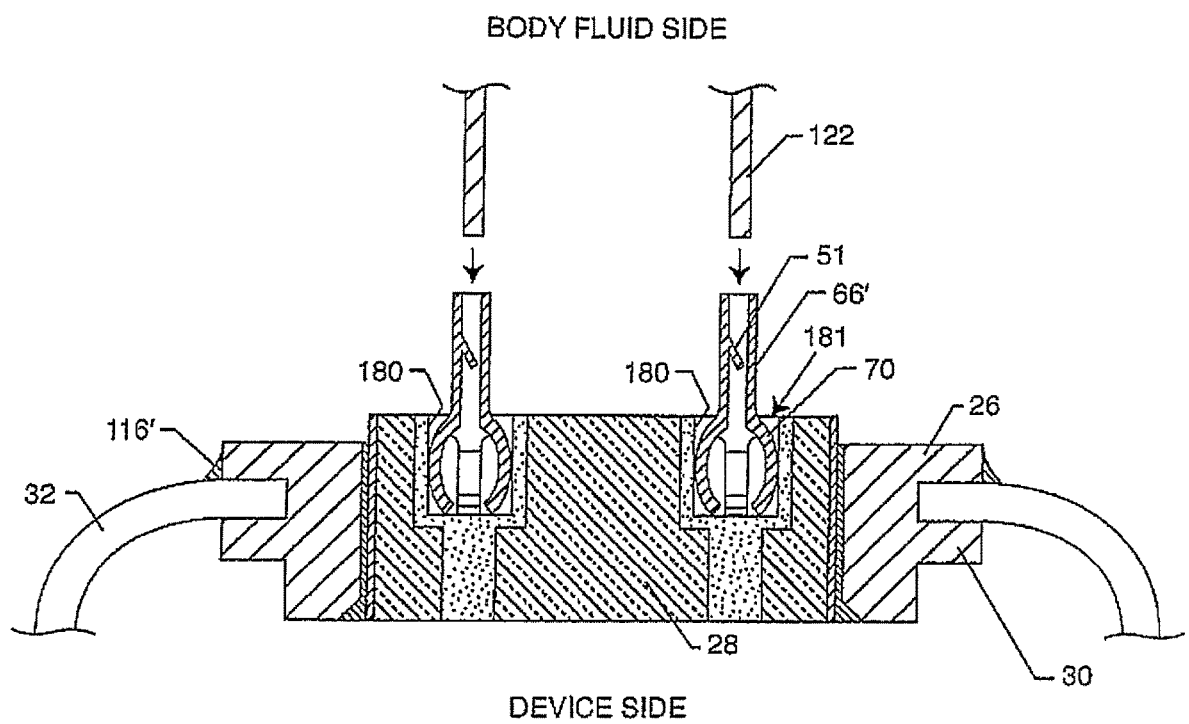
FIG. 23 shows a cross-sectional view of an alternative embodiment of an AIMD feedthrough connector assembly.

In an embodiment (not shown), it is understood that the structure of FIG. 5E illustrating the spring clip 64' could also be inserted into a bore or a counterbore of a co-sintered conductive via (for example, see FIGS. 22 and 23).

As illustrated in FIG. 7A, the housing bottom planar surface 98 (hidden underneath) of the connector housing 66 is designed to establish intimate electrical contact with an electrical connection pad 104 of an AIMD active electronic circuit board 106 of the active implantable medical device 12. As such, the connector housing 66 may be composed of an electrically conductive material or alternatively may be coated with an electrically conductive material, such as an electrically conductive foil, metallization, plating or vapor deposited film as previously disclosed for clip 64. The coating may additionally be used to facilitate joining processes, such as soldering or even welding. The coating may also comprise any one or more of the materials previously disclosed for clip 64.

Alternatively, a portion of the housing exterior surface 96' and a portion of the housing interior sidewall surface 86 of the connector housing 66 may be constructed of an electrically conductive material conducive to the joining processes of soldering and/or welding. The connector housing 66 is designed such that an electrical connection is made between the terminal pin 18 of the AIMD hermetically sealed feedthrough 14 and the AIMD active electronic circuit board 106 of the active implantable medical device 12.

Once again referring to FIG. 7A, the unfiltered or filtered AIMD connector feedthrough assembly 10 or the feedthrough connector capacitor assembly 20 is positioned within the active implantable medical device 12. The housing exterior surface 96' of the connector housing 66 may be electrically joined to an electrical connection pad 104 of the AIMD active electronic circuit board 106 by a laser weld 108' imparted by a joining instrument 108. Alternatively, the housing exterior surface 96' may be electrically connected to an electrical connection pad 104 of the AIMD active electronic circuit board 106 by a solder, using a soldering joining instrument (not shown). In either case, the joining process may be utilized to join at least a portion of the housing exterior surface 96' to the circuit board electrical connection pad 104.

The electrical connection 107' may be a laser weld 108', a solder, a thermal-setting conductive adhesive or even a ball grid array type approach where, before the connector housings 66 of the terminal pin connectors 16 are attached to the circuit board electrical connection pads 104, either a BGA (ball grid array) conductive epoxy or solder bump would be applied and then a robot would place the housing exterior surface 96' of the connector housing 66 of all the terminal pin connectors 16 in place, which, through a bulk reflow operation, the solder would be reflowed or the conductive epoxy would be cured. If a laser weld 108' is made, it is contemplated that the circuit board electrical connection pad 104 (or alternatively, a circuit board land or a circuit trace) would comprise a metallic pad, such as a Kovar pad, whereby, the laser weld 108' would include the melting and joining of the adjacent materials to form a solid mechanical metallurgical bond and a very low resistance and low impedance electrical connection 107'. Referring once again to FIG. 7A, one will note that there is a gold braze 46*b* that connects and mechanically and hermetically seals the active terminal pins 18 to the insulator 28. The right-hand side terminal pin 18 has a gold braze 46*bgnd*. In this case, the ground terminal pin 18*gnd* is shown gold brazed 46*bgnd* directly to the metallic ferrule 26. Alternatively, the ground terminal pin 18*gnd* could be a laser weld 108' that directly joins the ground terminal pin 18*gnd* to the metallic ferrule 26. In the case of a terminal pin laser weld 108' directly to the metallic ferrule 26, the ground terminal pin 18*gnd* would need to comprise an oxide-resistant material, or at least be coated with an oxide-resistant material once any oxides that form during laser welding are cleaned/removed from the ground terminal pin. The brazing or welding process grounds the terminal pin 18*gnd*. It is very common in pacemaker and ICD applications that the AIMD casing 32 (also known as a can or housing), which essentially comprises two can halves 112 and 114, can be used as one of the electrodes. For example, for an implantable cardioverter defibrillator, a defibrillation vector can be between the AIMD casing 32 and a distal shocking electrode (not shown), which is placed, for example, in the right ventricle area. To perform this function, the AIMD active electronic circuit board 106 is programmed to apply the ICD shock between a grounded pin, such as 18*gnd*, such that the pulse polarity is between the AIMD casing 32 and the single distal electrode. In various applications, the grounded pin may not extend into the body fluid side of the AIMD 12 as shown, however, in certain neurostimulators or other specialized applications, the grounded pin will extend into the boy fluid side of the AIMD 12.

It is understood to those skilled in the art that the terms AIMD "casing", "housing" and "can" are synonymous. As used throughout this specification, the terms "casing", "housing" and "can" can be applied to the overall AIMD hermetically sealed enclosure 32, which may have can halves 112, 114, or a lid (not shown), and which is generally conductive and forms an electromagnetic shield (Faraday cage). This is not to be confused with the housing 66 of the terminal pin connector 16 of the present invention. Hence, the use of similar terms "casing", "housing" and "can" must be taken in context with the structures to which these terms refer.

Figure 7B:
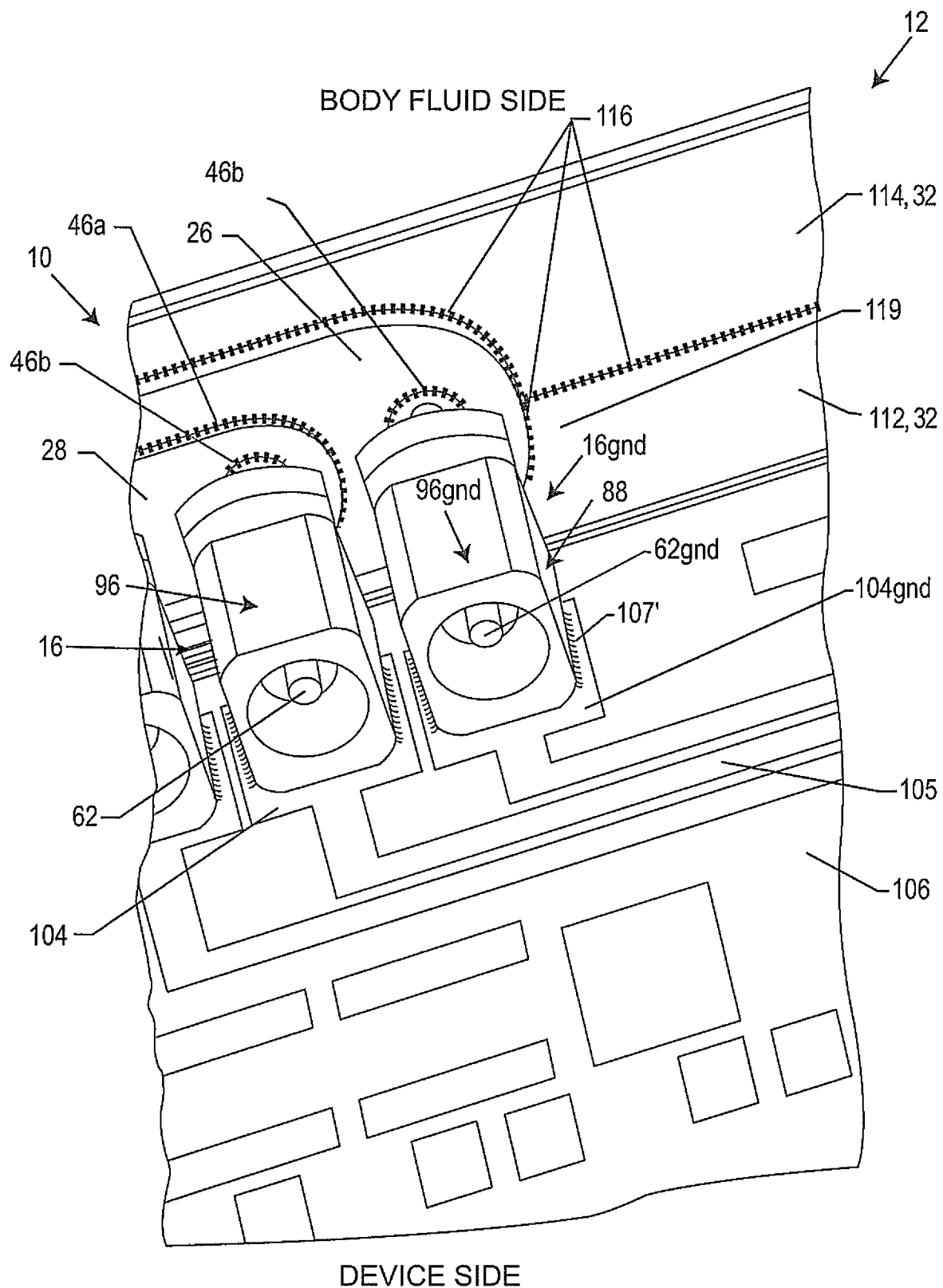
FIG. 7B illustrates an alternative embodiment of the terminal pin connector attached to an electrical connection pad of an AIMD active electronic circuit board.
Figure 7C:
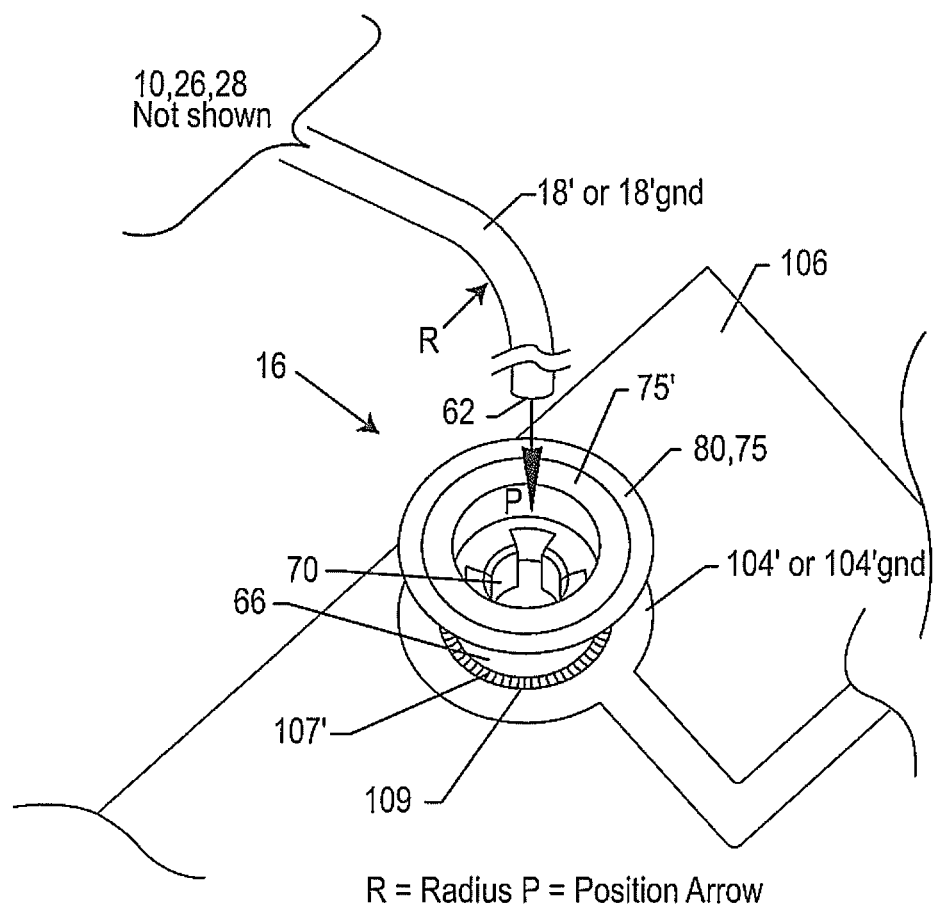
FIG. 7C illustrates an alternative embodiment of the connector assembly attached to a via hole of an AIMD active electronic circuit board.

Referring to FIGS. 7A and 7B, the circuit board electrical connection pad 104 could comprise a large circuit board via hole 109, which could be designed to accept and receive a round connector housing 66 (not shown). The round connector housing 66 would be mechanically and electrically attached to the circuit board via hole 109 by one of a press fit, a solder, an electrically conductive adhesive or other common circuit board via hole connection material and/or process, including crimps, and the like. This embodiment could position the connector housing 66 residing in the circuit board via hole 109 perpendicular to the position illustrated in FIGS. 7A and 7B. As such, the terminal pins 18 and 18*gnd* could have a 90° bend or other bend angle in order to align with a housing interior sidewall surface 86 such that the bent terminal pins 18 and 18*gnd* could slide along the housing interior sidewall surface 86 thereby 'plugging into' the circuit board connector housing 66. Using common multilayer circuit board trace techniques, these circuit board via holes 109 that receive connector housings 66 could be staggered in various patterns thereby enabling electrical connection of high count, high density and/or close pitched feedthrough conductors, including uniquely or other non-traditionally positioned feedthrough terminal pins 18, 18*gnd*, while preserving removability of circuit boards for rework or replacement should a circuit board be deemed defective.

Figure 19:
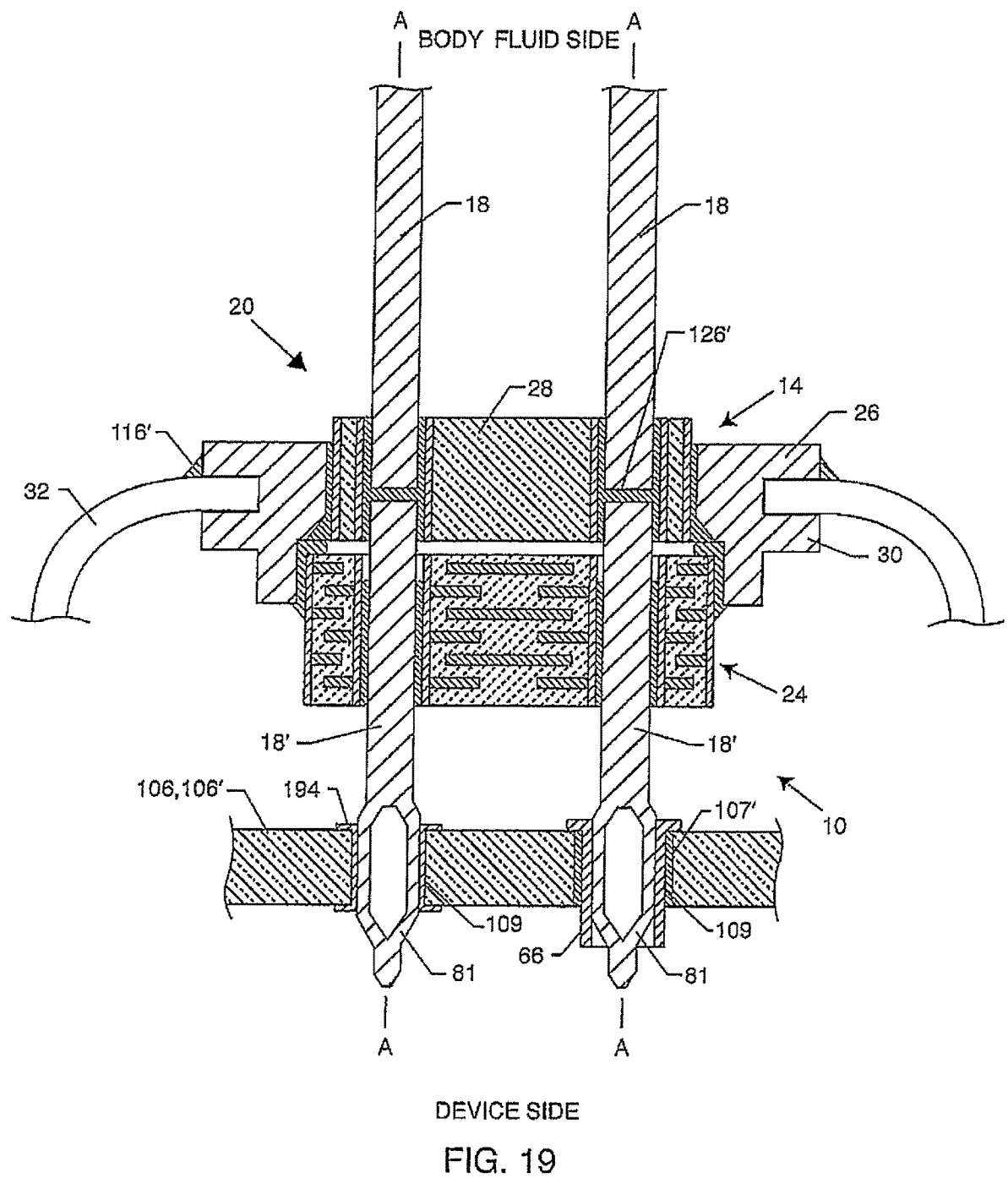
FIG. 19 shows a cross-sectional view of an alternative embodiment of a feedthrough capacitor connector assembly having terminal pins comprising a compliant termination structure.

Further regarding circuit board via holes 109, depending on the design of the circuit board, the terminal pin connector, the termination structure of terminal pin designs, or combinations thereof, terminal pins 18 and 18*gnd* may not require a bending operation. For example, FIG. 19 illustrates an embodiment of a feedthrough capacitor connector assembly 20 having circuit board via hole 109, within which a two-part pin resides. The two-part pin of FIG. 19 comprises a first pin comprising a terminal pin 18 partially residing in the insulator bore of the feedthrough conductive pathway, in this case, extending from the body fluid side of the insulator 28, and a second pin comprising a terminal pin 18' having a compliant termination structure 81, the second pin partially residing in the same insulator bore of the feedthrough conductive pathway, however, in this case, extending from the device side of the insulator 28. Both terminal pin 18 and terminal pin 18' residing within the same insulator bore of the feedthrough conductive pathway of the AIMD hermetically sealed feedthrough form the two-part pin. The compliant termination structure 81 of the terminal pin 18' extending from the device side insulator 28 is shown passing through the active capacitor dielectric bore of the externally grounded feedthrough capacitor 24', and then directly inserted through circuit board via hole 109 in-line with the longitudinal axis of the two-part pin, that is, terminal pins 18 and 18'. FIG. 19 illustrates terminal pin 18' directly electrically connected to the circuit board without a bending angle which can be a 90° or some other bending angle.

FIG. 7C is taken from section 7C-7C of FIGS. 7A and 7B. Illustrated is a terminal pin 18 bent to an angle (radiused R), which could be a radiused 90° right angle. A radiused bend is preferred for better shock and vibration resistance. Position arrow P illustrates how the bent terminal pin 18 would be inserted into the clip through-bore of connector housing 66 residing in the circuit board via hole 109 of the electrical connection pad 104. As previously described, the connector housing 66 would be attached to make an electrical connection 107'. In this case, the connector housing 66 is round along with a round alignment feature 75 comprising an alignment flange 71' at the proximal housing end 80 for accepting and receiving a terminal pin 18. Prong (s) 70 are shown residing within the connector housing 66. It is contemplated, particularly if the circuit board is thick enough, that the prong (s) 70 could instead alternatively reside on a terminal pin 18 and not within the connector housing 66. Terminal pins having compliant termination features could thereby plug directly into a connector housing 66 that are absent prongs. Such embodiments are illustrated in FIGS. 19, 19A through 19D, 20, and 21.

Referring once again to FIG. 7C, one will appreciate that the electrical connection 107' can comprise an electrically conductive circuit board via hole 109, which typically comprises circuit board via hole electrically conductive plating, eyelets and the like. In other words, connector housing 66 could be press-fitted into the circuit board via hole 109 of the electrical connection pad 104. The position arrow P illustrates how the terminal pin 18 is inserted into the clip through-bore to the prong (s) 70. The position arrow P could also alternatively be reversed such that the clip through-bore with the prong (s) 70 of the connector housing 66 of the AIMD active electronic circuit board 106 is aligned with a bent terminal pin distal end 62 and then a push force is applied so that the circuit board can be pushed onto the terminal pin 18.

The AIMD feedthrough connector assembly 10 or feedthrough capacitor connector assembly 20 may be designed for use with a "clam shell" style AIMD casing 32. A "clam shell" type AIMD casing 32 comprises two casing halves 112, 114 that are essentially mirror images of each other, meaning that the two casing halves appear almost identical, but are reversed in the direction perpendicular to the mirror surface. The two casing halves 112, 114 are brought together to form an AIMD casing 32. In embodiments illustrated in FIGS. 8 and 9, the AIMD feedthrough connector assembly 10 (or feedthrough capacitor connector assembly 20 not shown) is positioned within a casing inlet 110 of a first casing half 112 of the AIMD casing 32. The flange 30 of the ferrule 26 is typically welded to the casing half within the casing inlet 110. The terminal pin connectors 16, attached to their respective terminal pins 18 and 18gnd, are then positioned on the circuit board electrical connection pads 104 of the AIMD active electronic circuit board 106 and electrical connection 107' is made.

Referring to FIG. 7B, in an embodiment, the terminal pin connector 16 is positioned and attached to the circuit board electrical connection pads 104 of an AIMD active electronic circuit board 106 by an electrical connection material 107 (not shown), such as by soldering, thermal-setting conductive adhesives, brazing, welding or the like, to form electrical connection 107'. After the terminal pin connector 16 has been mechanically and electrically attached to the circuit board electrical connection pad 104, the hermetic seal assembly, including terminal pins 18 and 18gnd may be positioned, wherein the terminal pins are inserted into their respective terminal pin connector 16. Once the terminal pins 18 and 18gnd are correctly positioned, the flange 30 of the ferrule 26 may be tack welded 119 to the first casing half 112. This tack weld 119 positions and holds the ferrule 26 to the casing half 112. At this time, final visual and electrical inspections are made, and then, if inspection is passed, a second casing half 114 can be placed so that a continuous laser weld 116 is made between the casing halves and all around the ferrule 26 such that the entire AIMD casing 32 is mechanically and hermetically sealed. There is typically a step before the final hermetic seal is made involving vacuum baking of the AIMD casing 32 and back-filling the AIMD casing with an inert gas optionally having a tracer gas such as helium or argon. This step is well known in the prior art and will not be further described herein. Shown in FIG. 7B is an AIMD hermetically sealed feedthrough 14 that has terminal pins 18 hermetically sealed to an insulator 28 and a ground terminal pin 18gnd extending through the ferrule 26 of the AIMD hermetically sealed feedthrough 14 to a body fluid side and a device side. After the AIMD casing 32 is hermetically sealed by joining casing halves 112, 114, the device side is defined herein as inside the AIMD casing 32, and the body fluid side is defined herein as outside the AIMD casing 32.

Referring once again to FIG. 7A, one can see that after the terminal pins 18, 18gnd have been inserted into the terminal pin connectors 16, similarly to FIG. 7B above, the flange 30 of the ferrule 26 may be tack welded 119 to the first casing half 112, positioning and holding the ferrule 26 to the casing half 112, such that all of the circuit board connections can be made. The AIMD active electronic circuit board 106 is then tested, and if testing is passed, then the second casing half 114 can be positioned for laser welding. A continuous laser weld 116, 116' is made from the body fluid side of the AIMD casing 32. It is noted that, while FIG. 7A shows the AIMD components within the AIMD casing 32, once the second casing half 114 is laser welded to the first casing half 112 and to the ferrule 26 of the AIMD hermetically sealed feedthrough 14, none of the components inside the AIMD casing 32 would be visible. The laser welds 116, 116', forms a continuous seam that hermetically seals the two can halves 112, 114 and 116' the entire perimeter or circumference of the ferrule 26 of the AIMD. The continuous seam forming a complete hermetic seal thereby protects all of the AIMD electronic circuits and other components residing inside the AIMD casing 32, while also forming a Faraday shield (also called a Faraday cage), which is an effective electromagnetic shield against high frequency undesirable electromagnetic interference (EMI).

Referring now to FIG. 7C, illustrated is an embodiment comprising an alternative connector housing 66 to the connector housing having planar surfaces shown in 7C-7C of FIGS. 7A and 7B. In this case, the connector housing 66 is shown inserted into a circuit board via hole 109 instead of having a planar surface attached to an electrical connection pad 104 as taught in FIGS. 7A and 7B. The circuit board via hole 109 of FIG. 7C is further associated with round electrical connection pad 104'. It is contemplated that the electrical connection pad 104', which could also be square or any other geometry. A mechanical and electrical connection 107' is shown, which could comprise an electrical connection material 107 such as a solder, a thermal-setting conductive adhesive or the like. The elevated alignment feature 75 at the proximal housing end 80 of the connector housing 66 is an alignment flange 75' and is only shown elevated so that the mechanical and electrical connection 107' is visible in order to appreciate the connection joining structure. In reality, the alignment feature 75 is actually set down against the connection joining structure, which may comprise one of a press-fit, a solder or a thermal-setting conductive adhesive. When the alignment feature 75 is set down against the connection joining structure, the alignment flange 75' of the alignment feature will mimic a fillet or a rounding edge, which exists but is not actually shown in FIG. 7C. Further regarding the proximal housing end 80, prongs 70 are illustrated. It is contemplated, however, that any one of the elastically resilient conductive structures of the present application may be within the connector housing 66 instead of prongs 70. FIG. 7C illustrates a terminal pin 18 comprising a bend, the bend having a radius R. It is contemplated that the bend of the terminal pin 18 can be a radiused 90° bend or another suitable radiused angle such that the AIMD active electronic circuit board 106 and the terminal pin 18 can be removably attached. For example, a downward push force may be applied to the AIMD active electronic circuit board 106, while an upward push force can be applied to the terminal pin distal end 62 of the terminal pin 18 so that the terminal pin 18 is inserted into the connector housing 66 and grasped by the prongs 70 thus being mechanically and electrically captured by the prongs 70. If testing indicates that the AIMD active electronic circuit board 106 is defective, applying pull force opposite the insertion push force allows removal of the defective circuit board for either replacement or rework. The embodiment illustrated in FIG. 7C, has enhanced resistance to shock and vibration, and is also resilient to thermal forces that may be introduced by mismatched rates of thermal expansion due to the various different materials of construction within AIMD components or subassemblies, including the AIMD active electronic circuit board 106 and the AIMD casing 32. The radius R can be customized to accommodate various lead extensions, lengths, or orientations. Moreover, the radius allows for flexure during perturbations including thermal expansion mismatch movement, shock, vibration and even insertion/retraction forces. Referring once again to FIG. 7C, one will see that the connector housing 66 is round instead of rectangular or square, as illustrated in other embodiments herein, and has an alignment feature 75 and the alignment flange 75', both of which are also round. It is contemplated that other shapes could be used for the connector housing 66, alignment feature 75 and/or alignment flange 75' including square, rectangular, hexagonal, elliptical or the like. FIG. 7C also shows the terminal pin distal end 62 of the bent terminal pin 18 being pushed into the connector 66 in the direction indicated by the arrow representing a push force P. Radius R may be a single radius, as shown, or may comprise multiple radii all along the length of terminal pin 18, which extends from the device side of the insulator (not shown)

into the AIMD casing 32. In other words, the terminal pin 18 may be bent in various accommodating configurations in order for the terminal pin distal end 62 to engage the prong 70.

Figure 8:
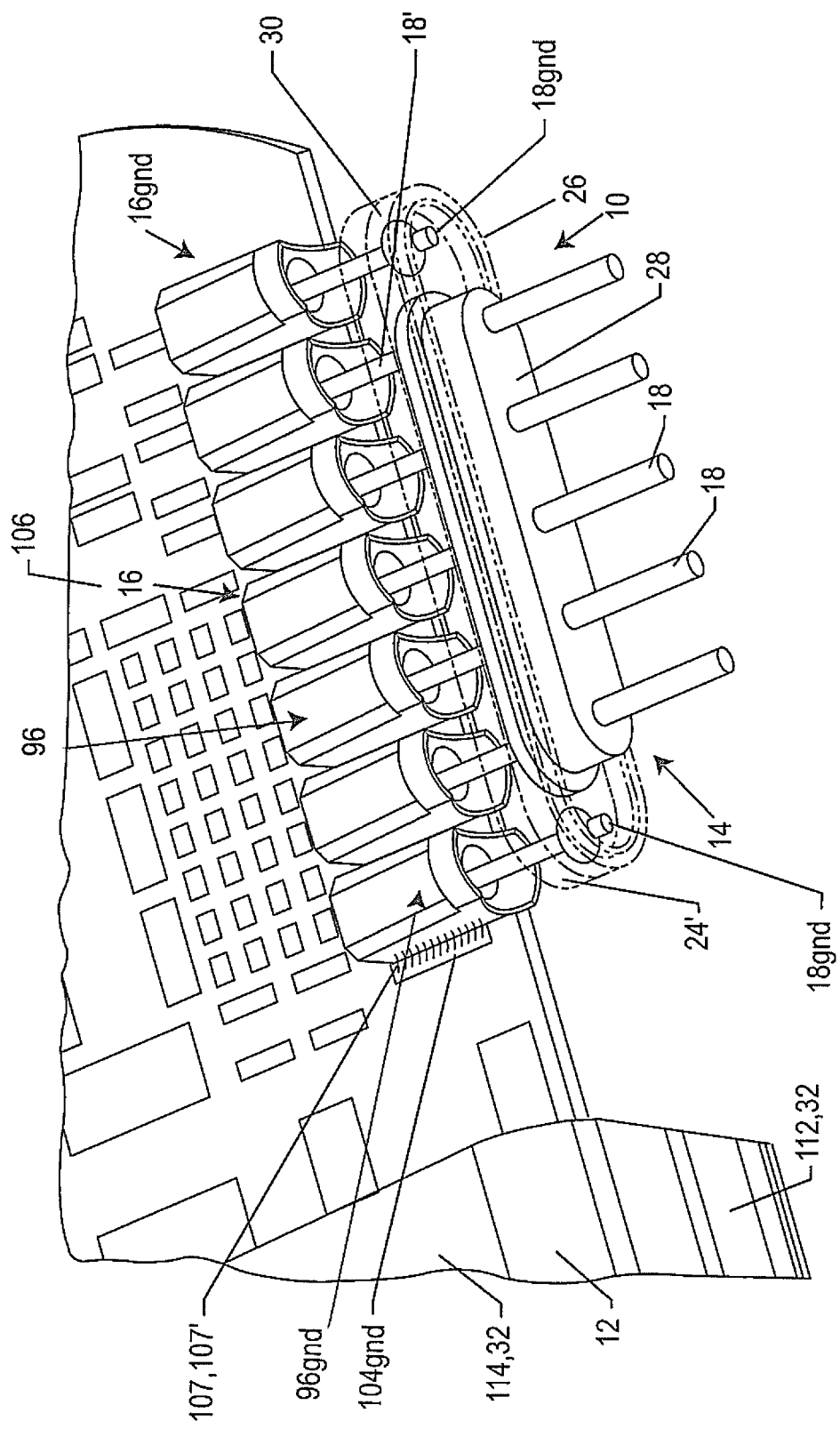
FIG. 8 shows an enlarged partial cross-sectional perspective view of an embodiment of an AIMD feedthrough connector assembly attached to the AIMD active electronic circuit.

FIG. 8 illustrates a cutaway view of an AIMD 12 showing the terminal pin connector 16 of the present invention, mechanically and electrically attached to the AIMD active electronic circuit board 106. The AIMD hermetically sealed feedthrough 14, 10 is shown with the corresponding terminal pins 18, 18 *gnd* plugged into the terminal pin connector 16. There is also an internally grounded feedthrough capacitor 24' that is disposed on the inside of the AIMD casing 32. In FIG. 8, the internally grounded feedthrough capacitor 24' does not have an external, perimeter or outer metallization layer; instead, the internally grounded feedthrough capacitor 24' is grounded to the terminal pins 18*gnd* residing at both ends of the ground terminal pins. These ground terminal pins 18*gnd* are either gold brazed, or laser welded directly to the ferrule 26 and provide a solid mechanical and low impedance RF ground for the internally grounded feedthrough capacitor 24'. This is a convenient way of providing grounds to the AIMD active electronic circuit board 106. In FIG. 8, there are five active terminal pins 18 and the two ground terminal pins each labeled 18*gnd*.

Referring once again to FIG. 8, illustrated is one casing half 112 of the AIMD casing 32, which can have a multiplicity of shapes, of which only one exemplary shape of many shape possibilities (including customized shapes) is shown.

Illustrated is a ferrule 26 fitted into an opening in an AIMD casing 32 such that a laser weld can be made hermetically sealing the AIMD pulse generator. It is noted that the ferrule 26 in FIG. 8 may comprise an H-flange 30 as shown in FIGS. 3, 3B and 3C, which captures the casing half 112, or alternatively, ferrule 26 may comprise an L-flange, an F-flange, an indent flange, or a barrel flange, including the flange configuration shown in FIG. 8. It will be appreciated that the ferrule 26 of FIG. 8 is only a non-limiting exemplary configuration, thus ferrule and AIMD casing configurations may vary.

FIG. 9 illustrates perspective view of a first casing half 112 with various components internal to an AIMD prior to hermetically sealing a second casing half thereby forming AMID casing 32 of an AIMD 12. Shown is a battery 130, which can be either a primary or a secondary battery. For example, in the case that the AIMD 12 is a cardiac pacemaker, the battery 130 could be a primary battery, while, in the case that the AIMD 12 is a neurostimulator, the battery 130 could be a secondary battery or rechargeable battery. The main AIMD active electronic circuit board 106 is also shown along with at least one microprocessor 131 and various other circuit board components 133. The AIMD active electronic circuit board 106 has a plurality of terminal pin connector housings 16 that have also been mechanically and electrically attached to the AIMD active electronic circuit board 106 and, importantly, to its circuit board inputs and outputs. Circuit boards contain the circuits that provide, for example, pacing pulses to simulate the natural biological signals of the heart, sending pacing pulses from the pacemaker circuit to a terminal pin, and then from the terminal pin to the distal electrodes of an implanted lead in order to treat cardiac arrhythmias (problems with a rate or rhythm of a heartbeat). Circuit boards can also comprise circuits that can sense biological signals received by sense amplifiers within a circuit of a microprocessor 131. Circuit boards may also comprise circuits for telemetry to which one or more RF telemetry pins are connected. In general, RF telemetry antennas would be included in an AIMD header block area (not shown), and the RF telemetry signal would pass from the RF telemetry antenna to the one or more RF telemetry pins, and then from the RF telemetry pin to the microprocessor of the circuit board. Accordingly, an AIMD is thereby enabled to sense, process, and adjust a pacing therapy in accordance with specific patient needs and/or to communicate data.

Referring once again to FIG. 9, one can see that the AIMD active electronic circuit board 106 has been 'plugged in' and connected to the hermetic seal terminal pins 18' of the AIMD hermetically seal feedthrough 14. The circuit board is also shown connected to the battery 130. As has been previously disclosed, there may be an internally grounded feedthrough capacitor 24' attached to the AIMD hermetically seal feedthrough 14 (not shown), or instead of a feedthrough capacitor, an EMI filter circuit board 106' (not shown) comprising one of an MLCC, an X2Y attenuator, a flat-thru capacitor or combinations thereof can be used.

Figure 9A:
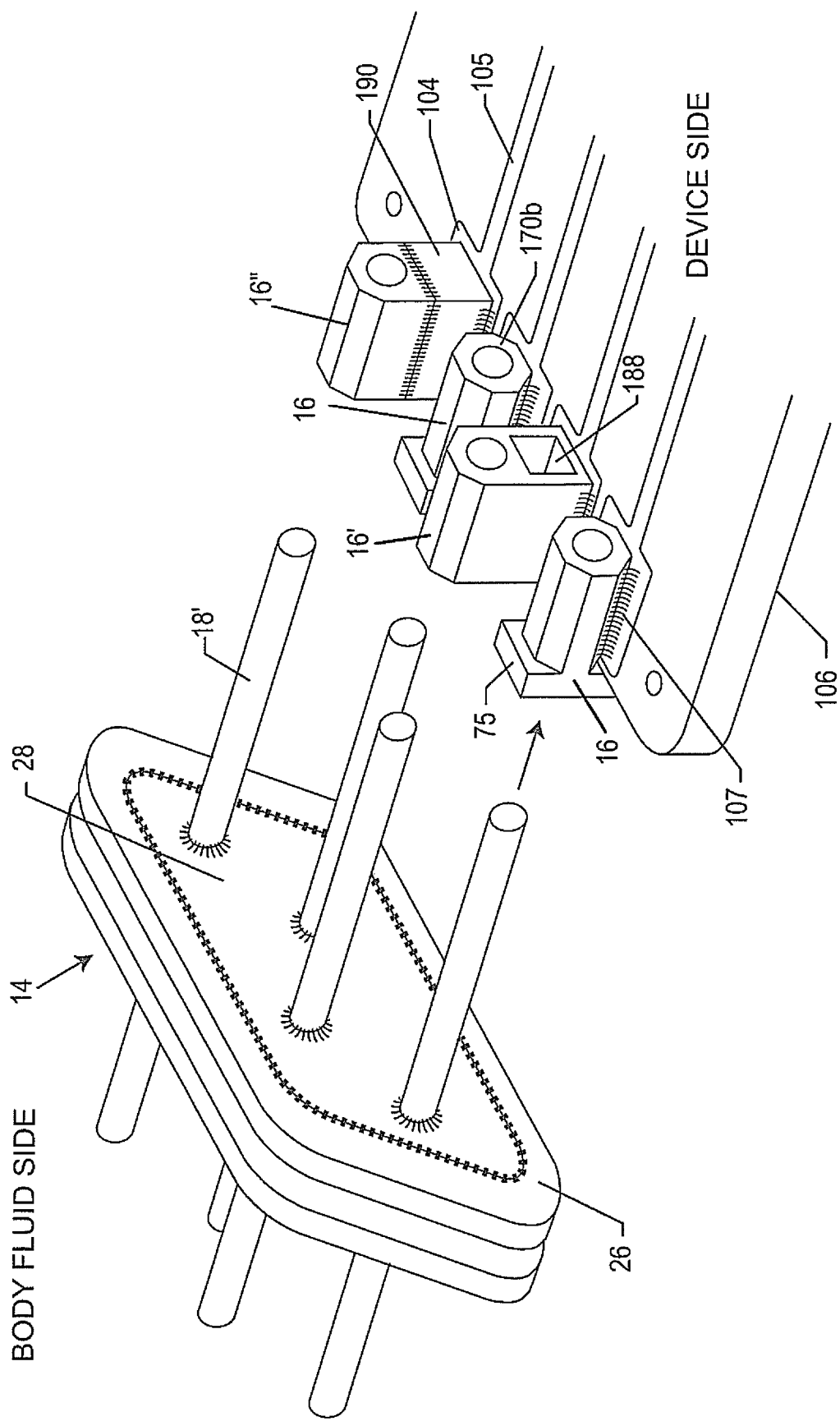
FIG. 9A illustrates a perspective view of an alternative embodiment of the terminal pin connector attachable to an AIMD hermetically sealed feedthrough having a staggered terminal pin configuration.

FIG. 9A illustrates embodiments of terminal pin connectors 16, 16' and 16" for use with an AIMD hermetically seal feedthrough 14 having a staggered terminal pin 18' configuration. It is understood by one skilled in the art that terminal pin connectors may be shaped, positioned, oriented, or otherwise mounted to accommodate any terminal pin configuration of an AIMD hermetically sealed feedthrough 14, including one of a staggered terminal pin configuration, a dual in-line terminal pin configuration, or a custom terminal pin configuration. Referring once again to the terminal pin connecters of FIG. 9A, terminal pin connector 16 is configured as previously disclosed in the present application. The embodiment of terminal pin connector 16' provides height to the terminal pin connector, thereby having an elevated insertion though-bore with respect to that of the terminal pin connector 16 so that the terminal pin connector 16' suitably aligns with a respective staggered terminal pin. To save weight, terminal pin connector 16' may comprise an optional cutout 188 as illustrated. The embodiment of terminal pin connector 16" essentially embodies the shape of the terminal pin connector 16', except that the terminal pin connector 16" comprises a flat cutoff that is attached to a conductive spacer block 190. The conductive spacer block 190 may be electrically attached to at least one of the circuit board electrical connection pad 104 as shown, a circuit board trace 105 (not shown) or a circuit board land (not shown). It is noted that the alignment feature 75 of the terminal pin connectors 16 of FIG. 9A are disposed so that the alignment feature 75 overhangs the edge of the AIMD active electronic circuit board 106 to facilitate a flat attachment for proper bonding and electrical connection 107' to the circuit board electrical connection pad 104. The circuit board electrical connection pad 104 area is sufficiently large to allow robotic dispensing of solder dots, ball grid arrays and the like.

Figure 9B:
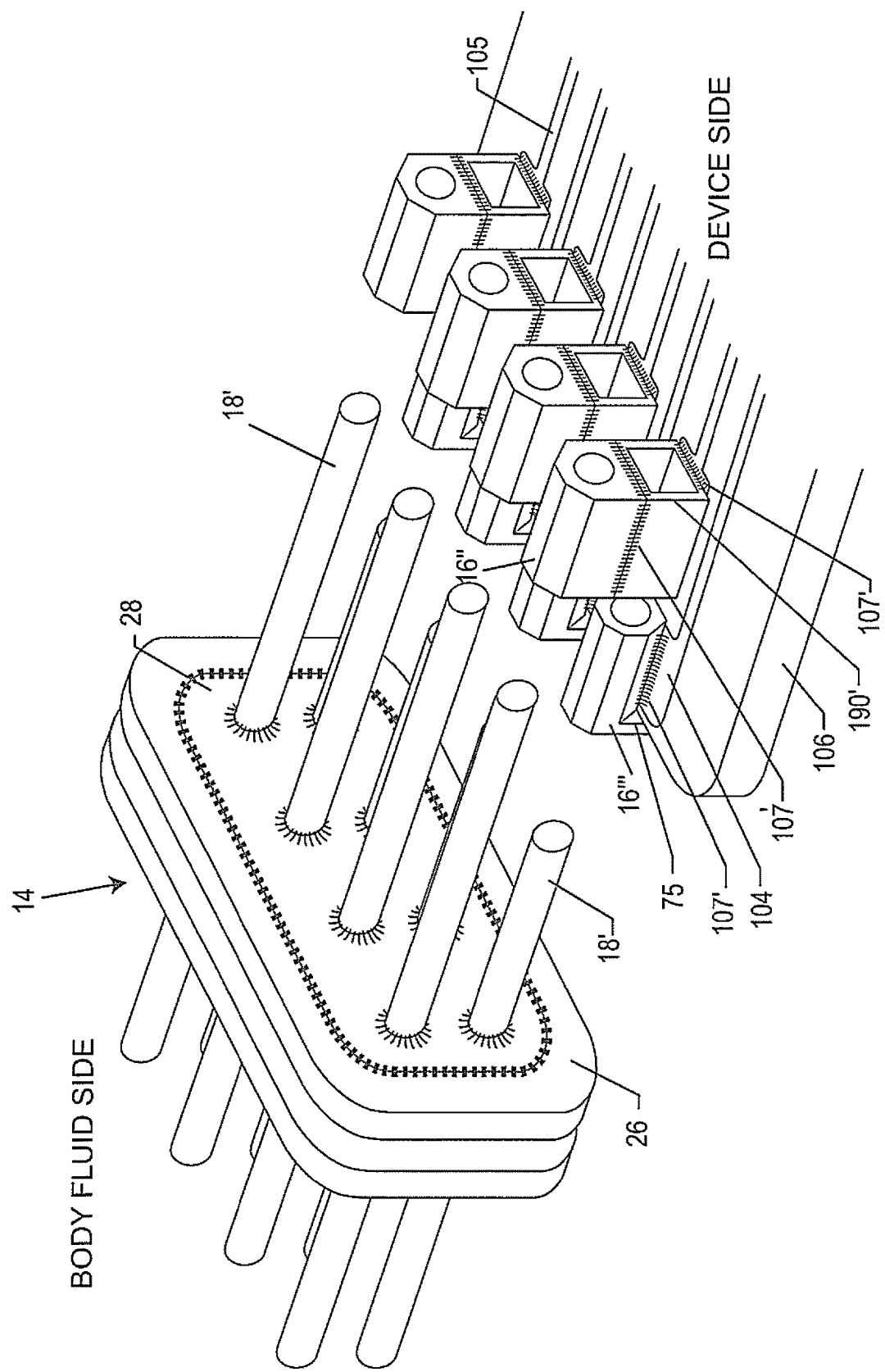
FIG. 9B illustrates a perspective view of an alternative embodiment of the terminal pin connector attachable to an AIMD hermetically sealed feedthrough having an orientation comprising aligned terminal pin pairs of different terminal pin lengths.

FIG. 9B illustrates an embodiment of a terminal pin connectors 16" and 16"" suitable for a dual in-line terminal pin 18 configuration. In this case, the terminal pins 18 are vertically aligned one above the other. The hermetically sealed feedthrough 14 of FIG. 9B comprises eight hermetically sealed terminal pins 18 extending through the insulator 28 of the AIMD hermetically sealed feedthrough 14 from a body fluid side to a device side. After the AIMD casing 32 is hermetically sealed by joining can haves 112, 114, the device side of the insulator 28 is inside the AIMD casing 32 and the body fluid side is outside the AIMD casing 32. The terminal pin connectors illustrated in FIG. 9B are staggered to accommodate insertion of each terminal pin of the dual in-line terminal pin configuration into its respective terminal pin connector. The terminal pin connectors can be attached either using a BGA dot or a thermal-setting conductive adhesive dot or an edge electrical connection. In the embodiment of FIG. 9B, terminal pin connector 16'''' accommodates the shorter terminal pins 18', while terminal pin connectors 16'' accommodates the longer terminal pins 18. The short and long terminal pin configuration ensures that only terminal pin 18' are inserted into terminal pin connector 16'''' and only terminal pin 18 are inserted into terminal pin connector 16''. Additionally, the height of terminal pin connectors 16'''' is defined such that terminal pins 18 will not make contact to terminal pin connectors 16''''. Terminal pin connectors 16'' have a separate open spacer block 190', however it is contemplated that terminal pin connectors 16'' can comprise a solid spacer block. Additionally, the terminal pin connectors 16'' may also be a one-piece structure instead of a multi-piece structure as shown. Multi-piece terminal pin connector structures will have an electrical connection 107' as shown. The spacer block 190' is attached to circuit board electrical connection pads 104 (or alternately to circuit traces or circuit board lands not shown) as previously described for terminal pin connector 16. The through-bore of the terminal pin connector 16'' is spatially aligned to line up along the axis of the length of the terminal pins 18 of the hermetic feedthrough seal 14 so that insertion of the terminal pin distal end can be made. Importantly, during insertion of the AIMD active electronic circuit board 106, terminal pins 18 and 18' should be assembled such that, when the AIMD active electronic circuit board 106 is attached to the terminal pins 18 and 18', the terminal pins will not substantially deflect or bend. Depending on the terminal pin material of construction, either the terminal pins can have an applied force such as by a fixture to prevent deflection and/or bending during the insertion process, or the terminal pins may have a specified material composition and/or properties, as terminal pin materials can then be specifically chosen based on a material's flexural strength, which is the amount of bending force a material can withstand without being substantially deflection or compromisingly bent.

Figure 10:
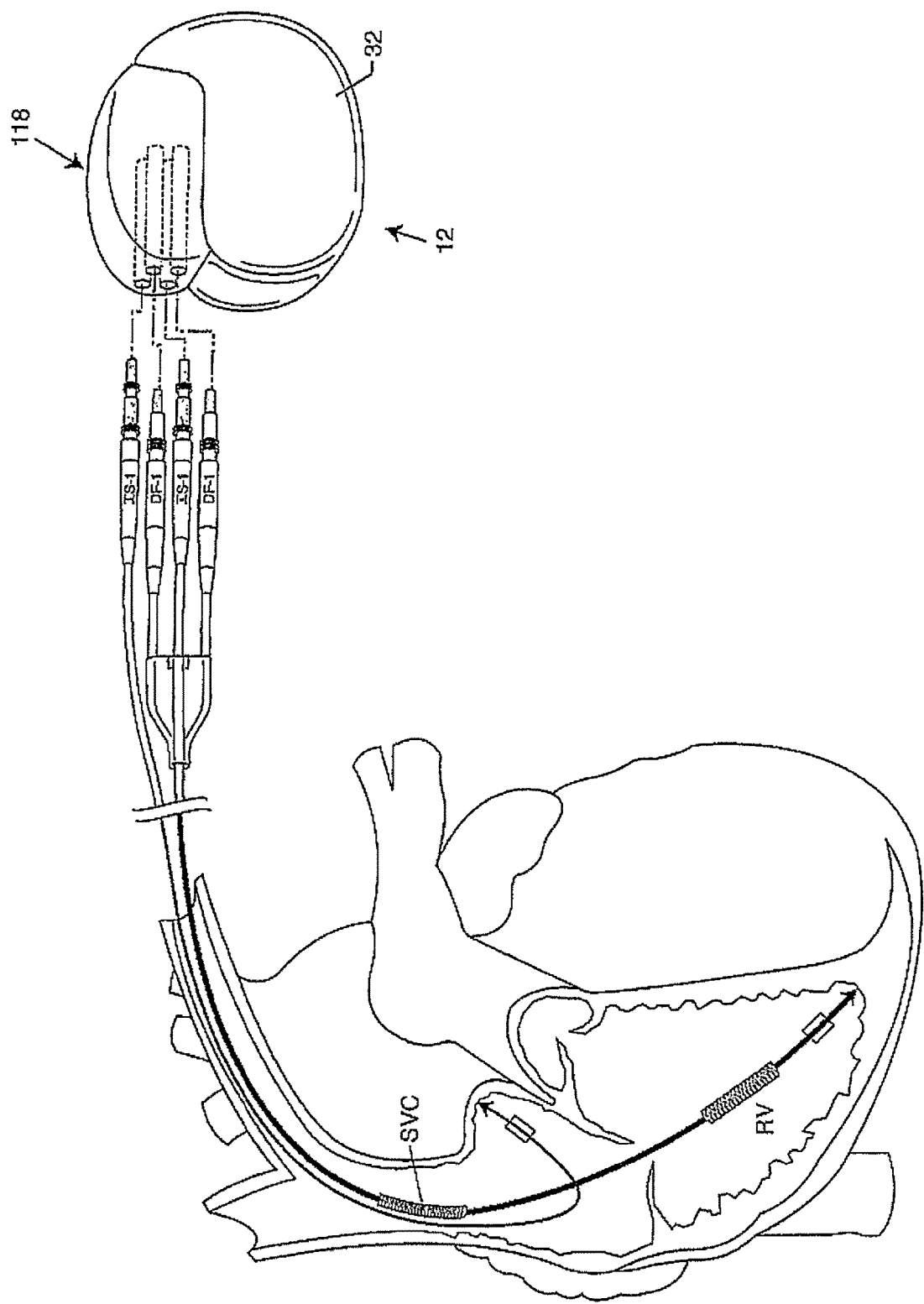
FIG. 10 illustrates an active implantable medical device connectable to a heart of a patient.

FIG. 10 illustrates an active implantable medical device 12 known as an implantable cardioverter defibrillator (ICD). An ICD has a hermetically sealed metallic AIMD casing 32 generally of titanium. An ICD also comprises an AIMD header block 118 into which therapy delivery leadwires routed to the heart are plugged as shown. Illustrated are ISO international standard industry lead connectors IS-1 and DF-1. An IS-1 lead connector is a low-voltage pacing/sensor lead connector. A DF-1 lead connector is a high-voltage shock lead connector. A first leadwire is shown routed to the right ventricle of the heart, which, in this case has one IS-1 lead connector and two DF-1 lead connectors, the three lead connectors joined together at a yoke integrating these lead connectors into the single lead body illustrated. The first leadwire comprises a coil electrode at the Superior Vena Cava (SVC), and both a coil electrode and a ring electrode in the right ventricle. The second leadwire comprising a ring electrode is shown routed to the right atrium. This embodiment represents a standard dual chamber pacing system with defibrillation capabilities. It is understood that a variety of therapy delivery leadwire configurations are possible as are a multitude of locations that electrodes can be routed transvenously to contact either the myocardium of the heart or that floats in the heart blood pool.

Regarding the AIMD header block 118, header blocks are generally the last thing to be placed on an AIMD and can be cast or molded directly to the AIMD 12 or, alternatively, pre-formed or pre-molded and then attached to the AIMD, either by biocompatible mechanical fastener (s) and/or adhesive (s). AIMD header blocks are typically made using a relatively hard, insulative polymer, such as, but not limited to Tecothane®. The AIMD header block 118, as FIG. 10 illustrates, usually has a thickness approximating the thickness of the AIMD casing 12 and includes a surface that conforms to the mating surface of the AIMD casing. AIMD header blocks, in their own right, are very complicated and comprise many components. Hence, there is a need for AIMD header blocks that easily plug into an AIMD. The header blocks of present day AIMDs are generally securely affixed to an AIMD casing such that the AIMD header block is not removable without causing damage to the AIMD; hence, if an AIMD header block is deemed defective after the AIMD header block is affixed to an AIMD casing, replacement, or rework of the defective AIMD header block is not possible, and so the entire AIMD is rejected and scrapped.

The Lim Patent Publication 2017/0266451 teaches a plug-in header block, the contents of which are fully incorporated herein by this reference. However, the header block of Lim includes a conductor assembly, a feedthrough coupled to the conductor assembly, and a polymer header that was injection molded about the conductor assembly and at least a portion of the feedthrough. The terminal pins of the feedthrough of the conductor assembly are plugged into electrical receptacles residing in the AIMD casing, and then the AIMD casing is welded to the plugged-in feedthrough. One problem with Lim's approach is that the welding process creates considerable heat, which could be damaging to the polymer material forming the header. Polymer materials easily carburize at high temperatures, which could cause deleterious electrically conductive areas in an otherwise insulative header block. Another problem with Lim's approach is that the feedthrough is subjected to three thermal perturbations in this order: (1) each terminal pin of the feedthrough is subjected to a joining temperature when the terminal pins of the feedthrough are welded to their corresponding electrically conductive component; (2) the feedthrough is additionally subjected to the injection molding temperatures; and (3) the feedthrough is again subjected to welding temperatures when the AIMD casing is welded to the plugged in feedthrough. Once the feedthrough is injection molded, hermeticity testing of the feedthrough is likely not doable. More importantly, since the feedthrough was incorporated into the header by the injection molding process, there is no way to determine if the feedthrough is still hermetic. Historically, feedthroughs have at times caused device recalls due to loss of feedthrough hermeticity.

Figure 11:
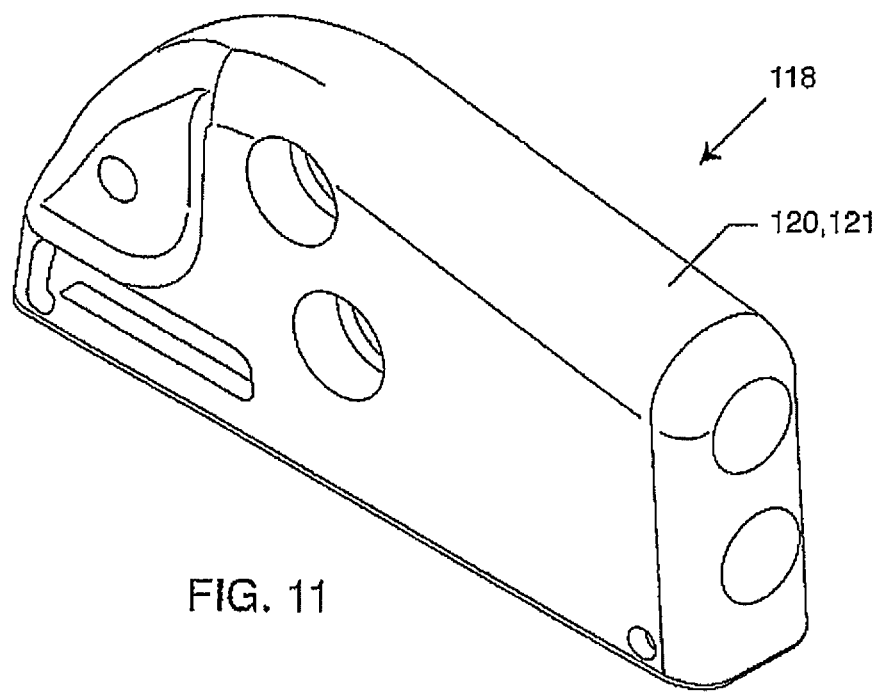
FIG. 11 shows a perspective view of an exemplary AIMD header block.
Figure 12:
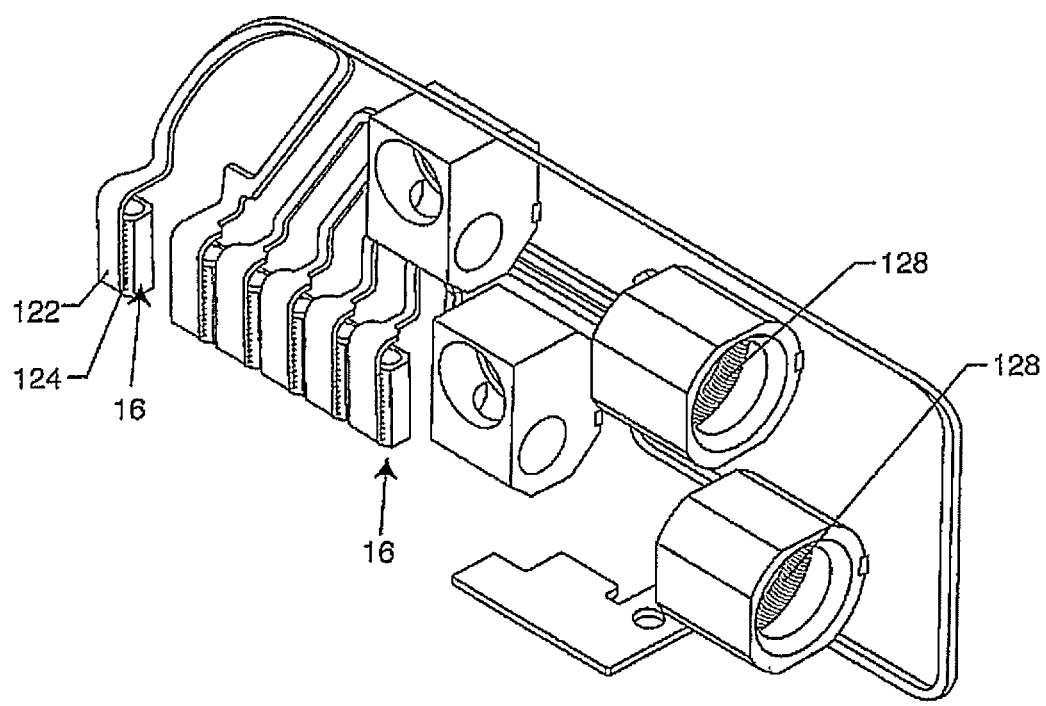
FIG. 12 illustrates a perspective first-side view of exemplary internal conductors, lead connectors and terminal pin connectors residing within the exemplary AIMD header block of FIG. 11.
Figure 13:
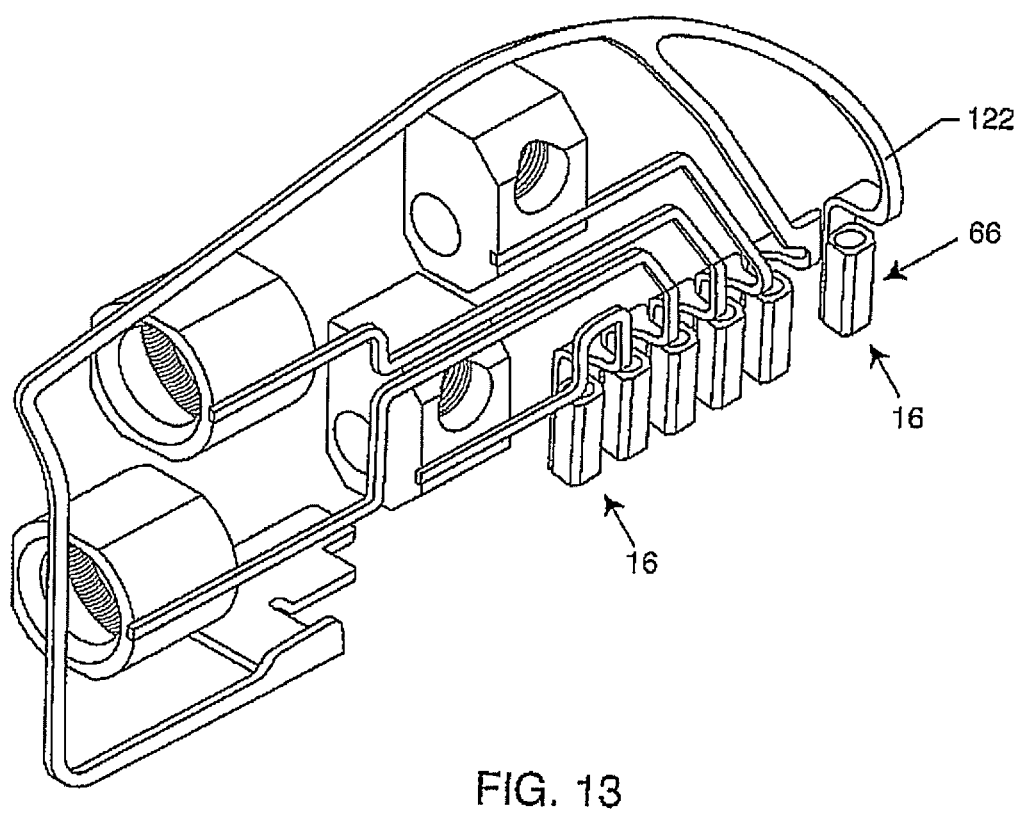
FIG. 13 illustrates a perspective second-side view of the exemplary internal conductors, lead connectors and terminal pin connectors of FIG. 12.

FIGS. 11, 12 and 13 of the present application are related to FIGS. 3, 4A and 4B of Lim, which are a representative header (FIG. 3) within which resides various electrically conductive components (FIGS. 4A and 4B). Illustrated in FIGS. 4A and 4B of Lim are the following electrically conductive components: an antenna (48), an RF anchor tab (50), and RF pin tabs (52) and (60). It is noted that the element numbers in parenthesis refer to those element numbers of the Lim publication. Given the Lim problems discussed above, the inventors resolve the issues associated with the Lim header connector assembly by providing an embodiment of a removable AIMD header block that does not require a feedthrough. Instead, the removable AIMD header block of the present application attaches to the terminal pins of present day AIMDs without having to change existing AIMD pulse generator manufacturing, inspection, or quality testing processes. Shown in FIGS. 12 and 13 of the present application are electrical conductors 122 to which are electrically connected to the terminal pin connectors 16 of the present invention. The electrical conductors 122, which are present within the header residing on the body fluid side of the AIMD 12, are shown laser welded 124 to the terminal pin connecters 16.

Referring once again to FIGS. 12 and 13, since the electrically conductive components will be exposed to body fluids when implanted, the electrically conductive components of the AIMD header block 118 comprises biocompatible, non-toxic, and biostable materials of construction. For example, the electrical conductors 122, the terminal pin connectors 16, and the other components shown in FIGS. 12 and 13 may comprise any of the biocompatible and biostable materials, as previously described in addition to stainless steel, particularly 316L stainless steel, MP35N®, Nitinol, cobalt chromium alloys, titanium, niobium, tantalum gold, platinum, and palladium. Also shown are ports with circumferential springs 128 such as made by BalSeal®, which are well known in the art, and cavities that are optionally present for set screws, fasteners, or other fastening/attachment medium.

FIG. 13 is very similar to FIG. 12, except that it has been rotated so that one can more clearly see the terminal pin connectors 16 of the present invention. One will appreciate that the connector housing 66, as illustrated, could be staggered to align with either a staggered terminal pin hermetic seal or a dual in-line terminal pin hermetic seal. This would mean that the conductors that they are attached to are also staggered.

Figure 19A:
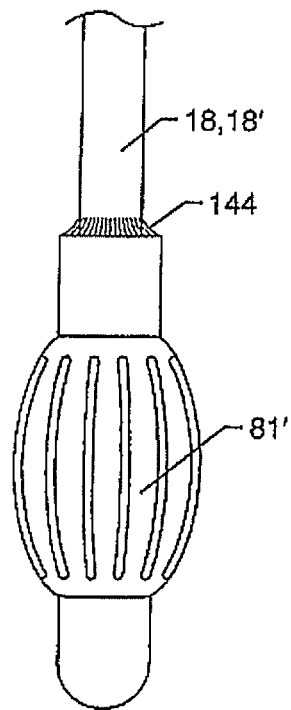
FIG. 19A illustrates an embodiment of a terminal pin having a compliant termination structure.
Figure 19B:
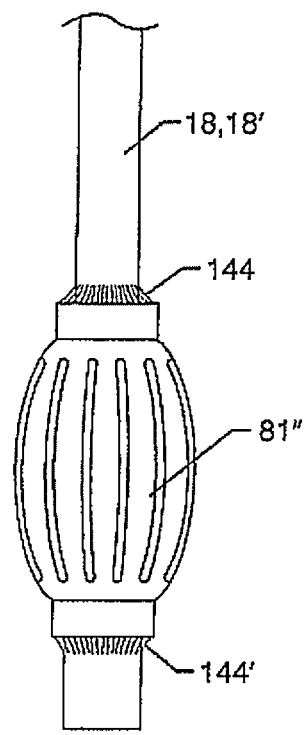
FIG. 19B illustrates an embodiment of a terminal pin with a compliant termination structure.
Figure 19C:
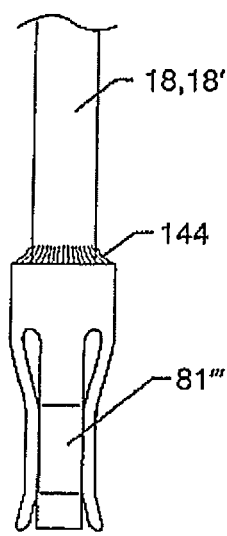
FIG. 19C illustrates an embodiment of a terminal pin with a compliant termination structure.
Figure 19D:
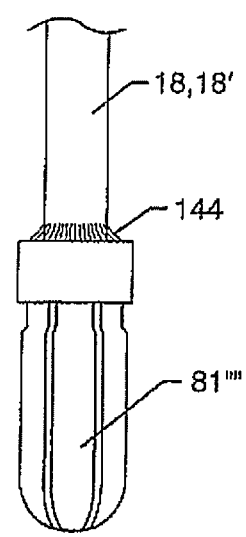
FIG. 19D illustrates an embodiment of a terminal pin with a compliant termination structure.
Figure 20:
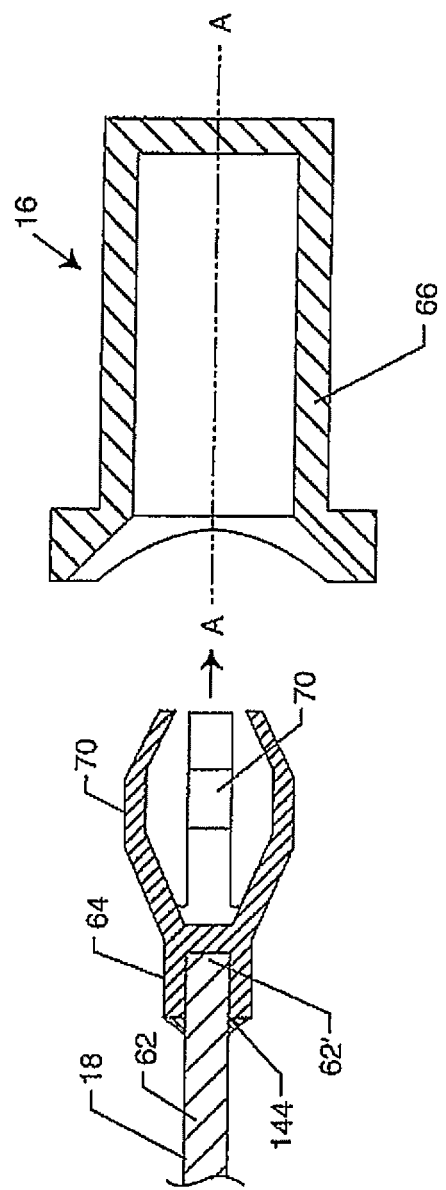
FIG. 20 shows a cross-sectional view of an alternative embodiment of a terminal pin connector.
Figure 21:
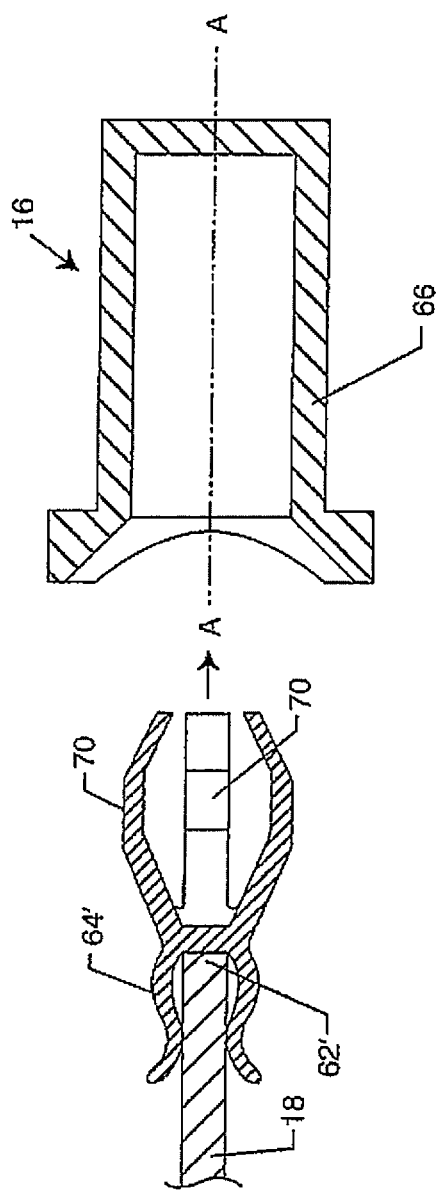
FIG. 21 shows a cross-sectional view of an alternative embodiment of a terminal pin connector.

Referring once again to FIGS. 12 and 13, it is contemplated that the terminal pin connectors 16, which are attached to the electrical conductors 122, could instead comprise any of the compliant termination structures 70' disclosed herein, even pin compliant termination structures 81, 81', 81", 81''', and 81'''' as illustrated in FIGS. 19 through 19D, and clip 64/prong 70 type pin compliant termination structures such as illustrated in FIGS. 20 and 21. Furthermore, adding any of the pin compliant termination structures of the present application to the electrical conductors 122 of FIGS. 12 and 13 enables feedthroughs comprising one or more cavities 180, as illustrated in exemplary FIGS. 22 through 24. Likewise, adding any of the pin compliant termination structures of the present application to the electrical conductors 122 of FIGS. 12 and 13 further enables feedthroughs having terminal pins attached to only a connector housing 66 (the connector housing is entirely absent any clip, prongs, or compliant termination structure), see, for example, the connector housings of FIGS. 20, 21, 25 and 26, to receive such pin compliant terminations.

Referring once again to circumferential springs, while circumferential springs 128 (often called BalSeal® springs) are used in prior art AIMD header blocks 118 for insertion of implanted lead distal ends, such circumferential springs being biocompatible, biostable, and non-toxic, it is contemplated, in accordance with the present invention, that the circumferential springs can be used in terminal pin connectors 16 or in compliant termination structures 70' as taught herein. Further regarding BalSeal® springs, example header block spring concepts are disclosed in U.S. Pat. Nos. 7,195, 523; 7,822,477; 8,096,838; and 8,437,855 all assigned to BalSeal, which, the contents of which are fully incorporated herein by these references. Such BalSeal header block circumferential springs are termed in-line garter springs (element 44 in U.S. Pat. No. 7,195,523), leaf springs (element 50 in U.S. Pat. No. 7,822,477), spring contact elements (element 54 in U.S. Pat. No. 8,096,838) and canted coil springs (element 28 of U.S. Pat. No. 8,437,855). It is noted that all element numbers shown in parenthesis are taken from the BalSeal patents. The BalSeal springs are shown spaced in line in slots in the header block in order to receive and electrically connect to a plurality of electrically conductive rings associated with the proximal plug of an implantable therapy delivery leadwire. These electrically conductive rings are placed at the proximal end of male therapy delivery leadwire connectors typically of AIMDs like cardiac pacemakers, implantable cardioverter defibrillators, neurostimulators and the like. By definition, the rings must be insulated from one another or AIMD functions would be shorted out. Accordingly, all of these in-line spring types are held within an insulative housing (58) as illustrated in the BalSeal '523 patent. The key distinction is illustrated in FIG. 3 of the '523 patent, in that, the leadwire (70) of the BalSeal feedthrough, which would be considered terminal pin 18 of the present application, is electrically and mechanically attached to an outside ring (40), in which a garter spring (44) resides. In no case, in the '523 patent, is it taught or suggested that the leadwire (70) of the '523 could be plugged into the center hole space (12) of the garter spring (44) thereby making a direct electrical connection to the garter spring (44). In summary, there are several key differences between the present invention and the BalSeal '523 invention, including the fact that the BalSeal's garter springs (44) are all spatially in-line and are all contained with an overall insulating body (58) to prevent the garter springs from shorting out to each other. Moreover, all of the leadwires (70) of the feedthrough are taught being attached to the outside ring (40). The feedthrough leadwires (70) are never shown plugged into the center through-bore of the garter spring (44). In contrast, the present application discloses that, whether the contact member is a spring, a prong or other elastically resilient conductive structure, and regardless of whether the contact member resides within a header block, a circuit board or the feedthrough itself, terminal pins are inserted into a central through-bore to connect to the inside of a conductive structure such as a connector housing 66, a terminal pin connector 16 or a cavity 152 within a co-sintered conductive paste-filled via 146. Moreover, the connector housing 66 and/or terminal pin connector 16 of the present invention, are not only electrically conductive, but are also designed for robotic placement on an AIMD active circuit board 106 or an EMI filter circuit board 106', which is not taught by any of the BalSeal patents. Such connector housings 66 and/or terminal pin connectors 16 of the present application are populated adjacently (such as, but not limited to, dual in-line as illustrated in FIG. 9B), or adjacent to each other in varying positions in order to receive terminal pins 18 of an AIMD hermetically sealed feedthrough 14 of an AIMD 12 regardless of the number of terminal pins or the design of the feedthrough. In this way, each terminal pin 18 is electrically connected to electrical conductor 122 of the AIMD header block 118 and the AIMD internal electronic circuitry by plugging in so that the connector housing 66, which is housed in a conductive structure of the AIMD header block 118 or in/on the circuit board, the conductive structure completing the circuit path by electrically connecting to a circuit board land, a circuit board pad, a circuit trace or the like and ultimately, through the terminal pins 18 and the attached AIMD header block 118, to the electrodes of the therapy delivery leads of the AIMD 12.

BalSeal U.S. Pat. No. 7,822,477 is similar to the '523, except that, in the '477 patent, instead of a garter spring (44 of the '523, also known as Gerber springs), a leaf spring (50) of a leaf spring contact element (28) is illustrated. For example, in FIGS. 1 through 4 of the '477 patent, shown is a therapy delivery lead termed a medical lead cable (12) having a male plug proximal end (19) with conductive ring electrical terminals (16) within which the leaf spring (50) resides. Such leaf springs are spaced along the length of the plug in insulative relationship with each other. As the proximal end of the medical lead cable is inserted into the housing (26) of the conductive ring of the '477 patent, the proximal end is inserted and compressed by the leaf spring (50) such that electrical contact is made. There is also an electrical circuit connection, in this case, lead (36), which is connectable to a feedthrough wire (not labelled) of an AIMD feedthrough (see '477 FIG. 11 element 36). The AIMD feedthrough of the '477 patent is inferred as there is no description of the hermetic feedthrough much less of an AIMD active circuit board in the '477 patent specification. Similar to the '523, these leaf springs are in-line and also must be insulated from each other by seal rings (24) or the leaf springs would short out to each other. There is no teaching or suggestion that the leaf springs could be separate individual electrical contacts capable of being populated on an AIMD active electronic circuit board 106 or an EMI filter circuit board 106'. Additionally, there is no teaching or suggestion that would indicate the leaf springs could be separated out and spaced apart in parallel and then individually connected to circuit board electrical connection pads 104, circuit traces 105 or generally to AIMD circuits.

The other FIGS. 5A through 11 of the '477 are very similar to FIGS. 1 through 4 illustrating a number of embodiments of leaf springs, leaf fingers, and prongs. All these embodiments are ultimately connected to a lead (36) extending from the base (52) of the contact element (28), which becomes part of the header block wiring and is routed to an input or output of an electrical circuit of the device. Similar to the '523 patent, the '477 patent also has no teaching or suggestion of the AIMD feedthrough terminal pin itself (terminal pin 18 of the present invention) being inserted into a through-bore of the leaf springs in order to connect to the inside of a conductive structure as taught by the present application. In addition, and in contrast to the teachings of the present application, the leaf springs of the '477 are all in-line and individually insulated to receive the proximal plug contact rings of multi-inductor implantable therapy delivery leadwires, providing only the lead (36) for connection between the header block and pulse generator of an AIMD.

The BalSeal '838 patent also teaches in-line header block spring contact elements to contact the rings of a proximal implantable lead plug. Referring to FIG. 3B of the BalSeal '838 patent, illustrated is a co-formed insulator 26 that electrically isolates the in-line electrical contacts from each other. Similarly to the '523 and '477 patents, there is no teaching or suggestion in the '838 patent that these spring contact elements could be separated out or that the AIMD feedthrough terminal pin itself could be inserted into a through-bore of a spring contact element in order to connect to the inside of an AIMD as taught by the present application, or that even the methods of insulation disclosed in the '838 would even be useful to the invention (s) of the present application.

The BalSeal '855 patent also teaches more of the same, namely in-line coaxial springs insulated from one another. There is no teaching or suggestion that such coaxial springs could be separated individually and populated on an AIMD active electronic circuit board 106 or an EMI filter board 106' as taught by the present application. There is no teaching or suggestion that would indicate separated individual coaxial springs could be spaced apart in parallel so that individual connection could even be made to circuit board electrical connection pads 104, traces 105 or circuits. There is also no teaching or suggestion that an AIMD feedthrough terminal pin itself could be inserted into a through-bore of a coaxial spring in order to connect to the inside of an AIMD as taught by the present application.

In summary, the present application teaches implantable terminal pins 18 of an AIMD hermetically sealed feedthrough 14 that can be inserted into novel terminal pin connectors 16, which may comprise compliant termination structures, including circumferential springs, thereby enabling a removable electrical connection so that replacement or rework of one of an AIMD active electronic circuit board 106, an EMI filter board 106", an AIMD header block 118, or combinations thereof can be done. Additionally, the AIMD active electronic circuit board 106, the EMI filter board 106", the AIMD header block 118, or combinations thereof can be further configured for optional removability so that decisions regarding the removability of any one or more of these components can be made.

For more variations of AIMD header blocks 118, one is referred to U.S. Pat. Nos. 8,437,855; 8,103,348; 8,065,009; 7,822,477; 7,751,893; 7,630,768; 7,295,123; 7,167,749; and 7,068,081, the contents of which are fully incorporated herein by these references. Additionally, U.S. Pat. No. 10,376,688 discloses neurostimulator interconnection apparatus and is also fully incorporated herein by this reference.

Figure 14:
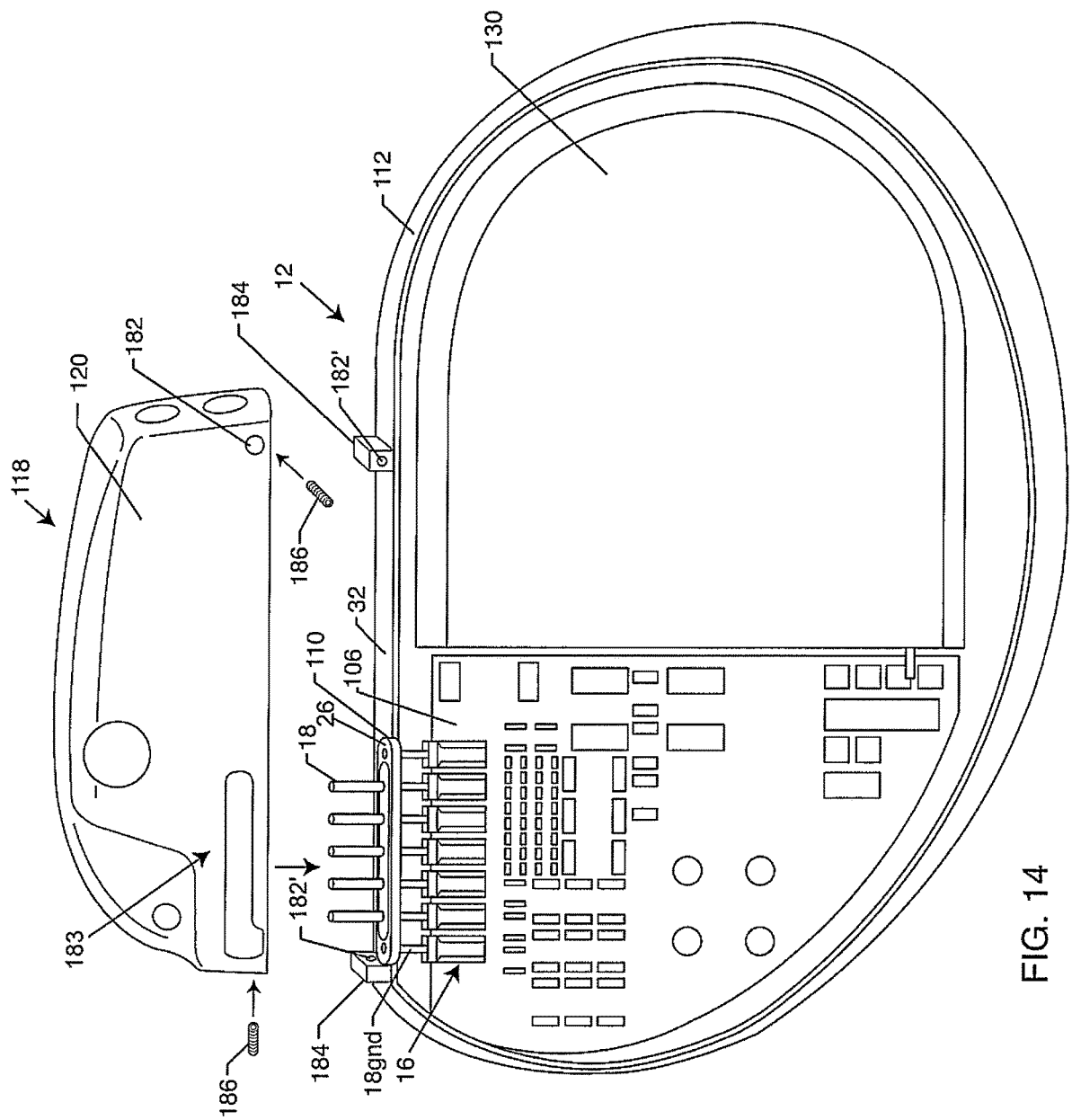
FIG. 14 illustrates the exemplary header block attachable to the AIMD pulse generator of FIG. 9, the AIMD header block comprising the exemplary components of FIGS. 11-13.

FIG. 14 illustrates an AIMD 12, which as previously disclosed, can be a variety of active implantable medical devices. The AIMD shown illustrates a metallic first casing half 112, which has been laser tack welded to the ferrule 26 of the AIMD hermetically sealed feedthrough 14. Only a first casing half 112 is illustrated so that the internal components of the AIMD 12 are visible. It is understood that a second casing half 114 is mated to the first casing half, which is then laser welded forming a continuous weld seam around the perimeters of the ferrule 26 and the first and second case halves, thereby forming a mechanical and hermetically sealed AIMD casing 32. Accordingly, FIG. 14 illustrates some internal components inside a mechanically and hermetically sealed AIMD casing, for example, an AIMD battery, an AIMD circuit board and exemplary terminal pin connectors 16 of the present application. In this embodiment, a push force is applied to the AIMD active electronic circuit board 106 such that each terminal pin 18 is inserted into its respective terminal pin connector 16.

Similarly, while it is understood that various components (see FIGS. 11-13) exist within the AIMD header block 118, for simplicity, the AIMD header block 118 only illustrates the formed insulating structure 120, an opening 183, and various holes such as hole 182 into which a threaded fastener 186 eventually secures the header block to a header fixation block 184. Traditionally, the opening 183 of the header block 118 is used to connect the terminal pins 18 extending from the body fluid side of the AIMD pulse generator to the electrical conductors (not shown) residing within the header block. Referring again to FIG. 14, the AIMD header block 118 of the present application, depending on the design of the AIMD hermetically sealed feedthrough 14, can comprise any of the terminal pin connector 16 embodiments of the present application. A push force is then applied to AIMD header block 118 such that the terminal pins 18 are each inserted into its respective terminal pin connector 16. The opening 183 now becomes an optional feature, as the formed insulating structure 120 does not require the opening 183 to connect the header to the terminal pins of the AIMD pulse generator. However, if the opening 183 is present, the opening can be closed by applying and curing a relatively hard, suitable insulative polymer as traditionally done. It is contemplated that a feedthrough capacitor 24, 24', or 24" (not shown) or an EMI filter circuit board 106' may be installed on or near the AIMD hermetically sealed feedthrough 14 of FIG. 14 on the device side between the terminal pins 18 and the terminal pin connectors 16. Alternately, the feedthrough capacitor 24, 24', or 24" (not shown) may be installed on the body fluid side of the AIMD hermetically sealed feedthrough 14, instead of on the device side. Once an AIMD header block 118 is plugged in place on the AIMD casing 32 and the terminal pins 18 of the AIMD hermetically sealed feedthrough 14 are inserted, it is important that the AIMD header block 118 be mechanically affixed in place so that the AIMD header block 118 does not come loose or fall off the AIMD pulse generator. This can be done by one of: using the threaded fastener 186 and the header fixation block 184, adding an adhesive (not shown), using connector features as indicated in FIG. 14A, and combinations thereof.

Figure 14A:
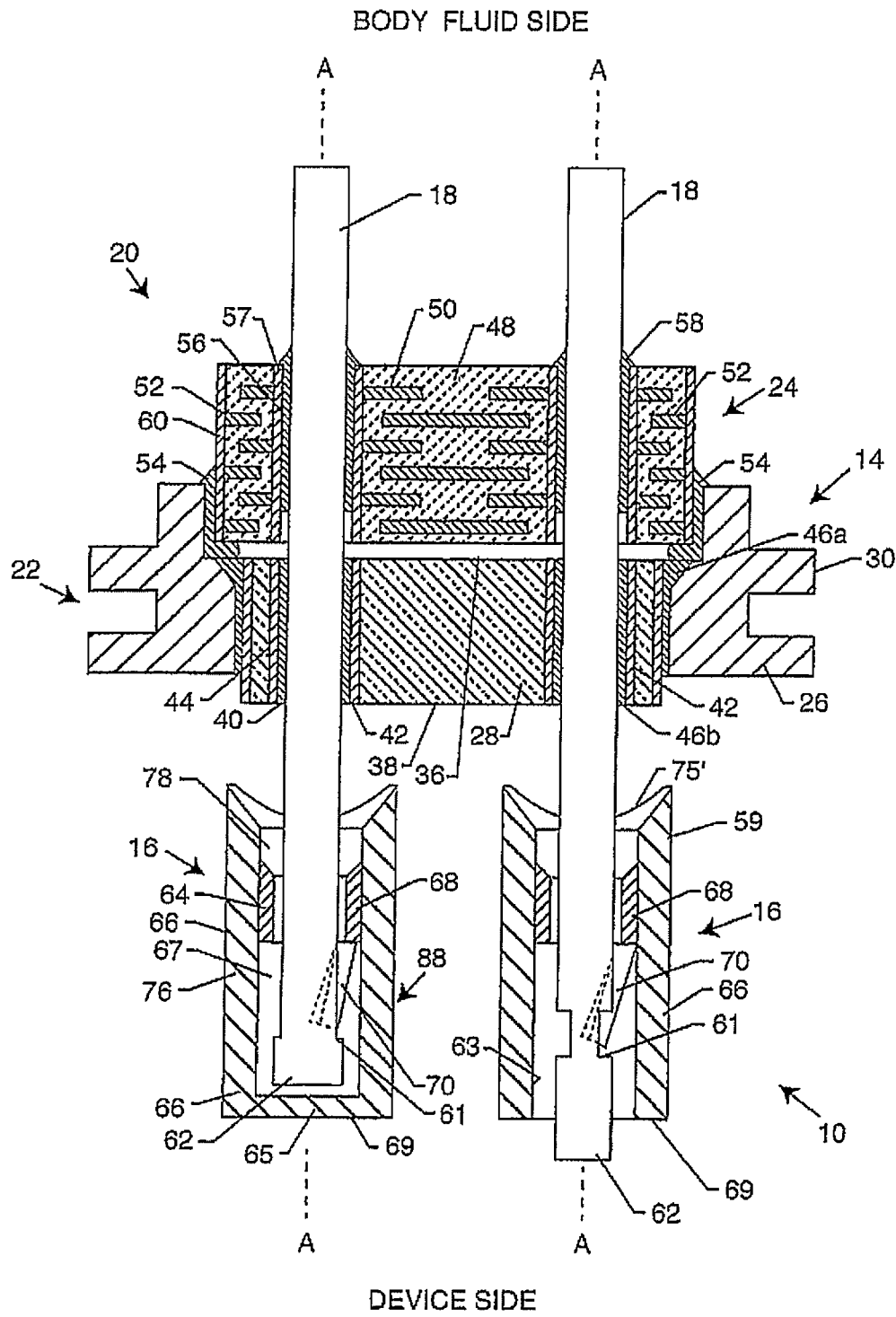
FIG. 14A shows a cross-sectional view of an alternative embodiment of a feedthrough capacitor connector assembly.

Referring now to FIG. 14A, one can see that the prongs 70 are captured in a notch 61 of the terminal pin 18. The notch of FIG. 14A illustrates corners that essentially have right angles. As such, the notch 61 enables the prongs 70 to more firmly grip the terminal pin 18. Such a firmer grip of the terminal pin 18 may require increased pull force of a terminal pin connector 16 for removal from the terminal pin 18. In the case of required increased pull force, removal of the terminal pin connector 16 can be facilitated by use of a tool, such as a slender tool inserted into and along the alignment flange 75' into the connector housing throughbore 78 of the connector housing 66 to push prong 70 outwardly from the terminal pin 18 thereby opening the prong 70 and facilitating release from the terminal pin 18. A tool is not illustrated, however, could be a structure similar to a dental pick or other a slender probe that could slide along the terminal pin 18 between the terminal pin and the prong 70, thereby opening the prong 70.

An alternative for releasing the prong 70 from the notch 61 of the terminal pin 18 of FIG. 14A would be to manufacture the prong of a shape-memory alloys such as, but not limited to: Nitinol (a nickel-titanium alloy: TiNi), or a Nitinol-based alloy, a copper-based shape-memory alloy (such as copper-aluminum-nickel alloy: Cu—Al—Ni or copper-zinc-aluminum alloy: Cu—Zn Al) or an iron-based shape-memory alloy (using iron alloyed with, for example, zinc, copper, and gold or an iron-manganese-silicon alloy: Fe—Mn—Si). Shape-memory alloys are stable and provide practicality of the terminal pin connectors 16 of the present application in that such shape-memory alloys possess superior thermo-mechanic performance. As such, shape-memory alloys can exist in two different phases, with three different crystal structures (i.e., twinned martensite, de-twinned martensite, and austenite), and six possible transformations. Shape-memory alloy phase transformation is only dependent on temperature and stress, thereby is a diffusionless transition between two phases that results in the special shape-memory properties of these alloys. It is a difference between a heating phase transition and a cooling phase transition where some of the mechanical energy within a formed structure is lost in the phase transition process. Hence, the material properties of the shape-memory alloy, such as the alloy's composition and work hardening, defines the temperatures required for a mechanical energy loss such that the deformation resultant from fabricating a structure can be reversed. Hence, shape-memory alloys are generally selected based on the needs of an application and an alloy's specific phase transformation temperatures. Such remarkable material properties are exactly why these shape-memory alloys are widely used in applications, including medical applications. For example, Nitinol is widely used for this reason in medical stents. Nitinol is a shape-memory alloy, so can 'remember' its original manufactured shape and can return to the original shape with a temperature change. Nitinol has low elastic modulus, and its effective strain range is large thereby having a wider optimal phase transformation force zone. Nitinol's low elastic modulus provides a greater range of phase transformation activation thus can be tuned for the transformation such that adjustments can be made to the temperature difference such that a prong 70 can be compositionally or harden adjusted such that the degree of grip of a prong 70 to a terminal pin 18 and/or the pull force required for removal of a prong 70 from a terminal pin 18 can be customized. In the example of stents, a Nitinol stent with a transition temperature of 30° C. can be compressed at a first temperature ≤20° C. The Nitinol stent will stay compressed until the temperature is increased to a second temperature >30° C. The Nitinol stent will then expand to its pre-set shape. If the Nitinol stent is kept cold during introduction into the body it will not expand, thereby facilitating navigation through the vasculature to the stent placement site within the vasculature. When the Nitinol stent is positioned at the desired location it warms to the second temperature by means of body heat and self-expands to its original size. Alternatively, when a first temperature ≤20° C. is prohibitive, pending the tissue within which the stent is being positioned, a self-expanding Nitinol stent could be built with a phase transition temperature of, for example, 40° C. and then inserted at a first temperature of ≥20° C. but less than ≤30° C. These stents would have to be heated after delivery to the site to make them expand, thereby achieving the same end result. Alternatively, when temperature change itself is prohibitive, deployment of a stent can leverage the super-elasticity properties of Nitinol, wherein the sent is compressed and constrained in a stent delivery system to prevent premature deployment, and then released of the compression and constraint when positioned within the tissue wherein the self-expanding stent then returns to its original shape. In addition to stents, the super-elasticity property of Nitinol is use in other medical applications, such as catheters, super-elastic needles, and even for reconnecting the intestine after removing a pathology. The medical industry leverages the super-elasticity of Nitinol in these applications, as the massive elasticity of Nitinol permits compression and constraint to an extremely small profile, and when the compression and constraint is released, the Nitinol device then returns to its original size. As such, medical procedures such as the procedures mentioned, are enabled by, for example, facilitating navigation of catheters in the vasculature, accurately positioning needles for biopsy, or even improving efficacy of intestinal reconnections. Hence, Nitinol can be leveraged not only for its thermal phase transformation properties, but also for its super-elasticity properties.

Referring once again to FIG. 14A, it is noted herein that environmental testing criteria for electronics/microelectronics of hermetically sealed AIMDs 14 are generally dictated by Military and Space Specification MIL-SPEC-883, which evaluates the ability of microcircuits (a part, a packaging, or a device) to sustain harsh environments. For example, to assess the resistance of a part to extremes of high and low temperatures, and/or to the effect of alternate exposures to temperature extremes, temperature cycling testing could be conducted. Such temperature cycling testing would be conducted, for example, on the AIMD header block 118, the AIMD active electronic circuit board 106, and the EMI filter circuit board 106' at temperatures ranging from −55° C. to +125° C. specified by the military standard. Hence, the terminal pin connector 16 and/or its components comprising a shape-memory alloy, such as the prong 70 of FIG. 14A, can be formed at a first temperature and opened to release from the terminal pin 18 at a second temperature different from the first temperature, the first and the second temperatures being within the temperature cycling test range. In summary, the full temperature range of −55° C. to +125° C. is usable to form a terminal pin connector 16 and/or its components comprising a shape-memory alloy at one temperature, and then remove the terminal pin connector 16 and/or its components at another temperature, when an assembly comprising the terminal pin connector 16 and/or its components is deemed defective and requires replacement or rework. In the example of prong 70 of FIG. 14A comprising a shape-memory alloy, the prong 70 would be capable of 'resetting' itself to an original shape so that release from terminal pin 18 can be facilitated.

Referring once again to FIG. 14, one can see that header fixation blocks 184 are attached to at least casing half 112 (header fixation blocks 184 can alternatively be attached to the AIMD casing 32 after laser welding) on the right-hand side and on the left-hand side. The header fixation blocks 184 can be attached by laser welding, gold brazing or the like. Prior art header blocks generally have one or more holes 182 such that a material (for example, a polymer) can be squeezed into hole 182 and around fixation blocks to affix and firmly secure a header block to the AIMD pulse generator. Such a prior art approach is a particular problem when an AIMD header block is deemed defective, for example, when a defective connector port, a defective BalSeal® spring, or a cosmetic defect is determined, as it becomes very difficult, if not impossible, to remove the AIMD header block for replacement without rejectable damage to the AIMD 12. Once the AIMD header block is affixed, the AIMD 12 is fully assembled, and includes all of its components, some substantially costly, such as the feedthrough, the battery, the electronics, and the casing among others. Consequently, when a fully assembled AIMD 12 is scrapped, a manufacturer takes a substantial financial hit to the bottom line.

As FIG. 14 illustrates, the header fixation blocks 184 comprise a hole 182', which is generally drilled and tapped with machined threads or equivalent such that when the AIMD header block 118 is positioned and aligned with holes 182', a threaded fastener 186 can be inserted into each hole and screwed in to attach the AIMD header block 118 to each header fixation block 184 forming a reliable mechanical attachment of the header block 118 to the AIMD casing 32. The threaded fastener 186 can comprise a set screw, the set screw comprising a head. The head of the set screw may comprise one of a Torx head, an Allen head, a hex head, or an equivalently structured head. The head of the set screw may alternately comprise a flat head. The hole 182 of the AIMD header block 118 may comprise a counter-bore such that, when the head is fastened tightly, the AIMD header block 118 is firmly squeezed against the header fixation block 184, which acts to prevent vertical dislocation of the AIMD header block 118 in addition to preventing the AIMD header block from wobbling. There are two header fixation blocks 184 illustrated in FIG. 14, one on the right-hand side and one on the left-hand side, each header fixation block illustrating different embodiments. The header fixation block 184 embodiment on the left-hand side of FIG. 14 illustrates hole 182' through the thickness of the long side of the header fixation block. The header fixation block 184 embodiment on the right-hand side of FIG. 14 illustrates hole 182' through the length of the long side of the header fixation block. Accordingly, the AIMD header block 118 would have a corresponding hole 182 for a threaded fastener 186 to be positioned and screwed through hole 182 of the header block 118 and hole 182' of the header fixation block 184, thereby removably affixing the AIMD header block 118 to the AIMD pulse generator forming a fully assembled AIMD 12. It is contemplated that different types, styles and designs of header fixation blocks can be used alternately to the header fixation blocks 184 shown in FIG. 14.

Referring once again to FIG. 14, when an AIMD header block 118 is connected to the terminal pins 18 of the AIMD hermetically sealed feedthrough 14 and is properly seated against the body fluid side surface of the AIMD pulse generator (not labelled), an electrically insulative sealant, such as an FDA-approved silicone or the like, generally resides between the AIMD header block 118 and the body fluid side surface of the AIMD pulse generator. The sealant is very important as the sealant prevents electrical currents from flowing through any body fluids that may migrate along either the terminal pins 18 of the AIMD hermetically sealed feedthrough of the AIMD 12 and/or into the terminal pin connectors 16. Accordingly, an appropriate amount of sealant is preferred to prevent undesirable stray electronic current leakage, to avoid unintended attenuation of biological sensing signals, or, in the case of a high voltage device like an implantable cardioverter defibrillator (ICD), to prevent high voltage flashovers. Having a suitable sealant is also important to a sustained biostability of materials present at this interface. For example, it is well known to those skilled in the art that gold under voltage bias in an actively functioning implanted AIMD is subject to electrolytic electromigration in the presence of body fluid. For electrolytic electromigration of a metal to occur, moisture on the surface of the metal and a high electric field across the metal are required. Such conditions are often caused by a combination of a voltage difference and a wet environment. It is noted herein that in the case of hermetic feedthroughs comprising gold braze, if the gold braze is under voltage bias and exposed to body fluid, the electrolytic electromigration can occur. When an AIMD is actively delivering electrical therapy, the gold braze of the hermetic feedthrough of the AIMD is under voltage bias, satisfying the voltage difference requirement for electrolytic electromigration. If the gold braze is also exposed to body fluid, then the wet environment requirement for electrolytic electromigration is satisfied. Exacerbating the conditions of electrolytic electromigration of the gold is that body fluids comprise electrolytes, which are minerals such as sodium, calcium, potassium, chloride, phosphate, and magnesium that carry an electric charge. Thus, the combination of the voltage bias across the gold braze and the presence of body fluid comprising electrolytes on the surface of the gold braze, migration of gold from the braze is enabled, such that the migrating gold can electroplate undesirably redepositing elsewhere along the surface of AIMD, and can cause life-threatening premature AIMD failure, premature power source depletion, or both. Sealants are therefore a critical adjunct of the present invention.

Figure 15:
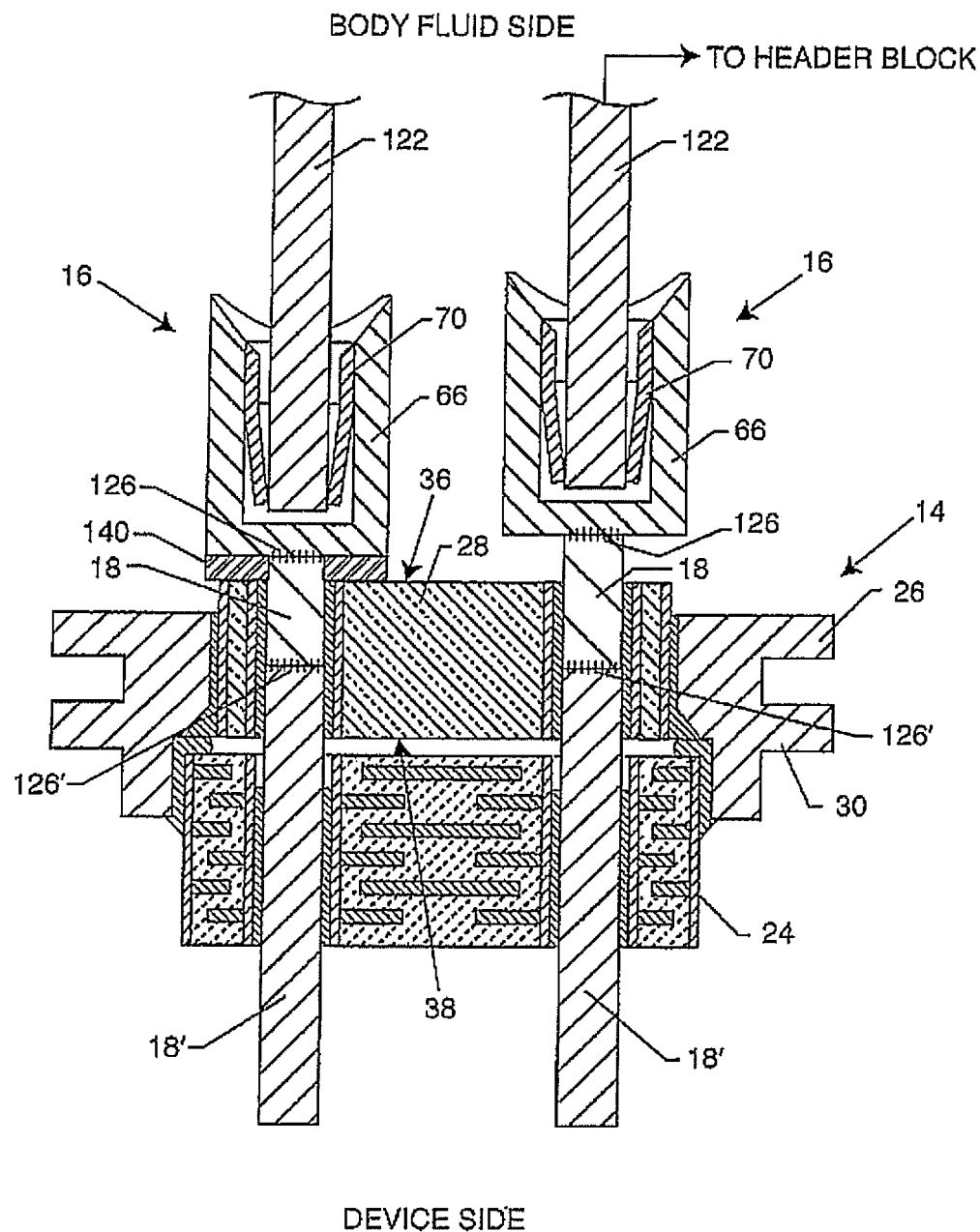
FIG. 15 shows a cross-sectional view of an alternative embodiment of a feedthrough capacitor connector assembly.

FIG. 15 is very similar to FIG. 3C in that we have an AIMD hermetically sealed feedthrough 14 with a feedthrough capacitor 24 disposed on the device side. On the body fluid side, we have the terminal pin connector 16 that is previously described which is now a part of an AIMD header block 118 (not shown). First of all, the terminal pins 18, 18' are two-part pins. Two-part pins are more thoroughly described in U.S. Pat. No. 10,272,252, the contents of which are fully incorporated herein by this reference. In this case, the AIMD header block 118 is different in that the terminal pin connectors 16 are not actually disposed inside the AIMD header block 118. Instead, the terminal pin connectors 16 are electrically and mechanically attached to the terminal pins 18 that are coming through to the body fluid side insulator surface 36 of the insulator 28 AIMD hermetically sealed feedthrough. On the right-hand side, illustrated are terminal pins 18 that extend outwardly beyond the body fluid side insulator surface 36 of the insulator 28 o which an electrical and mechanical connection 126 is made a terminal pin connector 16. Since the electrical connection 126 is on the body fluid side, the electrical connection must be biocompatible, hence, would typically be made by one of laser welding or brazing. However, other joining processes can be used to make electrical connection 126, including micro welding, micro TIG welding, ultrasonic welding, resistance welding, friction welding, butt welding, arc welding, gas welding, projection welding, flash welding, upset welding, solid state welding, diffusion welding, induction welding, percussion welding, electron beam welding, multi-stage brazing, or reactive brazing. On the left-hand side of FIG. 15, illustrated is a terminal pin connector 16 that is pressed down onto an insulating washer 140, which is in turn, is pressed down against the body fluid side insulator surface 36 of the insulator 28. The insulating washer 140 must also be biocompatible, biostable, and non-toxic so would typically be made of a polyimide or an adhesive-backed polyimide. There are a number of other biocompatible insulating washer materials that could be used as an alternative, such as biocompatible and biostable ceramics, plastics, polymers, paper, rubber, glass, glass fiber paper, glass ceramics, insulating metal oxides, diamond, and combinations thereof. The insulating washer 140 may further comprise alumina ($Al_2O_3$), zirconia ($ZrO_2$) and/or various stabilized or partially stabilized zirconia including ZTA and ATZ, fused silica, silicon nitride, alumina toughened zirconia, zirconia toughened alumina, zirconium dioxide, yttrium-toughened zirconium oxide (Y-TZP), aluminum nitride (AlN), magnesium oxide (MgO), piezoceramic materials, barium zirconium titanium doped oxide, barium cerium titanium doped oxide, sodium-potassium-niobate, calcium oxide, cerium oxide, titanium oxide, apatite-wollastonite (A-W) glass ceramic, boron nitride, alumina silicate, and combinations thereof. The insulating washer 140 may be rigid (resists bending and forced shaping) or flexible (capable of easily being shaped and/or bent without breaking). As previously described, the electrical conductors 122, illustrated in the exemplary FIG. 15 are leadwires, of the AIMD header block 118 must also be biocompatible, biostable, and non-toxic. Such electrical conductors 122 are selected from the group consisting of titanium, tantalum, platinum, palladium, niobium, tantalum, gold, silver, iridium, rhenium, rhodium, tungsten, vanadium, zirconium and alloys or combinations thereof. Additionally, the electrical conductors 122 of the AIMD header block 118 may further be an alloy selected from the group consisting of a cobalt chromium alloy, a cobalt chromium molybdenum alloy, a cobalt chromium nickel iron molybdenum manganese alloy, a cobalt chromium tungsten nickel iron manganese foil, a cobalt nickel chromium iron molybdenum titanium alloy, a cobalt nickel chromium iron molybdenum tungsten titanium alloy, a cobalt nickel chromium molybdenum alloy, a copper aluminum nickel alloy, a gold platinum palladium silver indium alloy, a nickel platinum alloy, Nitinol, a nickel titanium alloy, a nickel titanium aluminum alloy, a niobium-titanium alloy, a platinum iridium alloy, a platinum palladium gold alloy, a titanium aluminum vanadium alloy, a titanium based aluminum iron alloy, a titanium based aluminum molybdenum zirconium alloy, a titanium based molybdenum niobium alloy, a titanium based molybdenum zirconium iron alloy, a titanium based niobium zirconium alloy, a titanium based niobium zirconium tantalum alloy, a titanium molybdenum alloy, a titanium niobium alloy, a titanium platinum alloy, a titanium-based molybdenum zirconium tin alloy, MP35N®, Elgiloy® and biocompatible stainless steels, particularly 316L stainless steel. Referring now to the terminal pin connector 16, typically the connector housing 66, the clip 64 including its prongs 70 would be of titanium or similar biocompatible material, although any of the above biocompatible and biostable materials may alternatively be used as well. The MRI considerations previously discussed are also applicable to these terminal pin connectors and compliant termination structures.

It is contemplated that any of the terminal pin connectors and compliant termination structures disclosed in any of the drawings herein may comprise a shape-memory alloy, for example, but not limited to, Nitinol or a Nitinol-based alloy. As previously disclosed, Nitinol enables insertion at a first temperature and extraction at a second temperature. Additionally, the super-elasticity properties of Nitinol previously disclosed could be a substantially beneficial aspect during manufacturing, as the massive elasticity of Nitinol enables compression and constraint of AIMD components comprising Nitinol to a significantly smaller profile, even a smaller completely flat or curved profile, to facilitate insertion, and then when compression and constraint is released, the component returns to its original size. Moreover, Nitinol is capable of being locally modified to impart different spring constants at different points or locations on or about a specific site or area of a component, including terminal pin connectors and compliant termination structures taught herein.

Figure 16:
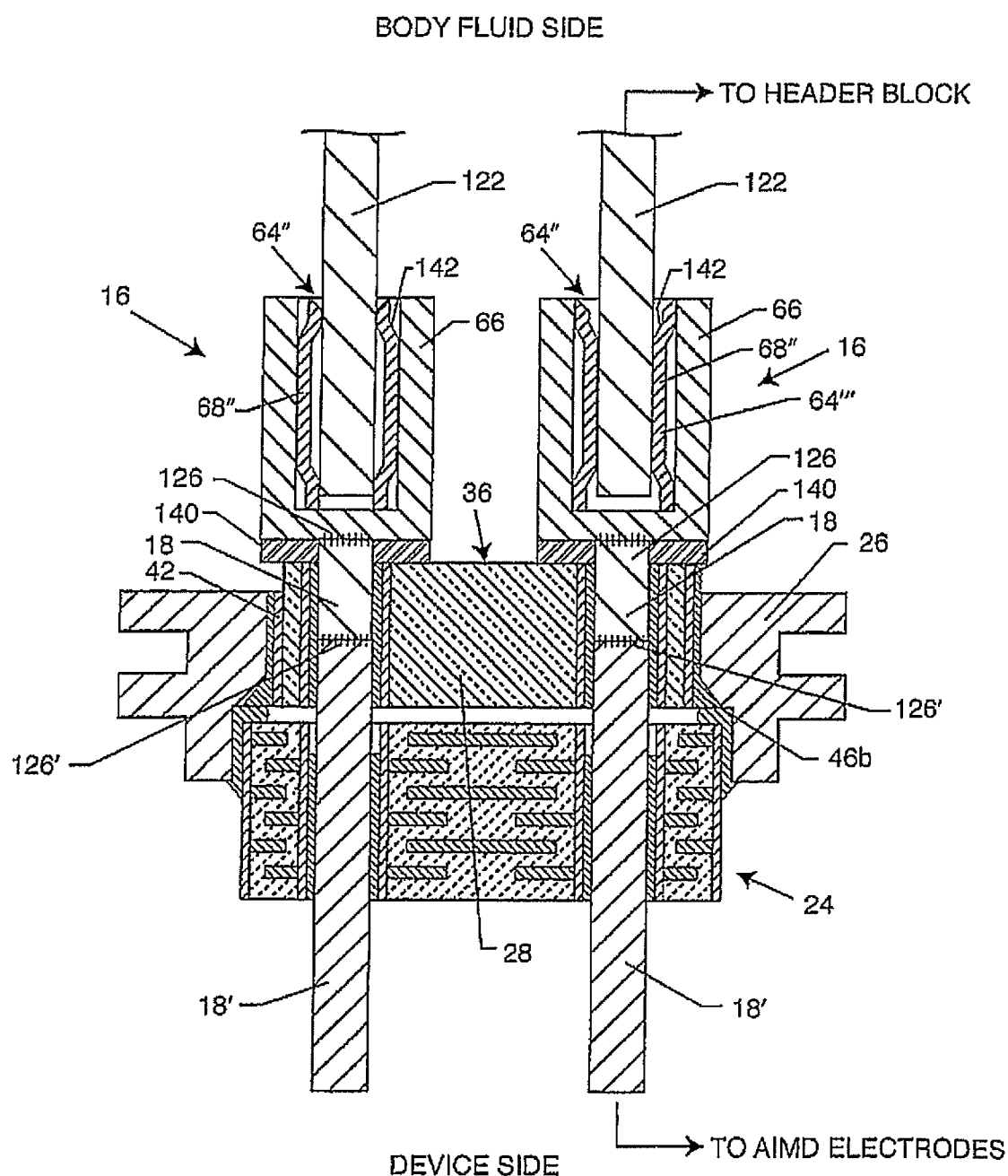
FIG. 16 shows a cross-sectional view of an alternative embodiment of a feedthrough capacitor connector assembly.

FIG. 16 is very similar to FIG. 15 except that both of the connector housings 66 have been pressed down against their respective insulating washers 140 against the body fluid side insulator surface 36 of the alumina insulator 28, and instead of clip 64, spring clips 64" and 64''' are illustrated. Insulating washers 140 of the present application may comprise a solid insulating structure (like mica, nylon, silicone rubber, plastic, ceramic, glass, composite, polytetrafluoroethylene, ethylene tetrafluoroethylene, polycarbonate, polyetherimide, polyoxymethylene, acetal, polyacetal, polyformaldehyde, phenolic and other similar non-metallic materials, and combinations thereof), a cured liquid insulating material (like epoxy, polyester, liquid silicone rubber, polyurethane, or other similar materials, and combinations thereof), or an insulating adhesive washer (like polyimide, silicone polyimide, polyurethane, silicone, polysulfide and other similar materials, and combinations thereof).

Referring to the left-hand side of FIG. 16, illustrated is a conductive sputter layer 42 (two sputter layers are illustrated by element 42 of FIG. 16, however, one sputter layer may alternatively be used), which is selectively applied to the perimeter of the insulator 28 such that the conductive sputter layer 42 does not extend outwardly beyond the surface of the ferrule 26, thereby does not contact the terminal pin connector 16. In this case, the insulating washer 140 could be removed because there is no longer a possibility of the connector housing 66 of the terminal pin connector 16 shorting out to the selectively applied metallization layer 42 of the insulator 28. Hence, the insulating washer 140 on the left-hand side can be eliminated, thereby enabling the terminal pin connector 16 to be dropped down onto the body fluid side insulator surface 36 of the insulator 28.

Referring to the right-hand side of FIG. 16, a conductive sputter layer 42 is applied to the full height of the perimeter of the insulator 28 such that the conductive sputter layer 42 is present around the entire perimeter surface of the insulator 28. In this case, the conductive sputter layer 42 (which is illustrated as two sputter layers but could be one sputter layer) contacts both the terminal pin connector 16 and the terminal ferrule 26. In this case, the insulating washer 140 is required to prevent shorting of the terminal pin connector 16 to the metallization layer 42; however, instead of insulating washer 140, the insulating washer 140 could be eliminated and alternatively, be replaced by insulating coatings on the bottom of the connector housing 66 such as an insulative paint, an insulative polymer, a sputtered layer of ceramic like alumina, an electrically insulating foil, or a vapor deposited insulating film. Other coating processes may include: plasma spraying, thermal spraying, spin coating, dip coating, foil lamination, and thin film deposited layers. The electrically insulating coating may comprise one or more layers.

The connector housings 66, as described herein, may be metallic and therefore, electrically conductive or may alternatively be an electrically insulating material that has an electrically conductive or a metallic coating on its surfaces. The latter would make possible miniature, sub-miniature and/or intricately designed connector housings 66, which could conceivably be required for AIMDs like intraocular implants, some brain stimulation devices, for example for babies or small children, or AIMDs having high count, high density and/or close pitched feedthrough conductor requirements. For example, the connector housing 66 could be plastic and then coated with conductive materials very much the same way that personal computers are made of plastic and then have a plated electromagnetic interference shield. Furthermore, the connector housing 66 could comprise a ceramic, a thermal-setting plastic, an injected molded plastic, polytetrafluoroethylene (PTFE), nylon, silicone rubber, plastic, ceramic, glass, composite, polytetrafluoroethylene, ethylene tetrafluoroethylene, polycarbonate, polyetherimide, polyoxymethylene, acetal, polyacetal, polyformaldehyde, phenolic and other similar non-metallic materials, and combinations thereof. The connector housing 66 could also comprise a fiberglass material. Irrespective of the insulating material, when an insulative material is used for the connector housing 66, it is contemplated that an electrically conductive coating must be applied. The electrically conductive coating may comprise an electrically conductive foil, a metallization, a plating, or a vapor deposited film. The electrically conductive coating may be applied either by painting, electroplating, bulk plating, or sputtering. As previously describe for clip 64, coating processes for applying an electrically conductive coating to an electrically insulating housing 66 may further include: physical vapor deposition, chemical vapor deposition, electrostatic spray assisted vapor deposition (ESAVD), electron beam physical vapor deposition (EBPVD), ion plating, ion beam assisted deposition (IBAD), magnetron sputtering, pulsed laser deposition, sputter deposition, vacuum deposition, pulsed electron deposition (PED), plating, electroless plating, electroplating, spraying, painting, plasma spraying, thermal spraying, spin coating, dip coating, metal foil lamination, and thin film deposited layers. The electrically conductive coating may comprise one or more layers. The one or more layers of the electrically conductive coating may further comprise, but is not limited to, copper, tin, aluminum, stainless steel, titanium, gold, platinum, palladium, carbon, palladium alloys, gold alloys, niobium, tantalum, palladium alloys, silver, silver alloys, zirconium, hafnium, Nitinol, Co—Cr—Ni alloys such as MP35N, Havar®, Elgiloy®, stainless steel, ZrC, ZrN, TiN, NbO, TiC and TaC, platinum alloys such as, but not limited to platinum iridium alloys, other associated alloys and the superalloys with nonlimiting examples such as the Hastelloys, Inconels, Monels, Waspaloys, and Renes, and combinations thereof. Body fluid side coated connector housing 66 would only include the biocompatible biostable materials within this list, including the biocompatible and biostable materials previously disclosed.

In the present invention, various spring-like elastically resilient and compliant termination structures are taught, including prongs 70, clip 64 and spring clips 64', 64", 64'" and the like. Generally, these would comprise one or more electrically conductive materials, however, could also be formed of various types of insulating materials described above for connector housing 66. It is understood that the materials, coatings, and processes disclosed for connector housing 66 above apply to all the spring-like elastically resilient and compliant termination structures described herein.

Referring once again to FIG. 16, in this embodiment, both the left-hand side and the right-hand side connector housings 66 incorporate spring clips 64" (on the left-hand side) and 64'" (on the right-hand side), neither spring clip comprising any prong(s) 70 as previously disclosed. The spring clip 64" and 64'" comprise elongated members 68" instead of prongs. The spring clip 64" on the left-hand side comprises a concave shape elongate member 68", which is opposite the elongate shape 68" of the spring clip 64'" on the right-hand side, which comprises a convex shape as previously introduced in FIG. 5E. As previously taught for FIG. 5E, either of these spring clips 64", 64'" can be slotted. The metallic connector housing 66 of FIG. 16 could be of titanium or other biocompatible conductive metallic material previously disclosed, or alternatively, a plastic, composite, ceramic or polymeric non-conductive material plated, coated or otherwise covered with an electrically conductive material, which can also be any of the previously disclosed materials; the spring clip 64" and 64'" reside within the connector housing 66 of the terminal pin connector 16. During AIMD header block 118 insertion, electrical conductor 122 is inserted into the connector housing 66 of the terminal pin connector 16, slides into spring clip 64'" on the right-hand side and is gripped by the elongated member 68", while the electrical conductor 122 inserted into spring clip 64" on the left-hand side is gripped by the radiused area 142 at the ends of the elongated member 68". It is noted herein that the grip of the electrical conductor 122 disclosed above for the right and left-hand sides clip embodiments also apply to the insertion of header block leadwires or AIMD terminal pins.

FIG. 17 is very similar to FIGS. 15 and 16, except in this case, the spring clip 64'" consists of one or more waved tines 79, as indicated. This is best shown in FIG. 18, which is an enlarged view of the spring clip 64'". FIG. 18 illustrates the waved tines 79 of the spring clip 64'" having a flat tine end, however, any configuration at the end of the tine may be used, such as curved, pointed or radiused. As previously described, it is very important that the spring rate be adjusted so that a tight grip be formed on the electrical conductor 122 (or leadwire or terminal pin) and at the same time, the elastic limit of the materials of 64'" are not exceeded. In other words, any permanent set to the times of spring clip 64''' of FIG. 18 should be avoided. Materials, such as constantan (a copper-nickel alloy) cannot be used for the structure shown in FIG. 18, as, in FIG. 18, the structure is shown on the body fluid side, and constantan is not biocompatible. The structure shown, however, when use on the device side can comprise constantan. Instead, on the body fluid, any of the biocompatible, biostable, and non-toxic materials disclosed previously for the electrical conductors 122 or leadwires of the AIMD header block 118 may be used as long as the design being used has a spring constant that supports the intent of the connection. The spring constant of any material used in any of the terminal pin connector 16 designs disclosed herein, including the design of the presently disclosed FIGS. 17 and 18 may be adjusted for optimal spring characteristics and durability by one of: varying material thickness, diameter, or size of the prongs, tines, fingers, or walls of the structure; plating with a complementary material or materials; heat treating; degree of engagement surface area; or combinations thereof. In the specific case of Nitinol, in addition to the above spring constant adjustment options, the spring constant of a monolithic Nitinol structure may also be adjusted by laser-processing, wherein a laser is used to change the composition of the Nitinol locally within the monolithic structure in order to add multiple memories within the monolithic Nitinol structure. By laser-processing, the localized compositional changes can provide customized elasticity and or phase transition temperature to each prong in the structure or can provided pairing of elasticities or phase transition temperatures between two or more prongs so that flexibility in force required for insertion or retraction is imparted to the monolithic structure. Further, if an AIMD application has special insertion and/or retraction requirements, one or more prongs can even be selectively removed from the monolithic Nitinol structure to achieve a target insertion and/or retraction force. While FIG. 18 shows a specific embodiment, it is understood by one skilled in the art that the shape of the prongs/tines can be of any configuration designed to achieve the required spring constants.

Referring now to U.S. Pat. No. 6,987,660, the contents of which are fully incorporated herein by this reference, one will see that the '660 patent teaches contact springs (136). The contact springs (136) are inserted into the active passageways of feedthrough capacitors (100, 400) to affect an electrical connection between a hermetic seal terminal pin (122) and the capacitor active passageways inside the diameter metallization (110), and, in turn, to the capacitor active electrode plates (106). The '660 patent teaches that the contact springs (136) are to facilitate low cost, high-speed manufacturing, and to also eliminate several expensive steps such as elimination of insulating washers and centrifuging of thermal setting conductive polymers, which are time consuming and messy processes. The '660 patent never suggests, teaches or otherwise mentions or anticipates removable AIMD active electronic circuit boards 106, EMI filter circuit boards 106' or AIMD header blocks 118 as taught by the present application. The words "circuit board" or "header block" never even appear in the '660 patent. At the time of filing, the '660 patent inventors did not contemplate or appreciate the need for removable AIMD circuit board (s) 106, 106' or a removable AIMD header block 118. Furthermore, the '660 patent teaches away from removability in that the feedthrough capacitor (100, 400) is not suggested or taught to ever be removable. As the '660 patent states in column 8, lines 38 to 40: "[t]here is no reason to remove the feedthrough capacitor (400) once it is installed", removability of the feedthrough capacitor was not considered, as the feedthrough capacitors of the '660 patent are not capable of removal without damaging them, thereby dispelling any notion of feedthrough capacitor removal.

Referring once again to FIGS. 16 and 17, the terminal pin connectors 16 are shown on the body fluid side, but it is contemplated that they could be attached to an AIMD active electronic circuit board 106, or an EMI filter circuit board 106' as implied by the device side portion of FIG. 17. Regarding the device side portion of FIG. 17, the circuit boards 106, 106' would reside inside the hermetically sealed casing 32 (not shown) of the AIMD 12 and the terminal pin connector 16 would, therefore, not need to be biocompatible. Accordingly, when disposed on the device side of an AIMD, the terminal pin connectors 16 of FIGS. 16 and 17 do not need to comprise biocompatible, biostable, and non-toxic materials, thus constantan could be effectively used.

In FIGS. 18 and 19, circuit board 106, 106' need not be perpendicular to the AIMD hermetically sealed feedthrough 14 and its terminal pins 18, 18' (two-part terminal pins). Alternatively, the terminal pins 18' (device side part of the two-part pin) could be bent at an angle (such as approximately a 90° angle) such that they could engage AIMD active electronic circuit board 106 that may be lying parallel to the AIMD hermetically sealed feedthrough 14.

FIG. 19 is another embodiment illustrating the terminal pin 18, 18' comprising a compliant termination structure 81 having a spring-like elastically resilient press-in zone that can be inserted or 'press fit' into a conductive plated or terminated circuit board via hole 109 having circuit traces (not shown) routed to them. Such a compliant termination structure 81 can be integrated with the device side portion of a two-part pin 18', while the body fluid side portion of a two-part pin 18 comprises a biocompatible biostable non-toxic terminal pin, thereby providing a unique cost-effective AIMD hermetically sealed feedthrough 14 embodiment. While the compliant termination structure 81 shown has a specific configuration, any compliant termination designs featuring an elastic-resilient spring-like behavior during insertion may be used. In this embodiment, the circuit board can comprise metallic eyelets 194, which are robust and allow for the insertion of the compliant termination structure 81 of the terminal pins 18'. It is understood that connector housings 66 could be used instead of metallic eyelets 194. Additionally, the AIMD active electronic circuit board 106 may comprise circuit board via holes 109, some of which can be eyelets 194, and some of which can be connector housings 66. In this case, the use of a two-part pin is ideal, as the terminal pin 18' disposed on the device side need not be biocompatible, thereby conductive material selection is unrestricted, allowing material selection to consider spring-rates conducive to ease of manufacture of potentially sensitive or complex compliant terminations 81 designs. Referring once again to FIG. 19, one will see that the orientation of the AIMD active electronic circuit board 106 is such that instead of lying parallel to and in-line with the longitudinal axis of the terminal pins 18', the circuit board 106 is positioned perpendicular to the longitudinal axis of the terminal pins 18'. Hence, as will be further described herein, either one of an AIMD active electronic circuit board 106, an EMI filter circuit board 106' or both an AIMD active electronic circuit board 106 and an EMI filter circuit board 106' can be disposed at, near or adjacent an AIMD hermetically sealed feedthrough. In this case, the feedthrough capacitor 24 would be removed and EMI filtering would be done by the EMI filter circuit board 106'.

Referring once again to FIG. 19, illustrated on the left-hand side is a via hole eyelet 194, which can be a formed eyelet (that is, a thin stamped, machined or the like) or, as shown on the right-hand side, an electroplated or metallized via hole 109 of any type known in the prior art can be provided into which a connector housing 66 may be inserted. Alternatively, on the right-hand side, a much heavier duty eyelet 194 can been inserted instead of connector housing 66, which can either be soldered (or otherwise equivalently electrically connected), or, depending on the size, material of construction and circuit board material and/or thickness, can be press-fit into via hole 109. A heavier duty eyelet 194 or a connector housing 66 serves to mitigate stresses imparted during pin insertion 18', thereby inhibiting crack initiation preventing cracking or damaging of delicate AIMD active electronic or EMI filter circuit boards 106, 106'. As such, in accordance with the embodiments of the present application, this heavier eyelet structure or the connector housing, may comprise at least a partial flange, as illustrated. While FIG. 19 shows a specific embodiment the compliant termination structure 81 of terminal pin 18' engaging the eyelet 194 or connector housing 66, it is understood by one skilled in the art that the shape of the terminal pin compliant termination structure 81 can be of any configuration designed to achieve the required eyelet 194 or connector housing 66 engagement.

FIG. 19A is another embodiment of a compliant termination structure 81'. The compliant termination structure 81' may be monolithically formed when terminal pins 18, 18' are formed (not shown), or alternatively may be separately formed and joined to terminal pins 18, 18' by a weld or a braze (the weld or braze is labelled 144 in FIG. 19A). Similarly, the embodiments of the compliant termination structures 81' of FIGS. 19 and 19B-19D can be monolithically formed when terminal pins 18, 18' are formed, or alternatively may be separately formed and joined to terminal pins 18, 18' by a weld or a braze.

FIG. 19B is another embodiment of a terminal pin 18, 18' with a compliant termination structure 81". In this embodiment, the terminal pin 18, 18' extends through the compliant termination structure 81" and illustrates a first weld or braze 144 and/or a second weld or braze 144' for attachment of the compliant termination structure 81" to terminal pin 18, 18'.

FIG. 19C is yet another embodiment of a terminal pin 18, 18' with a compliant termination structure 81'''. In this case, having inwardly angled prongs.

FIG. 19D is yet another embodiment of a terminal pin 18, 18' with a compliant termination structure 81'''' that has a rounded prong ends that facilitate insertion.

It is noted herein that, when any embodiments of terminal pin connectors 16, terminal pins 18, 18', 18gnd or the compliant termination structures 81' are used on the body fluid side of the AIMD, the embodiments must be made of biocompatible, nontoxic, and biostable materials. Likewise, when any embodiments of terminal pin connectors 16, terminal pins 18, 18', 18gnd or the compliant termination structures 81' are used on the device side, which is the inside of the AIMD, the embodiments do not need to be biocompatible, nontoxic, or biostable. It is also understood that any compliant termination structures disclosed herein including the compliant termination structures of FIGS. 19-19D can be separately manufactured from the terminal pin 18, 18', 18gnd or alternately could be made as part of the terminal pin 18, 18', 18gnd in one monolithic structure. It is also contemplated that any compliant termination structure disclosed herein including the compliant termination structures of FIGS. 19-19D can be integrated into any AIMD terminal pin or AIMD header block electrical conductor or leadwire for insertion into connector housings 66, circuit board eyelets 194, or cavities 180 taught herein.

FIG. 20 illustrates a connector housing 66 of an exemplary terminal pin connector 16 of the present application with an alternative prong 70, as illustrated. It is noted herein that any of the connector housing embodiments of the present application may be used instead of the connector housing shown. The prongs 70 of FIG. 20 are shown in cross-section. It is contemplated that they can be 2, 3, 4 or even "n" number of prongs. Prongs 70 could be laser welded or brazed 144 to clip 64, as indicated, or prongs 70 could alternately be crimped. If disposed on the device side (inside the hermetically sealed AIMD casing 32), then the mechanical and electrical connection of element 144 need not be biocompatible and could comprise solder, thermal-setting conductive adhesives and the like. However, if prongs 70 reside on the body fluid side, then mechanical and electrical would require a laser weld 144.

FIG. 21 is similar to FIG. 20, except in this case, the prongs 70 are now attached to a spring clip 64'. The spring clip 64' provides additional insertion capability to both sides of its structure such that prongs 70 can be inserted into a connector housing 66 as illustrated or into a circuit board via hole 109 or a cavity 181 (not shown) and terminal pin 18, as illustrated (or a two-part terminal pin either 18 or 18' not shown), can be inserted into spring clip 64'. In other words, there would no longer be a need for the mechanical and electrical connection previously labelled in FIG. 20 as element 144. The distal end 62' of the terminal pin 18 is inserted into the spring clip 64', making a robust, alternative mechanical and very low resistance electrical connection 181. When the prongs 70 are inserted inside the connector housing 66, the spring rate and the tolerances are adjusted such that the prongs 70 end up compressed very tightly against the inside diameter of the housing 66. This makes for a very robust alternative mechanical and electrical connection, which can either be on a circuit board or on an AIMD header block.

FIG. 22 illustrates an alternative AIMD hermetically sealed feedthrough comprising co-sintered conductive paste-filled vias 146, which are formed by co-sintering a conductive paste residing in the via of the insulator 28 at the same time that the insulator 28 is sintered. The co-sintered conductive paste-filled via 146 can be of a substantially pure platinum or a ceramic reinforced metal composite (CRMC). Co-sintered platinum filled vias are described by U.S. Pat. Nos. 8,653,384; 8,938,309; 9,233,253; 9,352,150; 9,511,220; 9,511,220; 9,889,306 and 9,993,650, the contents of which are fully incorporated herein by these references. Co-sintered ceramic reinforced metal composite (CRMC) conductive vias are described by U.S. Pat. Nos. 10,272,253 and 10,249,415, the contents of which are also fully incorporated herein by these references. Referring once again to FIG. 22, illustrated are two embodiments comprising a cavity 181, wherein the distal end of electrical conductor 122' comprises a compliant termination structure (a spring-like elastically resilient structure) having prongs 70 inserted into a counterbore 180 of the co-sintered conductive paste-filled vias 146 forming the cavity 181. The prongs 70, which are inserted into cavity 181, provide a robust, mechanical, and low resistance electrical connection.

Referring once again to FIG. 22, illustrated on the left-hand side of FIG. 22 is a co-sintered conductive paste-filled via 146 of the insulator 28 having two portions: a device side portion having a small diameter, and a body fluid side portion having a diameter larger than the device side portion.

Within the body fluid side portion, a counterbore 180 is made forming the cavity 181. The diameter of the cavity 181 is larger than the diameter of the device side portion of the co-sintered conductive paste-filled via 146, but smaller than the diameter of the device side portion of the co-sintered conductive paste-filled via 146. On the right-hand side of FIG. 22, illustrated is a co-sintered conductive paste-filled via 146 having a constant diameter over the length of the via of the insulator 28 (in other words, the same diameter from the body fluid side insulator to the device side insulator surface). The diameter of the co-sintered conductive paste-filled via 146 is larger than the diameter of cavity 181. Similar to the left-hand side, the prongs 70 are inserted into cavity 181 thereby providing a robust, mechanical, and low resistance electrical connection. The hole of co-sintered conductive paste-filled via 146 on both sides of the insulator 28 can be formed in the insulator 28 in a green state by one of a drilling, a punching, a machining, a waterjet cutting, or combinations thereof.

Referring once again to FIG. 22, forming the via configuration of co-sintered conductive paste-filled via 146 on the left-hand side may require a double forming (for example, a double drilling) or a multi-forming step. For the via configuration of the co-sintered conductive paste-filled via 146 on the right-hand side of insulator 28, wherein the via configuration on the right-hand side is of constant diameter, the entire via configuration of the co-sintered conductive paste-filled via 146 may be drilled through the thickness of the green insulator in one drilling step thus extending the via configuration of the insulator 28 to the device side insulator surface and to the body fluid side insulator surface. Once the via configuration is formed, both via configurations are then filled with a conductive paste-fill. Counterbore 180 may then be formed in either the left-hand side conductive paste-filled via, the right-hand side conductive paste filled via or both, forming the cavity 181, which is then followed by co-sintering of the conductive paste-fills with the sintering of the green insulator 28. Counterbore 180 alternatively may be formed in either the left-hand side conductive paste-filled via, the right-hand side conductive paste-filled via or both, after co-sintering with the sintering of the green insulator 28.

Instead of using one of the above formation processes to form the via configuration of the conductive paste-filled via after co-sintering the conductive paste-filled via with the sintering of the green insulator 28 thereby forming a co-sintered paste-filled via 146, the via configurations may be alternatively formed at the same time as the green insulator is formed by either pressing or molding the insulator 28 using appropriately designed fixtures and tooling designed to include the via configurations. Pressing may be done by one of hydro-static pressing, hot pressing, cold pressing, die pressing, or mechanical pressing. Molding may be done by powder injection molding, ceramic injection molding, or hot wax molding. Once the via configurations are co-formed with the green insulator 28, then one or more via configurations may be filled with a conductive paste-fill. The conductive paste-filling step may comprise filling the open volume of at least one entire via configuration or, alternatively, may at least partially fill at least one via configuration. Insulator 28 may comprise one or more via configurations, having an open via configuration volume that completely fills the available open via configuration volume; or, alternatively, each open via configuration may be filled with different volumes of the available open via configuration volume or all open via configurations may be filled to the same volume of the available open via configuration volume. At least one via configuration may be left open without any conductive paste-fill to later accommodate some other component, such as, but not limited to, a terminal pin 18. Counterbore 180 may be pre-formed in via configuration that has been filled with conductive paste-fill by adding additional pressing or molding steps and/or additional pressing and/or molding fixtures and/or tooling. Alternatively, counterbore 180 may be formed in the co-sintered conductive paste-filled via 146 after co-sintering with the sintering of the insulator 28 by one of drilling, punching, machining, waterjet cutting, or combinations thereof.

Referring once again to FIG. 22, it is understood that the electrical conductor 122' and the prongs 70 shown on the body fluid side must comprise a biocompatible, biostable, and non-toxic material. It is contemplated, however, that such conductors 122' and the prongs 70 could also be used on the device side, which is inside the AIMD casing 32, to attach components such as an AIMD active electronic circuit board 106 and/or an EMI filter circuit board 106' (not shown), wherein at least one conductor 122' would be attachable to a hermetically sealed feedthrough 14 having a corresponding cavity 181 on the device side. This would allow either of the circuit boards 106 and 106' or both the circuit boards 106 and 106' to be attachable to at least one electrical conductor 122' so that the prongs 70 of the electrical conductor 122' may be plugged into cavity 181 of the hermetically sealed feedthrough 14 as illustrated by FIG. 22. When the electrical conductor 122' is disposed on the device side inside the AIMD casing 32, it is contemplated that the electrical conductor 122' and its prongs 70 need not be biocompatible and could instead comprise less expensive cost-effective electrically conductive materials, including, but not limited to, gold-plated constantan, beryllium copper, or any of the previously disclosed electrically conductive materials. It is further contemplated that counterbore 180 may be formed on one of the body fluid side of a co-sintered conductive paste-filled via 146, on the device side of a co-sintered conductive paste-filled via 146, or on both the body fluid and the device sides of the co-sintered conductive paste-filled via 146. Likewise, any electrical conductor 122', regardless of the compliant termination structure may also be disposed on one of the body fluid side of a co-sintered conductive paste-filled via 146, on the device side of a co-sintered conductive paste-filled via 146, or on both the body fluid and the device sides of the co-sintered conductive paste-filled via 146. Additionally, it is also contemplated that any connector housing 66 disclosed herein may be inserted in at least one cavity 181 of a co-sintered conductive past-filled via 146 on one of the body fluid side of a co-sintered conductive paste-filled via 146 or on a device side of co-sintered conductive paste-filled via 146. In summary, FIG. 22 illustrates a way of plugging either an electrical conductor 122' of either an AIMD active electronic circuit board 106 or an EMI filter circuit board 106' or a body fluid side AIMD header block 118 or combinations thereof directly into at least one cavity 181 of a co-sintered conductive paste-filled via 146 of an insulator 28 of a hermetically sealed feedthrough 14 of an AIMD 12, thereby forming a mechanical and low resistance electrical connection.

Referring once again to FIG. 22, on the left-hand side, one can see that there are two layers to the co-sintered conductive paste-filled filled via 146. The two layers of the co-sintered conductive paste-filled filled via 146 may comprise one ceramic reinforced metal composite (CRMC) 147 and one essentially pure platinum 146. CRMCs 147 may encompass 1, 2 or even "n" number of layers in order to buffer any mismatches in thermal coefficients of expansion between the green alumina insulator 28 and the essentially pure platinum 146 during the co-sintering process and on cool-down to room temperature. CRMC pastes are more thoroughly described in U.S. Pat. No. 10,249,415 and its family, which are incorporated herein by reference. It is understood by one skilled in the art that the via configurations of the co-sintered conductive paste-filled vias shown on the body fluid side could alternately be used on the device side. Additionally, it is contemplated that the cavity 181 could be present on both sides by duplicating the body fluid side portion of the via configuration on the device side portion of the insulator 28. The teaching of cavity 181 and via configurations illustrated in FIG. 22 herein are not intended to be limiting in any way.

FIG. 23 is very similar to FIG. 22, except in this case, the electrical conductor 122 is inserted into the connector housing 66' such that the electrical conductor 122 is engaged with one or more spring fingers 51 making a mechanical and electrical connection with the electrical conductor 122. At the same time, the prong 70 makes an electrical connection with the cavity 181 formed by the counterbore 180 of a co-sintered conductive paste-filled via 146, as previously described for FIG. 22.

Figure 24:
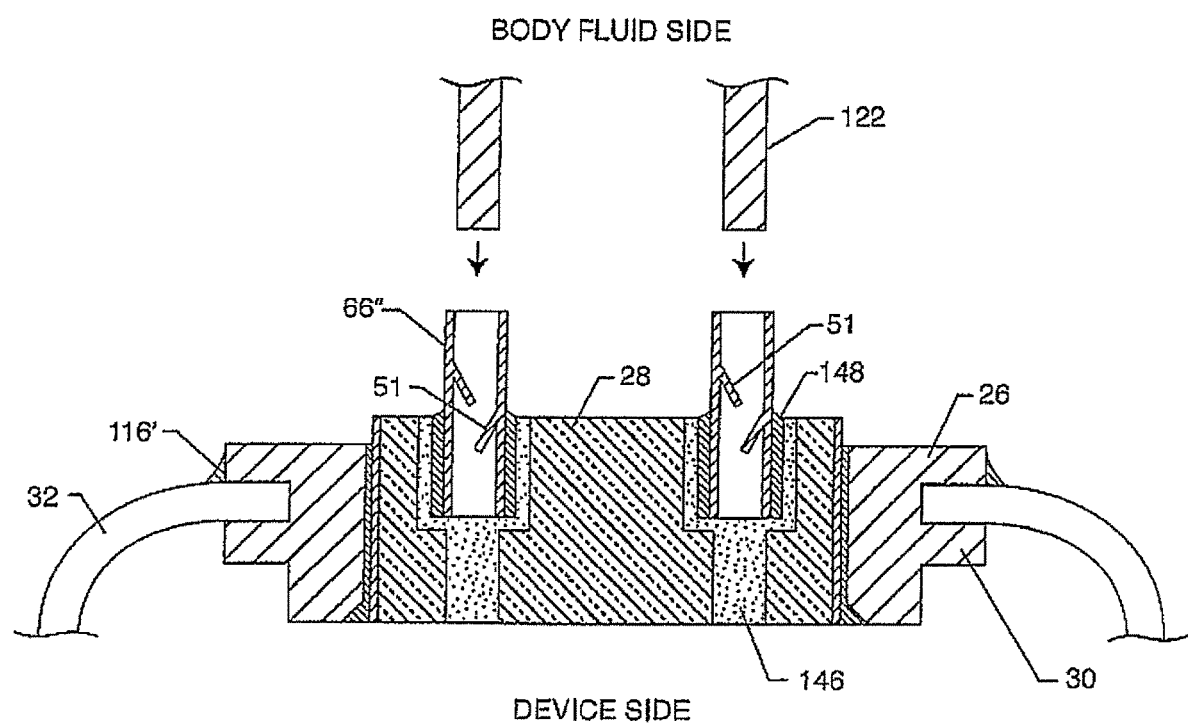
FIG. 24 shows a cross-sectional view of an alternative embodiment of an AIMD feedthrough connector assembly.

FIG. 24 is similar to FIG. 23, except in this case, the electrical conductors 122 are engaged in a connector housing 66" with one or more integrally formed spring fingers 51 that are oriented in different directions as illustrated. In this case, the connector housing 66" has been gold brazed 148 to the co-sintered conductive paste-filled via 146.

Referring now to FIGS. 22, 23 and 24, it is contemplated that a counterbore 180 can be made in any co-sintered conductive paste-filled via 146, either on the device side, on the body fluid side or on both the device and the body fluid sides of the co-sintered conductive paste-filled via 146; the counterbore 180 thereby forming a cavity 181, the cavity 181 capable of incorporating, for example, a spring clip 64''' having waved tines 79 (wavelike undulations), as illustrated in FIG. 18, or any other compliant termination structure taught herein. It will also be appreciated, referring back to FIGS. 4A, 4B and 4C, that the base 68 of clip 64 could be press fitted into the cavity 181 of a co-sintered conductive paste-filled via 146 formed by the counterbore 180 such that an electrical conductor 122 could be inserted. There are a number of embodiments that are possible in light of the teachings of this disclosure, the embodiments disclosed herein being only exemplary and not meant to be limiting in any way.

Figure 24A:
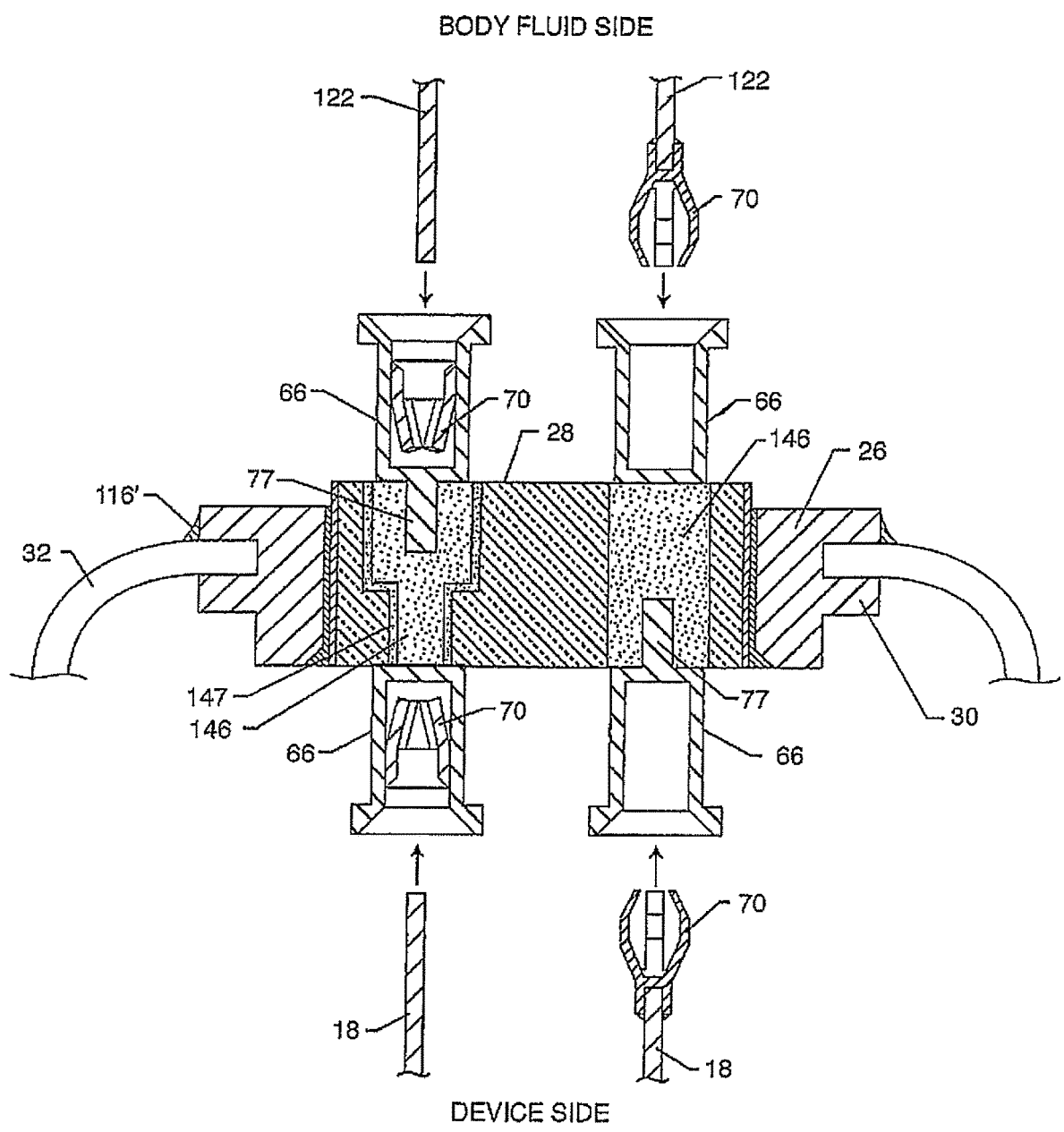
FIG. 24A shows a cross-sectional view of an alternative embodiment of an AIMD feedthrough connector assembly.

FIG. 24A is similar to FIGS. 22-24, except that now a connector housing 66 and/or a terminal pin connector 16 can be disposed either on the body fluid side or the device side of a. Such connector housings 66 and/or a terminal pin connectors 16 are electrically connected one or more co-sintered conductive paste-filled vias 146, the one or more co-sintered paste filled vias 16 comprising one of a pure platinum co-sintered conductive paste-filled via 146, a pure platinum co-sintered conductive paste-filled via 146 having a CRMC 147 co-sintered layer, or combinations thereof. FIG. 24A illustrates an embodiment where a connector housing 66 comprising an integrally formed post 77 co-sintered within a co-sintered conductive paste-filled via 146 (see the embodiment shown on the body fluid side of the left-hand side of FIG. 24A and the embodiment on the device side of the right-hand side of the co-sintered conductive paste-filled via 146 of FIG. 24A). Alternatively, the connector housing 66 may be brazed or welded for attachment to the co-sintered conductive paste-filled via 146 (see the embodiment shown on the body fluid side of the right-hand side of FIG. 24A and the embodiment on the device side of the left-hand side of the co-sintered conductive paste-filled via 146 of FIG. 24A). FIG. 24A also illustrates that either the connector housings 66 or the electrical conductors 122 can comprise compliant termination structures (see the exemplary clips comprising prongs 70 within connector housings 66 on the device and body fluids sides on the left-hand side of FIG. 24A, and prongs 70 of the compliant termination structure at the distal end of the terminal 18 on the right-hand side of FIG. 24A). When such compliant termination structures are used on the body fluid side, the compliant termination structures would be made of a biocompatible, nontoxic, and biostable material. Likewise, when the compliant termination structure is used on the device side inside the AIMD, the compliant termination structures do not have to comprise a biocompatible, non-toxic, or biostable material.

Figure 25:
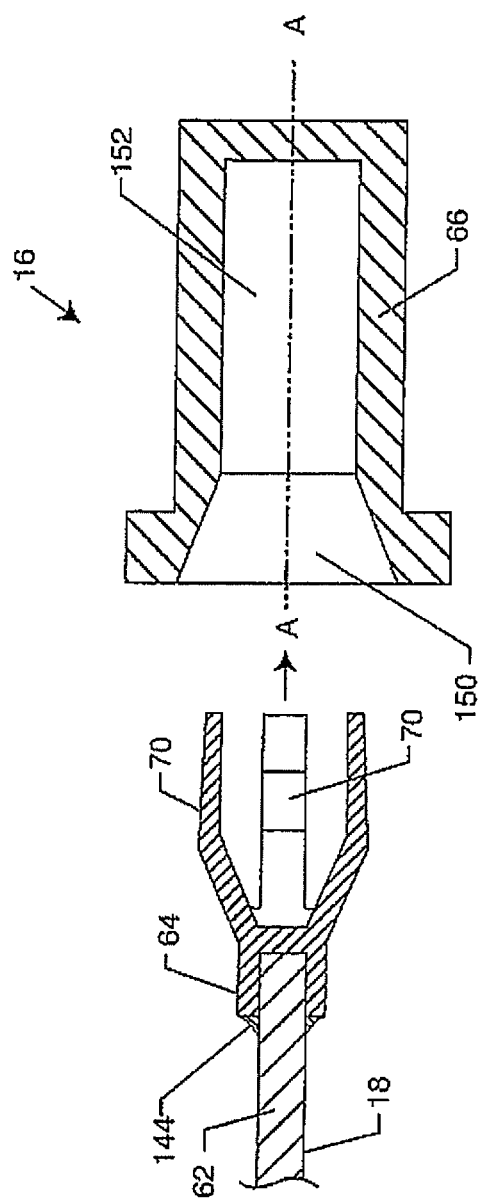
FIG. 25 shows a cross-sectional view of an alternative embodiment of a terminal pin connector assembly.

FIG. 25 is very similar to FIG. 20, except that the prongs 70 at the distal end 62 of terminal pin 18 have a different shape. One can see that the prongs 70 are relatively straight, but the connector housing 66 now has a chamfer 150. When the prongs 70 are inserted into the chamfer 150, the chamfer compresses the prongs 70, such that they are inserted into cavity 152 where they elastically contact the sidewalls of cavity 152 forming a robust mechanical and electrical connection. Referring once again to FIG. 25, illustrated is a closed bore connector housing 66, however, and an open bore connector housing 66 can alternatively be used. It will be appreciated that the embodiment illustrated in FIG. 25 could be disposed on the device side inside an AIMD casing 32 (not shown), wherein the connector housing 66 connects an AIMD feedthrough connector assembly 10 or a feedthrough capacitor connector assembly 20 and an AIMD active electronic circuit board 106 or an EMI circuit board 106' or both an AIMD active electronic circuit board 106 and an EMI circuit board 106'. Additionally, the embodiment illustrated in FIG. 25 could be disposed on the body fluid side of an AIMD 12 wherein the connector housing 66 connects an AIMD feedthrough connector assembly 10 or a feedthrough capacitor connector assembly 20 and an AIMD header block 118. The connector housing 66 can be disposed and/or attached in accordance with the embodiments and teachings disclosed herein.

Figure 26:
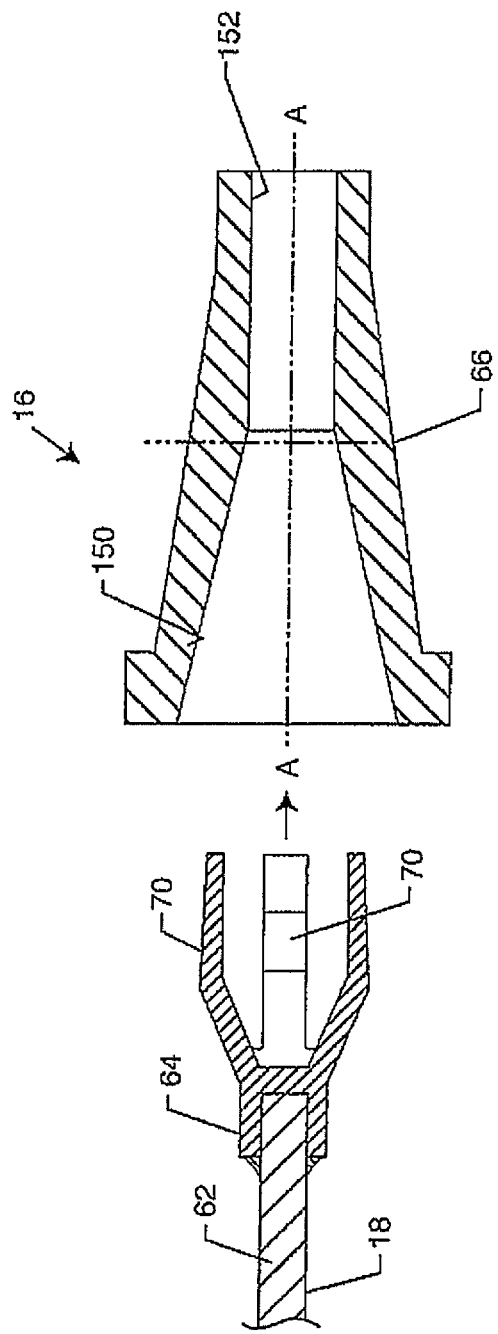
FIG. 26 shows a cross-sectional view of an alternative embodiment of a terminal pin connector.

FIG. 26 illustrates an embodiment similar to FIG. 25, except the chamfer 150 configuration of the connector housing 66 is different. When the prongs 70 at the distal end 62 of the terminal pin 18 are inserted into the chamfer 150 configuration of the connector housing 66 of FIG. 26, the prongs 70 are mechanically compressed as the prongs 70 slide along the chamfer 150 ultimately electrically engaging the inside diameter of the narrowed through-bore along longitudinal axis A-A.

Figure 27D:
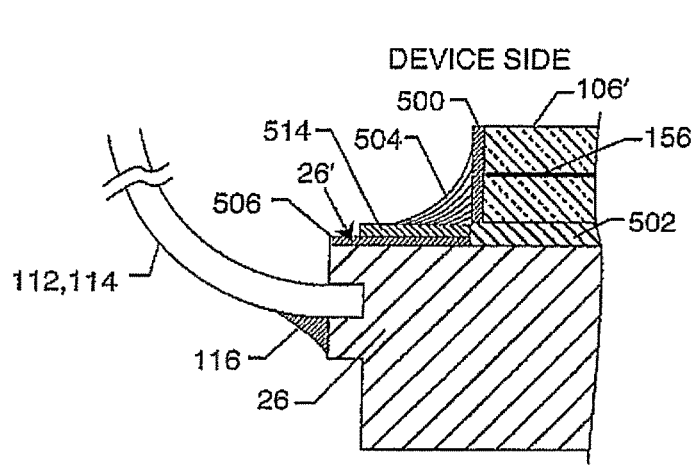
FIG. 27D illustrates an embodiment of an alternative electrical connection to the ground pin and the at least one ground electrode plate of an EMI filter circuit board.
Figure 27E:
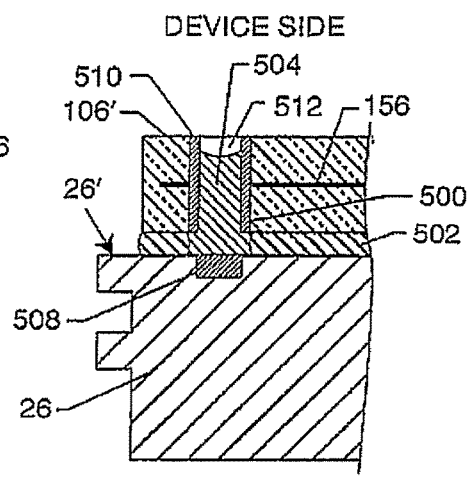
FIG. 27E illustrates an embodiment of an alternative electrical connection to the ground pin and the at least one ground electrode plate of an EMI filter circuit board.
Figure 27F:
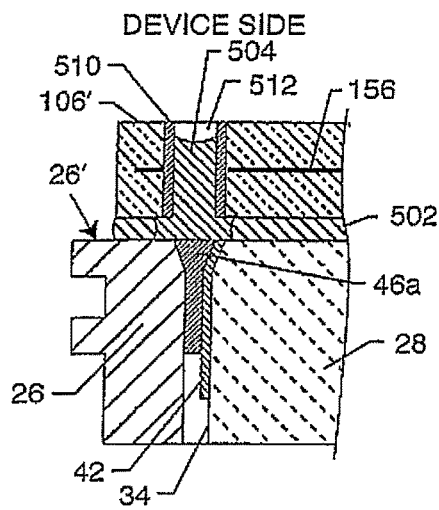
FIG. 27F illustrates an embodiment of an alternative electrical connection to the ground pin and the at least one ground electrode plate of an EMI filter circuit board.
Figure 27G:
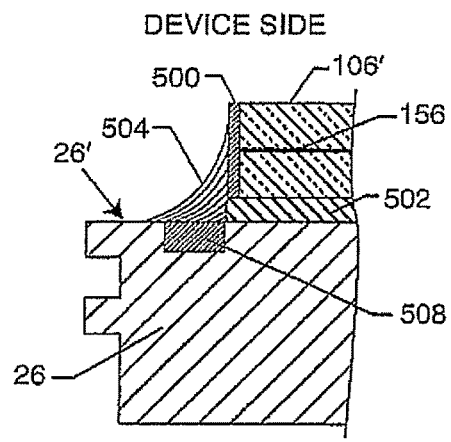
FIG. 27G illustrates an embodiment of an alternative electrical connection to the ground pin and the at least one ground electrode plate of an EMI filter circuit board.
Figure 27H:
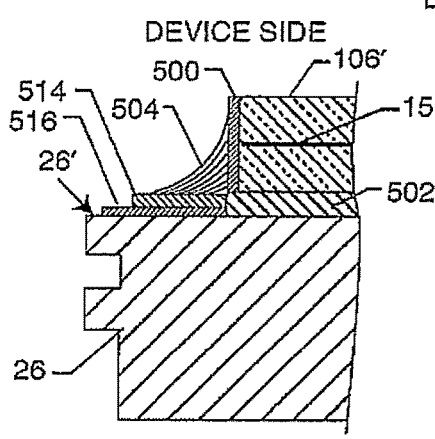
FIG. 27H illustrates an embodiment of an alternative electrical connection to the ground pin and the at least one ground electrode plate of an EMI filter circuit board.
Figure 28:
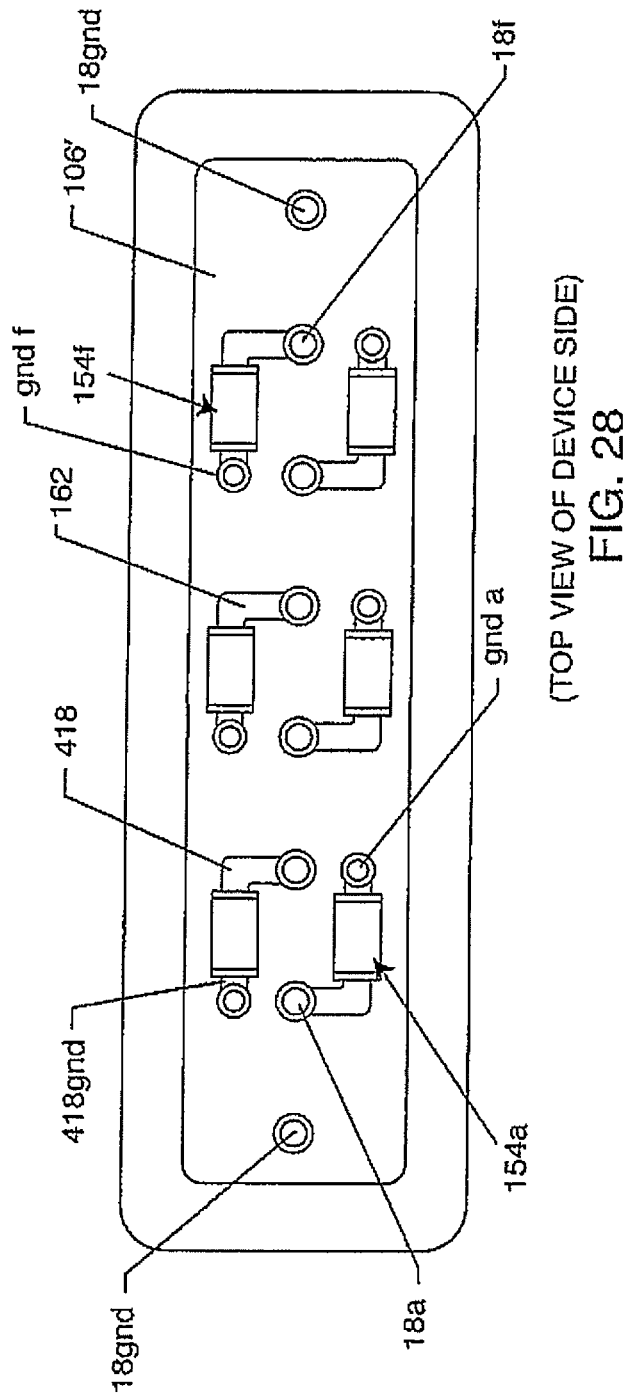
FIG. 28 is a top view taken along lines 28-28 of FIG. 27 showing multi-layer ceramic capacitors (MLCCs) populated on an EMI filter circuit board.

FIGS. 27 and 28 are taken from FIGS. 51 and 52 of U.S. Pat. No. 10,272,252, the contents of which are fully incorporated herein by this reference. Referring to FIG. 27, one can see that there is an AIMD hermetically sealed feedthrough 14 which may have one-part or two-part terminal pins 18, 18', as has been previously disclosed. Disposed on the device side is an EMI filter circuit board 106'. The EMI filter circuit board 106' may have one or more internal ground electrode plates 156, as illustrated. Circuit board ground electrode plates 156 are more thoroughly described in U.S. Pat. Nos. 8,195,295 and 10,272,252, the contents of which are fully incorporated herein by these references. Referring once again to FIG. 27, the EMI filter circuit board 106' may be disposed against at least one of the device side of the insulator 28 and/or the ferrule 26 or an insulating washer (not shown) may be disposed between the EMI filter circuit board 106' and at least one of the insulator 28 and the ferrule 26. Alternatively, the EMI filter circuit board 106' may be disposed along the terminal pins 18 and 18*gnd* at some distance from the ferrule 26 or the insulator 28 thereby providing a gap between the EMI filter circuit board 106' and at least one of the insulator 28 and the ferrule 26. As shown in FIG. 27, the EMI filter circuit board 106' is immediately adjacent both the alumina insulator 28 and the ferrule 26, but as has been stated, it need not be adjacent. Rather, it could be spaced away, even at some substantial distance, from one of the insulator 28, the ferrule 26, or both.

Referring once again to FIG. 27, one can see that there is a terminal pin connector 16 associated with each one of the active terminal pins 18 and also the ground terminal pins 18*gnd* and 18*gnd'*. It is contemplated that, while two ground terminal pins are illustrated, any number (n) of ground terminal pins can be present. As previously described, these terminal pin connectors 16 would be populated on the main AIMD active electronic circuit board 106 (not shown). Accordingly, each one of the active terminal pins 18 would be routed to active traces 162 of the AIMD active electronic circuit board 106. At least one ground terminal pin 18*gnd* (or 18*gnd'*) would be routed to an AIMD active electronic circuit board 106 ground electrode plate 52, ground trace or ground plane (not shown). As previously indicated, this is useful for AIMDs 12 that sometimes use the AIMD casing 32 as an electrode. The active pins are terminal pins 18*a* through 18*f*. The left-hand side ground terminal pin 18*gnd* resides in a ferrule counterbore. The ground terminal pin 18*gnd* may alternatively be attached to the device side ferrule surface 26' and may even comprise a nail head feature to facilitate ground terminal pin attachment (not shown). The right-hand side ground terminal pin 18*gnd'* goes all the way through the hermetically sealed feedthrough 14 such that it can also be connected on the body fluid side. Some of these active terminal pins 18*a*-18*f* may be used to sense biological signals. Others may be used to provide therapeutic pulses or in the case of an implantable cardioverter defibrillator (ICD), pairs of these leads could be used to provide high voltage cardioversion therapy to cardiovert the heart from dangerous rhythms to normal sinus rhythm. Referring once again to FIG. 27, it is contemplated that in an ICD application, terminal pin 18*a* could be routed to a distal shocking electrode, for example, in the right ventricle of the superior vena cava. The AIMD active electronic circuit board 106 could be programmed such that the opposite polarity of the shocking biphasic wave form could be applied to terminal pin 18*gnd*. This is called a 'hot can' wherein, the shocking vector would be between the distal electrode located inside the heart, back to the AIMD casing 32. So, by having terminal pin 18*gnd* connected to the AIMD active electronic circuit board 106 (not shown), this provides for a number of alternatives. Pacing vectors like this are also very important for spinal cord stimulators where sometimes the AIMD casing 32 itself is used as part of the pacing vector.

Referring once again to FIG. 27, one will see that the EMI filter circuit board 106' has a number of filter capacitors 154. As described in U.S. Pat. Nos. 10,272,252 and 8,195,295, these could be MLCCs 154, otherwise known as monolithic multilayer ceramic capacitors, or X2Y attenuators 300 or flat-thru capacitors 400. Each one of these capacitors 154, 300, 400 has one or more active electrode plates that are electrically connected to active terminal pins 18*a* through 18*f*. Referring once again to FIG. 27, this particular embodiment has six (6) poles (6 active terminal pins) with two (2) ground terminals 18*gnd* and 18*gnd'*. As illustrated in FIG. 27, the ground terminal pins 18*gnd* and 18*gnd'* are either laser welded 160 or gold brazed 165 to the ferrule 26. Brazing or welding the ground pins 18*gnd* and 18*gnd'* permits penetration through any oxides present on the ferrule 26 thus forming a very low resistance metallurgical electrical connection. This metallurgical electrical connection has been shown to be very stable and generally will not form oxides over time. Further, by using ground pins comprising a suitable oxide-resistant material, such as platinum, a further essentially oxide-free electrical connection can be made to the ground pin. For example, in addition to the already mentioned AIMD components, that is, circuit boards or header blocks, and the electrical components: MLCCs, X2Y attenuators or flat-thru capacitors, the essentially oxide-free electrical connection can be made between the oxide-resistant ground pins 18*gnd* and 18*gnd'* to a ground electrode, a ground circuit trace, a ground via of a circuit board, or to an edge ground metallization of the circuit board or of the electrical components. The essentially oxide-free electrical connection can be a direct electrical connection to the oxide-resistant ground pin, or, alternatively, the electrical connection may be made using an electrical connection material such as a solder, a thermal-setting conductive adhesive or the like. Hence, for the above reasons, all ground terminal pins of the AIMD device can comprise an oxide-resistant, namely an essentially oxide-free, material. For example, the oxide-resistant ground terminal pins 18*gnd* and 18*gnd'* can comprise a noble metal. Additionally, the oxide-resistant ground pins 18*gnd* and 18*gnd'* can comprise platinum, gold, tungsten, iridium, palladium, niobium, tantalum, ruthenium, rhodium, silver, osmium, and alloys or combinations thereof. Further, the oxide-resistant ground pins 18*gnd* and 18*gnd'* can comprise platinum-based materials including platinum-rhodium, platinum-iridium, platinum-palladium, or platinum-gold, including naturally occurring alloys such as platiniridium (platinum-iridium), iridiosmium and osmiridium (iridium-osmium). It is important to note herein that the oxide-resistant ground pins are hermetic (see 118*gnd*) and provide strong mechanical and low resistance electrical attachment to the ferrule 26. Importantly, such attachment of oxide-resistant ground pins 18*gnd* to the ferrule 26 further provides very low impedance connections at high frequencies, which is necessary to divert dangerous electromagnetic interference (EMI) signals. Of significance is that oxide-resistant ground terminal pins 18*gnd* and 18*gnd'* can themselves provide for connections having low resistance and low impedance at high frequencies regardless of the metal used to form the ferrule, providing new design opportunities not only for AIMDs, but other types of "smart" medical devices, whether implanted, temporarily implanted, or external the body, for example, sensors, monitors, identification tags, recorders, controller, artificial organs and the like. Such oxide-resistant materials should also be capable of high processing temperatures to sustain oxide formation resistance.

FIG. 27A is taken from section 27A-27A of FIG. 27. It shows an alternative connection to connect the ground pin 18*gnd* to the at least one ground plate 156 of the EMI filter circuit board 106'. In this case, the EMI filter circuit board 106' has a circuit board edge metallization 500, which is electrically connected to its at least one ground plate 156, in this case, an internal ground plate. It should be noted that there may be a plurality of internal ground plates and/or there may also be one or more external ground plates, for example, the external ground plates are disposed either on the top surface, on the bottom surface or on both the top and the bottom surfaces of an EMI filter circuit board 106'. Importantly, these ground plates 156 provide a low impedance path for the filters (an MLCC capacitor 154, an X2Y attenuator 300, a flat-thru capacitor 400, and combinations thereof) to divert dangerous EMI currents while at the same time, shielding the insulator 28 AIMD hermetically sealed feedthrough 14 from direct penetration of high frequency RF-radiated noise (EMI). Referring once again to FIG. 27A, one can see that there is an electrical connection material 504 that electrically connects the edge metallization 500 of the circuit board (which is also an external metallization) to the ground terminal pin 18gnd. This electrical connection material 504 may comprise a solder, a thermal-setting conductive adhesive, a conductive epoxy, or any other suitable type of electrical connection material 504. In addition, the ground terminal pin 18gnd could be wire bonded to the circuit board edge metallization 500 or to a conductive pad (not shown).

FIG. 27B is taken from section 27B-27B of FIG. 27. This illustrates the EMI filter circuit board 106' with edge metallization 500 as previously described in FIG. 27A. In this case, the electrical connection material 504, is a thermal-setting conductive adhesive, including conductive polyimides and conductive epoxies, which has been used to connect the circuit board edge metallization 500 directly to the device side ferrule surface 26'. For active implantable medical devices 12, ferrules 26 are typically of titanium. While being biocompatible and biostable, titanium tends to form oxides on its surface. Such an oxide layer 506 is shown in FIG. 27B. It would be appreciated that these oxide layers 506 would appear on all the surfaces of the titanium ferrule but are shown only on the device side ferrule surface 26' for convenience. This oxide layer 506 can be present at the time electrical connection material 504 is applied or it could occur later, particularly during laser welding 116 of the ferrule 26 to the AIMD casing 32 or casing halves 112, 114. When conducting a laser weld 116, 116', substantial localized heat may be generated, which can accelerate oxide layer 506 formation.

It is generally believed that oxide layer 506 will not form on titanium components internal the AIMD casing 32 once hermetically sealed, mostly because AIMDs 12 can be assembled in or back-filled with an inert gas, such as helium, nitrogen, or argon with the intent of inhibiting oxidation of sensitive metals like titanium. This belief is erroneous. Materials of construction used in the manufacture of AIMDs, such as polymers, plastics, adhesives, elastomers and the like, and even the printed circuit boards (PCBs) themselves, generally have some level of gases trapped within their structure, for example, moisture, oxygen, other oxygen-containing gases, or even undetected residues comprising same, that eventually outgas during the operating life of the device. Furthermore, processes that could involve increased temperature like welding, curing or other temperature shifts are possible during shipping and can accelerate such outgassing. Hence, even if an AIMD is manufactured in an inert gas environment, or backfilled with an inert gas, such 'heating' of certain materials of construction can release oxygen, oxygen-containing gases or water vapor into an otherwise hermetically sealed environment causing the formation of oxide layers 506 on conductive surfaces. The formation of this oxide layer 506 increases the RF ground impedance, which does seriously degrade EMI filter performance. This is why, during EMI filter initial design qualification (the EMI filters comprising a feedthrough filter 24, 24', an MLCC capacitor 154, an X2Y attenuator 300, a flat-thru capacitor 400, and combinations thereof), the filter performance metrics at pre- and post-AIMD casing 32 laser welding 116, 116' should be recorded to be sure there is no filter performance degradation. These filter performance metrics must include: Equivalent Series Resistance (ESR) above 10 MHz and, in particular, at 64 MHZ (MRI RF pulsed frequency of a 1.5 T scanner), and insertion loss (IL) sweeps in dB on a network analyzer from 10 MHz to 3000 MHZ, including 64 MHZ (1.5 T MRI scanner) and 128 MHZ (3 T MRI scanner). For more detail referring the effects of oxide layer formation on EMI filtering, refer to the paper entitled, "Dissipation Factor Testing is Inadequate for Medical Implant EMI Filters and Other High Frequency MLC Capacitor Applications", ISSN: 0887-7491, presented at CARTS 2003: 23rd Capacitor and Resistor Technology Symposium, Mar. 31-Apr. 3, 2003, incorporated herein by this reference. In summary, the presence of an oxide layer 506 can seriously degrade EMI filter performance (in dB), particularly at high frequencies or at MRI RF-pulsed frequencies where the diverter filters must conduct a substantial amount of high frequency current. Accordingly, the inventors have found that an electrical ground connection, such as illustrated in FIG. 27B, is a highly undesirable approach.

FIG. 27C and FIG. 27D are taken from sections 27C-27C and 27D-27D of FIG. 27. FIG. 27C illustrates that the ferrule device side surface 26' has been cleaned of the oxide layer 506. Such an oxide layer 506 may comprise several layers, with any one or more layers further comprising one or more titanium oxide compositions. As mentioned, these oxide layers 506 are undesirably insulative and can also cause potentially undesirable semi-conductor behavior. One approach that the inventors have tried in the past is to clean the oxide layers 506 from the ferrule device side surface 26' using abrasive mechanical and chemical removal processes, including grit-blasting, mechanical grinding, sanding, and hydrofluoric acid cleaning. It should be noted that titanium oxides, once formed, are very stable and very hard to remove. Titanium oxides are so stable that they are commonly used as paint pigments. Referring once again to FIG. 27C, the inventors first cleaned the oxide layers 506 from the device side ferrule surface 26' and then formed a stripe or a coating of an electrically conductive adhesive (ECA stripe 514). The ECA stripe 514 may comprise a thermal-setting conductive epoxy, a thermal-setting elastomer, or a thermal-setting conductive polyamide. The inventors then connected the edge metallization 500 of feedthrough filter capacitors 24 directly to the ECA stripe 514 with electrical connection material 504. This seemed to work very well in high frequency electrical measurements, including insertion loss (IL), impedance, ESR and inductance, all initially measuring very low and within acceptable specification limits. However, out of a thousand pieces of prototype pieces evaluated, two exhibited higher impedances and were worrisome.

FIG. 27D is taken from section 27D-27D of FIG. 27, which illustrates in cross-section the AIMD casing halves 112, 114 and laser weld 116 to ferrule 26. It is generally understood that titanium has two properties that greatly influence its weldability: 1) titanium has a great chemical affinity for combining with oxygen; and 2) titanium doesn't have a great affinity for combining with any other chemicals. It is generally understood that, in open air, freshly machined or cleaned titanium quickly forms a layer of oxides. This formation of oxides creates a natural passivity that inhibits the reactions with other chemicals, such as salt or oxidizing acid solutions. The result is that titanium has superior corrosion resistance. However, when heated during welding, these oxides form even faster, and as the temperature reaches titanium's melting point (1668° C., 3034° F.), the oxides dissolve into solution and contaminate the weld pool, causing an impure and very weak weld. For this reason, special care is generally taken to minimize exposure of the titanium pieces to oxygen during welding. Hence, AIMD 12 manufacturing processes typically employ a shield gas such as argon or helium. Titanium can also be reliably welded in a full vacuum (as is the case with electron beam welding). Regardless, laser welding can cause heating along the weld seam, which may also involve heating of the device side ferrule surface 26'. Hence, it is conceivable that when exposed to such heating from laser welding, the titanium ferrule 26, and in particular the device side ferrule surface 26', can undesirably re-oxide. The inventors studied the effect of such protective laser welding on feedthrough filters, measuring ESR/IL pre- and post-laser welding. The inventors observed that post-laser welding, the ESR measurements of some feedthrough filters 24 of a very large lot increased from the pre-laser welding measurement by orders of magnitude. To this day, when attachment is made directly to titanium or other oxidizable metal without the presence of an oxide-resistant intermediary between the titanium and the electrical attachment material, the inventors have found that, while most parts in a 1000-piece production lot remain within ESR/IL specification post-laser welding 116. There are consistently some parts in the same lot that fail ESR/IL horribly. Thus, since failing ESR measurements remain unpredictable even under protective laser welding protocols, attaching to an ECA stripe 514, as illustrated in FIG. 27C, is a highly undesirable practice. Accordingly, the generally accepted belief that oxide layer 506 will not form on titanium components internal the AIMD casing 32 once hermetically sealed, simply because AIMDs 12 can be assembled in or back-filled with an inert gas as commonly thought for inhibition of oxidation of sensitive metals like titanium is flawed and inaccurate.

In summary, the deposition of an ECA stripe 514 proved to be a highly unreliable electrical connection, which is prone to increasing in resistance, whether occurring over time or when exposed to laser welding during installation into an AIMD casing even when a shield gas is used or if the laser weld is made in full vacuum.

Referring once again to FIGS. 27C and 27D, the inventors have conceived a novel concept by which the ECA stripe 514 can be effective. To render the ECA stripe 514 effective, a low resistance and low impedance connection at high frequencies must be made. To achieve such a low resistance and low impedance connection, especially for high frequencies, two very important steps are required: Step 1) at least the ferrule side device surface 26' must be cleaned of all oxides; and Step 2) an oxide-resistant layer 516, as shown in FIG. 27H, must be disposed on the ferrule surface device side 26' at least in the area of the ECA stripe 514. As described previously, cleaning of the ferrule device side surface 26' can be done mechanically or chemically by either abrasive grit blasting, such as by alumina blasting, mechanical grinding, sanding processes, hydrofluoric acid cleaning, or combinations thereof, which would remove oxide layers 506 from the ferrule 26, or at least the ferrule device side surface 26'. Once the ferrule 26, and in particular, its device side top surface 26' have been essentially cleaned of oxides, time becomes important. If the cleaned ferrule is left lying around at room temperatures, or worse yet, exposed to elevated temperatures, intentionally or unintentionally, these oxides will undesirably re-form. Accordingly, the inventors have tested and determined that an oxide-resistant layer 516, such as a noble metal layer must be deposited soon after at least the ferrule device side surface 26' is cleaned of oxides.

One preferred method of depositing an oxide resistant layer 516 on the ferrule device side surface 26' includes sputtering, including sputtering of such materials as gold, platinum, rhodium, or palladium. Other ways of disposing an oxide-resistant layer would be by physical vapor deposition, chemical vapor deposition, electrostatic spray assisted vapor deposition (ESAVD), electron beam physical vapor deposition (EBPVD), ion plating, ion beam assisted deposition (IBAD), magnetron sputtering, pulsed laser deposition, sputter deposition, vacuum deposition, pulsed electron deposition (PED), plating, electroless plating, electroplating, spraying, painting, plasma spraying, thermal spraying, spin coating, dip coating, metal foil lamination, and thin film deposited layers, either fully or selectively disposed. The electrically conductive coating may comprise one or more layers. These processes may be used to deposit materials such as gold, gold alloys, rhodium, rhodium alloys, platinum, platinum alloys, platinum-iridium alloys, palladium, palladium alloys, nitinol, cobalt-chromium alloys and combinations thereof. Additionally, selective electro-plating can be used. For example, a layer of nickel would first be deposited on top of the essentially oxide-free titanium surface at least in the area of where the ECA stripe 514 is intended to be deposited on the ferrule surface device side 26'. Then, an oxide resistant layer 516, such as a layer of gold, platinum, rhodium, or any of the materials disclosed above, would be plated on top of an optional nickel layer. The purpose of the nickel layer is to prevent titanium from migrating through an oxide-resistant layer. For example, even a thin film gold layer is highly resistant to forming oxides and is highly conductive. However, a thin film gold layer may be relatively "porous", which could allow titanium to migrate through the thin film gold layer to its free surface. Researchers have shown that, when a thin film gold layer is disposed on an essentially oxide-free titanium surface, the titanium can diffuse along the grain boundaries at the gold/titanium interface to the free surface of the thin film gold layer, where the titanium is oxidized. Accordingly, laying down a layer of nickel or other suitable material that prevents migration of titanium through it, would be required. In another embodiment, the nickel layer could be omitted with a suitably thick layer of gold, platinum or the like, such that they sustain oxide resistance.

FIG. 27E is taken from section 27E-27E of FIG. 27 and illustrates an alternative embodiment that also provides a very reliable low impedance electrical connection. Shown, is an EMI filter circuit board 106' of the present invention with a ground via hole 512. The ground via hole 512 is spatially aligned over an oxide-resistant pocket pad 508. Gold pocket pads are disclosed in U.S. Pat. No. 10,350,421, the contents of which are fully incorporated herein by this reference; however, pocket pads may comprise other oxide-resistant materials such as platinum. Noble metals, such as gold and platinum, are used as jewelry for this reason, as gold and platinum do not tarnish or oxidize over time. The pocket pad 508 may comprise a number of oxide-resistant materials, such as gold, gold alloys, rhodium, rhodium alloys, platinum, platinum alloys, platinum-iridium alloys, palladium, palladium alloys, nitinol, cobalt-chromium alloys, and combinations thereof. In the case of a gold pocket pad, co-brazing the pocket pad 508 at the same time that the AIMD hermetically sealed feedthrough 14 is formed saves time and is very efficient. As such, a low impedance and low resistance electrical connection to the ferrule 26 may be formed from the ferrule through the gold pocket pad 508 to the electrical connection material 504 and then, in turn, to the EMI filter circuit board 106' edge metallization 500. Only a few oxide-resistant pocket pads 508 need be disposed on the device side ferrule surface 26' to provide for a very low resistance and low impedance electrical connection. During machining or formation of the ferrule 26, the oxide-resistant pocket pads 508 can be formed as small circles or rectangles. They do not need to be very deep. Accordingly, they can be made of thin gold preforms, which are relatively inexpensive.

FIG. 27F is taken from section 27F-27F of FIG. 27. In a similar manner to FIG. 27E, the EMI filter circuit board 106' illustrates a via hole 512. In FIG. 27F, however, instead of the via hole 512 being spatially aligned to an oxide-resistant pocket pad, the via hole 512 is spatially aligned over the braze material 46a, which is a gold braze that provides a robust mechanical connection between the ferrule 26 and the insulator 28 of the AIMD hermetically sealed feedthrough 14. Electrical connection material 504 residing in the via hole 512 connects the via hole metallization 510, which is electrically connected to the one or more ground plates 156 and to the braze material 46a. This forms a reliable low resistance and low impedance electrical connection and a stable ground path.

FIG. 27G is taken from section 27G-27G of FIG. 27 and illustrates that the oxide-resistant pocket pad 508 can also be used for electrical connection to a circuit board edge metallization 500. In this case, as illustrated, the circuit board edge metallization 500 is connected using electrical connection material 504. The electrical connection material 504 may comprise various solders and/or thermal-setting conductive adhesives for connecting both the device side ferrule surface 26' and the gold pocket pad 508. It is not important that the electrical connection material 504 make contact directly to the device side ferrule surface 26', but it is critical that the connection material 504 at least partially contacts the oxide-resistant gold pocket pad 508.

FIG. 27H is similar to FIG. 27C, except that an oxide-resistant layer 516 is shown in addition to the ECA stripe 514. The oxide-resistant layer 516 may comprise one or more layers. As previously described, either a single oxide-resistant layer 516 may be used or a first layer of nickel and then a suitable oxide-resistant second layer 516, such as a second layer comprising gold, may be disposed over the first layer of nickel (not shown), to achieve a low resistance and low impedance electrical connection between two AIMD components. Referring to the ECA stripe 514 of FIG. 27H, it is contemplated that, for some applications wherein ECA electrical connection may not be needed to provide an electrical connection between at least two AIMD components, the ECA stripe 514 could be eliminated if the oxide-resistant layer (s) 516 is/are robust enough to prevent titanium migration and oxidation, thereby allowing attachment of the electrical connection material 504 directly to the oxide-resistant layer 516. In other words, either an oxide-resistant layer (s) could be used to make the ECA stripe 514 an effective low resistance and low impedance connection or the oxide-resistant layer (s) alone can be used instead of the ECA stripe 514. It will be appreciated that the ECA stripe 514 and/or the metallization layer 516 may also be used to provide suitable grounding, not just for circuit boards 106, 106', but also for all types of filter capacitors, including feedthrough filters 24, 24', hybrid feedthrough capacitors 24", MLCC capacitors 154, X2Y attenuators 300, and flat-thru capacitors 400.

The ECA stripe 514 over an oxide-resistant layer 516, or an oxide-resistant layer 516 without the ECA stripe 514, can be electrically connected directly to a ground edge metallization or at least one ground via hole of any of a flat-thru shielded circuit board filter as taught and disclosed in U.S. Pat. No. 8,195,295, the contents of which are fully incorporated herein by this reference.

Thus, the ECA stripe 514 disposed directly atop the ferrule device side surface 26', which was subjected to substantial testing, does not provide a reliable, low resistance connection. The inventors have tested ECA stripe 514 after laser welding, and after high reliability testing, including burn-in and life testing at elevated temperatures. In all test cases, some percentage of the devices had an undesirable increase in the ESR of the EMI filter and a reduced filter performance. Disposing one or more oxide-resistant layers 516 atop the ferrule device side surface 26', with or without an ECA stripe 514, results in a reliable low resistance and low impedance electrical connection, including a low resistance and low impedance ground connection for various types of filter capacitors: feedthrough filters 24, 24', hybrid feedthrough capacitors 24", MLCC capacitors 154, X2Y attenuators 300, flat-thru capacitors 400, and the flat-thru EMI filter circuit boards taught by the '295 patent.

Referring once again to FIGS. 27 and 27A, it is important that the terminal pin 18$gnd$ be of suitable oxide resistant material, such as rhodium, rhodium alloys, platinum, platinum alloys, platinum-iridium alloys, palladium, palladium alloys, nitinol, cobalt-chromium alloys, and combinations thereof. This is so that terminal pin 18$gnd$ can either be laser welded or gold brazed to the ferrule 26, thereby providing an oxide-resistant structure for electrical connection material 504 so that a low resistance and low impedance electrical connection is made to the EMI filter circuit board 106' and the ferrule 26.

Referring to FIG. 27A, the ground terminal pin 18$gnd$ could be laser welded anywhere on the device side ferrule surface 26' or the edge of the ferrule 26 (not shown). What is important is that the terminal pin 18$gnd$ makes a low resistance metallurgical connection and is itself oxide-resistant, which means essentially oxide-free, to the ferrule 26 and also at the same time, provides for an oxide resistant surface to which circuit boards or EMI filters connect.

Referring to FIGS. 27, 27A-27H, the embodiments comprising connection to an oxide-resistant layer 516 as shown FIGS. 27, 27A, 27E, 27F, 27G and 27H are preferred. The embodiments illustrated in FIGS. 27B, 27C and 27D, which do not comprise an oxide-resistant layer 516, are all undesirable attachment configurations that ultimately result in unreliable electrical connections prone to oxidation and increases in resistance and RF impedance over time (particularly when exposed to elevated temperatures).

FIG. 28 is taken from section 28-28 of FIG. 27 illustrating the top view of the EMI filter circuit board 106' disposed at, near or distant from the ferrule 26. In this case, each one of the capacitors 154a-154f is directly connected either through a circuit trace 162, as shown, or a direct solder connection or thermal-setting conductive adhesive connection or the like, from the MLCC 154 active electrode plates to each of the six active terminal pins 18. The ground electrode plates of the MLCC's 154 are connected to via holes which communicate with the at least one internal ground electrode plate 156 of the EMI filter circuit board 106'. In this way, the capacitors are connected both to the active pins and to the effective RF ground, which diverts unwanted high frequency energy from the terminal pins 18 through the filter capacitor to the ground plate and in turn, to the ferrule 26 and then to the AIMD casing 32, which together acts as an overall Faraday shield. This Faraday shield prevents the EMI from entering the AIMD casing 32 and instead causes the dangerous unwanted EMI RF energy to circulate harmlessly as eddy currents in the AIMD casing 32 without penetrating inside the AIMD casing where it could undesirably couple to sensitive AIMD circuitry and cause AIMD malfunction. It is noted herein that certain AIMD malfunctions can be life-threatening to a patient.

Referring once again to FIG. 28, one can see that each of the MLCCs 154 are grounded to a via hole or a circuit trace labeled gnd a-gnd f. These via holes are disposed through the circuit board and contact at least one ground electrode plate 156, which as previously described, is connected to the ferrule 26, thereby, providing a low impedance RF ground.

Referring once again to FIG. 28, the exemplary circuit traces 162 only show one embodiment, in this case, for MLCCs 154. It is contemplated that, for the X2Y attenuators 300, the circuit traces would be modified to make at least two active connections to the X2Y attenuator, which would then have at least one ground connection. For example, MLCCs 154 could also be replaced by flat-thru capacitors 400. In this case, the circuit traces would be different, in that, there would be a third terminal connected to the flat-thru capacitors 400, which would be grounded, and the circuit trace currents would go through the flat-thru capacitor. Such flat-thru capacitors are all more thoroughly disclosed in U.S. Pat. No. 10,272,252, which is incorporated herein by reference.

Figure 28A:
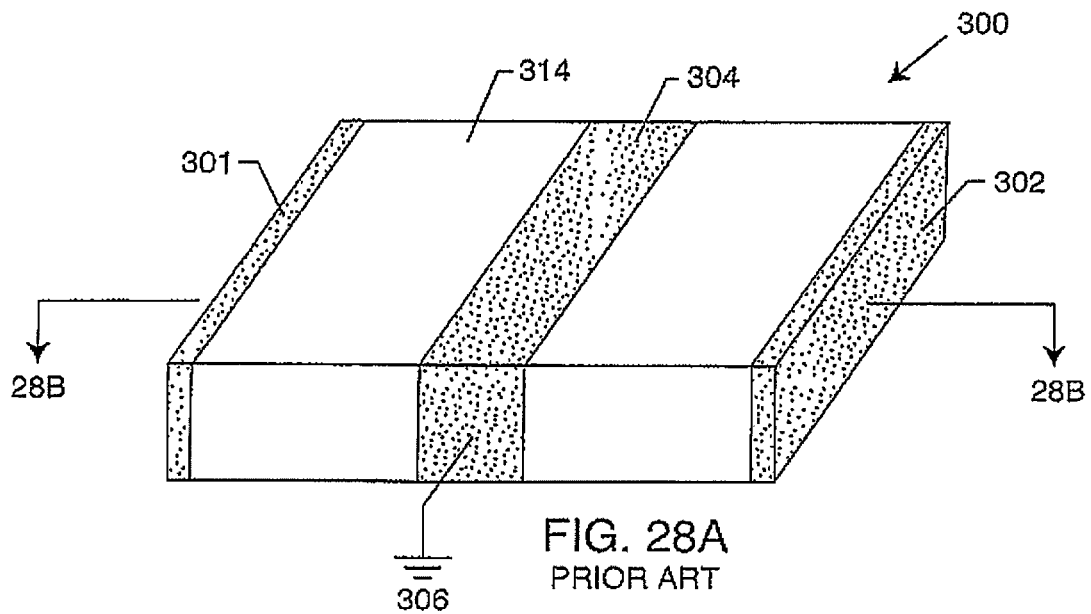
FIG. 28A is a perspective view of a prior art surface mounted capacitor known as an X2Y attenuator.

FIG. 28A is an isometric view of a prior art surface mounted capacitor that is also known by those skilled in the art as an X2Y attenuator 300. The X2Y attenuator was originally invented by the X2Y Attenuator® company. The X2Y attenuators are sold by Knowles/Syfer® and the Knowles/Syfer online catalogs are publicly accessible. In addition, the X2Y Attenuator company has approximately 72 patents assigned to them, some of which have been licensed to Knowles/Syfer. There are many variations to the X2Y attenuator 300 and only one embodiment is shown herein (see FIG. 28A). FIG. 28C illustrates how X2Y attenuator 300 can be attached to the EMI filter circuit board 106' of the present application. It will be understood by one skilled in the art that variations of the X2Y attenuators, including those described in the X2Y patents, could be used by adjusting the circuit board 106' circuit traces and the related physical embodiments disclosed herein. X2Y attenuators are so well known in the prior art that the inventors have not described all of the variations and shapes that are possible so as not to obfuscate the present application.

Referring once again to FIG. 28A, illustrated is an X2Y attenuator 300 having a dielectric body 314 comprising metallized terminations 301 and 302. As will be further described, the metallized terminations 301 and 302 are electrically conductive and solderable and will also accept a thermal-setting conductive adhesive such that these metallized terminations 301 and 302 can be connected to terminal pins 18, 18gnd or to circuit traces 418, 418gnd. Referring once again to FIG. 28A, one will see that there is a ground termination 304, as shown. This ground termination 304 of FIG. 28A comprises a continuous metallization band centrally located all of the way around the surface mounted X2Y attenuator, however, it is appreciated that the ground metallization 304 about the surface mounted X2Y attenuator could also be discontinuous. A ground connection 306 is made such that electromagnetic interference (EMI) signals from conductors attached to the metallized terminations 301 and 302 can be capacitively decoupled at the ground connection 306 to a system ground (not shown), which, for an AIMD application, can comprise the ferrule 26 or the flange 30 of the ferrule 26, which is designed to be electrically connected to the overall AIMD casing 32 of the AIMD 12.

As previously disclosed, this overall AIMD casing 32 adds an electromagnetic shield or Faraday cage to which undesirable high-frequency EMI signals may be diverted or decoupled (filtered).

Figure 28B:
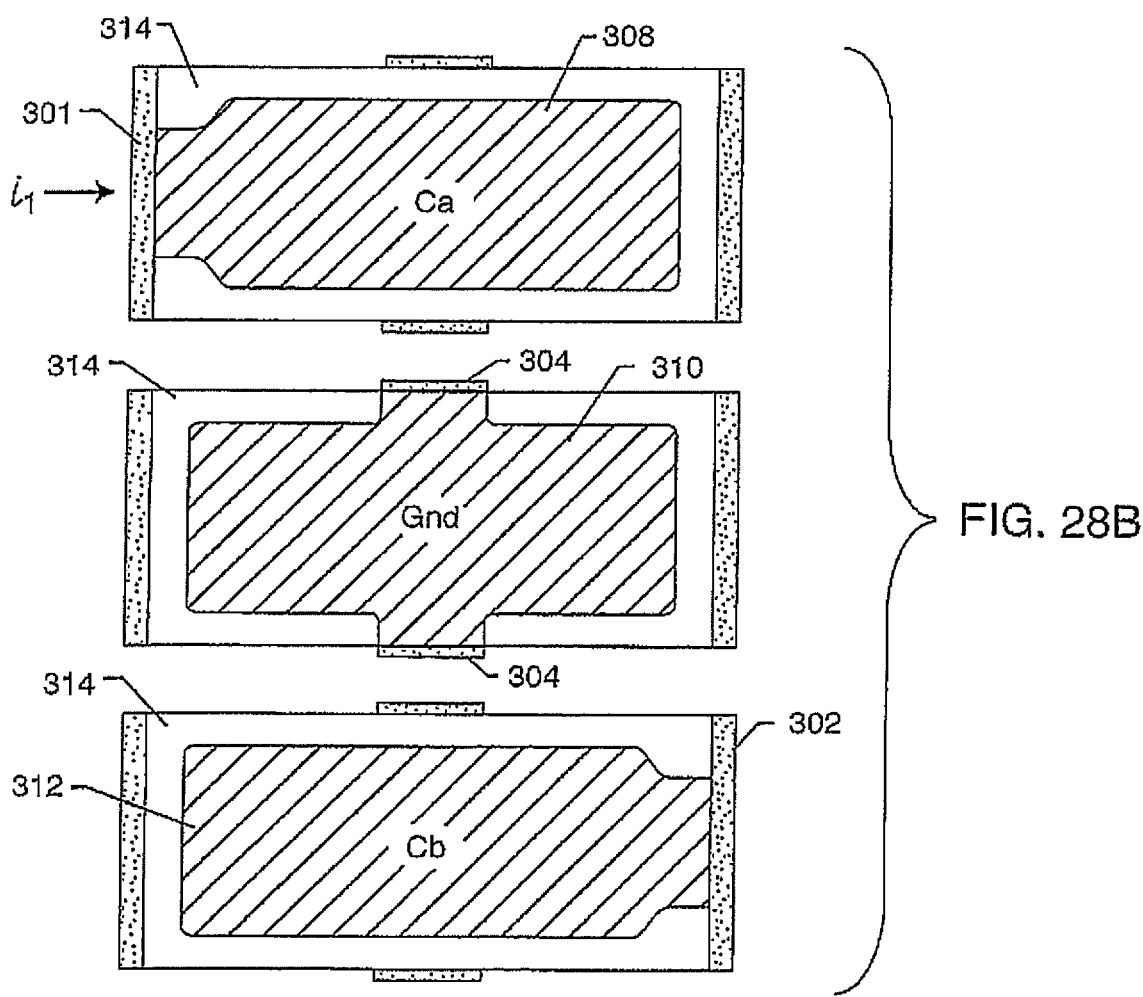
FIG. 28B is a sectional view taken along lines 28B-28B of FIG. 28A showing the active and ground electrode plates of the X2Y attenuator.
Figure 28C:
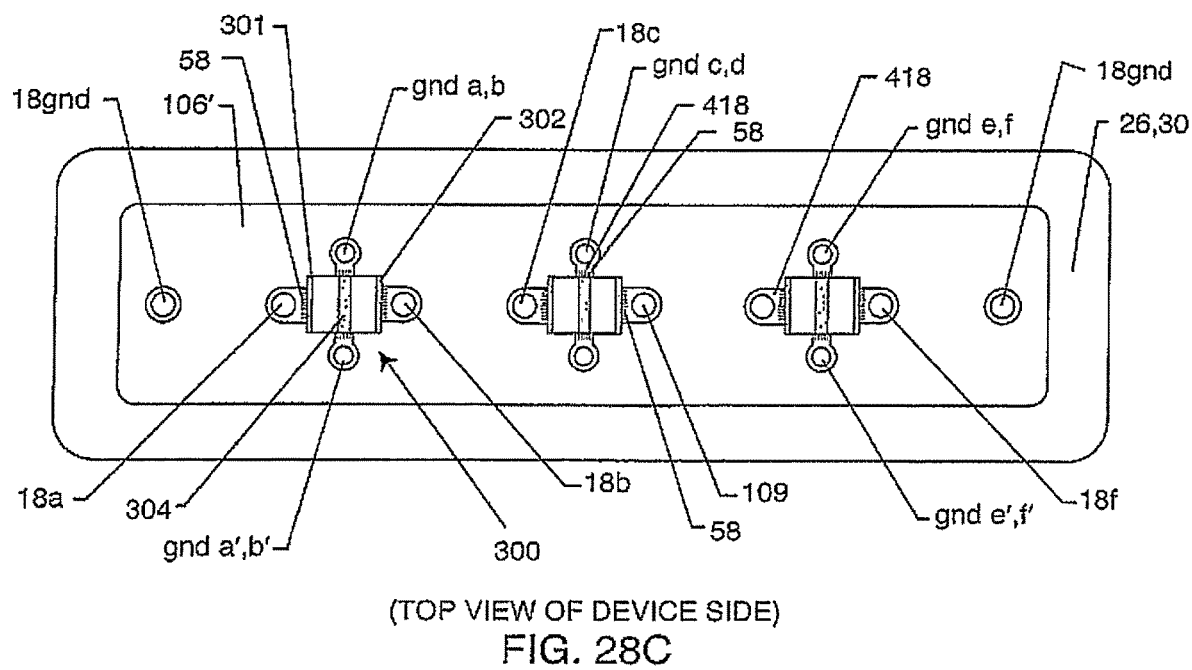
FIG. 28C is similar to FIG. 28 except that illustrated are X2Y attenuators populating the EMI filter circuit board instead of MLCCs.

FIG. 28B is taken from section 28B-28B of FIG. 28A. The sections illustrated in FIG. 28B represent different depths of the X2Y attenuator of FIG. 28A showing various layers through section 28B-28B. Referring back to FIG. 28A, the X2Y attenuator 300 has a dielectric body 314 as indicated. The dielectric body 314 may be a ceramic dielectric, such as a barium titanate, a strontium titanate or the like. In low capacitance values, the dielectric body 314 could even be an alumina ceramic or any type of ceramic structure. The dielectric body 314 may also comprise various insulative films, such as mylar (otherwise known as a stack-fill capacitor), Kapton® or many other types of film capacitors. It will also be appreciated that the dielectric body 314 could comprise a tantalum capacitor or an electrolytic capacitor. Referring now to FIG. 28B, one can see the active electrode plate 308 in the illustration at the top of FIG. 28B is associated with capacitance area Ca. The active electrode plate 308 is a conductive layer, which is connected to the metallized termination 301. The conductive layer shown in the middle illustration of FIG. 28B is a ground electrode plate 310 configured to be connected to the metallization termination 304. It is noted herein that the metallization terminations 304 and 306 of the X2Y attenuator of FIG. 28A can be continuous as shown or discontinuous (not shown). The conductive layer shown at the bottom of FIG. 28B is an active electrode plate 312, which is connected to metallization termination 302 and is associated with capacitance area Cb. It is the overlap of the active electrode plate 308 with ground electrode plate 310 that forms the capacitance Ca. Likewise, it is the overlap of active electrode plate 312 with the ground electrode plate 310 that forms the capacitance Cb. As will be shown, by selectively eliminating the ground electrode plate, an electrode plate stack up may comprise ten, twenty, thirty or even hundreds of conductive layers. In so doing, one can form and/or tailor a capacitance between the capacitance Ca and the capacitance Cb. FIG. 28B presently illustrates a ground electrode plate 310 that electrostatically shields the capacitance area Ca of the active electrode plate 308 from the capacitance area Cb of the active electrode plate 312. Therefore, the line-to-line capacitance Ca-b would be trivially small. So, it is only when one selectively removes the ground electrode plate 310, that one achieves a high effective capacitance area between active electrode plates 308 and 312 such that significant line-to-line capacitance will be achieved.

FIG. 28C is a top view of the device side of the EMI filter circuit board 106' showing a more common version of the X2Y attenuator 300, previously described in FIG. 28A, previously described in FIGS. 27 and 28. The X2Y attenuator 300, illustrated in FIG. 28C, is electrically attached by its left-hand side active metallization termination 301 and electrical attachment material 58 to active terminal pin 18a. On the right-hand side of the X2Y attenuator 300, the active metallization termination 302 is electrically connected to active terminal pin 18b. The specific type of electrical connection is not important as it may encompass a circuit trace (not shown), a circuit trace landing pad (not shown), direct connection to vias/via holes (only partially shown), or plated or metallized vias. Referring once again to FIG. 28C, one can see the ground metallization termination 304 of the X2Y attenuator 300. In order to provide very low impedance RF grounding, the ground metallization termination 304 has been electrically connected to two grounded via holes gnd a, b and gnd a', b'. Short circuit traces 418 are shown between the ground via holes and the ground metallization termination 304 of the X2Y attenuator 300. These circuit traces 418 may be long or may be eliminated simply by moving the ground via holes closer to the capacitor ground metallization termination 304 such that a direct connection can be made to the via holes. Such a change to the active traces can similarly be made.

Figure 28D:
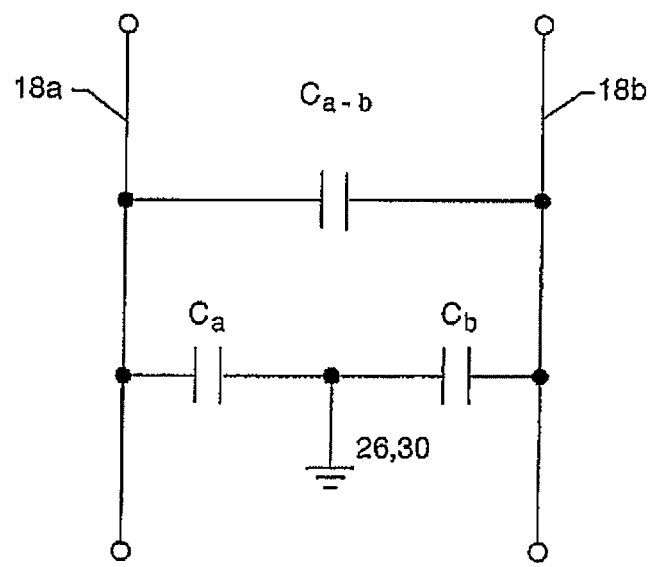
FIG. 28D is an electrical schematic for the configuration of FIG. 28C.

Now referring to FIG. 28D, illustrated is a schematic of the X2Y attenuators 300 previously described in FIGS. 28A, 28B and 28C. One can see that capacitances Ca and Cb are both connected to ground 26, 30. Ground 26, 30 is a ground to the ferrule 26, which becomes the system ground once the ferrule is welded to the AIMD casing 32. Referring once again to FIG. 28D, a line-to-line capacitance Ca-b may be formed between terminal pins 18a and 18b. As previously described in FIG. 28B, this line-to-line capacitance Ca-b would be made by selective elimination of ground electrode plates 310 such that an effective capacitance area (ECA) develops between Ca and Cb. It is noted herein that not all of the ground electrode plates 310 can be removed. If this were the case, then Ca and Cb capacitance would not even exist. Therefore, ground electrode plates 310 may only judiciously removed selectively. To EMI specialists, such judicious elimination of ground electrode plates is known as balancing the common mode filter attenuation with the differential mode filter attenuation. Differential mode means a differential signal between terminal pins 18a and 18b. This is understood more simply if one was to put a high-frequency voltmeter between terminal pins 18a and 18b, where one would read a voltage. The purpose of capacitance Ca-b is to divert the voltage so that the voltage cannot get into the inside the AIMD 12. This is called differential mode filter attenuation. Referring once again to FIG. 28D, capacitances Ca and Cb are shown both connected to ground 26, 30. Because they are both connected to a common point, this means they are also connected to each other as the schematic illustrates. The schematic, however, could be changed so that Ca and Cb are separated, with each connected to a ground symbol. It will be understood that such a connection is the same thing. This configuration is to protect against differential mode EMI. This is also easy to understand if one were to take a volt meter, say, on terminal pin 18a and place it between the terminal pin and the ferrule and one measured a high-frequency AC voltage, then the purpose of capacitance Ca is to attenuate or divert that differential mode EMI to the ferrule so that dangerous EMI will not enter into terminal pin 18a into the inside of the AIMD 12 where the EMI could therefore disrupt the proper operation of the electronic circuits of the AIMD.

Figure 28E:
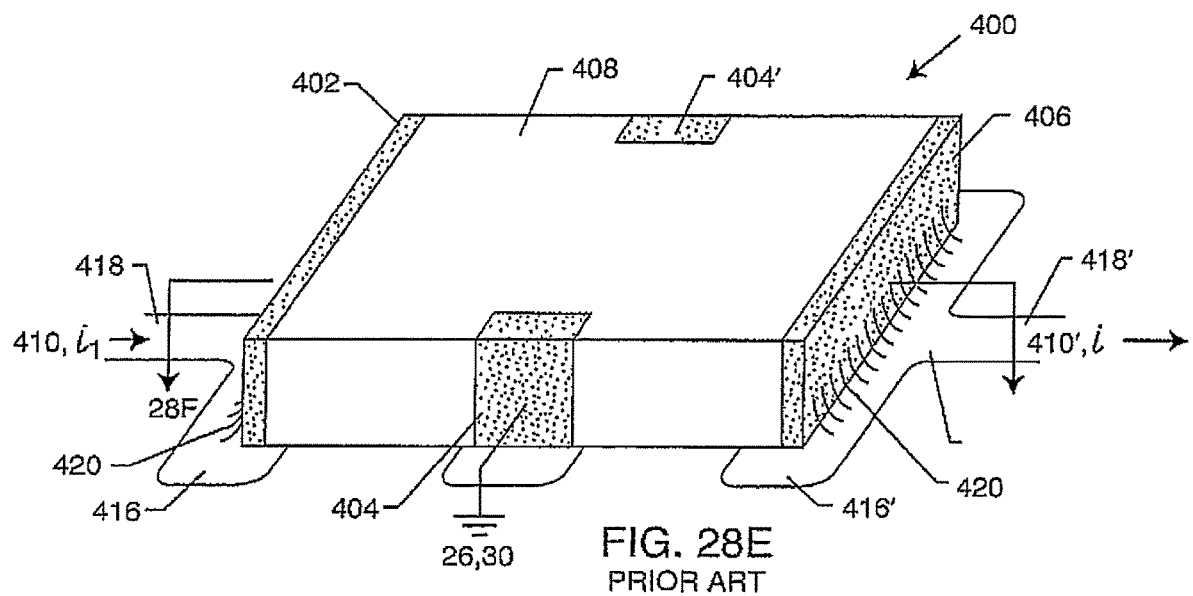
FIG. 28E is a perspective view of a prior art surface mounted capacitor known as a flat-thru capacitor.

FIG. 28E is known in the prior art as a flat-thru capacitor 400. This term was coined by one of the inventors, Robert A. Stevenson, when he was working on his master's thesis. This term also appears in a number of patents, including U.S. Pat. No. 8,195,295. This type of capacitor is unique in that circuit current actually passes through the electrodes of the capacitor itself. These capacitors are also commonly known in the prior art and are public sold online, including online catalogs for same that are also publicly accessible.

Referring once again to FIG. 28E, one can see that the flat-thru capacitor 400 is similar to the X2Y attenuator 300 in that a first active metallization termination 402 and a second active metallization termination 406 resides at both ends of the flat-thru capacitor 400. The flat-thru capacitor 400 also has ground metallization terminations 404 and 404'. The ground metallization termination, in this case, 404 and 404' is shown discontinuous, but like for the X2Y attenuator, it is contemplated that this termination 404 and 404' could comprise a continuous band all the way around the capacitor, as illustrated for the X2Y attenuator of FIG. 28A. Current 410, $i_1$ is shown entering in from a circuit trace 418 to a circuit board landing pad 416 to which the metallization termination 402 is electrically connected using electrical connection material 420. The electrical connection material 420 is better shown on the right-hand side of the flat-thru capacitor 400 where the metallization termination 406 is electrically connected to circuit board landing pad 416'. The current 410, $i_1$ is conducted all the way through the capacitor very much like a feedthrough capacitor, except in this case as will be shown, the current passes through the capacitor's electrode plates. This makes the flat-thru capacitor very unique in the prior art. The circuit current 410, $i_1$, passes through the capacitor then exits on the right-hand side as the same circuit current 410', i, this time from circuit trace 418'.

Figure 28F:
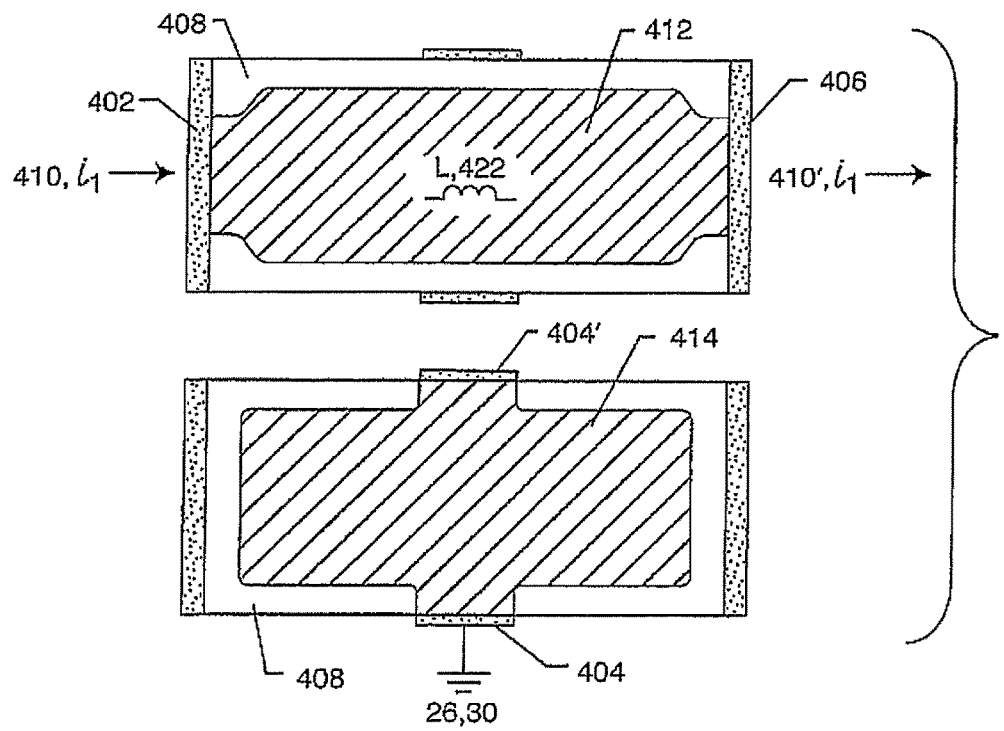
FIG. 28F is a sectional view taken along lines 28F-28F of FIG. 28E showing the active and ground electrode plates of the flat-thru capacitor.

FIG. 28F is taken generally from section 28F-28F of FIG. 28E. One will appreciate that electrode plate 412, when building a monolithic ceramic capacitor structure 408, have to be thin and lacey, so the structure does not de-laminate and remains monolithic. As used herein, the term "lacey," as it refers to an electrode plate, means that, instead of being a solid thick metal sheet, the electrode plate has a plurality of open spaces through its thickness (more like a window screen) through which grain growth can infuse and traverse the bulk ceramic dielectric during sintering. The distribution of open spaces doesn't have to be homogeneous like a window screen, but there does have to be sufficient amount of open space areas in the electrode plate so that during sintering, the grain growth of the bulk ceramic dielectric will penetrate through the electrode such that the entire capacitor anchoring the electrode plate to the bulk ceramic thereby forming a truly solid and monolithic conductive layer. This is in contrast to a bologna sandwich analogy, where the layers of bread and bologna easily separate and delaminate or otherwise are taken apart one from the other. For more information on delamination, one is referred to the paper entitled "DUAL ELECTRODE PLATE MLCC FOR HIGH VOLTAGE PULSE APPLICATIONS" presented at the Capacitor and Resistor Technology Symposium held on Mar. 6-10, 2000, at Huntington Beach, California, (ISSN 0887-7491), the contents of which are fully incorporated herein by this reference.

Figure 28G:
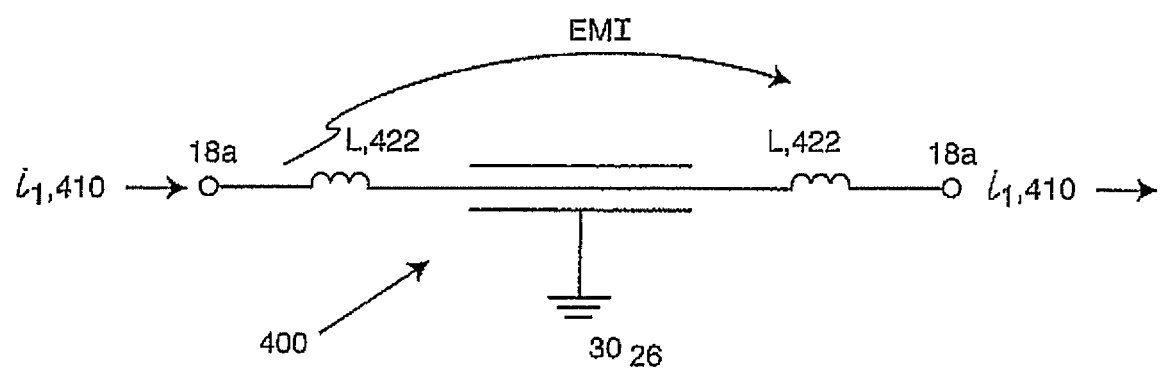
FIG. 28G is an electrical schematic for the configurations of FIGS. 28E and 28H.

Electrode plate 412 is the active electrode plate through which the circuit current 410, $i_1$ passes all the way through. Therefore, it is desirable that there be a relatively high number of active electrode plates 412 stacked up in interleaved relationship such that sufficient cross-sectional area exists to thereby preclude a high resistance to the flow of the current 410, $i_1$. It is also desirable that active electrode plats 412 be relatively wide (possibly much wider than shown) such that the circuit current 410, $i_1$ does not encounter excessive resistance or inductance. Actually, in the case of FIG. 28F, the inductance of the electrode plates 412 is desirable in that the inductance is in series with the electromagnetic filtering of the flat-thru capacitor 400. As is well known to EMI engineers, series inductance can help reduce the amount of electromagnetic energy that can get inside of a structure, in this case, the AIMD casing 32. The inductance L, 422 of the embodiment of FIG. 28F is therefore highly desirable. Normally, for prior art feedthrough capacitors and MLCCs, an inductance is undesirable, as the inductance, as shown in the schematic of FIG. 28G, would be in series between the capacitance and ground thereby degrading filter performance at high frequencies. However, in the case of FIG. 27E, as will be shown, the inductance shows up in series with the terminal pin, thereby, providing increasing inductive reactance at high frequencies which consequently improves filter performance.

Referring again to FIG. 28F, one can see the ground electrode plate 414 that is connected to the ground metallization terminations 404 and 404'. As previously disclosed, such ground metallization terminations are configured to be attached to a system ground, which is the AIMD casing 32.

FIG. 28G is the schematic of the prior art flat-thru capacitor 400. The flat-thru geometry has an enormous advantage in that, any stray or parasitic inductance of the electrode plates shows up in series with the terminal pin 18 (18a). As previously described, this series inductance helps to attenuate undesirable EMI. The flat-thru capacitor 400 is grounded through the ground symbol to the ferrule 26 and in turn, to system ground (namely, the AIMD casing 32), as previously disclosed. A deficiency of the flat-thru capacitor is also illustrated in FIG. 28G. That is, at extremely high frequency, EMI can couple (radiate) through the air between metallization terminations 402 and 406, or worse yet, from circuit trace 418 to circuit trace 418'. EMI cross-coupling depends on the geometry of the circuit, the spacing and size of the circuit traces and the size of the flat-thru capacitor, but, in general, such undesirable EMI cross-coupling does not happen until one is in the GHz frequency range, such as 3 GHZ. Fortunately, the human body effectively absorbs and reflects EMI in the GHz region, particularly above 3 GHZ, such that it is very difficult for extremely high frequency energy to penetrate very far inside the human body. Accordingly, the flat-thru capacitor 400 is an acceptable EMI filter tradeoff for use in active implantable medical devices that are designed to be placed inside the human body with leadwires also disposed inside the human body. The human skin, muscle and fats tend to reflect and absorb such extremely high energy, thereby compensating for the flat-thru capacitor's tendency for EMI to couple across the flat-thru capacitor 400.

Figure 28H:
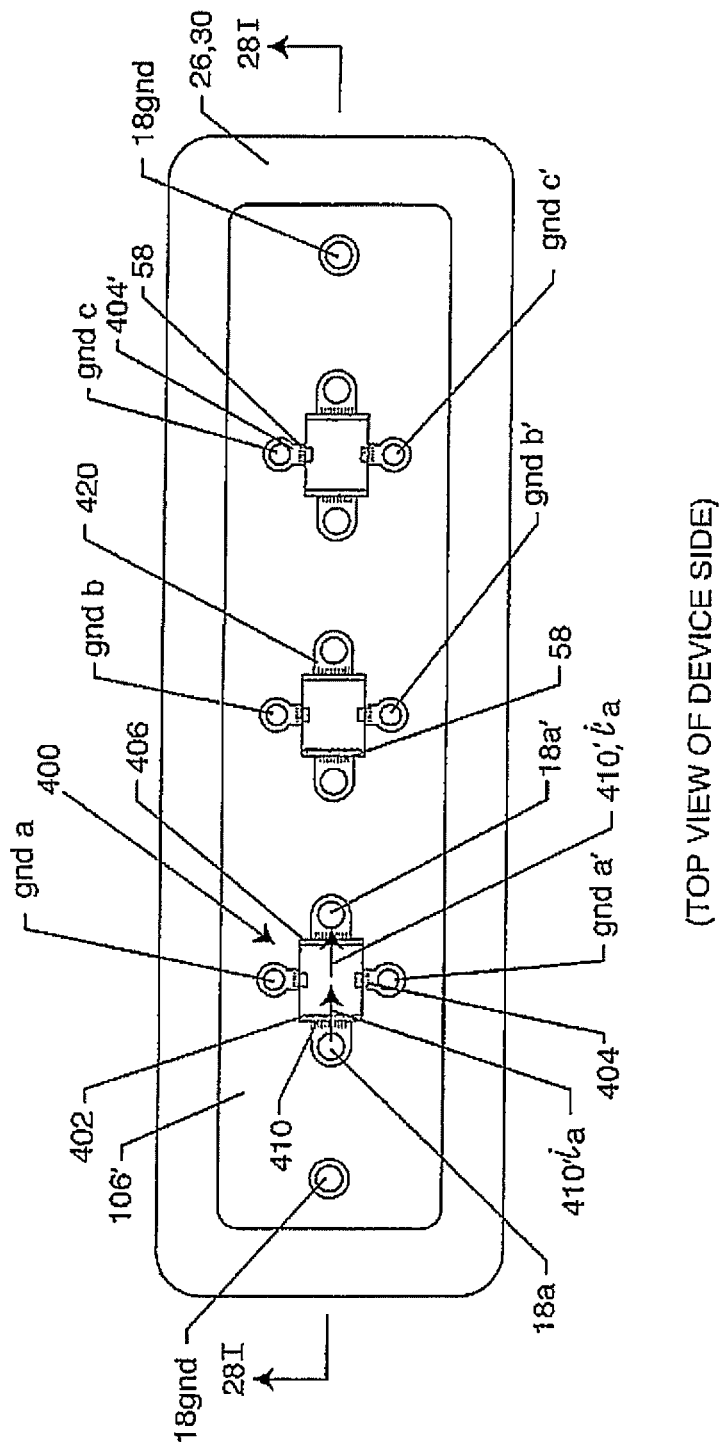
FIG. 28H is similar to FIG. 28C except that illustrated are flat-thru capacitors populating the EMI filter circuit board instead of X2Y attenuators.

FIG. 28H is very similar to FIGS. 28 and 28C in that, the embodiment of FIG. H shows the top view of the device side of an EMI filter circuit board 106', comprising three flat-thru capacitors mounted to the top surface of the EMI filter circuit board 106'. One can see flat-thru capacitor 400 disposed between terminal pins 18a and 18a'. Circuit current enters terminal pin 18a as undesirable EMI energy from the body fluid side (not shown) up to the top of terminal pin 18a and then the circuit current passes through the capacitor body of the flat-thru capacitor 400 to terminal pin 18a' and is then directed to the circuit board active electronic circuits of an AIMD active electronic circuit board 106. Metallization termination 402 is electrically connected with electrical connection material 420, such as a solder or a thermal-setting conductive adhesive to circuit via hole 18a. This electrical connection may comprise a circuit board landing pad, a circuit board trace or even internal circuit board traces (not shown). There are many ways to make an electrical connection between the flat-thru capacitor's metallization terminations 402 and 406 to the corresponding leads 18a and 18a' thereby electrically connecting to the metallization terminations. The ground electrode plates 414 of the flat-thru capacitor 400 are electrically connected to ground vias gnd a and gnd a'. In the embodiment of FIG. 28H, there are short circuit traces shown, but as previously described for the X2Y attenuator, these short circuit traces are not necessary as the via holes gnd a and gnd a' could be moved immediately adjacent the metallization terminations 404 and 404' such that a direct electrical connection is made to the via holes gnd a and gnd a'. In addition, ground vias gnd a and gnd a' could even comprise a single bump underneath the flat-thru capacitor 400 wherein a robotic dispenser could accurately place a BGA dots such that the ground electrical connection would be invisible beneath the flat-thru capacitor 400. Those skilled in the art will appreciate that there are many possible ways to make the electrical connections to the flat-thru capacitor 400. BGA dots can alternatively be solder bumps or dots of a conductive thermal-setting adhesive.

Figure 28I:
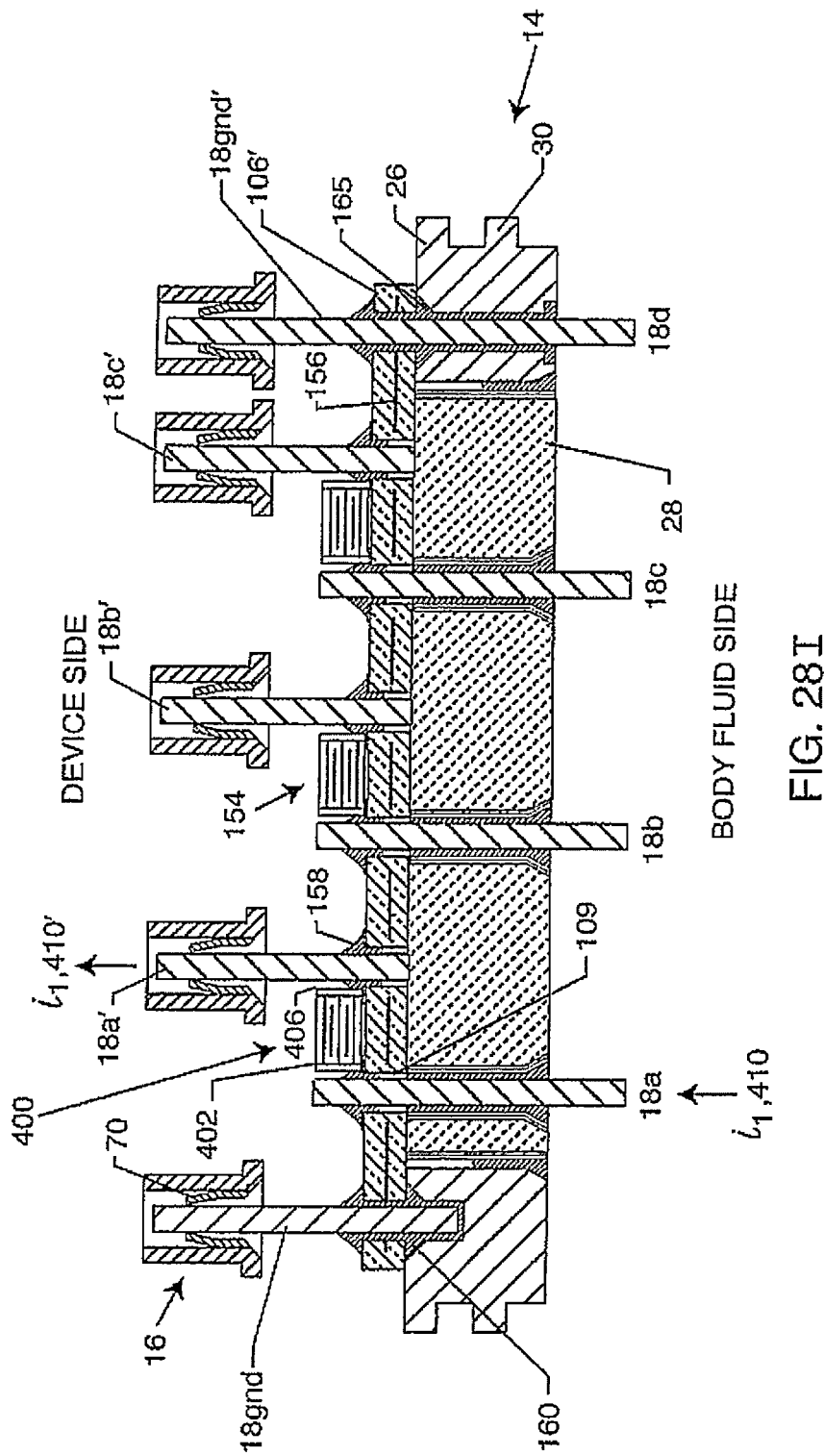
FIG. 28I shows a cross-sectional view of an alternative embodiment of a feedthrough connector assembly taken along lines 28I-28I. Illustrated are terminal pin connectors attached to terminal pins. It is noted that the terminal pins are actually also attached to an AIMD active electronic circuit board (not shown) of the device side of an AIMD.

FIG. 28I is a sectional view taken from section 28I-28I of FIG. 28H. The embodiment of FIG. 28I illustrates terminal pin 18a passing through the insulator 28 of an AIMD hermetically sealed feedthrough 14 and a via of an EMI filter circuit board 106' and electrically connected to the flat-thru capacitor 400 left-hand side active metallization termination 402. Terminal pin 18a must be discontinuous of terminal pin 18a' because, for the flat-thru capacitor 400 to function such that unwanted high frequency electrical interference is effectively diverted, the circuit current $i_1$,410 must pass right through the electrode plates of the flat-thru capacitor 400. Accordingly, on the right-hand side of the flat-thru capacitor 400, the active metallization termination 406 is electrically connected to terminal pin 18a'. As previously discussed, terminal pin 18a could be disposed in an EMI filter circuit board 106' via hole 109. So as one traces the circuit current $i_1$,410, from the body fluid side, one will appreciate that the circuit current $i_1$,410, if it is a low frequency or DC current, low frequency meaning low frequency biologic signals, or low frequency therapeutic pacing pulses, such as cardiac pacing pulses, would pass from the body fluid side or from the device side from terminal pin 18a through the active electrode plates 412 of the flat-thru capacitor 400 and in turn, to the device side terminal pin 18a' as $i_1$,410'.

Further regarding the embodiment of FIG. 28I, the terminal pin connectors 16 on the device side of the embodiment illustrated in FIG. 28I are attached to circuit board lands on an AIMD active electronic circuit board 106 (not shown). If therapeutic low frequency pulses flow through the circuitry of the AIMD active electronic circuit board 106 with the intention of travelling to the distal electrodes in contact with human tissue, then the therapeutic pacing pulses would come from the device side of the AIMD into terminal pin 18a' and would then flow through flat-thru capacitor 400 unattenuated, and then flow out through terminal pin 18a on the body fluid side of the AIMD, through the leads (not shown) connected on the body fluid side of the AIMD, to the distal electrodes of the leads thereby stimulating a body tissue, for example, the myocardium of a heart. On the other hand, if terminal pin 18a was intended for sensing low frequency biologic signals, such low frequency biological signals sensed by a distal electrode of a lead enters terminal pin 18a on the body fluid side, then passes through the flat-thru capacitor 400 unattenuated or minimally attenuated, and then desirably flows to terminal pin 18a' to a circuit board circuit trace of the AIMD active electronic circuit board 106 (not shown). The sense signal would be assessed, and stimulation therapy appropriately adjusted such that the adjusted therapeutic low frequency pulses can flow through the circuitry of the AIMD active electronic circuit board 106, travelling the original therapy delivery path disclosed above.

There is a third type of signal that is very important and that is a high frequency dangerous EMI signal. If that signal is picked up by the body fluid side leads and distal electrodes, the undesirable EMI current would enter into terminal pin 18a, on the body fluid side and then would pass through the active electrode plates 412 of the flat-thru capacitor 400. Ideally, the flat-thru capacitor would divert (or capacitively decouple) this dangerous high frequency EMI energy through the capacitive reactance of the flat-thru capacitor 400 to the ferrule 26 and then, in turn, to the AIMD casing 32, which acts as a Faraday cage. In this way, the flat-thru capacitor 400 allows low frequency pacing and biological sensing signals to freely pass, while attenuating or filtering dangerous high frequency EMI.

FIG. 28J illustrates a different embodiment of a flat-thru capacitor 400' comprising four poles, which is known as a quad polar flat-thru capacitor. Instead of a monopolar or one-pole flat-thru capacitor 400 as shown in FIGS. 28E-28I, FIG. 28J indicates that flat-through capacitors could embody many poles in a monolithic dielectric body. Flat-thru capacitors can have any number of poles in various geometric configurations. This is better understood by referring to FIG. 28K, where one can study the four active electrode plates 412a through 412d illustrated. As disclosed for the monopolar flat-thru capacitor 400 of FIGS. 28E-28I, the circuit current $i_1$ must pass through the four active electrode plates 412a through 412d as indicated for active electrode plate 412 a, in an overlap relationship with ground electrode plates 414. The metallization terminations 404 and 404' would be connected to system ground (that is, to the ferrule 26 and in turn, to the AIMD casing 32 not shown). The overlap of the active layers 412a through 412d with the ground electrode plate 414 creates four flat-thru capacitances. Flat-thru capacitors can greatly vary in geometry and shape and are similar to X2Y attenuators in that flat-thru capacitors can also include 1, 2 or even "n" number of attenuators (poles) in a monolithic package.

FIG. 29 is very similar to FIG. 27, in that the EMI filter circuit board 106' has at least one ground electrode plate 156, which can be internal or external. However, in the embodiment of FIG. 29, the ground electrode plate 156 is not grounded to a pin that is welded or brazed to the ferrule 26. Instead, there is a circuit board metallized via hole that traverses the at least one internal ground electrode plate 156 thereby is electrically connected to the at least one internal ground electrode plate 156. The via hole is spatially aligned such that the via hole sits at least partially atop the gold braze 46a of the hermetic seal between the insulator 28 and the ferrule 26. Illustrated is an electrical connection material 158gnd, which is disposed either filling the via hole or on the internal sidewall of the via hole traversing the at least one internal ground electrode plate 156, thereby completing an electrical connection from the ground electrode plate 156 (in this FIG. shown as an internal ground electrode plate) to the gold braze 46a. Ground electrode plate 156 can be any number 'n' electrode ground plates, the 'n' ground electrode plates being either all internal ground plates or internal and external ground electrode plates. As previously disclosed herein, it is very important that the ground electrical connection be to a ferrule 26 comprising an oxide resistant surface, one embodiment shown previously in FIG. 27. An oxide-resistant surface may further comprise an oxide-resistant (essentially oxide-free) ground terminal pin. In the case of FIG. 29, the ground via hole is spatially aligned atop gold braze 46a, however, a plurality of via holes can be aligned strategically over the gold braze 46a of the hermetic seal. Referring once again to FIG. 29, a ground via hole of the EMI circuit board 106', may comprise an electrical connection comprising an electrically conductive solid filled via hole, the electrically conductive solid filled via hole comprising a BGA, a solder, a solder bump, a conductive epoxy, a conductive epoxy bump or an anisotropic conductive film (ACF). It is contemplated that many of the electrical connections disclosed herein can also alternatively be used. One is also referred to FIGS. 92 and 93 of U.S. Pat. No. 8,195,295, which illustrates a circuit board (192) having internal ground electrode plates (194) and (194') grounded through via holes directly connected to the gold braze (124) of a hermetic seal. As previously noted, the element numbers in parenthesis are the element numbers of the '295 patent. One is also referred to FIG. 94 of the '295 patent for another example of a solid filled via hole and electrical connection material (260) that contacts the hermetic seal gold braze (124). One is also referred to FIGS. 95, 96 and 97 of the '295 patent for examples of (196) pins or structures (270) over which a circuit board ground via can be placed and electrically attached. U.S. Pat. No. 8,195,295 is fully incorporated herein by this reference.

Figure 30:
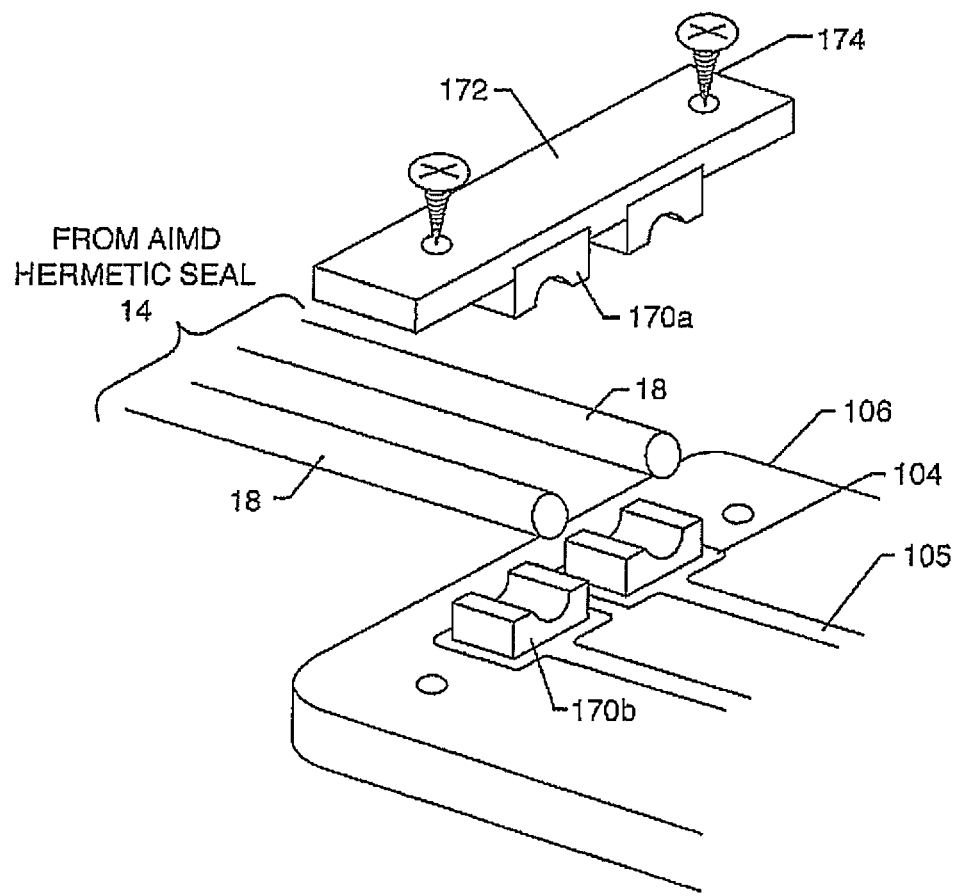
FIG. 30 shows a perspective view of an alternative embodiment of a terminal pin connector.

FIG. 30 illustrates an exemplary embodiment of a bus-bar-like terminal pin connector for providing electrical connection between one or more components of the AIMD and one or more feedthrough conductive pathways, wherein the one or more feedthrough conductive pathways are selected from the group consisting of a terminal pin, a pin, a leadwire, a lead wire, a two-part pin, a lead conductor, a sintered paste-filled via, a co-sintered via, a co-sintered via with one or more metallic inserts, or combinations thereof, and wherein the component of the AIMD comprises one of a circuit, a circuit board, an electrical component, a header, a header block, or combinations thereof. The embodiment of FIG. 30 simulates a bus-bar in that the embodiment shown is capable of providing multiple feedthrough conductive pathway connections uses a single top capture pad 172 capable of capturing a group of feedthrough conductive pathways such that electrical current or sensing signals can travel between the AIMD pulse generator and the distal electrodes of an implanted lead in contact with body tissue. For simplicity, the exemplary embodiment of FIG. 30 illustrates only two feedthrough conductive pathway connection points, each feedthrough conductive pathway point connectable from either an AIMD hermetically sealed feedthrough or an AIMD hermetically sealed feedthrough comprising a feedthrough filter or an EMI filter circuit board (not shown) to an AIMD component, which, in the embodiment of FIG. 30, is an AIMD active electronic circuit board 106, The AIMD active electronic circuit board 106 illustrated comprises two electrically conductive terminal pin half pads 170b, each terminal pin half pad mechanically and electrically attached to circuit board landing pads 104 of the circuit trace 105. Such terminal pin half pads 170b are alternatively attachable to circuit board pad, a circuit board via hole, a circuit board land, or a circuit trace. Such terminal pin half pads 170b could be made of any electrically conductive material as the terminal pin half pads 170b reside inside of the hermetically sealed AIMD casing 32, therefore do not need to be biocompatible. The terminal pin half pads 170b illustrated are routed to other AIMD circuitry within the AIMD 12. The terminal pin half pads 170b residing on the AIMD active electronic circuit board 106 positions the AIMD active electronic circuit board beneath the terminal pins 18 such that a top capture pad 172 is attachable to the AIMD active electronic circuit board 106 using fasteners 174 as shown. The top capture pad 172 comprises an insulative frame with two electrically conductive terminal pin half pads 170a insulated from each other. Illustrated is a bipolar system, but it is understood that the embodiment of FIG. 30 could be unipolar, quad polar, or "n" polar. Referring once again to FIG. 30, the diameter of terminal pin 18 would typically be slightly larger than the diameter formed when the terminal pin half pad 170a and the terminal pin half pad 170b engages terminal pin 18. When the fasteners 174 screwed in so that the top capture pad 172 is attached to the AIMD active electronic circuit board 106, a small gap between the terminal pin half pad 170a and the terminal pin half pad 170b surrounding the terminal pin 18 is present. As such, the terminal pin 18 is captured such that longitudinal movement is prevented, resulting in a robust mechanical and electrical attachment. In one embodiment, the terminal pin half pads 170a and 170b could be any suitably electrically conductive material, including insulative materials coated or plated with an electrically conductive material as previously disclosed herein. During the laser welding of the AIMD can halves 112, 114, as previously disclosed, may exhibit some degree of terminal pin longitudinal movement so that undo stresses and strains cannot build up if expansion and contraction occurs between the can halves and the circuit board due to mismatch of thermal coefficients of expansion. Thermal coefficient of expansion mismatch may also cause residual stresses and strains during laser welding of the ferrule 26, the AIMD can half 112 and the AIMD can half 114, as inhomogeneous temperature distributions may arise, potentially causing a terminal pin 18 to expand and push against the terminal pin half pads 170a and 170b.

Figure 30A:
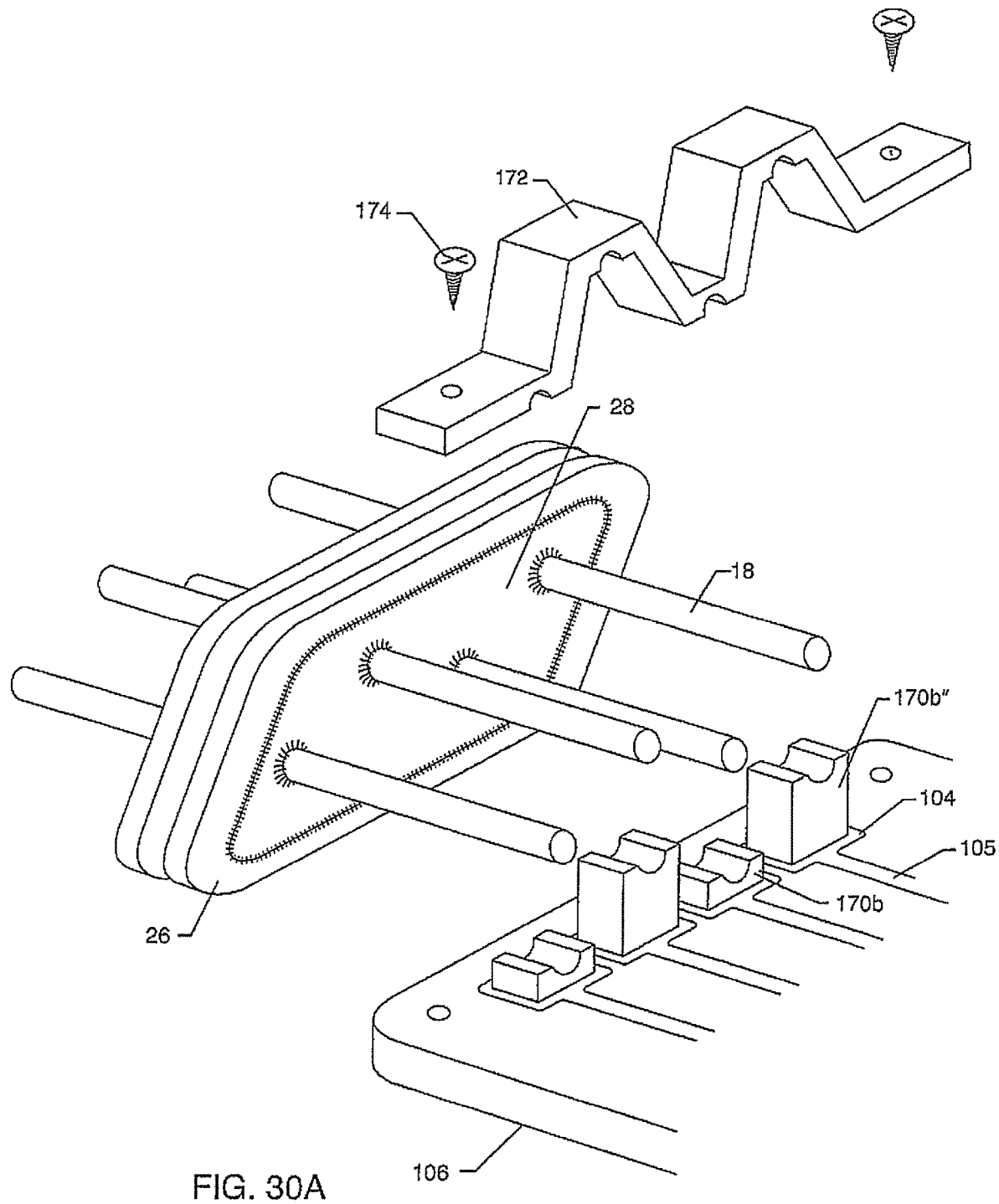
FIG. 30A is a perspective view of an alternative embodiment of an AIMD feedthrough connector assembly attachable to an AIMD hermetically sealed feedthrough having a staggered terminal pin configuration.

FIG. 30A is very similar to FIG. 30, except that in the embodiment of FIG. 30A, the top capture pad 172 is staggered to accommodate dual in-line terminal pin configurations. As illustrated, some of the terminal pin half pads 170b are shorter and other terminal pin half pads 170b" are taller than illustrated in FIG. 30. Such height variations of the terminal pin half pads are made so that each one of the staggered terminal pins 18 hermetically sealed to the insulator 28 are appropriately spatially aligned within their respective terminal pin half pads 170b and 170b" so that the top capture pad 172 can be fastened to the AIMD active electronic circuit board 106, thereby capturing each terminal pin 18 between the terminal pin half pads 170b or 170b" and the top capture pad 172.

Figure 31:
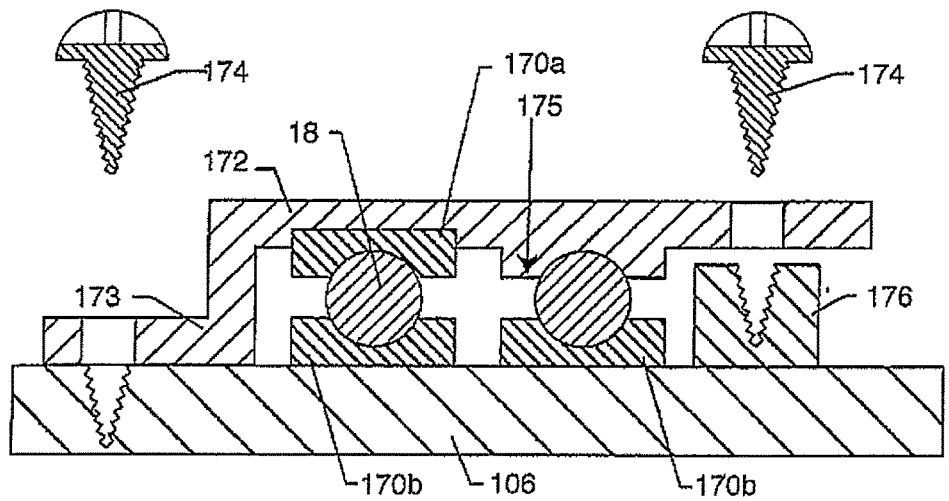
FIG. 31 is a cross-sectional view an alternative embodiment of an AIMD feedthrough connector.

FIG. 31 is a cross-sectional view of an exemplary bus-bar-like terminal pin connector embodiment. This terminal pin connector embodiment illustrates two terminal pins 18 each uniquely captured by the terminal pin connector, two fastening configurations for attaching the top capture pad 172 to an AIMD active electronic circuit board 106, and a uniquely configured top capture pad 172. Referring now to the fasteners 174, illustrated are simple slotted screws. Alternatively, the fasteners 174 can be selected from the group consisting of Allen screws, Torx screws, hex screws, star screws and combinations thereof. The fasteners 174 are optionally fastenable using a torque wrench.

Referring to the embodiment of the fastening configuration on the right-hand side of FIG. 31, illustrated is a female screw thread receptacle 176 affixed to the surface of the AIMD active electronic circuit board 106, the female screw thread receptacle in this embodiment is shown positioned at, near or adjacent a terminal pin half pad 172b. The top capture pad 172 comprises a via hole on the right-hand side that is spatially aligned with a threaded opening of the female screw thread receptacle 176. When the fastener 174 is inserted through the via hole of the top capture pad 172 and into the threaded opening of the female screw thread receptacle 176, the top capture pad 172 is fastened to the AIMD active electronic circuit board 106. As such, this optional fastening configuration enables AIMD assembly such that an AIMD casing half 114 (not shown) can be positioned to physically contact the surface of the fastener 174 so that the fastener 174 cannot come loose or back out from the female screw thread receptacle 176.

Referring to the embodiment of the fastening configuration on the left-hand side of FIG. 31, the top capture pad 172 is illustrated stepped down, wherein the step portion 173 of the top capture pad 172 on the left-hand side comprises a via hole. When the top capture pad 172 is seated on the AIMD active electronic circuit board 106, the via hole is spatially aligned with a threaded opening of the AIMD active electronic circuit board 106. When the fastener 174 is inserted through the via hole of the step portion 173 of the top capture pad 172 and into the threaded opening of the AIMD active electronic circuit board 106, the step portion 173 of the top capture pad 172 is fastened to the AIMD active electronic circuit board.

Referring to the embodiment on the left-hand side for capturing a terminal pin 18, illustrated are two electrically conductive terminal pin pad halves, a terminal pin pad half 170a attached to the top capture pad 172 and a terminal pin pad half 170b attached to the AIMD active electronic circuit board 106. When the top capture pan 172 is fastened, terminal pin 18 is captured by terminal pin pad halves 170a and 170b similarly to the embodiment of FIG. 30.

Referring to the embodiment for capturing a terminal pin 18 to the left of the female screw thread receptacle 176 of FIG. 31, illustrated is an electrically conductive terminal pin pad half 170b attached to the AIMD active electronic circuit board 106 and an insulator pad 175 monolithically extending from the top capture pad 172. The insulator pad 175, which is formed during the manufacturing of the top capture pad 172, is configured to mate with a portion of the diameter of the terminal pin 18. When the top capture pan 172 is fastened, terminal pin 18 is captured by terminal pin pad half 170b and the insulator pad 175.

Referring to the exemplary embodiment of the top capture pad 172 of FIG. 31, it is noted herein that variations of the top capture pad 172 can be made to satisfy the specific needs of an application. For example, it is contemplated that step portion 173 of the top capture pad 172 could optionally comprise a compliant spring-like material. The step portion 173 of the top capture pad 172 could also optionally be angled, or thinner than the overall thickness of the top capture pad 172, or curved, in order to apply less force to one or more terminal pins 18 or to flex so as to accommodate varying tolerancing or to permit some degree of longitudinal movement should mismatches of coefficient of expansion exist during thermal assembly processes. The top capture pad 172 may comprise one of only terminal pin half pads, only monolithic insulator pads, or combinations thereof. The top capture pad 172 may be insulative only or selectively electrically conductive. While the embodiments of FIG. 31 are exemplary, the embodiments are not meant to be limiting. Accordingly, a specific configuration of a top capture pad 172 may comprise one or more of any of the embodiments disclosed within the present application.

Figure 32:
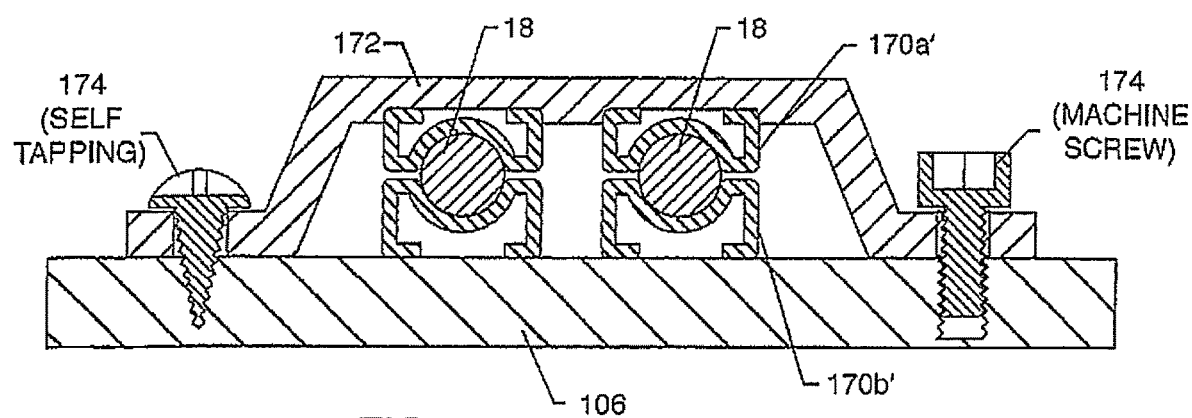
FIG. 32 is a cross-sectional view an alternative embodiment of an AIMD feedthrough connector.

FIG. 32 illustrates a cross-sectional view of yet another embodiment of an exemplary bus-bar-like terminal pin connector. Illustrated are compliant terminal pin half pads 170a' and 170b' in accordance with the definition of the term "compliant" previously defined herein. In the compliant embodiment of FIG. 32, has elastic resilience permitting longitudinal movement of terminal pins 18 if needed. As previously disclosed for other compliant components herein, the compliant terminal pin half pads 170a' and 170b' may be plated to enhance a particular property of the compliant terminal pin pads. For example, plating may be provided to enable electrical conductivity, increase strength and durability, allow solderability, improve electrical conductivity, increase surface hardness, provide wear resistance, impart anti-galling properties, afford antifriction properties, offer movement lubricity, or increase friction to impart resistance to movement or to enhance grip. The plating may be of the same materials and by the same processes previously disclosed herein.

Referring once again to FIG. 32, both terminal pin half pads are illustrated being compliant terminal pin half pads 170a' and 170b', however, it is contemplated that one or the other terminal pin half pads may be compliant while its corresponding terminal pin half pad is not compliant. Furthermore, it is irrelevant as to whether the compliant terminal pin half pad is attached to the top capture pad 172 or the AIMD active electronic circuit board 106. need not be at the top and bottom. In other words, the upper terminal pin half pad could be a compliant terminal pin half pads 170a' and the bottom terminal pin half pad could be the non-compliant terminal pin half pad 170b of FIG. 31.

Referring to the fasteners, it noted herein that the fasteners 174 of FIGS. 31 and 32 are merely illustrative. While the fasteners of FIG. 32 are self-tapping or machine screw fasteners, any type of fastener may be used that preserves removability of defective AIMD components for replacement or reworked and re-installation. Additionally, in the spirit of removability, the fasteners disclosed herein may further comprise lock washers, a removable LOC TITE®, nylocks or other such components that employ special design to ensure a snug and secure attachment while still remaining removable. Such component additions to a fastener can prevent a fastener from backing out, inadvertent or component mishandling detachments, and compliance to industry shock, vibration and drop test requirements. It will be appreciated that a threaded opening as illustrated may instead be a tapped hole. Alternatively, a threaded opening may be replaced by a threaded post, a threaded insert, or a threaded connector housing of an AIMD component without departing from the spirit and the scope of the subject matter of the present application.

Referring once again to FIGS. 31 and 32, it is understood that the top capture pad 172 can be insulative and incorporate an electrically conductive terminal pin half pad 170a or an electrically conductive compliant terminal pin pad 170a'; or the top capture pad 172 could comprise an electrically insulative top capture pad 170 or an electrically insulative compliant terminal pin pad 170a'. Electrical connection can be made to terminal pin 18 by only contacting the terminal pin 18 to the terminal pin half pad 107b or the compliant terminal pin half pad 107b'. Electrically insulative terminal pin half pads may be integral to the top capture pad 172 or separately attached to the top capture pad 172. An insulating material may be selected from the group consisting of polyimide, acrylic, glass, fiberglass, rubber, polyester, polyether imide, polytetrafluoroethylene, polyethylene, polyetheretherketone (PEEK), polyethylene napthalate, polyvinyl chloride (PVC), fluoropolymers, copolymers, ceramic, a laminate, a resin, papers, films, foams, silicone, sponge, rubber, soft ceramic-filled silicone, a silicone coated fabric or mesh, a silicone foam, an open-cell foam such as, but not limited to, a polyurethane, a reticulated polyurethane foam, a closed cell foam such as, but not limited to, polyethylene, a cross-linked polyethylene foams, or combinations thereof.

Generally regarding electrical connection to terminal pin 18, some terminal pin materials are subject to oxidation over time. If a terminal pin 18 is pre-disposed to oxidation, the terminal pin may require a "tin-dip" or a plating such that a robust electrical connection can be consistently achieved. Any of the previously disclosed materials may be used in accordance with the teachings herein regarding whether the terminal pin resides on the body fluid side or on the device side of the AIMD.

The terminal pin half pads 170b and 170b', as illustrated in FIGS. 31 and 32, are readily populated by robots during population of other components on the AIMD active circuit board 106. The terminal pin half pads may be attached to one of a circuit board landing pad, a circuit trace, a bond pad, a circuit board land by currently available attachment methods, including robotic dispensing of BGA (ball grid array), which can encompass solder or electrically conductive thermal-setting adhesives and the like.

Figure 33:
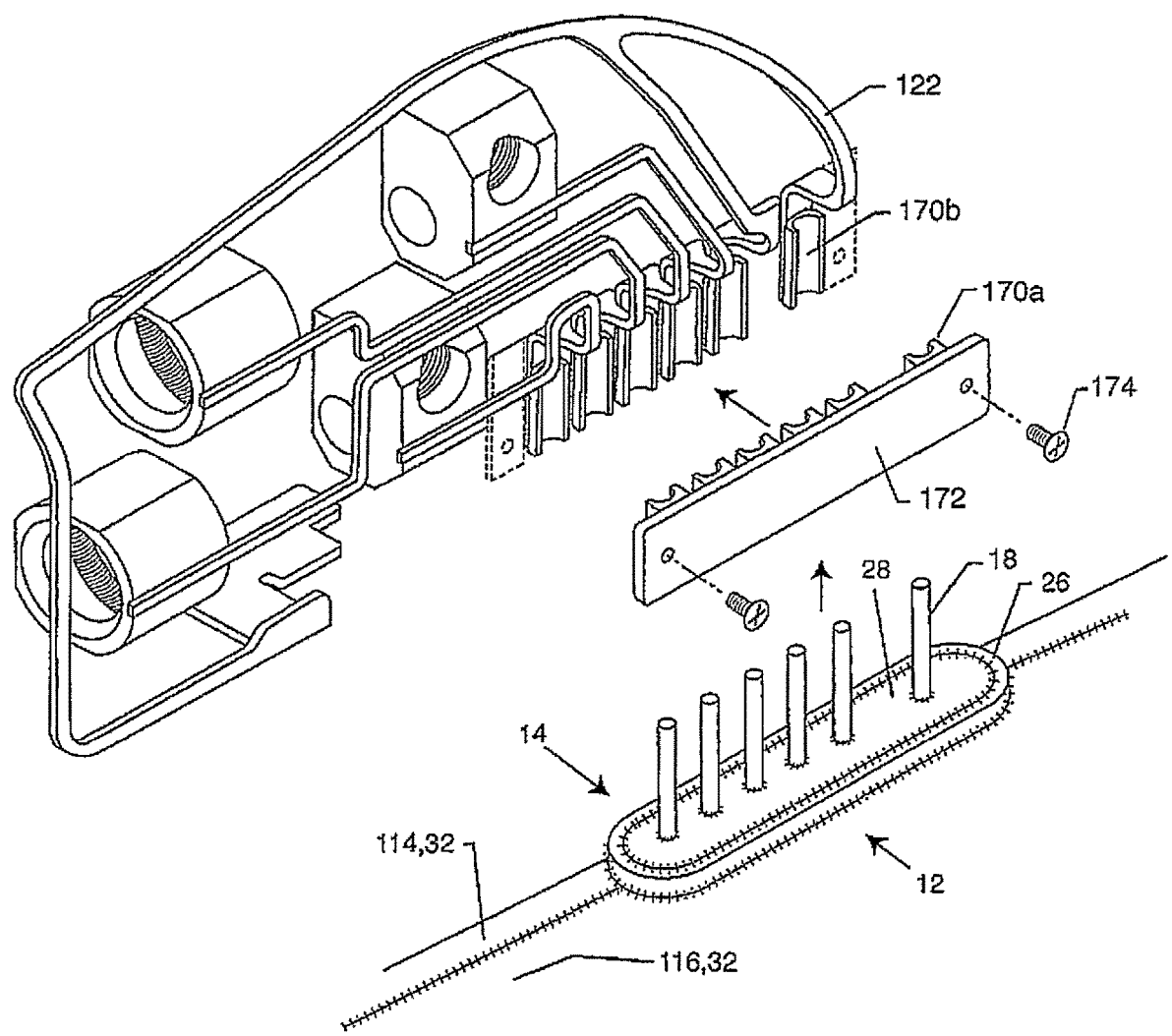
FIG. 33 is a perspective view of exemplary internal conductors, lead connectors and terminal pin connectors residing of an AIMD header block attachable to an AIMD hermetically sealed feedthrough.

FIG. 33 illustrates an embodiment of a bus-bar-like terminal pin connector for use with an AIMD header block. An AIMD header block 118 is previously described in FIGS. 10, 12 and 13. Referring once again to FIG. 33, illustrated are terminal pin half pads 170b attached to each electrical conductor 122 residing within a formed insulating structure 120 of an AIMD header block 118 (not shown). In the embodiment of FIG. 33, the terminal pin half pads 170b must be electrically conductive, biocompatible, biostable, and non-toxic. In an embodiment, the terminal pin half pads 170b would be of the same material as the electrical conductors 122. In an embodiment, the terminal pin half pads would be a different material than the electrical conductors 122. The terminal pin half pads of FIG. 33 may be metallic and therefore, electrically conductive or may alternatively be an electrically insulating material that has an electrically conductive or a metallic coating on its surfaces. The terminal pin half pads 170b of FIG. 33 may further comprise any of the biocompatible, biostable, and non-toxic materials previously described for the electrical conductor of FIGS. 12 and 13. Similarly, the terminal pin half pads 170b of FIG. 33 may further comprise the biocompatible, biostable, and non-toxic insulating materials and electrically conductive or metallic coatings also previously disclosed herein for the various AIMD components disposed on the body fluid side of the AIMD. Similar to the terminal pin half pads disclosed for the device side of the AIMD, the terminal pin half pads 170b of FIG. 33 are designed to capture terminal pins 18 passing through the insulator 28 of the AIMD hermetically sealed feedthrough 14 extending to the body fluid side of the AIMD. In FIG. 33, the top capture pad 172 would be entirely insulative and is fastened to the header block using fasteners 174, as shown. It is contemplated that the fasteners 174 can be selected from the group consisting of Allen screws, Torx screws, hex screws, star screws and combinations thereof. The fasteners 174 may be screwed directly into the formed insulation structure 120 (not shown) of the AIMD header block 118, or to vias in the electrical conductor 122 as illustrated.

Referring once again to FIG. 33, it is contemplated that the terminal pin half pads 170b could be eliminated and instead, the ends of the electrical conductors 122 could be formed into a semi-circular configuration for engaging with the terminal pin 18. In this embodiment, the conductors 122 may comprise an electrically conductive biocompatible coating or plating so that, when the top capture pad 172 is affixed and compressed against terminal pins 18, a low resistance electrical connection be made. The electrically conductive biocompatible coating or plating may be any one of the biocompatible electrically conductive materials previously disclosed herein, which may be applied by any of the processes also previously disclosed herein.

Referring once again to FIG. 33, it is understood that other components having threaded holes could be added to or within the AIMD header block 118 such that fasteners 174 could be used to fasten the top capture pad 172 to the AIMD header block. It is also understood that the entire top capture pad 172 and the terminal pin half pads 170a could all be insulative, offering a cost-effective attachment option. Referring once again to FIG. 33, of importance is that the terminal pin half pads 170b be electrically conductive. This would mean that electrically conducting materials subject to surface oxidation like tantalum, niobium or titanium must be coated or plated with a suitable higher conductivity preferably oxide-resistant material, such as pure gold or pure rhodium (which are also biocompatible). In an embodiment, the terminal pin half pads 170b could be made of a biocompatible highly conductive material, such as pure platinum or gold; however, these may be prohibitively expensive. The terminal pin half pads 170b may comprise any of the biocompatible materials previously disclosed herein. The terminal pin half pads 170b may comprise a coating or a plating comprising the biocompatible materials and application processes also previously disclosed herein. The coating or plating may be applied to increase strength and durability, allow solderability, or to improve electrical conductivity. Additionally, the terminal pin half pads 170b may comprise a gold flash over any plated material.

Figure 34:
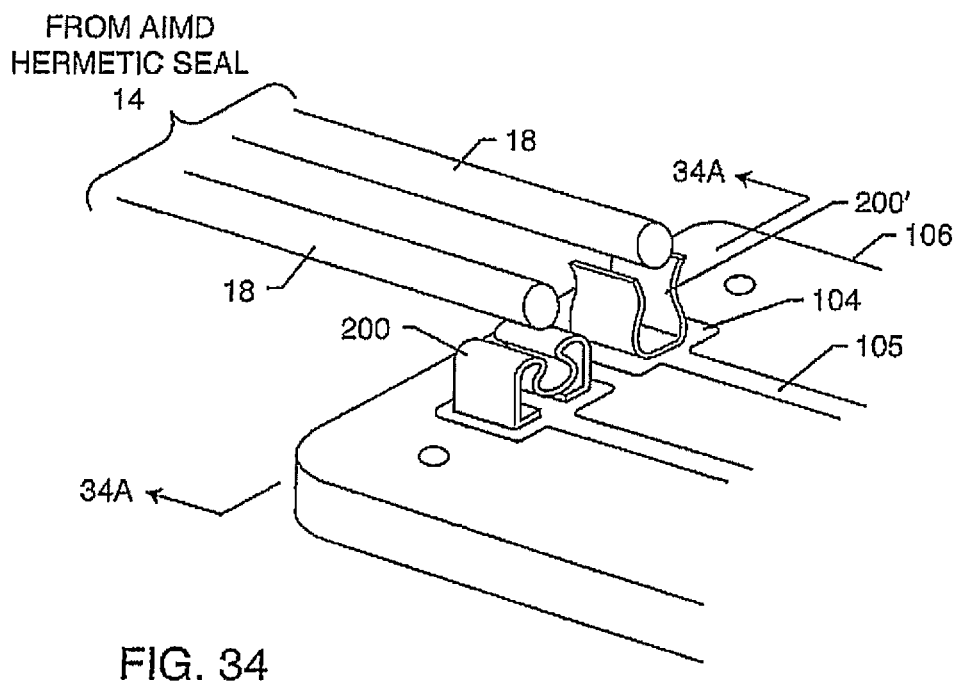
FIG. 34 is perspective view of alternative embodiments of clips of a terminal pin connector attached to electrical connection pads of an AIMD active electronic circuit board.

FIG. 34 illustrates an embodiment, wherein clips 200 or 200' have been populated onto an electrical connection pad 104 of an AIMD active electronic circuit board 106. Clips 200 and 200' are compliant clips in accordance with the definition of the term "compliant" previously defined herein. As clips 200, 200' are on the device side inside the hermetically sealed AIMD casing 32, sad clips 200, 200' need not be biocompatible, and could comprise any elastically resilient material, for example, beryllium copper or the like. The clips 200, 200' in the embodiment of FIG. 34 may be populated by a circuit board manufacturing robot along with all the other circuit board components (such as the microprocessor and other components not shown). Additionally, a robotic dispensing of a BGA dot, which could be a solder, or a solder paste, or a thermal-setting conductive adhesive dot, could also be robotically dispensed onto the electrical connection pad 104 for clip attachment. It is contemplated that during manufacturing, the solder would be reflowed, or the conductive epoxy would be cured, thereby firmly affixing clips 200 and 200' to the electrical connection pad 104 of the AIMD active electronic circuit board 106. In any of the embodiments disclosed in the present application, a circuit board electrical connection pad 104 may either be part of a circuit trace 105 as shown or comprise a circuit board land connected to one or more internal circuit traces (not shown) or may even directly connected to an electronic component (not shown).

The electrical connection pad 104 and circuit trace 105 are manufactured using known circuit board manufacturing techniques. The electrical connection pad 104, also known as a bond pad, may further comprise an affixed metal pad, such as a Kovar pad and the like. Affixing a Kovar pad (not shown) to the electrical connection pad 104 that is gold plated can provide high surface area for soldering to the electrical connection pad 104 or could facilitate laser welding or brazing of the clips 200, 200' to the electrical connection pad 104.

Referring once again to FIG. 34, the compliant clips 200, 200' can be plated or coated with a suitable material, such as gold or rhodium, which are high conductivity materials. Rhodium also has the advantage of wear resistant thereby allowing multiple terminal pin 18 insertions and retractions.

Figure 34A:
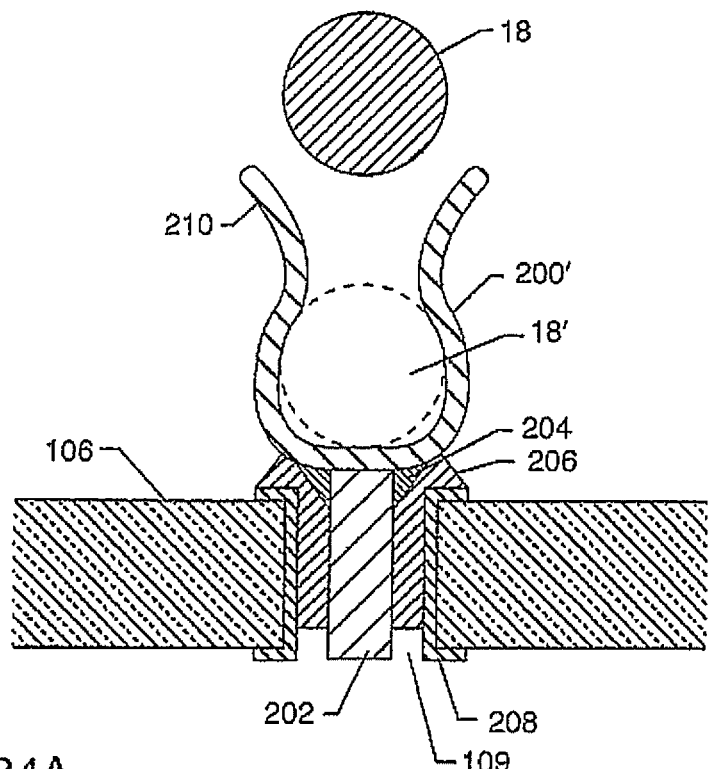
FIG. 34A is a sectional view of an alternative embodiment of a clip residing in a circuit board via hole that is attachable to a terminal pin. The clip comprises a post that secures attachment to an AIMD active electronic circuit board.

FIG. 34A is a sectional view taken along lines 34A-34A of FIG. 34 illustrating an alternative embodiment of clip 200'. In the embodiment of FIG. 34A, an electrically conductive post 202 is added to the clip 200' of FIG. 34. The clip 200' of FIG. 34A is mechanically and electrically attached to the AIMD active electronic circuit board 106 by inserting the post 202 of the clip 200' into to a via hole 109 of the AIMD active electronic circuit board 106. An electrical connection 206 electrically connects the post 202 to the metallization 208 of the via hole 109, the electrical connection 206 firmly securing the post 202 and the clip 200' to the AIMD active electronic circuit board 106. The post 202 may be affixed to the clip 200' by co-forming as one piece, or the post 202 and the clip 200' may be connected 204 by welding, brazing, soldering, or an equivalent process. The clip 200' and post 202 may also be made using 3-D printing processing. The post 202 could be of the same material as the clip 200' or a material different from the clip 200'. Clip 200' with attached post 202 may optionally be coated or plated as previously disclosed herein. As clip 200' is inside the AIMD, neither the clip 200', the coating or the plating need to be biocompatible. AIMDs must satisfy shock, vibration and drop test requirements as described by ISO 14708-1, which sets the general standards for all implantable medical devices, and the specific shock, vibration, and drop test requirements of ISO 14708-2 and ISO 14708-6, which sets the particular requirements for implantable cardiac pacemakers and implantable cardioverter defibrillators including an impact requirement (the example typically describing impact being an AIMD implanted within a pectoral pocket getting hit by a baseball). The embodiment of FIG. 34A offers a robust option for meeting such requirements.

Referring again to FIG. 34A, illustrated is an electrical connection 206 of the clip 200' with post 202 to an electrically conductive circuit board via hole 109, which typically comprises an electrically conductive plating, metallization, eyelet and the like. The via hole 109 of FIG. 34A illustrates an eyelet 208. The electrical connection 206 between the clip 200' with post 202 and the eyelet 208 may be a reflowed solder or a cured thermal-setting conductive adhesive. It is contemplated that electrical connection 206 could also be a thermal-setting conductive epoxy or even a low temperature braze.

The design of the compliant clip 200' of FIGS. 34 and 34A is important in that the spring rate and the curvature of the wings 210 of the clip 200' must be such that the terminal pin 18 can be pressed into and then firmly gripped by the wings 210. The insertion of terminal pin 18 spreads the wings 210 of the clip 200', as shown in FIG. 34A, so that the wings 210 open enough to snugly seat the terminal pin 18 within the wings 210 of the clip 200' and positioned and firmly gripped as shown by dashed circle 18'. The design considerations above also apply to clip 200 of FIG. 34.

Referring once again to FIGS. 34 and 34A, it will be appreciated that the plating or coating that may optionally be placed on the clips 200 and 200' is also important. For example, if the coating or plating are lubricious or smooth, insertion and retraction of the terminal pin 18 is facilitated. Likewise, if the coating and the plating is coarse, insertion and retraction of the terminal pin 18 is impeded. Accordingly, in accordance with the present invention, the surface roughness of the coating on the clips 200, 200' can be adjusted to a desired push and pull force. For example, the coating could be deliberately placed down, shot in or plasma-etched to provide a relatively higher degree of surface roughness to tailor tolerance to shock, vibration, drop and impact loads such that the terminal pin 18 does not undesirably detach from the clip 200, 200'.

Figure 34B:
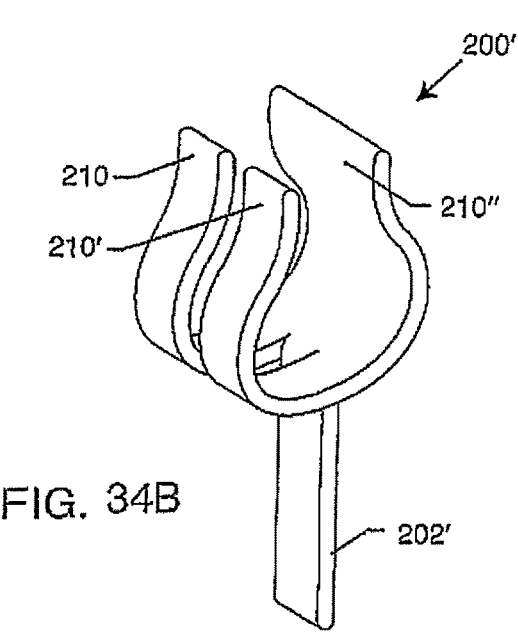
FIG. 34B is a perspective view of an alternative embodiment of a clip attachable to a terminal pin.

Referring to FIG. 34B, the clip 200' has been co-formed during a stamping process to include a post 202'. This embodiment allows the dual wings 210, 210' to be formed at the same time as the opposing wing 210" and at the same time as the post 202'. It will be appreciated that the post 202' of FIG. 34B, is configured for insertion into and connection to the circuit board via hole 109 in the same manner as disclosed for post 202 of FIG. 34A.

Figure 34C:
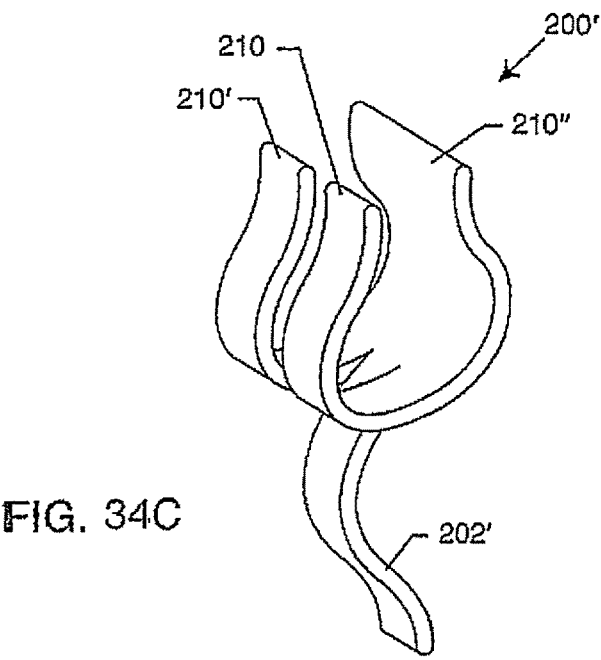
FIG. 34C is a perspective view of an alternative embodiment of a clip attachable to a terminal pin.

FIG. 34C illustrates an embodiment similar to FIG. 34B, except that the post 202' of the embodiment of FIG. 34C comprises a curved structure so that when the post 202' is inserted into the via hole 109 in the same manner as disclosed for post 202 of FIG. 34A, the curved structure of the post 200' compresses against opposing sidewalls of the via hole 109 such that the post 202' is held firmly in place. As such, the firm holding in place of the clip 200' by the curved post 202' facilitates application and flow of a solder, a thermal-setting conductive adhesive, a thermal-setting epoxy, or a braze during a reflow, a curing or a brazing process that forms the electrical connection 206 between the clip 200' with curved post 202' and electrically conductive via hole 109 of the AIMD active electronic circuit board 106. Those skilled in the art will understand that, when a very low weight structure, such as clip 200' and post 202', sits in liquifying solder or braze or is in a dispensed liquid adhesive or epoxy, there is a tendency for the entire structure to float in the liquid. The unique curving to the post 202' of clip 200' of the embodiment of the present application such that the post is mechanically 'clipped' (in other words pinned) to the via hole, thereby preventing the clip 200' from floating or moving during reflow, brazing, or curing processes, provides an effective economical connection option, which otherwise would require more costly and time-consuming production fixturing, such as pogo springs that push down on the structure during the attachment process. It will be appreciated that the clip 200' with the curved post 202' of FIG. 34C, is co-formed in the same manner as disclosed for FIG. 34B. It will also be appreciated that curved post 202' is inserted into the circuit board via hole 109 in the same manner as disclosed for post 202 of FIG. 34A.

Figure 34D:
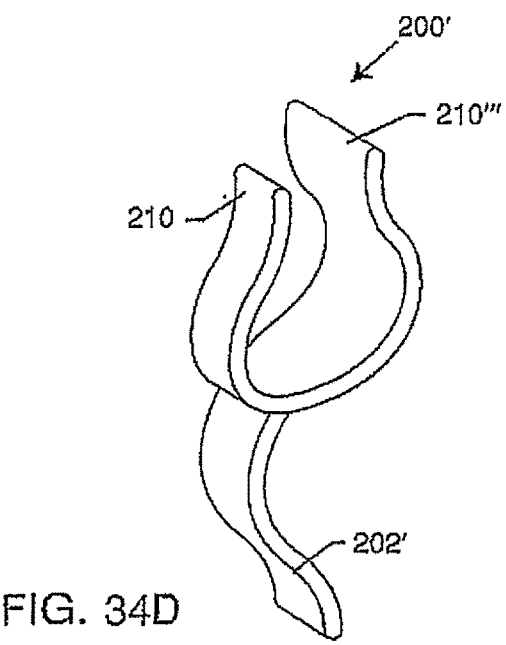
FIG. 34D is a perspective view of an alternative embodiment of a clip attachable to a terminal pin.

FIG. 34D illustrates an embodiment of clip 200' having a single wing 210 instead of the double wings 210, 210' of the clip 200' of FIGS. 34B and 34C. The single wing 210 of FIG. 34D is opposed by a larger wing 210'''. The post 202' of the clip 200' of FIG. 34D comprises the curved structure of FIG. 34C. It will be appreciated that the curved post 202' of the embodiment of FIG. 34D provides another effective economical connection option in the same manner as disclosed for the curved post 202' of FIG. 34C. It will also be appreciated that the clip 200' with the curved post 202' of FIG. 34D, is co-formed in the same manner as disclosed for FIG. 34B and is inserted into the circuit board via hole 109 in the same manner as disclosed for post 202 of FIG. 34A.

Figure 34E:
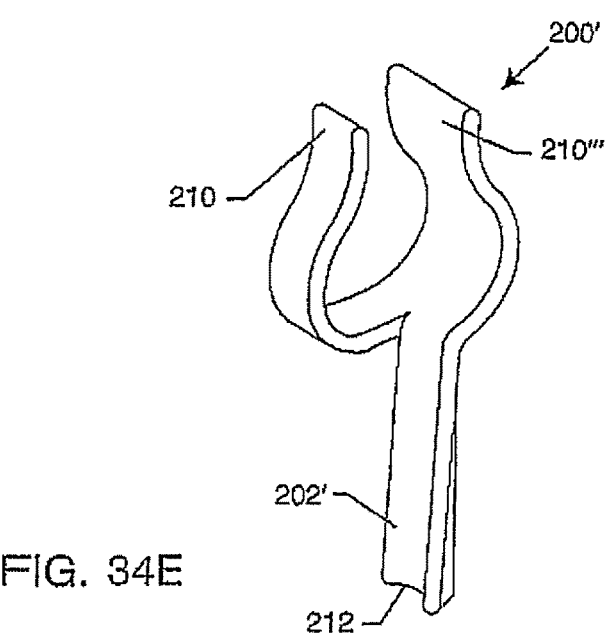
FIG. 34E is a perspective view of an alternative embodiment of a clip attachable to a terminal pin.

FIG. 34E illustrates an embodiment of clip 200' that is very similar to the clip 200' of FIG. 34D, except that in the embodiment of FIG. 34E, the positions of the single wing 210 and the post 202' are reversed compared to the positions of the single wing 210 and the post 202' of FIG. 34D, and the post 202' of FIG. 34E has a radius of curvature 212, as shown, instead of having a curved structure as shown in the curved post 202' of FIG. 34D. The radius of curvature 212 of the post 202' of clip 200' of FIG. 34E is carefully designed such that it is slightly larger than the radius of curvature of the via hole 109 of the AIMD active electronic circuit board 106 of FIG. 34A. The slightly larger radius of curvature 212 of the post 202' of FIG. 34E allows insertion of the radiused post 202' into the via hole 109 such that the radiused post 202' compresses against opposing sidewalls of the via hole 109 holding the clip 200' firmly in place. As such, the firm holding in place of the clip 200' by the radiused post 202' facilitates application and flow of a solder, a thermal-setting conductive adhesive, a thermal-setting epoxy, or a braze during a reflow, a curing or a brazing process that forms the electrical connection 206 between the clip 200' with radiused post 202' and electrically conductive via hole 109 of the AIMD active electronic circuit board 106 similarly to the curved post 202' of FIGS. 34C and 34D. It will be appreciated that the radiused post of the embodiment of FIG. 34E provides yet another effective economical connection option in the same manner as disclosed for the curved post of FIGS. 34C and 34D. It will also be appreciated that the clip 200' with the radiused post 202' of FIG. 34E, is co-formed in the same manner as disclosed for FIG. 34B and is inserted into the circuit board via hole 109 in the same manner as disclosed for post 202 of FIG. 34A.

Referring once again to FIGS. 34 through 34E, the material of construction of any of the stamped or co-formed clips of FIGS. 34 through 34E could be any suitable compliant elastically resilient material disclosed herein. Additionally, any of the clips of FIGS. 34 through 34E could comprise an insulating material instead of an electrically conductive material. Suitable insulating materials are high temperature (have melting and deflection temperatures above approximately 204° C.), high strength materials and capable of withstanding a sustained high temperature soldering process without deforming. There are a wide variety of polymers and plastics that can withstand high temperatures. Insulating materials may be selected from the group consisting of acrylonitrile butadiene styrene (ABS), polytetrafluoroethylene (PTFE), perfluoroalkoxy (PFA), polyamide-imide (PAI), polyether ether ketone (PEEK™), polyaryletherketone (PAEK), stereolithography (SLA) resin, polyetherimide (PEI), polyimide (PI), polyamide (PA). polyphenylsulfone (PPSU), polysulfone (PSU), polybenzimidazole (PBI), thermoplastic polyimide (TPI), polyethersulfone (PES), polyether ketone (PEK), polyphenylen sulfide (PPS), polychlorotrifluoroethylene (PCTFE), ethylene chlorotrifluoroethylene (ECTFE), polyvinylidene fluoride (PVDF), fluoropolymer (FP), and combinations thereof. Insulating materials may also be selected from the group consisting of Teflon®, Rulon™, Torlon®, Ultem®, Vespel®, Radel®, Celazole®, molded plastics, 3 dB plastics, among others. Such clips comprising insulating material would require an electrically conductive coating or plating. The electrically conductive coating or plating may be any one of the electrically conductive materials previously disclosed herein, which may be applied by any of the processes also previously disclosed herein. It will also be appreciated that a plating or coating could be applied to clip 202' to impart supplemental properties also as previously disclosed herein. It is understood that the embodiments shown in FIGS. 34 through 34E are low-cost options for electrically connecting terminal pins 18 to AIMD components.

As defined herein and used throughout, an AIMD circuit board 106 is a circuit board enclosed within the hermetically sealed AIMD casing 32 that contains active electronic circuits, including, in most cases, a microprocessor among many other components. An AIMD either has a primary battery or a secondary (rechargeable) battery that drives the circuit board or a that drives the circuit board electronics or another source of energy, such as an energy harvesting mechanism from body motions, thermal energy or externally induced ultrasonic energy and the like. Hence, an AIMD circuit board 106 is an active electronic circuit board and not a circuit board containing only passive electronic components. On the other hand, an EMI filter circuit board is a circuit board that may comprise MLCCs, X2Y attenuators or flat-thru capacitors placed on, near, adjacent, or slightly away from an AIMD hermetic seal, which is disposed in an opening of the AIMD casing. So, there is a clear distinction between a removable AIMD active electronic circuit board and a removable EMI filter circuit board again, as the AIMD active electronic circuit board has at least one active electronic component.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, while this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

What is claimed is:

1. A feedthrough terminal pin connector assembly, comprising:
    a) a first terminal pin connector comprising a first sidewall having a first exterior surface spaced from a first interior surface defining a first connector opening extending along a first longitudinal axis, wherein at least a first portion of the first sidewall comprising the first exterior and interior surfaces is electrically conductive and supports a first electrically conductive compliant structure in the first connector opening;
    b) at least a second terminal pin connector comprising a second sidewall having a second exterior surface spaced from a second interior surface defining a second connector opening extending along a second longitudinal axis, wherein at least a second portion of the second sidewall comprising the second exterior and interior surfaces is electrically conductive and supports a second electrically conductive compliant structure in the second connector opening;
    c) a common housing containing the first and second terminal pin connectors; and
    d) an insulative material contained inside the common housing to electrically isolate the electrically conductive first and second portions of the first and second sidewalls of the first and second terminal pin connectors from each other.

2. The feedthrough terminal pin connector assembly of claim 1, wherein the electrically conductive first and second portions of the first and second sidewalls of the respective first and second terminal pin connectors have at least one first and second planar exterior surface.

3. The feedthrough terminal pin connector assembly of claim 2, wherein the insulative material does not coat the first and second planar exterior surfaces.

4. The feedthrough terminal pin connector assembly of claim 1, wherein the common housing comprises a metallic structure, a ceramic structure, or a structure comprising a ceramic and a metal.

5. The feedthrough terminal pin connector assembly of claim 1, wherein the common housing comprises alumina.

6. A circuit board connector assembly for use in an active implantable medical device (AIMD), the circuit board connector assembly comprising:
    a) a circuit board having at least a first electrical circuit and a second electrical circuit; and
    b) a feedthrough terminal pin connector assembly, comprising:
        i) a first terminal pin connector comprising a first sidewall having a first exterior surface spaced from a first interior surface defining a first connector opening, wherein at least a first portion of the first sidewall comprising the first exterior and interior surfaces is electrically conductive and supports a first electrically conductive compliant structure in the first connector opening;
        ii) at least a second terminal pin connector comprising a second sidewall having a second exterior surface spaced from a second interior surface defining a second connector opening, wherein at least a second portion of the second sidewall comprising the second exterior and interior surfaces is electrically conductive and supports a second electrically conductive compliant structure in the second connector opening;
        iii) a common housing containing the first and second terminal pin connectors; and
        iv) an insulative material contained inside the common housing to electrically isolate the first and second electrically conductive sidewall portions of the first and second terminal pin connectors from each other, and
    c) wherein the feedthrough terminal pin connector assembly is supported on the circuit board with the electrically conductive first and second sidewall portions of the respective first and second terminal pin connectors contained in the common housing being electrically connected to the respective first and second electrical circuits.

7. The feedthrough terminal pin connector assembly of claim 1, wherein the insulative material is selected from silicone, polyurethane, polyester, polyethylene, polypropylene, polyimide, polyamide, synthetic polyamide, acrylic, polyacrylates, perfluoroalkoxy (PFA), fluorinated ethylene-propylene (FEP), polyetheretherketone (PEEK), polyamide imide (PAI), polyphenylsulfone (PPSU), polyetherimide (PEI), polymethyl methacrylate (PMMA), acrylonitrile butadiene styrene (ABS), polycarbonate (PC), polyoxymethylene (POM), polystyrene (PS), thermoplastic elastomer (TPE), polyethylene terephthalate (PET), ethylene-vinyl acetate (EVA), polyethylene-vinyl acetate (PEVA), and combinations thereof.

8. The feedthrough terminal pin connector assembly of claim 1, wherein the insulative material includes nanoparticles selected from $Al_2O_3$, BaO, CaO, $CeO_2$, MgO, $Zro_2$, $SiO_2$, $TiO_2$, $Al_2SiO_{53}$, $BaTiO_3$, $SrTiO_2$, ZnO, $Si_3N_4$, zirconia toughened alumina (ZTA), alumina toughened zirconia (ATZ), Yttrium stabilized zirconia (YSZ), yttrium-toughened zirconia (YTZP), aluminum nitride (AlN), silicon nitride ($Si_3N_4$), boron nitride (BN), carbon nitride (CN), and combinations thereof.

9. The feedthrough terminal pin connector assembly of claim 8, wherein the nanoparticles range in size from greater than about 100 nanometers (0.1 microns) to about 40,000 nanometers (40 microns).

10. The feedthrough terminal pin connector assembly of claim 8, wherein a nanoparticle loading in the insulating material ranges from >0% to about 40%, by weight.

11. The feedthrough terminal pin connector assembly of claim 1, wherein the first and second electrically conductive compliant structures supported by the respective electrically conductive first and second sidewall interior surfaces are selected from at least two prongs angled from at least one of the first and second interior surfaces toward the first and second longitudinal axes in the respective first and second connector openings, a wavy tine, and a spring clip.

12. The feedthrough terminal pin connector assembly of claim 1, wherein the common housing contains at least a third terminal pin connector.

13. The circuit board connector assembly of claim 6, wherein electrically conductive first and second portions of the first and second sidewalls of the respective first and second terminal pin connectors have at least one first and second planar exterior surface, and wherein the insulative material does not coat the first and second planar exterior surfaces.

14. The circuit board connector assembly of claim 6, wherein the first and second terminal pin connectors are individually selected from an active terminal pin connector and a ground terminal pin connector.

15. The circuit board connector assembly of claim 13, wherein the circuit board has first and second electrical connection pads that are electrically connected to the respective first and second electrical circuits, and wherein, with the common housing being supported on the circuit board, the first and second planar exterior surfaces of the electrically conductive portions of the first and second terminal pin connectors contact the respective first and second electrical connection pad electrically connected to the respective first and second electrical circuits.

16. The circuit board connector assembly of claim 15, wherein the first and second electrical connection pads are individually selected from a land, a trace, and an edge connection.

17. The circuit board connector assembly of claim 13, wherein the first electrical circuit is an active electrical circuit and the second electrical circuit is a ground electrical circuit, and wherein the first planar exterior surface of the first connector housing is connected to the active electrical circuit and the second planar exterior surface of the second connector housing is connected to the ground electrical circuit of the circuit board, and wherein the insulative material is configured to prevent flashover, avalanche discharge, carbon tracking, catastrophic failure, and microcoulomb discharge between the first and second connector housings.

18. The circuit board connector assembly of claim 13, wherein first and second alignment flanges extend outwardly from the first and second electrically conductive portions of the first and second terminal pin connectors, and wherein, with the first and second planar exterior surfaces of the first and second electrically conductive portions of the first and second terminal pin connectors being electrically connected to the respective first and second electrical circuits, the first and second alignment flanges contact an edge of the circuit board.

19. An active implantable medical device (AIMD), comprising:
  a) an AIMD housing;
  b) a circuit board contained inside the AIMD housing, the circuit board comprising at least a first and a second electrical circuits;
  c) a feedthrough terminal pin connector assembly contained inside the AIMD housing, the feedthrough terminal pin connector assembly comprising:
    i) a first terminal pin connector comprising a first sidewall having a first exterior surface spaced from a first interior surface defining a first connector opening, wherein at least a first portion of the first sidewall comprising the first exterior and interior surfaces is electrically conductive, and wherein the electrically conductive first portion of the first sidewall supports a first electrically conductive compliant structure in the first connector opening and has at least one first planar exterior surface;
    ii) at least a second terminal pin connector comprising a second sidewall having a second exterior surface spaced from a second interior surface defining a second connector opening, wherein at least a second portion of the second sidewall comprising the second exterior and interior surfaces is electrically conductive, and wherein the electrically conductive second portion of the second sidewall supports a second electrically conductive compliant structure in the second connector opening and has at least one second planar exterior surface;
    iii) a common housing containing the first and second terminal pin connectors; and
    iv) an insulative material contained inside the common housing to electrically isolate the first and second electrically conductive sidewall portions of the first and second terminal pin connectors from each other; and
  d) a feedthrough, comprising:
    i) an electrically conductive ferrule comprising a ferrule opening, wherein the ferrule is sealed in an opening in the AIMD housing;
    ii) an insulator hermetically sealed to the ferrule in the ferrule opening, wherein the insulator has an insulator body fluid side opposite an insulator device side, the insulator body fluid and device sides residing outside and inside the AIMD housing, respectively;
    iii) at least a first and second insulator passageways extending through the insulator; and
    iv) first and second electrically conductive terminal pins hermetically sealed to the insulator in the respective first and second insulator passageways, wherein the first and second terminal pins extend outwardly beyond the insulator device side,
  e) wherein, with the feedthrough terminal pin connector assembly mounted on the circuit board, the first and second planar exterior surfaces of the electrically conductive first and second sidewall portions of the respective first and second terminal pin connectors contained in the common housing are electrically connected to the respective first and second electrical circuits of the circuit board, and
  f) wherein the feedthrough terminal pin connector assembly is configured to allow multiple insertions and retractions of the first and second terminal pins into and out of the respective first and second electrically conductive compliant structures of the first and second terminal pin connectors to thereby electrically connect and disconnect the first and second terminal pins from the first and second electrical circuits.

20. The AIMD of claim 19, wherein the first and second terminal pin connectors are individually selected from an active terminal pin connector and a ground terminal pin connector.

21. The AIMD of claim 19, wherein the insulative material does not coat the first and second planar exterior surfaces.

22. The AIMD of claim 19, wherein first and second alignment flanges extend outwardly from the first and second electrically conductive portions of the first and second terminal pin connectors, and wherein, with the first and second planar exterior surfaces of the first and second electrically conductive portions of the first and second terminal pin connectors being electrically connected to the respective first and second electrical circuits, the first and second alignment flanges contact an edge of the circuit board.

23. The AIMD of claim 19, further including a feedthrough capacitor comprising at least one active electrode plate interleaved in a capacitive relationship in a capacitor dielectric with and at least one ground electrode plate, wherein the active electrode plate is electrically connected to at least one of the first and second terminal pins and the at least one ground electrode plate is electrically connected to the ferrule.

* * * * *